(12) United States Patent
Oleksiewicz et al.

(10) Patent No.: US 7,749,697 B2
(45) Date of Patent: Jul. 6, 2010

(54) METHOD FOR LINKING SEQUENCES OF INTEREST

(75) Inventors: Martin B. Oleksiewicz, Bronshoj (DK); Lars S. Nielsen, Niva (DK); Peter S. Andersen, Vanlose (DK); Margit H. Hansen, Copenhagen (DK)

(73) Assignee: Symphogen A/S, Lyngby (DK)

( * ) Notice: Subject to any disclaimer, the term of this patent is extended or adjusted under 35 U.S.C. 154(b) by 524 days.

(21) Appl. No.: 10/572,431

(22) PCT Filed: Sep. 17, 2004

(86) PCT No.: PCT/DK2004/000633

§ 371 (c)(1),
(2), (4) Date: Mar. 20, 2006

(87) PCT Pub. No.: WO2005/042774

PCT Pub. Date: May 12, 2005

(65) Prior Publication Data

US 2007/0141048 A1   Jun. 21, 2007

Related U.S. Application Data

(60) Provisional application No. 60/504,589, filed on Sep. 18, 2003, provisional application No. 60/504,455, filed on Sep. 18, 2003.

(30) Foreign Application Priority Data

Dec. 17, 2003   (DK) ............... 2003 01867
May 15, 2004    (DK) ............... 2004 00782

(51) Int. Cl.
*C12Q 1/68* (2006.01)
*C12P 19/34* (2006.01)
*C07H 21/04* (2006.01)

(52) U.S. Cl. ............... 435/6; 435/91.2; 536/24.33
(58) Field of Classification Search ............... 435/6, 435/91.2, 91.21; 536/23.1
See application file for complete search history.

(56) References Cited

U.S. PATENT DOCUMENTS

| | | |
|---|---|---|
| 4,683,202 A | 7/1987 | Mullis |
| 5,698,435 A | 12/1997 | Robinson et al. |
| 5,882,856 A | 3/1999 | Shuber |
| 5,912,172 A | 6/1999 | Eshhar et al. |
| 6,096,878 A | 8/2000 | Honjo et al. |
| 6,111,166 A | 8/2000 | van de Winkel |
| 6,258,529 B1 | 7/2001 | Berdoz et al. |
| 6,538,124 B1 | 3/2003 | Idusogie et al. |
| 6,849,259 B2 | 2/2005 | Haurum et al. |
| 6,867,021 B2 | 3/2005 | Maes et al. |
| 6,994,963 B1 | 2/2006 | Murphy et al. |
| 2001/0027249 A1 | 10/2001 | Le et al. |
| 2002/0102604 A1 | 8/2002 | Edwards et al. |
| 2003/0096343 A1 | 5/2003 | Robinson et al. |
| 2003/0175837 A1 | 9/2003 | Le et al. |
| 2004/0067532 A1 | 4/2004 | Zhu et al. |
| 2006/0275766 A1 | 12/2006 | Haurum et al. |
| 2007/0003515 A1 | 1/2007 | Leonard et al. |
| 2008/0131882 A1 | 6/2008 | Rasmussen et al. |
| 2009/0017017 A1 | 1/2009 | Rasmussen et al. |

FOREIGN PATENT DOCUMENTS

| | | |
|---|---|---|
| WO | WO 92/15678 A1 | 9/1992 |
| WO | WO 9215678 A1 * | 9/1992 |
| WO | WO 93/03151 A1 | 2/1993 |
| WO | WO 9303151 A1 * | 2/1993 |
| WO | WO 93/20227 A1 | 10/1993 |
| WO | WO 94/08008 A1 | 4/1994 |
| WO | WO 95/20401 A1 | 8/1995 |
| WO | WO 96/08564 A1 | 3/1996 |
| WO | WO 98/057994 A2 | 12/1998 |
| WO | WO 99/16904 A1 | 4/1999 |
| WO | WO 99/029888 A1 | 6/1999 |
| WO | WO 01/89563 A1 | 11/2001 |
| WO | WO 01/92291 A2 | 12/2001 |
| WO | WO 2004/061104 A2 | 7/2004 |
| WO | WO 2006/007850 A1 | 1/2006 |

(Continued)

OTHER PUBLICATIONS

Poddar, SK. Influenza virus types and subtypes detection by single step single tube multiplex reverse transcription-polymerase chain reaction (RT-PCR) and agarose gel electrophoresis. J. Virol Methods, vol. 99, pp. 63-70, 2002.*

Ray, PF et al. Single cell multiplex PCR amplification of five dystrophin gene exons combined with gender determination. Molecular Human Repro., vol. 7, No. 5, pp. 489-494, 2001.*

Wang, X et al. Human immunoglobulin variable region gene analysis by single cell RT-PCR. J immunological Methods, vol. 244, pp. 217-225, 2000.*

Database Biotechno, Accession No. 1999:29089942, Abstract for Akatsuka, Y., et al., "Rapid screening of T-cell receptor (TCR) variable gene usage by multiplex PCR: Application for assessment of clonal composition," *Tissue Antigens* 53:122-134, Blackwell Publishing, Inc. (1999).

(Continued)

*Primary Examiner*—Suryaprabha Chunduru
(74) *Attorney, Agent, or Firm*—Sterne, Kessler, Goldstein & Fox P.L.L.C.

(57) ABSTRACT

Multiplex overlap-extension RT-PCR provides an efficient method of linking two or more nucleotide sequences encoding for domains or subunits of a heteromeric protein, in a single reaction. Especially, the linkage of variable region encoding sequences from e.g. immunoglobulins, T cell receptors or B cell receptors is eased with the method of the present invention. This allows for a more efficient way of generating libraries of variable region encoding sequences. The capability to perform the multiplex overlap-extension RT-PCR using template derived from an isolated single cell enables the generation of cognate pair libraries in a high-throughput format.

29 Claims, 38 Drawing Sheets

FOREIGN PATENT DOCUMENTS

WO     WO 2006/007853 A2     1/2006

OTHER PUBLICATIONS

Database Biotechno, Accession No. 1999:29445017, Abstract for Cheng, L., et al., "Expression in normal human tissues of five nucleotide excision repair genes measured simultaneously by multiplex reverse transcription-polymerase chain reaction," *Cancer Epidemiology Biomarkers and Prevention* 8:801-807, American Association for Cancer Research (1999).

Database Biotechno, Accession No. 1999:29223369, Abstract for Tanabe, R., et al., "Expression of myosin heavy chain isoforms in porcine muscles determined by multiplex PCR," *Journal of Food Science* 64:222-225, Institute of Food Technologists (1999).

Altman, J.D., et al., "Phenotypic Analysis of Antigen-specific T Lymphocytes," *Science* 274:94-96, American Association for the Advancement of Science (1996).

Babcook, J.S., et al., "A novel strategy for generating monoclonal antibodies from single, isolated lymphocytes producing antibodies of defined specificities," *Proc. Natl. Acad. Sci. USA* 93:7843-7848, The National Academy of Science (1996).

Barbas, C.F., et al., "Assembly of combinatorial antibody libraries on phage surfaces: The gene III Site," *Proc. Natl. Acad. Sci. USA* 88:7978-7982, The National Academy of Sciences (1991).

Callan, M.F.C., et al., "Direct Visualization of Antigen-specific $CD^+$ T Cells during the Primary Immune Response to Epstein-Barr Virus In Vivo," *J. Exp. Med.* 187:1395-1402, The Rockefeller University Press (1998).

Campbell, M.J., et al., "Use of Family Specific Leader Region Primers for PCR Amplification of the Human Heavy Chain Variable Region Gene Repertoire," *Mol. Immunol:* 29:193-203, Pergamon Press plc (1992).

Chapal, N., et al., "In-Cell Assembly of scFv from Human Throid-Infiltrating B Cells," *BioTechniques* 23:518-524, Eaton Publishing Company (1997).

Chin, J., et al., "Production of neutralizing human monoclonal antibody directed to tetanus toxin in CHO cell," 31:45-53, Elsevier Science Ltd. (Mar. 2003).

Compton, J., "Nucleic acid sequence-based amplification," *Nature* 350:91-92, Nature Publishing Group (1991).

Coronella, J.A., et al., "Amplification of IgG VH and VL (Fab) from single human plasma cells and B cells," *Nucleic Acids Res.* 28:e85, Oxford University Press (2000).

de Haard, H.J., et al., "A Large Non-Immunized Human Fab Fragment Phage Library That Permits Rapid Isolation and Kinetic Analysis of High Affinity Antibodies," *J. Biol. Chem.* 274:18218-18230, The American Society for Biochemistry and Molecular Biology, Inc. (1999).

Den W., et al., "A bidirectional phage display vector for the selection and mass transfer of polyclonal antibody libraries," *J. Immunol. Meth.* 222:45-57, Elsevier Science B.V. (1999).

de Wildt, R.M.T., et al., "Antibody arrays for high-throughput screening of antibody-antigen interactions," *Nat. Biotechnol.* 19:989-994, Nature America Inc. (2000).

Embleton, M.J., et al., "In-cell PCR from mRNA: amplifying and linking the rearranged immunoglobulin heavy and light chain V-genes within single cells," *Nucleic Acids Res.* 20:3831-3837, Oxford University Press (1992).

Fitzgerald, K., "In vitro dislay technologies—new tools for drug discovery," *Drug Discovery Today* 5:253-258, Elsevier Science Ltd. (2000).

Guatelli, J.C., et al., "Isothermal, in vitro Amplification of nucleic acids by a multioenzyme reaction modeled after retroviral replication," *Proc. Natl. Acad. Sci. USA* 87:1874-1878, The National Academy of Sciences (1990).

Gherardi, E. and Milstein, C., "Original and artificial antibodies," *Nature* 357:201-202, Nature Publishing Group (1992).

Henegariu, O., et al., "Multiplex PCR: Critical Parameters and Step-by-Step Protocol," *Biotechniques* 23:504-511, Eaton Publishing Company (1997).

Horton, R.M., et al., "Engineering hybrid genes without the use of restriction enzymes: gene splicing by overlap extension," *Gene* 77:61-68, Elsevier Science Publishers B.V. (1989).

International Search Report and Written Opinion of the International Search Authority for International Application No. PCT/DK2004/000633, European Patent Office, Netherlands, mailed Apr. 29, 2005.

European Search Report for European Application No. EP 04 02 1764, European Patent Office, Netherlands, mailed Jan. 10, 2006.

Kang, A.S., et al., "Linkage of recognition and replication functions by assembling combinatorial antibody Fab libraries along phage surfaces," *Proc. Natl. Acad. Sci. USA* 88:4363-4366, The National Academy of Sciences (1991).

Kuroiwa, Y., et al., "Cloned transchromosomic calves producing human immunoglobulin," *Nat. Biotechnol.* 20:889-894, Nature Publishing Group (2002).

Lakew, M., et al., "Combined immunomagnetic cell sorting and ELISPOT assay for the phenotypic characterization of specific antibody-forming cells," *J. Immunol. Meth.* 203:193-198, Elsevier Science B.V. (1997).

Liu, A.H., et al., "Sequencing heavy- and light-chain variable genes of single B-hybridoma cells by total enzymatic amplification," *Proc. Natl. Acad. Sci. USA* 89:7610-7614, The National Academy of Sciences (1992).

Marks, J.D., "Human Monoclonal Antibodies from V-Gene Repertoires Expressed on Bacteriophage," in *Antibody Engineering, 2nd Ed.*, Borrebaeck, C., ed., Oxford University Press, New York, pp. 53-88 (1995).

Marks, J.D., et al., "By-passing Immunization," *J. Mol. Biol.* 222:581-597, Academic Press Limited (1991).

Markoulatos, P., et al., "Mutliplexing Polymerase Chain Reaction: A Practical Approach," *J. Clin. Lab. Anal.* 16:47-51, Wiley-Liss, Inc. (2002).

Mullinax, R.L., et al., "Expression of a Heterodimeric Fab Antibody Protein in One Cloning Step," *BioTechniques* 12:864-869, Eaton Publishing (1992).

Nielson, H., et al., "Identification of prokaryotic and eukaryotic signal peptides and prediction of their cleavage sites," *Protein Eng.* 10:1-6, Oxford University Press (1997).

Novak, E.J., et al., "MHC class II tetramers identify peptide-specific human $CD4^+$ T cells proliferating in response to influenza A antigen," *J. Clin. Invest.* 104:R63-R67, American Society for Clinical Investigation (1999).

Sharon, J., et al., "Recombinant Polyclonal Antibody Libraries," *Comb. Chem. High Throughput Screen.* 3:185-196, Bentham Science Publishers (2000).

Thirion, S., et al., "Mono- and bispecific single-chain antibody fragments for cancer therapy," *Eur. J. Cancer Preven.* 5:507-511, Rapid Science Publishers (1996).

Traggiai, E., et al., "An efficient method to make human monoclonal antibodies from memory B cells: potent neutralization of SARS coronavirus," *Nat. Med.* 10:871-875, Nature Publishing Company (Aug. 2004).

Walker, G.T., et al., "Strand displacement amplification—an isothermal, in vitro DNA amplification technique," *Nucleic Acids Res.* 20:1691-1696, Oxford University Press (1992).

Wang, X. and Stollar, B.D., "Human immunoglobulin variable region gene analysis by single cell RT-PCR," *J. Immunol. Meth.* 244:217-225, Elsevier Science B.V. (2000).

Willcox, B.E., et al., "Production of soluble $\alpha\beta$ T-cell receptor heterodimers suitable for biophysical analysis of ligand binding," *Protein Sci.* 8:2418-2423, Cambridge University Press (1999).

Wu, D.Y. and Wallace, R.B., "The Ligation Amplification Reaction (LAR)-Amplification of Specific DNA Sequences Using Sequential Rounds of Template-Dependent Ligation," *Genomics* 4:560-569, Academic Press, Inc. (1989).

Written Opinion of the International Preliminary Examining Authority (PCT Rule 66) for International Application No. PCT/DK2004/000633, European Patent Office, Netherlands, mailed Sep. 19, 2005.

International Preliminary Report on Patentability (PCT Article 36 and Rule 70) for International Application No. PCT/DK2004/000633, European Patent Office, Netherlands, mailed Dec. 19, 2005.

Burgart, L.J., et al., "Multiplex Polymerase Chain Reaction," *Mod. Path.* 5:320-323, U.S. and Canadian Acad. Path. (1992).

Kurokawa, M., et al., "Paired cloning of the T cell receptor α and β genes from a single T cell without the establishment of a T clone," *Clin. Exp. Immunol.* 123:340-345, Blackwell Sci. Ltd. (2001).

Meijer, P.-J., et al., "Isolation of human Antibody Repertoires with Preservation of the natural heavy and light chain pairing," *J. Mol. Biol.* 358:764-772, Elsevier Ltd. (2006).

Orlandi, R., et al., "Cloning immunoglobulin variable domains for expression by the polymerase chain reaction," *Proc. Natl. Acad. Sci. USA* 86:3833-3837, The National Academy of Sciences (1989).

Orum, H., et al., "Efficient method for constructing comprehensive murine Fab antibody libraries displayed on phage," *Nuc. Acids Res.* 21:4491-4498, Oxford University Press (1993).

Wrammert, J., et al., "Rapid cloning of high-affinity human moncolonal antibodies against influenza virus," *Nature* 453:667-71, Nature Publishing Group (2008).

Xiaocong, Y., et al., "Neutralizing antibodies derived from the B cells of 1918 influenza pandemic survivors," *Nature* 455:532-6, Nature Publishing Group (2008).

Chapal, N., et al., "Human anti-thyroid peroxidase single-chain fragment variable of Ig isloated from a combinatorial library assembled in-cell: insights into the in vivo situation," *J Immunol.* 164(8): 4162-9, American Association of Immunologists, United States (Apr. 2000).

Harris, E. et al., "Typing of dengue viruses in clinical specimens and mosquitoes by single-tube multiplex reverse transcriptase PCR," *J Clin Microbiol.* 36(9): 2634-9, American Society for Microbiology, United States (Sep. 1998).

Lang, A.B. et al., "Polyclonal preparatiosn of anti-tetanus toxoid antibodies derived from a combinatorial library confer protection," *Biotechnology* 13(7): 683-5, Nature Pub Co., United States (Jul. 1995).

Ardavin, C., "B Cell Response After MMTV Infection: Extrafollicular Plasmablasts Represent the Main Infected Population and Can Transmit Viral Infection," *J. Immunol.* 162: 2538-2545, The American Association of Immunologiest, United States (1999).

Kumar, S., et al., "Molecular cloning and expression of the Fabs of human autoantibodies in *Escherichia coli*. Determination of the heavy or light chain contribution to the anti-DNA/-cardiolipin activity of the Fab," *J. Biol. Chem.* 275(45): 35129-36, American Society for Biochemistry and Molecular Biology, United States (Nov. 2000).

Liu, A.Y., et al., "Expression of the mouse::human immunoglobulin heavy-chain cDNA in lymphoid cells," *Gene* 54: 33-40, Elsevier Science, Netherlands (1987).

Requena, L., et al., "Cutaneous Involvement in Multiple Myeloma: A Clinicopathologic, Immunohistochemical, and Cytogenetic Study of 8 Cases," *Arch Dermatol.* 139: 475-486, American Medical Association, United State (2003).

Rudikoff, S., et al., "Single amino acid substitution altering antigen-binding specificity," *Proc. Natl. Acad. Sci. USA.* 79(6): 1979-83, National Academy of Sciences, United States (Mar. 1982).

Smith-Gill, S.J., et al., "Contributions of immunoglobulin heavy and light chains to antibody specificity for lysozyme and two haptens," *J. Immunol.* 139(12): 4135-44, American Association of Immunologists, United States (Dec. 1987).

Söderlind, E., et al., "Complementarity-determining region (CDR) implantation: a theme of recombination," *Immunotechnology* 4(3-4): 279-85, Elsevier, Netherlands (Mar. 1999).

Söderlind, E., et al., "Domain libraries: synthetic diversity for de novo design of antibody V-regions," *Gene* 160(2): 269-72, Elsevier/North-Holland, Netherlands (Jul. 1995).

Song, M.K., et al., "Light chain of natural antibody plays a dominant role in protein antigen binding," *Biochem. Biophys. Res. Commun.* 268(2): 390-4, Academic Press, United States (Feb. 2000).

Ward, E.S., et al., "Binding activities of a repertoire of single immunoglobulin variable domains secreted from *Escherichia coli*," *Nature* 341(6242): 544-6, Nature Publishing Group, United States (Oct. 1989).

Weissenhorn, W., et al., "Chimerization of antibodies by isolation of rearranged genomic variable regions by the polymerase chain reaction," *Gene* 106: 273-277, Elsevier Science, Netherlands (1991).

Office Action mailed Apr. 2, 2010, in U.S. Appl. No. 12/074,066, Kastrup et al., filed Feb. 29, 2008.

\* cited by examiner

Figure 1
I
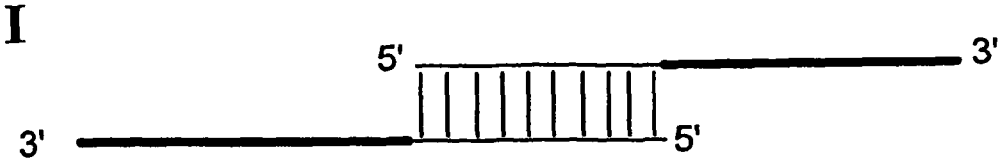
II
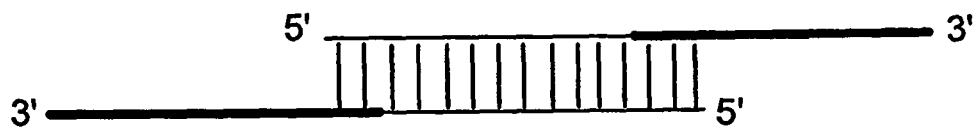
III

Figure 5
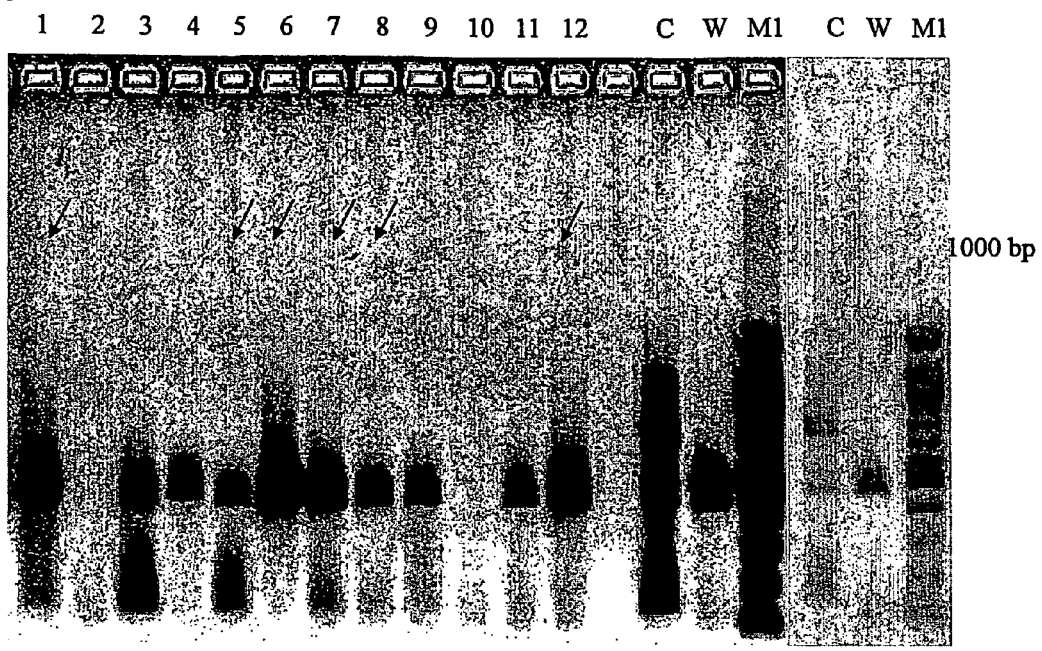
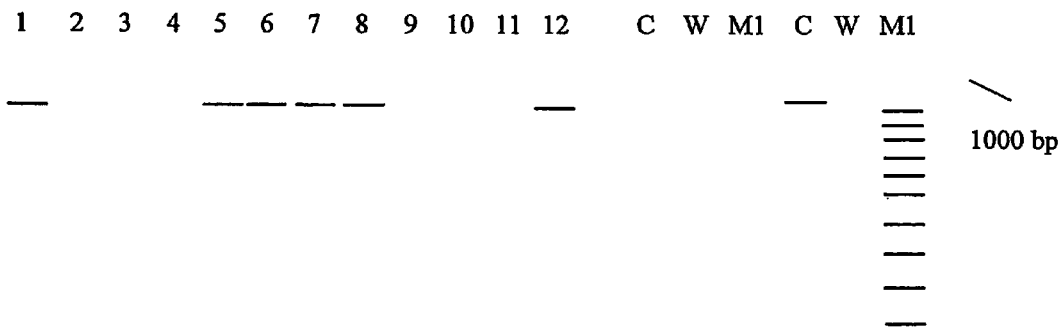

Figure 22a

```
                                                        20
SEQ ID NO. 229  g060a03.hcp  :  GRA VQLVQSGPELKKPGASVRISCKASG
SEQ ID NO. 262  g060g03.hcp  :  GRAEVQLVQSGPEVKKPGASVRVSCKASG
SEQ ID NO. 227  g060a01.hcp  :  GRAQVQLVQSGPEVKKPGASVRVSCKASG
SEQ ID NO. 239  g060b12.hcp  :  GRAQVQLVQSGGGLVKPGGSLRLSCAASG
SEQ ID NO. 240  g060c03.hcp  :  GRAKVQLVESGGGLVKPGGSLRLSCAASG
SEQ ID NO. 248  g060d08.hcp  :  GRAKVQLVESGGGLVKPGGSLRLSCAASG
SEQ ID NO. 256  g060f06.hcp  :  GRA*VQLQQSGGGLVKPGGSLRLSCAASG
SEQ ID NO. 245  g060d04.hcp  :  GRAKVQLVESGAEVKKPGSSVKVSCKASG
SEQ ID NO. 269  g060h02.hcp  :  GRAEVQLVQSGAEVKKPGSSVKVSCKASG
SEQ ID NO. 271  g060h10.hcp  :  GRAEVQLVESGAEVKKPGSSVKVSCKASG
SEQ ID NO. 267  g060g11.hcp  :  GRAEVQLVESGAEVKKPGSSVKVSCKASG
SEQ ID NO. 246  g060d05.hcp  :  GRAKVQLVESGAEVKKPGSSVKVSCKTSG
SEQ ID NO. 258  g060f09.hcp  :  GRAEVQLVQSGAEVKKPGSSVKVSCKTEG
SEQ ID NO. 242  g060c07.hcp  :  GRAKVQLVQSGAEVKKPGESLKISCQASG
SEQ ID NO. 249  g060d11.hcp  :  GRAKVQLVQSGAEVKKPGESLKISCQASG
SEQ ID NO. 261  g060g02.hcp  :  GRAEVQLVQSGAEVKKPGESLKISCQASG
SEQ ID NO. 231  g060a09.hcp  :  GRAQVQLQESGPEVKKPGASVKVSCKASG
SEQ ID NO. 263  g060g04.hcp  :  GRAEVQLVQSGPGLVKPSETLSLTCAVSG
SEQ ID NO. 270  g060h04.hcp  :  GRAEVQLVQSGPGLVKPSETLSLTCAVSG
SEQ ID NO. 232  g060a10.hcp  :  GRAQITLKESGPTLVKPTQTLTLTCTLSG
SEQ ID NO. 273  g060h12.hcp  :  GRAQVTLKESGPTLVKPTQTLTLTCTLSG
SEQ ID NO. 237  g060b09.hcp  :  GRAQVQLQESGPTLVKPTQTLTLTCSFSG
SEQ ID NO. 259  g060f10.hcp  :  GRAQVTLKESGPTLVKPTQTLTLTCTFSG
SEQ ID NO. 255  g060f05.hcp  :  GRAQVQLVESGAEMKKPGSSVKVSCQASG
```

Figure 22b

```
              40                    60
KCDI------HWVRQAPGQGLEWMG---WISADDGGTTTALNER
YSLK--NYGIHWVRQAPGQGLEWMG---WISADNGDTTTALNER
YSFK--NYGIHWVRQAPGQGLEWMG---WISADNGDTTTALNER
FSES--NNNMNWVRQTPGKGLEWVA---SISFGSHYISYADSVK
SSES--NNNMNWVRQTPGKGLEWVA---SISFGSHYISYADSVK
FSES--NNNMNWVRQTPGKGLEWVA---SISFGSHYISYADSVK
FSES--NNNMNWVRQTPGKGLEWVA---SISFGSHYISYADSVK
GSES---TYAITWVRQAPGQGLEWMG---GIIPIFASRDYAQKFQ
GSES---TYAITWVRQAPGQGLEWMG---GIIPIFASRDYAQKFQ
GSES---TYAITWVRQAPGQGLEWMG---GIIPIFASRDYAQKFQ
GSES---TYIFTWVRQAPGQGLEWMG---GINPIFATRDYPKKFQ
GSES---TYSITWVRQAPGQGLEWMG---GINPIFATRDYAQKFQ
GTES---TYVISWMRQAPGQGLEWMG---GIVPIFNTPNYAQKFQ
YGFT---VYWIGWVRQPPGKGLEWLG---IIYPGDSDTRYNPSFQ
YGFT---VYWIGWVRQPPGKGLEWLG---IIYPGDSDTRYNPSFQ
YGFT---VYWIGWVRQLPGKGLEWLG---IIYPGDSDTRYNPSFQ
YTEN---SYGIAWVRQVPGQGLEWMG---WISPYSGHTNYAEKVQ
ASVSGGDYYWSWIRQPPGKALEWIG---YIYYIGSTNYNPSLK
ASVSGGDYYWSWIRQPPGKALEWIG---YIYYIGSTNYNPSLK
FSLYTTGVGVGWIRQPPGKALEWLA---RIYWDDDERYNPSLK
FSLYTTGVGVGWIRQPPGKALE*LA---RIYWDDDERYNPSLK
FSLGTTGVNVGWIRQPPGKALEWLA---LISWDGGKHYSPSLN
FSLGTTGVNVGWIRQPPGKALEWLA---LISWGGGKHYSPSLN
GTFS--NYGINWVRHAPGQGLEWMG---GIVPIYGPPKYAQKFQ
```

Figure 22c

```
                 80                   100               .
GRVSMTTDRATN-TVYMELKSLRSDDTATYFCAR---------
GRVSMTTDTSTN-TVYMEVKSLRSDDTATYFCAR---------
GRVSMTTDTSTN-TVYMEVKSLRSDDTATYFCAR---------
GRFTISRDNARN-AVYLQMNSLRVEDTAVYYCTR--------C
GRFTISRDNARN-AVYLQMNSLRVEDTAVYYCTR--------C
GRFTISRDNARN-AVYLQMNSLRVEDTAVYYCTR--------C
GRFTISRDNARN-AVYLQMNSLRVEDTAVYYCTR--------C
RVTVTADESTR-TVYMELSSLRSDDTAVYYCAR---------V
RVTITADESTR-TVYMEPRSLRSEDTAVYYCAR---------V
RVTITADESTR-TVYMELSSLRSDDTAVYYCAR---------V
RVTITADESTR-PVYMELSSLTSEDTAVYYCAR---------V
RVTITADESTR-TVYMELRNLRSEDTAVYYCAR---------V
GRVTITADRSTS-TAYMELRSLGSEDTAVYYCAR---------V
CQVTISADKSVS-ITYLQWSSLKASDTATYYCAR--HLDSYDV
CQVTISADKSVS-ITYLQWSSLKASDTATYYCAR--HLDSYDV
CQVTISADKSVS-ITYLQWSSLKASDTATYYCAR--HLDSYDV
RVTMTTDTATS-TACMELTSLRSDDTAVYFCAR---------
SRLSLSVDTAKS-QFSLKLSSVTAADTATYFCAR-------AR
SRLSLSVDTAKS-QFSLKLSSVTAADTATYFCAR-------AR
SRLTITKDASKN-QVVLKMTNMDPVDTATYYCAR---------
SRLTITKDASKN-QVVLKMTNMDPVDTATYYCAR---------
SRLTLTKDASREQVVVPTMTNMDPADTGRYYCAR---------
SRLTLTKDASREQVVVLTMANMDPVDTGRYYCAR---------
GRVTITADTSTS-TAYMELSSLSSDDTAVYYCAR-LSRTVFGS
```

Figure 22d

```
          120                 .
        DFYSGTYRSFDYWGQGTLVTVS : 119
        DFYSGSYRSFDYWGQGTLVTVS : 123
        DFYSGSYRSFDCWGQGTLVTVS : 123
        RGGTRTYYYMDVWGKGTLVTVS : 124
        RGGTRTYYYMDVWGKGTLVTVS : 124
        RGGTRTYYYMDVWGKGTMVTVS : 124
        RGGTRTYYYMDVWGKGTLVTVS : 123
        LGGTRLYYALNVWGQGTMVTVS : 124
        LGGTRLYYALNVWGQGTLVTVS : 124
        LGGTRLYYALNVWGQGTTVTVS : 124
        LGGTRLYYALNVWGQGTTVTVS : 124
        FGGTRLYYALNVWGQGTLVTVS : 124
        VGGTRSYYALGFWGQGTTVTVS : 124
        FTGYNLGGYMDVWGKGTLVTVS : 130
        FTGYNLGGYMDVWGKGTLVTVS : 130
        FTGYNLGGYMDVWGKGTMVTVS : 130
        --DYSSPYHFDYWGQGTWSPSR : 121
        RTYSGYDSAFDYWGQGTLVTVS : 126
        RTYSGYDSAFDYWGQGTLVTVS : 126
        --TMGVVLPFDYWGQGTLVTVS : 122
        --TMGVVLPFDYWGQGTLVTVS : 121
        ----IVGTHGFDYWGQGTLVTVS : 122
        ----IVGTHGFDYWGQGTLVTVS : 122
        GTYRPGYYYMDVWGIGTTVTVS : 131
```

Figure 22e

```
                             .        20
g060f11.hcp : GRAEVQLVQSGGGVVRPGGSLRLSCAGSG
g060g12.hcp : GRAEVQLVQSGGGVVRPGGSLRLSCAGSG
g060f01.hcp : GRAQVQLQQSGGGVVQPGRSLRLSCAASG
g060a11.hcp : GRAKVQLVESGGGLVKPGGSLRLSCVVSG
g060c12.hcp : GRAKV*LVQSGGGLVKPGGSLRLSCVVSG
g060f03.hcp : GRA*VQLVQSGGGLVKPGGSLRLSCAASG
g060a02.hcp : GRAQVQLQQSGGGLVKPGGSLRLSCAASG
g060d03.hcp : GRAQMQLVQSGAEVKKPGTSVRVSCKTSG
g060f08.hcp : GRAKVQLVQSGAEVKKPGTSVRVSCKTSG
g060b05.hcp : GRAQVQLVQSGAEVKKLGTSVRVSCKTPG
g060b07.hcp : GRAEVQLVESGAEVKKPGTSVRVSCKTSG
g060f04.hcp : GRAKVQLVQSGAEVKKPGTSVRVSCKTPG
g060g10.hcp : GRAEVQLVQSGAEVKKPGTSVRVSRKTPG
g060d07.hcp : GRAEVQLVQSGAEVKKPGTSVRVSCKTPG
g060e05.hcp : GRAQVQLVESGAEVKKPGSSVKVSCKSSG
g060f02.hcp : GRAKVQLVQSGAEVKKPGTSVRVSCKTSG
g060g09.hcp : GRAKVQLVQSGAEVKKPGSSVKVSCKSSG
g060c04.hcp : GRAQMQLVQSGAEVKKPGSSVKVSCQSSG
g060g07.hcp : GRAQVQLQQSGPGLVKPSETLPLTCTVSG
g060h11.hcp : GRAQVTLKESGPTVVKPTQTLTLTCSLSG
g060b06.hcp : GRAQVQLQESGGGVVQPGTSLRLSCVVSG
g060a04.hcp : GRAKVQLVESGGGVVQPGTSLRLSCVVSG
g060b10.hcp : GRAKVQLVESGAEVKKPGATVRVSCKASG
```

Figure 22f

```
             .         40                     .        60                .
           FTFD--EYAMSWVRQAPGKGLEWVA--FINWNGDSTYYADSVK
           FTFD--EYAMSWVRQAPGKGLKWVA--FINWNGDSTYYADSVK
           FAFR--DYAMHWVRQAPGKGLEWMG--VISFNGDQIFYADSMK
           FPLN--RYTMNWVRQAPGKGLEWLS--SISSTSSYIYYADSVK
           FPLN--RYIMNWVRQTPGKGLEWLS--SISSTSSYIYYADSAK
           FTFS--NAWMSWVRQAPGKGLEWVGHVKSMTDGGTTDYAAPVK
           FTFS--SYSMNWVRQAPGKGLEWVS--SISSSSSYIYYADSVK
           GYVF------SWVRQAPGQGPEWMG--GIINFGTTNYAQKFQ
           GYVF------SWVRQAPGQGPEWMG--GIINFGTTNYAQKFQ
           GYVF------SWVRQAPGQGPEWMG--GIINFGTTNYARKFQ
           GYVF------SWVRQAPGQGPEWMG--GIISFGTTSYAQKFQ
           GYVF------SWVRQAPGQGPEWMG--GIINFGTTNYARKFQ
           GYVF------SWVRQAPGQGPEWMG--GIINFGTTNYARKFQ
           GYVF------SWVRQAPGQGPEWMG--GIINFGTTNYARKFQ
           GYVF------SWVRQAPGQGLEWMG--GISNFRTAEYARKFQ
           GYVF------SWVRQAPGHGPEWMG--GIINFGTATYAQKFQ
           GYVF------SWVRQAPGQGLEWMG--GISNFHTAEYAQKFQ
           GPPK--SYTLSWVRQAPGQGPEWMG--GILIFGPPNYAQKFQ
           GSFS--TYYWSWIRQSPEKGLEWIG---YQNSVNTNYNPSLK
           FALGTTGVAVGWIRQPPGKALEWLG---IDWNDDRRYRPSLK
           FTFR--TYGMNWVRQAPGKVLEWLA--FVSSDGSDEFYADSVK
           FTFR--TYGMNWVRQAPGKGLEWLA--FLSSDGSDEFYADSVK
           YRFN--DYCISWVRQAPGQGLEWMG--WINGNNADTFYAPKLQ
```

Figure 22g

```
                    80                    100
GRFTVSRTNAKN-SLYLQMNSLRAEDTAFYYCAR--------D
GRFTVSRSNAKN-SLYLQMNSLRAEDTAFYCCAR--------D
GRFTISRENSKN-TLHLRMNSLRPEDTAVYYCAR------ARL
GRFTISRDNAKN-SLFLQMNSLRADDTALYFCAS---------
GRFTISRDNAKN-SLFLQMNSLRAEDTGLYYCAS---------
GRFTISRDDSEN-TLYLQMNSLKTDDTAVYYCTT---------
GRFTISRDNAKN-SLYLQMNSLRAEDTAVYYCAR------RPG
GRVTITADKSTN-TVYMDLSNLTSEDTAVYYCAR--APRGTST
GRVTITADKSTN-TVYMDLSNLTSEDTAVYYCAR--APRGTST
GRLTVTADKSTN-TVYMDLSNLASEDTAVYYCAR--APRGTST
GRVTITADKATN-TVYMDLSDLTSEDTAIYYCAR--APRGTST
GRITVTADKSTN-TVYMDLSNLASEDTAVYYCAR--APRGTST
GRITVTADKSTN-TVYMDLSNLASEDTAVYYCAR--APRGTST
GRITVTADKSTN-TVYMDLSNLASEDTAVYYCAR--APRGTST
GRVTMTADTSTN-TIYMELTSLTSEDTAVYFCVS--APRDTST
GRVSITADTSTN-TFYMDLNNLKSDDTAVYYCAS--APRDTST
GRVTMTADTSTN-TIYMELTSLTSEDTAVYFCVS--APRDTST
DRLTITADKSTN-TVYMELSSLRSDDTAMYYCVT--APDDTGT
SRVIISVDTSNN-QFSLKLRSVTAADTAVYYCAR-------VS
TRLTITQDMSRN-QVVLRLTNLDPLDTGTYFCAR---------
GRFTVSRDNSKS-TLFLKMNSLRADDTAVYYCARDRGAQITLF
GRFTVSRDNSKS-TLFLKMNSLRPDDTAVYYCARDRGAQITLF
GRVTMSTDTSTS-TAYMELRNLRSDDTAVYFCAR-DRGRITLF
```

Figure 22h

```
        120              .
PRTKLGMSYFDYWGQGTLVTVS  : 124
PRTKLGMSYFDYWGQGTLVTVS  : 124
LFCSGGRCDMDSWGQGTLVTVS  : 126
-------GNTHDYWGQGTLVTVS  : 117
-------GNTHDYWGQGTLVTVS  : 116
----------HDYWGQGTLVTVS  : 115
WAATRAAGAFDIWGQGTMVTVS  : 126
IAARFNRYFDSWGQGTLVTVS   : 126
IAARFNRYFDSWGQGTLVTVS   : 126
IAARFNRYFDSWGQGTLVTVS   : 126
IAARFNRYFDSWGQGTLVTVS   : 126
IAARFNRYFDSWGQGTLVTVS   : 126
IAARFNRYFDSWSQGTLVTVS   : 126
IAARFNRYFDSWGQGTLVTVS   : 126
IAARFNRYFDTWGQGTLVTVS   : 126
IAARFNRYFDFWGPGTLVTVS   : 126
IAARFNRYFDIWGQGTLVTVS   : 126
ILARHNRYYFDSWGQGTLVTVS  : 130
GWGPRGGIYFDYWGQGTLVTVS  : 124
-SVVPATRAFDFWGQGTLVTVS  : 123
GAPLIRPSSFDSWGQGTLVTVS  : 132
GAPLIRPSSFDSWGQGTLVTVS  : 132
GEVILRAGWFDSWGQGTLVTVS  : 131
```

Figure 23a

```
                                                              20
SEQ ID NO. 276   g060a03.lcp  :  LADVVMTQSPSSLSASLGDRVSITCRASQ
SEQ ID NO. 309   g060g03.lcp  :  LADVVMTQSPSSLSASLGDRVTITCRASQ
SEQ ID NO. 274   g060a01.lcp  :  LAEIVLTQSPSSLSASLGDRVTITCRASQ
SEQ ID NO. 286   g060b12.lcp  :  LAEIVLTQSPGTLALSPGDRATLSCGASQ
SEQ ID NO. 287   g060c03.lcp  :  LAEIVMTQSPGTLALSPGDRATLSCGASQ
SEQ ID NO. 295   g060d08.lcp  :  LADVVMT*SPGTLALSPGDRATLSCGASQ
SEQ ID NO. 303   g060f06.lcp  :  LAEIVMTQSPGTLALSPGDRATLSCGASQ
SEQ ID NO. 292   g060d04.lcp  :  LADVVMTQFPSSLSASVGDRVTITCRASQ
SEQ ID NO. 316   g060h02.lcp  :  LAEIVLTQSPSSLSASVGDRVTITCRASQ
SEQ ID NO. 318   g060h10.lcp  :  LADIQLTQSPSSLSASVGDRVTITCRASQ
SEQ ID NO. 314   g060g11.lcp  :  LAEIVMTQSPSSLSASVGDRVTISCRASQ
SEQ ID NO. 293   g060d05.lcp  :  LADVVMTQSPSSLSASVGDRVTITCRASQ
SEQ ID NO. 305   g060f09.lcp  :  LADIQLTQSPSSLSASVGDSVTITCRASQ
SEQ ID NO. 289   g060c07.lcp  :  LAETTLTQSPGTLSLSPGERATLSCRASQ
SEQ ID NO. 296   g060d11.lcp  :  LAETTLTQSPGTLSLSPGERATLSCRASQ
SEQ ID NO. 308   g060g02.lcp  :  LADIQLTQSPGTLSLSPGERATLSCRASQ
SEQ ID NO. 278   g060a09.lcp  :  LADVVMTQSPSSLSASVGDRVTISCRASQ
SEQ ID NO. 310   g060g04.lcp  :  LADVVMTQSPSSLSASVGDRVSITCRASR
SEQ ID NO. 317   g060h04.lcp  :  LADVVMTQSPSSLSASVGDRVSITCRASR
SEQ ID NO. 279   g060a10.lcp  :  LAEIVLTQSPSTLSASVGDRVTITCRASQ
SEQ ID NO. 320   g060h12.lcp  :  LADIQLTQSPSTLSASVGDRVTITCRASQ
SEQ ID NO. 284   g060b09.lcp  :  LAEIVLTQSPSFLSASVGDRVTITCRASQ
SEQ ID NO. 306   g060f10.lcp  :  LAEIVMTQSPSFLSASVGDRVTITCRASQ
SEQ ID NO. 302   g060f05.lcp  :  LADIQMTQSPDSLAVSLGERATINCKSSQ
```

Figure 23b

```
              40              60
HISNY------INWYQQKPGKAPKLLIYAASTLQSGVPSRFTG
HISNY------LNWYQQKPGKAPKLLIYAASSLQSGVPSRFTG
HISNY------LNWYQQKPGKAPKLLICAASSLQSGVPSRFTG
SVFGD------FLAWYQHKPGQAPRLLIYGASTRATGIPDRFSG
SVFGD------FLAWYQHKPGQAPRLLIYGASTRATGIPDRFSG
SVFGD------FLAWYQHKPGQAPRLLIYVASTRATGIPDRFSG
SVFGD------FLAWYQHKPGQAPRPLIYGASTRATGIPDRFSG
GISNI------LAWYQQKPGKVPELLIYGASTLQSGVPSRFSG
GISNI------LAWYQQKPGKVPELLIYGASTLQSGVPSRFSG
GISNI------LAWYQQKPGKVPELLIYGASTLQSGVPSRFSG
GISNI------LAWFQQKPGQVPKLLIYVASTLQSGVPSRFSG
GISNI------LAWHQQKPGQVPKLLIYGASTLQSGVPSRFSG
GISNI------LAWYQKKPGKVPRLLIYGASTLQSGVPSRFSG
SVSTN------YLAWYRQKPGQAPRLLIHGASSRATGIPDRFSG
SVSTN------YLAWYRQKPGQAPRLLIHGASSRATGIPDRFSG
SVSTN------YLAWYRQKPGQAPRLLIHGASSRATGIPDRFSG
PISTY------LNWYQQKPGKAPKLLIEGASRLQSGVPSRFSG
SVKTY------LNWYQQKPGKAPKLLVYGSSSLESGVPSRFSG
SVKTY------LNWYQQKPGKAPKLLVYGSSSLESGVPSRFSG
SIGSW------LAWYQQKPGKAPKLLIYKASTLQSETPSRFRG
SIGSW------LAWYQQKPGKAPKLLIYKASTLQSETPSRFRG
GIGNI------LAWYQQKPGKAPKLLISGASTLQSWVPSRFSG
GIGNI------LAWYQQKPGKAPKLLISGASTLQSWVPSRFSG
SLLYSSNNKNYLAWYQQKPGQPPKLLIYWASTRESGVPDRFSG
```

Figure 23c

```
                80                  100
SGSGADYTLTITSLQPEDFATYYCQQSYGTS-WTFGQGTTVET
SGSGADYTLTISSLQPEDFATYYCQQSYSTS-WTFGQGTTVGI
SGSGADYTLTISSLQPEDFATYYCQQSYSTS-WTFGQGTTVEI
SGAGTDFTLTISRLEPEDFAVYFCQ*YGDSV-FTFGQGTKLGI
SGAGTDFTLTISRLEPEDFAVYFCQQYGDSV-FTFGQGTKLEI
SGAGTDFTLTISRLEPEDFAVYFCQQYGDSV-FTFGQGTKLEI
SGAGTDFTLTISRLEPEDFAVYFCQQYGDSV-FTFGQGTKLEI
SGSGAEFTLTINSLQPEDVATYYCQKYDSGLRFTFGPGTKVDI
SGSGTDFTLTINSLQPEDVATYYCQKYDSGLRFTFGPGAKVDI
SGSGTEFTLTINSLQPEDVATYYCQKYDSGLRFTFGPGTKVDI
SGSGTDFSLTINGLQPEDVATYYCQRYDSGLIFTFGPGTKVEI
SGSGTDFTLTINGLQPEDVATYYCQKYDSGLIFTFGPGTRVEI
SGSGTDFTLTISSLQPEDVATYYCQEYSNALIFTFGPGTKVHI
SGSGTDFTLTISRLEPEDFAVYFCQQYGSSP-QTFGQGTRLEI
SGSGTDFTLTISRLEPEDFAVYFCQQYGSSP-QTFGQGTRLEI
SGSGTDFTLTISRLEPEDFAVYFCQQYGSSP-QTFGQGTRLEI
SGSGTDFSLTITSLQPEDFATYICQQSKSPP-YNFGRGTKLEI
SGSGTDFTLTISSLQPEDFATYLCQQSFGTP-YTFGQGTKLDT
SGSGTDFTLTISSLQPEDFATYYCQQSFGTP-YTFGQGTKLDI
SGSGTEFTLTISSLQDDFATYYCQQFNSFSPWTFGQGTKVEF
SGSGTEFTLTISSLQDDFATYYCQQFNSFSPWTFGQGTKAEF
RGSGTEFTLTISSLQPEDFATYYCQQLNRYPPYTFGQGTKLEI
RGSGTEFTLTISSLQPEDFATYYCQQLNRYPPYTFGQGTKLEI
SGSGTDFTLTISSLQAEDVAVYYCQQYSTP-PMFGQGTRVEI
```

```
                                                    20
g060f11.lcp : LAEIVMTQSPSSLSASVGDRVTITCRASQ
g060g12.lcp : LADIQMTQSPSSLSASVGDRVTITCRASQ
g060f01.lcp : LAEIVMTQSPSFLSASVGDRVTITCRASQ
g060a11.lcp : LADVVMTQSPSSLSASVGDRVTITCRASQ
g060c12.lcp : LAEIVLTQSPSSLSASVGDRVTTICRTSQ
g060f03.lcp : LAEIVMTQSPPFLSASVGDRVTITCRASQ
g060a02.lcp : LAEIVLTQSPSSLSASVGDRVTITCRASQ
g060d03.lcp : LADIQMTQSPGTLSLSPGERATLSCRASQ
g060f08.lcp : LADVVMTQSPGTLSLSPGERATLSCRASQ
g060b05.lcp : LADVVMTQSPDSLAVSLGERATINCKSSQ
g060b07.lcp : LAEIVLTQSPDSLAVSLGERATINCKSSQ
g060f04.lcp : LAEIVLTQSPDSLAVSLGERATINCKSSQ
g060g10.lcp : LADIQMTQSPDSLAVSLGEKATINCKSSQ
g060d07.lcp : LADVVMTQSPDSLAVSLGERATINCKSSQ
g060e05.lcp : LAEIVLTQSPGTLSLSPGERATLSCRASR
g060f02.lcp : LADVVMTQSPGTLSLSPGERATLSCRASQ
g060g09.lcp : LAEIVLTQSPGTLSLSPGERATLSCRASR
g060c04.lcp : LAEIVLTQSPGTLSLSPGQRATLSCRASQ
g060g07.lcp : LADIQMTQSPSSLSASVSDRVTITCRASQ
g060h11.lcp : LADIQMTQSSSTLSASVGDRVTITCRASQ
g060b06.lcp : LAEIVLTQSPSSLSASVGDRITITCQASQ
g060a04.lcp : LADVVMTQSPSSLSASVGDRVTITCQASQ
g060b10.lcp : LAEIVMTQSPSSLSASVGDRVTITCQASQ
```

Figure 23f

```
              40                    60              .
TISNH------LNWYQQKPGRAPKLLIYVGSSLQSGVPSRFSG
TISNH------LNWYQQKPGRAPKLLIYVGSSLRSGVPSRFSG
DIITY------LAWYQQKPGKAPEVLIFGASTLQSGVPSRFSG
SININ------LNWFQQKPGKAPNLLIYSASTLQTGVPSRFSG
SIFIN------LNWFQQKPGKAPKLLIYSASTLQTGVPSRFSG
GLSTY------LAWYQVKPGKAPKLLIYAASTLQSGVPSRFSG
GISNY------LAWYQQKPGKVPKLLIYAASTLQSGVPSRFSG
SVNSD-----NLAWYQQKPGQAPRLLMSGATSRATDVPDRFSG
SVNSD-----NLAWYQQKPGQAPRLLMSGATSRATDIPDRFSG
SLLYSSNNKNYLAWYQQKPGQPPKLLIYWASTRESGVPDRFSG
SLLYSSNNKNYLAWYQQKPGQPPKLLIYWASTRESGVPDRFSG
SLLYSSNNKNYLAWYQQKPGQPPKLLIYWASTRESGVPDRFSG
SLLYSSNNKNYLAWYQQKPGQPPKLLIYWASTRESGVPDRFSG
SLLYSSNNKNYLAWYQQKPGQPPKLLIYWASTRESGVPDRFSG
SVNSN-----NLAWYQQKPDQAPRLLMYGASSRATGIPDRFTG
SVNSN-----NLAWYQQKPGQAPRLLVSGATNRATDIPDRFSG
SVYSN-----NLAWYQQKPDQAPRLLMYGASSRATGIPDRFTG
SVNRD-----YLAWYQQKPG*APRLLIYGASSRATGIPDRFSG
SINKF------LNWYQQKPGKAPQLLIYAATNLQSGVPSRFSG
NININ------LAWYQQKAGKAPKLLIYKASTLERGVPSRFSG
DITNY------LNWYQQKPGKAPKLLIYDASNLQPGVPSRFSG
DITNY------LNWYQQKPGKAPKLLIYDASNLQPGVPSRFSG
DISKY------LNWYQQKPGRAPKLLIYEASNLETGVPPRFSG
```

Figure 23g

```
                80                       100                  .
SGSGTDFTLTISGLQPEDFATYYCQQSYSPS-YTFGQGTKVEI
SGSGTDFTLTISGLQPEDFATYYCQQSYSPS-YTFGQGTKVEI
SGSGTEFTLTISSLQPEDFATYYCQQIIRYP-RTFGQGTRVEI
SGSGTEFTLTISSLQPEDFATYYCQQIYSHV-RTFGQGTKVEI
SGSGTEFTLTISSLQPEDFATYYCQQIYSQV-RTFGQGTKVEI
SGSGTEFTLTINSLQPEDFATYYCQQLDTYP-LTLGGGTKVEI
SGSGTDFTLTISSLQPEDVATYYCQKYNS-APYTFGQGTKLEI
SGSGTEFTLTISRLEPEDFAVYYCHQYGSSD-NTFGQGTKLEI
SGSGTDFTLTISRLEPEDFAVYYCHQYGSSD-NTFGQGTKLEI
SGSGTDFTLTISSLQAEDVAVYYCQQYYSTP-PMFGQGTKVEI
SGSGTDFTLTISSLQAEDVAVYYCQQYYSTP-PMFGQGTKVEI
SGSGTDFTLTISSLQAEDVAVYYCQQYYSTP-PMFGQGTKVEI
SGSGTDFTLTISSLQAEDVAVYYCQQYYSTP-PMFGQGTKVEI
SGSGTDFTLTISSLQAEDVAVYYCQQYYSTP-PMLGQGTKVEI
SGSGTDFTLTISRLEPEDFAVYYCHQYGASD-NTFGQGTKLEI
SGSGTDFTLTISRLEPEDFAVYYCHQYGSSE-NTFGQGTKLEI
SGSGTDFTLTISRLEPEDFAVYYCHQYGASD-NTFGQGTKLEI
SGSGTDFTLTISRLERDDFAVYFCHQYGSSP-NTFGQGTKLEI
SGSGTDFTLTISSLQTEDFATYYCQQSYDMP-RTFGQGTKVEI
SGSGTEFTLTITGLRDDFGSYYCQHYDGNS-LTFGQGTRVDI
SRSGTDFTFTISSLRPEDIATYYCQQYDGPV-LTFGGGTKVEI
SGSVTDFTFTISSLRPEDIATYYCQQYDGPV-LTFGGGTKVEI
SGSGTHFTFTITGLQPEDIATYYCQQCDSLP-PVFGQGTKLEV
```

METHOD FOR LINKING SEQUENCES OF INTEREST

This application is a National Stage of International Application No. PCT/DK2004/000633, filed Sep. 17, 2004 and published in the English language May 12, 2005, which claims the benefit of U.S. Provisional Application No. 60/504,589, filed Sep. 18, 2003, U.S. Provisional Application No. 60/504,455, filed Sep. 18, 2003, Danish Application No. PA 2003 01867, filed Dec. 17, 2003, and Danish Application No. PA 2004 00782, filed May 15, 2004. The entirety of each of these documents is fully incorporated by reference herein.

TECHNICAL FIELD OF THE INVENTION

The present invention relates to a multiplex molecular amplification procedure capable of linking nucleotide sequences of interest in connection with the amplification, in particular polymerase chain reaction (multiplex PCR). The method is particularly advantageous for the generation of cognate pair libraries as well as combinatorial libraries of variable region encoding sequences from immunoglobulins, T cell receptors or B cell receptors.

BACKGROUND OF THE INVENTION

Antigen binding proteins involved in the immune response are present in mammals as large polyclonal repertoires representing a broad diversity of binding specificities. This diversity is generated by rearrangement of gene sequences encoding variable regions of these binding proteins. Such variable region binding proteins include soluble and membrane-bound forms of the B cell receptor (also known as immunoglobulins or antibodies) and the membrane-bound T cell receptors (TcR). With respect to immunoglobulins, their affinity is enhanced subsequent to recognition of an antigen by a B cell antigen receptor, through a process termed affinity maturation which involves cycles of somatic hypermutation of these variable genes.

Notably, immunoglobulins or fragments thereof, such as Fab fragments, Fv fragments and single chain Fv (scFv) molecules have been subject to cloning and recombinant expression. However, all other variable region binding proteins can in principle also be cloned and expressed using the same concepts as for antibodies.

Known approaches for isolating antibodies with a desired binding specificity most often involves generation of hybridomas from immunized hosts followed by screening for specific clones or involves the generation of combinatorial expression libraries in E. coli composed of immunoglobulin variable domains, which are subsequently enriched using techniques such as, for example, phage display.

The main restriction in the use of the hybridoma technology for making therapeutic antibodies is the absence of a human lymphoma suitable as fusion partners for human B lymphocytes. Heterohybridomas (i.e., fusion of human B cells with mouse lymphomas) are notoriously unstable and thus rarely lead to suitable cell lines for production purposes. Human B cells immortalized through infection with Epstein-Barr virus exhibit similar challenges of instability. The lack of robust cellular methodology for making human antibodies for therapy can be compensated with more recent advantages in molecular biology.

The use of combinatorial libraries and phage display allows for generation of large repertoires of antibody clones with a potential diversity in excess of $10^{10}$. From this repertoire selection for binding to a specific target can be performed thereby generating a sub-library. This sub-library can be used to generate either polyclonal or monoclonal antibodies. The variable region encoding sequences (for example immunoglobulin heavy chain variable region and light chain variable region encoding sequences) which constitute the library can be amplified from lymphocytes, plasma cells, hybridomas or any other immunoglobulin expressing population of cells. Current technologies for generating combinatorial libraries involve separate isolation of the variable region encoding sequences from a population of cells. Thus, the original pairing of for example immunoglobulin heavy chain variable region and light chain variable region encoding sequences will be lost. Rather, in a combinatorial library said sequences are randomly paired and the original combinations of these variable sequences will only occur by chance. Thus, in order to isolate variable region encoding sequences responsible for a desired binding specificity, a considerable amount of screening is necessary. This is typically performed in combination with methods for enrichment of clones exhibiting a desired specificity, such as ribosome display or phage display. Even then, the diversity achieved might not be sufficiently large to isolate variable region encoding sequence pairs giving rise to binding proteins of similar high affinity as those found in the original cells. Further, the enrichment procedures normally used to screen combinatorial libraries introduce a strong bias e.g. for polypeptides of particular low toxicity in E. coli, efficient folding, slow off-rates, or other system dependent parameters, that reduce the diversity of the library even further. In addition, clones derived from such combinatorial libraries will be more prone to produce binding proteins with cross-reactivity against self-antigens because they as pairs, in contrast to original pairs (hereafter called cognate pairs), never have been through in vivo negative selection against self-antigens, such as it is the case for B and T lymphocyte receptors during particular stages of their development. Therefore, the cloning of original pairs of variable region encoding sequences is a desirable approach. Moreover, the frequency of clones exhibiting a desired binding specificity is expected to be considerably higher within a library of cognate pairs, than in a conventional combinatorial library, particularly if the starting material cells are derived from a donor with high frequency of cells encoding specific binding pairs e.g. immune or immunized donors. It follows that the size of a cognate pair library will not need to be as large as a combinatorial library: a cognate pair library size of $10^4$ to $10^5$ clones or even as small as $10^2$ to $10^3$ clones derived from a donor with a relevant ongoing immune response might very well suffice in order to obtain binding proteins representing a broad diversity of desired binding specificities.

In order to generate cognate pair libraries the linkage of the variable region encoding sequences derived from the same cell is required. At present, two different approaches which can achieve cognate pairing of variable region encoding sequences have been described.

In-cell PCR is an approach where a population of cells is fixed and permeabilized, followed by in-cell linkage of heavy chain variable region and light chain variable region encoding sequences from immunoglobulins. This linkage can be performed either by overlap-extension RT-PCR (WO 93/03151) or by recombination (Chapal, N. et al. 1997 BioTechniques 23, 518-524). The amplification process as described in these publications is a three or four step process consisting of i) reverse transcription utilizing constant region primers generating immunoglobulin cDNA, ii) PCR amplification of the heavy and light chain variable region encoding sequences utilizing primer sets containing either overlap-extension design or recombination sites, iii) linkage by recombination, if this approach is chosen, iv) nested PCR of the products generating restriction sites for cloning. Since the cells are permeabilized there is a considerable risk that amplification products might leak out of the cells, thereby introducing scrambling of the heavy chain variable region and light chain variable region encoding sequences, resulting in the loss of cognate pairing. Therefore, the procedure includes washing steps after each reaction which makes the process laborious and reduces the efficiency of the reactions.

More generally, the in-cell PCR is notoriously inefficient, resulting in low sensitivity. Accordingly, the in-cell PCR linkage technique has never found widespread usage, and the original study has in fact never been reliably repeated in a way which can be used to verify that the linkage actually occurs within the cell. This, however, is absolutely crucial to avoid scrambling of the heavy chain variable region and light chain variable region encoding sequences and thereby disrupting the cognate pairs.

A different in-cell approach is described in WO 01/92291. This approach is based on RNA trans-splicing, and achieves joining of $V_H$ and $V_L$ encoding mRNA within the cell. This approach requires the presence of a DNA construct driving the trans-splicing within the cells.

Single-cell PCR is a different approach to achieve cognate pairing of heavy chain variable region and light chain variable region encoding sequences (see, for example, Coronella, J. A. et al. 2000 Nucleic Acids Res. 28, E85; Wang, X., et al. 2000 J. Immunol. Methods 20, 217-225). In these publications a population of immunoglobulin expressing cells are distributed by diluting to a density of one cell per reaction, thereby eliminating scrambling of heavy chain variable region and light chain variable region encoding sequences during the cloning process. Basically, the process described is a three to four step procedure consisting of i) reverse transcription utilizing oligo-dT-, random hexamer- or constant region primers generating cDNA, ii) fractionating the cDNA product into several tubes and performing PCR amplification on the individual variable chain encoding sequences (in separate tubes) with primer sets containing restriction sites for cloning, iii) nested PCR of the products generating restriction sites for cloning (optionally) and iv) linking the heavy chain variable region and light chain variable region encoding sequences from the separate tubes by cloning them into an appropriate vector, which in itself is a multi-step process.

In humans there are two types of light chains: lambda (λ) and kappa (κ). This means that with the cDNA generated from every single cell at least three separate PCR reactions must be performed followed by analysis and cloning of the appropriate fragments into a single vector to achieve the cognate pairing. Thus, the single-cell PCR approach as described requires a large number of manipulations to generate a library of cognate pairs. Although, a cognate pair library does not need to be as large as a combinatorial library in order to obtain binding proteins representing a broad diversity of binding specificities it would still be a laborious task to generate a library of for example $10^4$ to $10^5$ clones by the described single-cell PCR approach. Further, the large number of manipulations highly increases the risk of contamination and human error.

In order to obtain high affinity binding proteins corresponding to the affinities normally observed during an immune response, cognate pairing of the variable region sequences in association with their amplification is highly advantageous. To generate a library of large diversity it is necessary to have a cloning technique that can be fitted to a high-throughput format and where the risk of contamination and scrambling is minimal.

A reduction of the number of cloning steps allowing the generation of combinatorial libraries to be fitted to a high-throughput format, is likewise desired.

DISCLOSURE OF CONTRIBUTION

The present invention provides an efficient method of linking two or more nucleotide sequences of interest, e.g. variable region encoding sequences, utilizing a multiplex molecular amplification procedure, such as multiplex overlap-extension RT-PCR or multiplex RT-PCR followed by linkage by ligation or recombination. The method is applicable on a single cell, thereby enabling cloning of cognate pairs in a high-throughput format.

DESCRIPTION OF THE FIGURES

FIG. 1 is a diagram illustrating the different types of overlap-extension tails. The bold line corresponds to a gene-specific part of the primer and the regular line corresponds to the overlapping tail. The vertical bars illustrate complementary regions. The primers facilitate the linkage of two nucleotide sequences of interest. FIG. 1 (I) illustrates two varieties of the type I overlap-extension tails where only the extension tails overlap, either completely or partially; FIG. 1 (II) illustrates the type II overlap-extension tails where some of the 5'-nucleotides of the first primer extension tail are complementary to the gene-specific part of the neighboring primer; FIG. 1 (III) illustrates the type III overlap-extension tails where the entire overlap-extension tails are complementary to the gene-specific region of the neighboring primer.

FIG. 3A is a diagram illustrating a head-to-head orientation of the products. FIG. 3B is a diagram illustrating a tail-to-tail orientation. FIG. 3C is a diagram illustrating a head-to-tail orientation with the light chain encoding sequence first. FIG. 3D is a diagram illustrating a head-to-tail orientation with the heavy chain encoding sequence first.

FIG. 5A is an electrophoretic gel showing the results from a two-step multiplex overlap-extension RT-PCR followed by a semi-nested PCR. The amplification products are derived from cDNA isolated from single CHO Flp-In pLL113 cells. Lanes 1-12 are sample lanes and the arrows indicate correct nested multiplex-overlap-extension RT-PCR products of 1076 bp; M1 is a 100 bp ladder. W is water used as negative control template. C is a positive cDNA control template derived from cell-line HB-8501. In a separate panel the same lanes W, C and the 100 bp ladder have been depicted with less contrast in order to resolve the individual DNA fragments. FIG. 5B is a sketch of the gel shown in FIG. 5A, illustrating the relevant fragments from the gel.

FIG. 6A is an electrophoretic gel showing the amplification products derived from lysate corresponding to 100, 10, 1 or 0 cells. The arrow indicates the overlap-extension product. FIG. 6B is a sketch of the gel in FIG. 6A. FIG. 6C is an electrophoretic gel verifying the presence of overlap-extension product in the 100 and 1 cell lanes in FIG. 6A. FIG. 6D is an electrophoretic gel showing restriction enzyme cleavage with NheI and NcoI, respectively, of the overlap-extension product from the 1 cell lane in FIG. 6C.

FIG. 22 shows alignment of variable heavy chain protein sequences from TT antigen-binding clones from plate G060. The degree of sequence homology was represented by different shadings; 100%, 80% and 60% were depicted with black, gray and light gray, respectively. CDR1 is located at alignment position 34 to 41. CDR2 is located at alignment position 55 to 73. CDR3 is located at alignment position 107 to 127. Premature stop codons were denoted by an asterisk. The alignment is divided into 8 separate Figures (a-h) distributed in two rows from left to right with FIG. 22a to d in the top row and FIG. 22e to h in the bottom row.

FIG. 23 shows alignment of variable light chain protein sequence from TT antigen-binding clones from plate G060. The degree of sequence homology was represented by different shadings; 100%, 80% and 60% were depicted with black, gray and light gray, respectively. CDR1 is located at alignment position 26 to 42. CDR2 is located at alignment position 58 to 64. CDR3 is located at alignment position 97 to 106. Premature stop codons were denoted by an asterisk. The alignment is divided into 8 separate Figures (a-h) distributed in two rows from left to right with FIG. 23a to d in the top row and FIG. 23e to h in the bottom row.

DESCRIPTION OF THE INVENTION

Figure 2:
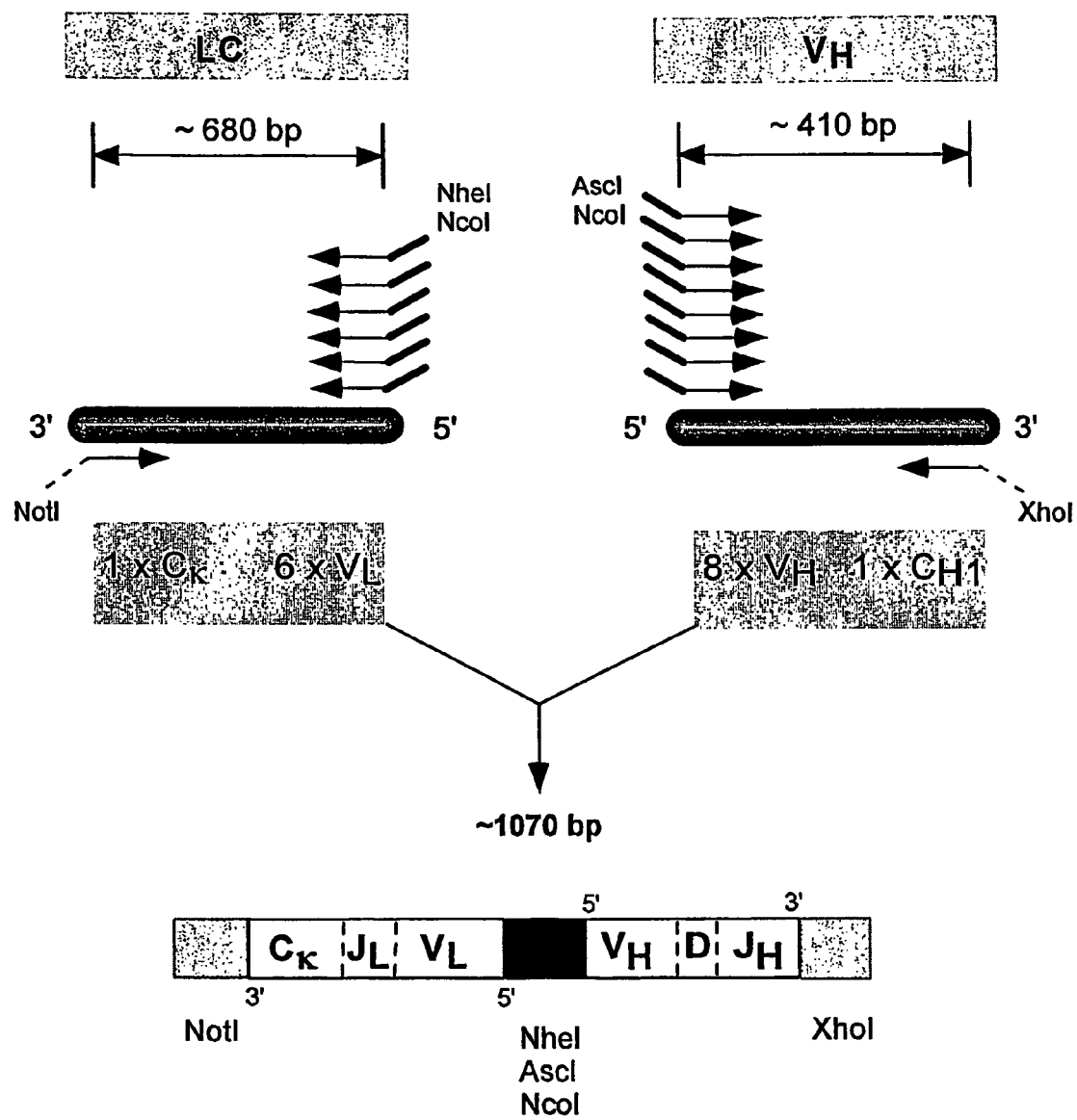
FIG. 2 is a diagram showing a schematic overview of a multiplex overlap-extension primer mix applicable in the linkage of immunoglobulin variable region encoding sequences. The cDNA encoding the light chain (LC) and the heavy chain variable region ($V_H$) to be linked are illustrated as tubes with indication of their sense strand 5' and 3'ends as well as the expected size of the amplified product. The multiplex overlap-extension primer sets used to amplify the encoding sequence are illustrated by the arrows. The bended arrow tails with dashed 5' overhangs illustrate the cloning tails. The overlap-extension tails are in bold. The restriction sites present in the tails are named in connection with the tail. The total number of primers in the multiplex overlap-extension primer mix is sixteen, distributed on the outer primers comprising one $C_\kappa$ and one $C_{H1}$ primer and the overlap extension primers comprising Six $V_L$ and eight $V_H$ primers. The $C_{H1}$ primer anneal at the 5' end of the heavy chain constant domain 1. The product resulting from the multiplex overlap-extension RT-PCR is expected to be approximately 1070 bp constituting the entire kappa light chain composed of the constant region, joining gene and variable gene ($C_\kappa+J_L+V_L$) and the heavy chain variable region, composed of the variable gene, diversity segment and joining gene ($V_H+D+J_H$). 5' and 3' indicates the direction of the open reading frame. Only a small portion of the $C_{H1}$ region encoding sequence is amplified by this multiplex overlap-extension primer mix, because the annealing position of the $C_{H1}$ primer is close to the heavy chain J-region.

The present invention sets out to provide an amplification and linkage process of two or more non-contiguous nucleotide sequences of interest which enables the cloning of such sequences to be fitted to a high-throughput format. This is basically achieved by reducing the number of steps necessary to amplify and link sequences to be cloned.

One aspect of the invention is a method of linking a plurality of non-contiguous nucleotide sequences comprising amplifying, in a multiplex molecular amplification procedure, nucleotide sequences of interest using a template derived from an isolated single cell, a population of isogenic cells or a population of genetically diverse cells and effecting a subsequent linkage of the amplified sequences. If the template is an isolated single cell or a population of isogenic cells, the linkage results in a nucleic acid segment comprising nucleotide sequences of interest associated with each other in a cognate manner. If the template is a population of genetically diverse cells, the linkage results in a library of segments where each segment comprise nucleic acid sequences of interest associated in a random manner, this is also termed a combinatorial library.

In one embodiment of the present invention this multiplex molecular amplification procedure is a multiplex PCR amplification, preferably preceded by a reverse transcription step. In a preferred embodiment reverse transcription, amplification and linkage are performed in a single step, using multiplex overlap-extension RT-PCR or alternatively in two steps using multiplex RT-PCR followed by linkage by ligation or recombination.

A further embodiment of the present invention relates to the generation of libraries of cognate pairs comprising linked variable region encoding sequences, in particular heavy chain variable region and light chain encoding sequences or T cell receptor (TcR) alpha chain encoding sequences and beta chain encoding sequences. The process involves obtaining a lymphocyte-containing cell fraction from at least one suitable donor and optionally enriching for a particular lymphocyte population from this fraction, for example B lymphocytes or T lymphocytes, depending on whether variable region encoding sequences from immunoglobulins or TcRs are desired. The lymphocyte-containing cell fraction or the enriched cell fraction is distributed into an array of vessels, obtaining one cell in each vessel. The array of single cells are subjected to a reverse transcription (RT) step or an alternative cDNA generating procedure, using the nucleic acids derived from the population of single cells as template. The RT step is followed by multiplex molecular amplification procedure and linkage of pairs of variable region encoding sequences generated from each cell according to one of the methods of the present invention.

The cloning techniques disclosed in the present invention omit laborious and inefficient cloning approaches and additionally reduces the risk of contamination and loss of diversity during multiple cloning steps.

Another aspect of the invention relates to libraries of cognate pairs produced by the multiplex molecular amplification and linkage process. The initial library of cognate pairs (parent library) generated by the method of the present invention can be subjected to screening, thereby generating a sub-library of cognate pairs encoding target-specific binding protein variable domains or full-length binding proteins.

In a further embodiment of the invention, the libraries and sub-libraries of the present invention can be used in the expression of recombinant monoclonal or polyclonal proteins, where the original binding affinities and specificities present in the donor are preserved.

DEFINITIONS

The term "cognate pair" describes an original pair of non-contiguous nucleic acids of interest that are contained within or derived from a single cell. In preferred embodiments, a cognate pair comprises two variable region encoding sequences which together encode for a binding protein variable domain and which gene sequences are derived from the same cell. Thus, when expressed either as a complete binding protein or as a stable fragment thereof, they preserve the binding affinity and specificity of the binding protein originally expressed from this cell. A cognate pair can for example be comprised of an antibody variable heavy chain encoding sequence associated with a variable light chain encoding sequence from the same cell, or a T cell receptor α chain encoding sequence associated with a β chain encoding sequence from the same cell. A library of cognate pairs is a collection of such cognate pairs.

The term "hot-start polymerase" describes polymerases that are inactive or have very low activity at temperatures used for reverse transcription. Such polymerases need to be activated by high temperatures (90 to 95° C.) to become functional. This is for example an advantage in single-step RT-PCR procedures, since this prohibits interference of the polymerase with the reverse transcriptase reaction.

The term "isogenic population of cells" describes a population of genetically identical cells. In particular, an isogenic population of cells derived by clonal expansion of an isolated single cell is of interest in the present invention.

The term "isolated single cell" describes a cell that has been physically separated from a population of cells corresponding to "a single cell in a single vessel". When distributing a population of cells individually among a plurality of vessels, a population of isolated single cells is obtained. As specified in the section entitled "Template sources" the proportion of vessels with a single cell is not necessarily a 100% in order to call it a population of single cells.

Terms derived from "link" or "linkage" in relation to amplification describes the association of the amplified nucleic acid sequences encoding the nucleic acid sequences of interest into a single segment. In relation to cognate pairs a segment comprises nucleic acid sequences encoding a variable domain, e.g. an antibody heavy chain variable region associated with an antibody light chain variable region encoding sequence, derived from the same cell. The linkage can either be achieved simultaneously with the amplification or as an immediate step following the amplification. There are no requirements to the form or functionality of the segment, it may be linear, circular, single stranded or double stranded. Nor is the linkage necessarily permanent, one of the nucleic acid sequences of interest may be isolated from the segment if desired, one of the variable region encoding sequence may for example be isolated from a cognate pair segment. However, as long as the original variable regions constituting the cognate pair are not scrambled with other variable regions, they are still considered a cognate pair, although not linked together into a single segment. The linkage is preferably a nucleotide phosphodiester linkage. However, linkage can also be obtained by different chemical cross linking procedures.

The term "multiplex molecular amplification" describes the simultaneous amplification of two or more target sequences in the same reaction. Suitable amplification methods include the polymerase chain reaction (PCR) (U.S. Pat. No. 4,683,202), ligase chain reaction (LCR), (Wu and Wallace, 1989, Genomics 4, 560-9), strand displacement amplification (SDA) technique (Walker et al., 1992, Nucl. Acids Res. 20, 1691-6), self-sustained sequence replication (Guatelli et al., 1990, Proc. Nat. Acad. Sci. U.S.A., 87, 1874-8) and nucleic acid based sequence amplification (NASBA) (Compton J., 1991, Nature 350, 91-2). The latter two amplification methods involve isothermal reactions based on isothermal transcription, which produce both single stranded RNA (ss-RNA) and double stranded DNA (dsDNA).

The term "multiplex PCR" describes a variant of PCR in which two or more target sequences are amplified simultaneously, by including more than one set of primers in the same reaction, e.g. one primer set adapted for amplification of the heavy chain variable region and one primer set adapted for amplification of the kappa chain variable region in the same PCR reaction. Additionally a primer set adapted for amplification of the lambda chain variable region may be combined with these primer sets.

The term "multiplex RT-PCR" describes a multiplex PCR reaction, which is preceded by a reverse transcription (RT) step. The multiplex RT-PCR, can either be performed as a two-step process with a separate RT step prior to the multiplex PCR, or as a single-step process where all components for both RT and multiplex PCR are combined in a single tube.

The terms "multiplex overlap-extension PCR" and "multiplex overlap-extension RT-PCR" implies that the multiplex PCR or multiplex RT-PCR is performed utilizing a multiplex overlap-extension primer mix to amplify the target sequences, thereby enabling simultaneous amplification and linkage of the target sequences.

The term "a plurality of vessels" describes any object (or collection of objects) which enables the physical separation of a single cell from a population of cells. This may be tubes, multiwell plates (e.g. 96-well, 384-well, microtitter plates or other multiwell plates), arrays, microarrays, microchips, gels, or a gel matrix. Preferably the object is applicable for PCR amplification.

The term "polyclonal protein" or "polyclonality" as used herein, refers to a protein composition comprising different, but homologous protein molecules, preferably selected from the immunoglobulin superfamily. Thus, each protein molecule is homologous to the other molecules of the composition, but also contains one or more stretches of variable polypeptide sequence, which is/are characterized by differences in the amino acid sequence between the individual members of the polyclonal protein. Known examples of such polyclonal proteins include antibody or immunoglobulin molecules, T cell receptors and B cell receptors. A polyclonal protein may consist of a defined subset of protein molecules, which has been defined by a common feature such as the shared binding activity towards a desired target, e.g. a polyclonal antibody exhibiting binding specificity towards a desired target antigen.

The term "a population of genetically diverse cells" as used herein, refers to a cell population where the individual cells in the population differ among each other on the genomic level. Such a population of genetically diverse cell is for example a population of cells derived from a donor, or a fraction of such cells, e.g. a B lymphocyte or a T lymphocyte containing cell fraction.

The term "primer set" is used interchangeably with the term "primer pair" and describes two or more primers which together are capable of priming the amplification of a nucleotide sequence of interest (i.e., one member of a cognate pair). A primer set of the present invention might be designed to prime a family of nucleotide sequences containing variable region encoding sequences. Examples of different families are antibody kappa light chains, lambda light chains, heavy chain variable regions, and α, β, γ, or δ T cell receptor variable regions. A primer set for the amplification of a family of nucleotide sequences containing variable region encoding sequences often constitutes a plurality of primers where several primers can be degenerate primers.

The term "sequence identity" is expressed as a percentage which indicates the degree of identity between to nucleic acid sequences over the length of the shortest of the two sequences. It can be calculated as $(N_{ref}-N_{dif}) \times 100/N_{ref}$, wherein $N_{ref}$ is the number of residues in the shorter of the sequences, and wherein $N_{dif}$ is the total number of non-identical residues in an $N_{ref}$ long optimally aligned match between the two sequences. Hence, the DNA sequence AGTCAGTC will have a sequence identity of 75% with the sequence T AATCAATCGG (Ndif=2 and Nref=8) (underlining shows the optimal alignment, and bold indicates the two non-identical residues out of 8).

The terms "randomly" or "random" with respect to linkage refers to linkage of nucleotide sequences which are not derived from the same cell but are linked transversely among a population of genetically diverse cells. If the nucleotide sequences of interest are variable region encoding sequences, this will result in a combinatorial library of linked sequences. If, on the other hand, the nucleotide sequences of interest encode for a non-diverse heteromeric protein the randomly linked sequences will appear similar to sequences linked from a single cell.

The term "template derived from an isolated single cell," with regard to reverse transcription, relates to the nucleic acids within such an isolated cell. The nucleic acids can for example be in the form of RNA, mRNA, DNA or genomic DNA. The nucleic acids can either be isolated from the cell or still be with the remaining contents of the cell, where the cell is in an intact form or a lysed form.

The Amplification and Linkage Process

One feature of the present invention reduces the number of tubes necessary to amplify the nucleotide sequences of interest, utilizing a variant of PCR in which two or more target sequences are amplified simultaneously in the same tube, by including more than one set of primers, for example all the primers necessary to amplify variable region encoding sequences, in the same reaction. Generally this approach is known as multiplex polymerase chain reaction (multiplex PCR).

Multiplex PCR amplification and multiplex PCR preceded by reverse transcription (multiplex RT-PCR) are well known techniques within the diagnostic field, for example in the analysis of mutations, deletions and polymorphisms of DNA, for quantitative assays of mRNA levels and for identification of viruses, bacteria and parasites (reviewed in Markoulatos, P. et al. 2002. J. Clin. Lab. Anal. 16, 47-51). However, there are only very few examples where immunoglobulin light chain variable region encoding sequences has been amplified in the same vessel as immunoglobulin heavy chain variable region encoding sequences using a multiplex primer mix composed of more than four primers constituting a $V_\kappa$ and/or $V_\lambda$ primer set together with a $V_H$ primer set (Chapal, N. et al. 1997. BioTechniques 23, 518-524; Liu, A. H. et al. 1992. Proc. Natl. Acad. Sci. U.S.A. 89, 7610-7614; Embleton, M. J. et al. 1992. Nucleic Acids Res. 20, 3831-3837). The reason for this, might be that primer sets adapted for the amplification of sequences encoding the variable domains of antigen binding proteins generally are constituted of a plurality of degenerate primers in order to capture the diversity of these variable region encoding sequences. Thus, the complexity of the PCR reaction is highly increased when performing multiplex PCR amplification on variable region encoding sequences.

A further feature of the present invention is that two or more target sequences amplified by multiplex PCR are linked in close proximity to the amplification process. In particular cognate pairs of variable region encoding sequences are linked by this process.

One embodiment of the present invention exploits that a multiplex primer mix can be designed to work in an overlap-extension PCR procedure, resulting in a simultaneous amplification and linkage of nucleotide sequences of interest. This multiplex overlap-extension PCR technique serves to reduce the number of reactions necessary to isolate and link nucleotide sequences of interest, in particular cognate pairs of linked variable regions.

Other embodiments of the present invention apply linkage by ligation or by recombination as an alternative to linkage by multiplex overlap-extension PCR. In these procedures, the linkage is not performed simultaneously with the multiplex PCR amplification, but as an immediate step following the amplification. However, linkage can still be performed in the same tube as the multiplex PCR was performed in.

In order to perform multiplex overlap-extension PCR, the presence of two or more primer sets (a multiplex primer mix), where at least one primer of each set is equipped with an overlap-extension tail is needed. The overlap-extension tails enable the linkage of the products generated by each of the primer sets during amplification. Such a primer mix is called a multiplex overlap-extension primer mix. The multiplex overlap-extension PCR, differ from conventional overlap-extension PCR in that the sequences to be linked are generated simultaneously in the same tube, thereby providing immediate linkage of the target sequences during amplification, without any intermediate purification. Further, conventional overlap-extension PCR requires a separate linking PCR reaction either with an outer primer set or a nested primer set in order to generate the linked product (Horton, R. M. et al. 1989. Gene 77, 61-68). Such an additional amplification step is optional in the multiplex overlap-extension PCR of the present invention.

A further feature of the present invention is a reverse transcription (RT) step preceding the multiplex PCR or multiplex overlap-extension PCR amplification, utilizing a template derived from an isolated single cell or a population of isogenic cells.

A further feature of the present invention is the use of nucleotide sequences derived from an isolated single cell or a population of isogenic cells as template for the multiplex PCR amplification. Preferably, RNA from a single cell is reverse transcribed into cDNA prior to the multiplex PCR. For the amplification of some nucleic acid sequences of interest genomic DNA may be used as an alternative to mRNA. By using isolated single cells or a population of isogenic cells derived by clonal expansion of an isolated single cell as template source, it is possible to avoid scrambling of nucleotide sequences encoding a heteromeric protein of interest, with nucleotide sequences derived from different cells within a population of cells. This is of importance if one wishes to obtain the original composition of the sequences of interest. Especially for the generation of a cognate pair of variable region encoding sequences, is the use of an isolated single cell or a population of isogenic cells as template source an important feature.

Multiplex overlap-extension PCR is a rarely used technology. WO 99/16904 discloses the linkage of exons from a genomic sequence in a single reaction, thereby generating cDNA without utilizing reverse transcription. The process as described, utilized one primer set (constituted of two primers) per exon to be linked, thereby composing a multiplex overlap-extension primer mix. Each individual primer set was capable of overlapping with the adjacent primer set by complementary overlap-extension tails. The cDNA was generated from a template of genomic DNA by performing an overlap-extension PCR reaction utilizing the multiplex overlap-extension primer mix followed by a nested PCR, which was described as a necessary step.

The generation of cDNA from the exons of genomic DNA as described in WO 99/16904 is a different field than the cloning of sequences encoding for heteromeric proteins. First of all, heteromeric proteins are generally expressed from different genes, whereas the exon linkage as described in WO 99/16904 relates to the linkage of exons from a single gene. Additionally, the present invention facilitates the generation of libraries of linked nucleic acid sequences of interest, in particular combinatorial libraries and libraries of cognate pairs of variable regions; a completely different situation than linking a series of exons from a single gene, resulting in a single non-variable cDNA. Further, the present invention utilizes nucleic acids derived from single cells, preferably in the form of RNA that does not need to be isolated from the remaining cell contents before it can be utilized as template.

There are few publications, where multiplex overlap-extension RT-PCR has been described in relation to linkage of variable region encoding sequences.

The most simple form of multiplex overlap-extension RT-PCR was described for the isolation of a scFv encoding sequence from a hybridoma cell line (Thirion, S. et al. 1996. Eur. J. Cancer Prev. 5, 507-511 and Mullinax, R. L et al. 1992. BioTechniques 12, 864-869). The methods described by Thirion and Mullinax utilized reverse transcription of mRNA with oligo-dT primers on total RNA extracted from the hybridoma cell line followed by a separate linkage step. The linkage step was performed with a total of four primers, constituting two primer pairs for amplification of heavy chain variable region and light chain variable region encoding sequences, respectively. The $V_L$ forward primer and the $V_H$ or $C_H$ reverse primer contained complementary overlap-extension tails, thereby enabling simultaneous amplification and linkage of the heavy chain variable region and light chain variable region encoding sequences. These methods did not use a nested PCR to increase the sensitivity of the linkage method.

The other example of multiplex overlap-extension RT-PCR in relation to linkage of variable region encoding sequences was described in the previously mentioned WO 93/03151, providing a method of cloning heavy chain variable region and light chain variable region encoding sequences originating from the same cell without having to isolate single cells prior to the cloning. The method described in WO 93/03151 required washing between the RT step and the multiplex overlap-extension PCR step. Further, one of the specific aims brought about by WO 93/03151, was to solve the problem of having to isolate single cells in order to obtain cognate pairs of variable region encoding sequences.

None of these known multiplex overlap-extension RT-PCR techniques were developed to function on template derived from an isolated single cell. Neither were any of the methods able to perform as single-step RT-PCR reactions.

One embodiment of the present invention encompasses the linkage of a plurality of non-contiguous nucleotide sequences of interest. The method comprises amplifying, in a multiplex PCR or multiplex RT-PCR amplification procedure, nucleotide sequences of interest using a template derived from an isolated single cell or a population of isogenic cells and effecting linkage of the amplified nucleotide sequences of interest. Further, the method comprises an optional step of performing an additional amplification of the linked products.

A further embodiment of the present invention encompasses a method of producing a library of cognate pairs comprising linked variable region encoding sequences. The method comprises providing a lymphocyte-containing cell fraction from a donor, which is optionally enriched for a particular lymphocyte population from said cell fraction. Further, a population of isolated single cells is obtained by distributing cells from the lymphocyte-containing cell fraction, or the enriched cell fraction, individually among a plurality of vessels. Multiplex molecular amplification (multiplex RT-PCR amplification) of the variable region encoding sequences contained in the population of isolated single cells is performed and linkage of pairs of variable region encoding sequences, wherein an individual pair is derived from a single cell, within the population of isolated single cell, is effected. Further, the technique comprises two optional steps: in the first step the individual isolated single cell in the population of single cells is expanded to a population of isogenic cells prior to performing multiplex RT-PCR amplification. Thereby obtaining a plurality of vessels with a diverse population of isogenic cells (one population of isogenic cells in one vessel). The second optional step encompasses performing an additional amplification of the linked variable region encoding sequences.

In preferred embodiments of the present invention, an individual member of said library of cognate pairs comprised of an immunoglobulin light chain variable region encoding sequence is associated with an immunoglobulin heavy chain variable region encoding sequence, originating from the same cell or of sequences encoding a T cell receptor binding domain, constituted of an alpha chain variable region associated with a beta chain variable region or a gamma chain variable region associated with a delta chain variable region, where the associated variable regions originate from the same cell.

The multiplex RT-PCR amplification of the present invention can be performed either as a two-step process, where reverse transcription (RT) is preformed separate from the multiplex PCR amplification (or alternative multiplex molecular amplification), or as a single-step process, where the RT and multiplex PCR amplification steps are performed with the same primers in one tube.

The reverse transcription (RT) is performed with an enzyme containing reverse transcriptase activity resulting in the generation of cDNA from total RNA, mRNA or target specific RNA from an isolated single cell. Primers which can be utilized for the reverse transcription are for example oligo-dT primers, random hexamers, random decamers, other random primers, or primers that are specific for the nucleotide sequences of interest.

The two-step multiplex RT-PCR amplification procedure, allows for the cDNA generated in the RT step, to be distributed to more than one vessel permitting for the storage of a template fraction before proceeding with the amplification. Additionally, the distribution of cDNA to more than one tube, allows for the performance of more than one multiplex PCR amplification of nucleic acid derived from the same template. Although, this results in an increased number of separate reactions, it opens for the possibility to decrease the complexity of the multiplex primer mix if this should be desired. This two-step approach can for example be applied to amplify and link heavy chain variable region and kappa light chain variable region encoding sequences in one tube and heavy chain variable region and lambda light chain variable region encoding sequences in a different tube utilizing the same template. A single cell usually only expresses one of the light chains. However, it will often be easier to perform the reactions simultaneously instead of awaiting the result of one of the reactions before performing the other. Further, the amplification of both kappa and lambda serves as an internal negative control, since it would be expected that only kappa or lambda amplify from a single cell.

In the single-step multiplex RT-PCR procedure, reverse transcription and multiplex PCR amplification is carried out in the same vessel. All the components necessary to perform both the reverse transcription and the multiplex PCR in a single step are initially added into the vessels and the reaction is performed. Generally, there is no need to add additional components once the reaction has been started. The advantage of single-step multiplex RT-PCR amplification is that it reduces the number of steps necessary to generate the linked nucleotide sequences of the present invention even further. This is particular useful when performing multiplex RT-PCR on an array of single cells, where the same reaction needs to be carried out in a plurality of vessels. Single-step multiplex RT-PCR is performed by utilizing the reverse primers present in the multiplex primer mix needed for the multiplex PCR amplification as primers for the reverse transcription as well. Generally, the composition needed for the single-step multiplex RT-PCR comprises a nucleic acid template, an enzyme with reverse transcriptase activity, an enzyme with DNA polymerase activity, deoxynucleoside triphosphate mix (dNTP mix comprising dATP, dCTP, dGTP and dTTP) and a multiplex primer mix. The nucleic acid template is preferably total RNA or mRNA derived from an isolated single cell either in a purified form, as a lysate of the cell or still within the intact cell. Generally, the exact composition of the reaction mixture requires some optimization for each multiplex primer mixture to be used with the present invention. This applies both for the two-step and the single-step multiplex RT-PCR procedures.

In alternative embodiments of the present invention it may be appropriate to use genomic DNA instead of RNA as template. In such cases the reverse transcription step is omitted, and the remaining steps of the invention are performed as described throughout the application.

For some single-step multiplex RT-PCR reactions it may be an advantage to add additional components during the reaction. For example, addition of the polymerase following the RT step. Other components could for example be a dNTP mixture or a multiplex primer mix possibly with a different primer composition. This can then be considered as a one-tube multiplex RT-PCR, which generally has the same advantages as the single-step multiplex RT-PCR, since it also limits the number of tubes necessary to obtain the desired linked products.

The nucleotide sequences of interest, amplified by the multiplex RT-PCR, can be linked to one another by several methods, such as multiplex overlap-extension RT-PCR, ligation or recombination, using different multiplex primer mixes. Preferably the multiplex RT-PCR amplification and linkage process is a single step or a two step process. However, the linkage process may also be performed as a multi step process, using for example a stuffer fragment to link the nucleic acid sequences of interest, either with PCR, ligation or recombination. Such a stuffer fragment may contain cis-elements, promoter elements or a relevant coding sequence or recognition sequence. In a preferred embodiment the linkage process is performed in the same vessel as the multiplex RT-PCR amplification.

In one embodiment of the present invention the linkage of a plurality of non-contiguous nucleotide sequences of interest is performed in association with the multiplex PCR amplification, utilizing a multiplex overlap-extension primer mix. This results in the combined amplification and linkage of the target sequences. Generally, the composition needed for the multiplex overlap-extension PCR comprises, a nucleic acid template, an enzyme with DNA polymerase activity, deoxynucleoside triphospate mix (dNTP mix comprising dATP, dCTP, dGTP and dTTP) and a multiplex overlap-extension primer mix.

In a particular embodiment of the present invention, the linkage of a plurality of non-contiguous nucleotide sequences of interest is performed by multiplex overlap-extension RT-PCR using a template derived from an isolated single cell or a population of isogenic cells. Further, the method comprises an optional step of performing an additional molecular amplification of linked products. Preferably, the multiplex overlap-extension RT-PCR is performed as a single-step/one-tube reaction.

A multiplex overlap-extension primer mix of the present invention comprises at least two primer sets capable of priming the amplification and linkage of at least two variable region encoding sequences, for example, amplification and linkage of sequences from immunoglobulin heavy chain variable region families with kappa or lambda light chain variable region families, or amplification and linkage of sequences from T cell receptor families $\alpha$, $\beta$, $\gamma$, or $\delta$.

In another embodiment of the present invention the plurality of nucleotide sequences of interest, amplified by multiplex RT-PCR, are linked by ligation. To achieve this, the multiplex primer mix used for the multiplex RT-PCR, is designed such that the amplified target sequences can be cleaved with appropriate restriction enzymes, and covalent linkage by DNA ligation can be performed (the primer design is described in the section "Primer Mixtures and Design"). Following multiplex RT-PCR amplification with such a multiplex primer mix, the restriction enzymes needed to form compatible ends of the target sequences, are added to the mixture together with the ligase. No purification of the PCR products is needed prior to this step, although purification may be performed. The reaction temperature for the combined restriction cleavage and ligation is approximately between 0 and 40° C. However, if the polymerase from the multiplex PCR reaction is still present in the mixture, an incubation temperature below room temperature is preferred, most preferred are temperatures between 4 and 16° C.

In yet another embodiment of the present invention, the plurality of nucleotide sequences of interest, amplified by multiplex RT-PCR, are linked by recombination. In this approach, the target sequences amplified can be joined using identical recombination sites. Linkage is then performed by adding the recombinases facilitating recombination. Some suitable recombinase systems are Flp recombinase with a variety of FRT sites, Cre recombinase with a variety of lox sites, integrase $\Phi$C31 which carries out recombination between the attP site and the attB site, the $\beta$-recombinase-six system as well as the Gin-gix system. Linkage by recombination has been exemplified for two nucleotide sequences ($V_H$ linked with $V_L$) (Chapal, N. et al. 1997 BioTechniques 23, 518-524), hereby incorporated by reference.

In a preferred embodiment of the present invention, the nucleotide sequences of interest comprise variable region encoding sequences and the linkage generates a cognate pair of variable region encoding sequences. Such a cognate pair may comprise one or more constant region encoding sequences in addition to the variable regions.

In an even more preferred embodiment of the present invention, the nucleotide sequences of interest comprise immunoglobulin variable region encoding sequences and the linkage generates a cognate pair of light chain variable region and heavy chain variable region encoding sequences. Such a cognate pair may comprise one or more constant region encoding sequences in addition to the variable regions. Further, such a cognate pair may be isolated from template derived from cells of the B-lymphocyte lineage enriched from a lymphocyte-containing cell fraction, such as whole blood, mononuclear cells or white blood cells.

In a just as preferred embodiment of the present invention, the nucleotide sequences of interest comprise TcR variable region encoding sequences and the linkage generates a cognate pair of α chain variable region and β chain variable region encoding sequences or γ chain variable region and δ chain variable region encoding sequences. Such a cognate pair may comprise one or more constant region encoding sequences in addition to the variable regions. Further, such a cognate pair may be isolated from template derived from cells of the T-lymphocyte lineage enriched from a lymphocyte-containing cell fraction, such as whole blood, mononuclear cells or white blood cells.

Another aspect of the present invention, is to utilize the multiplex RT-PCR with a population of genetically diverse cells as template source. The majority of heteromeric protein encoding sequences do not vary from cell to cell as is the case with variable region encoding sequences from binding proteins. Thus, when utilizing the present invention for the cloning of such non-variable heteromeric protein encoding sequences there is no need to perform an initial isolation of single cells.

In this embodiment of the present invention, a plurality of non-contiguous nucleotide sequences of interest are linked randomly by a method comprising, performing multiplex RT-PCR amplification of nucleotide sequences of interest using a template derived from a population of genetically diverse cells and effecting linkage of the amplified nucleotide sequences of interest. Further, the method comprises an optional step of performing an additional amplification of the linked products. As with the single cell approach the linkage can either be performed utilizing a multiplex overlap-extension primer mix for the amplification or alternatively by ligation or recombination. Preferably the template derived from the population of cells is not strictly contained within the cells. The population of cells may for example be lysed.

Application of the process of random linkage on a population of cells expressing variant binding proteins, allows for a simplified generation of combinatorial libraries of variable region encoding sequences. Preferably, the population of cells constitutes cells that express variable region binding proteins, such as B lymphocytes, T lymphocytes, hybridoma cells, plasma cells, or a mixture of these cells.

The population of cells in the above mentioned embodiment can for example be permeabilized or lysed, without additional purification, or the template nucleic acids can be isolated from the cells by standard procedures. The single-step multiplex RT-PCR procedure is preferred. However, the two-step procedure may also be used in the embodiment.

The invention also provides a combinatorial library comprised of linked pairs of immunoglobulin light chain variable region and heavy chain variable region encoding sequences.

An efficient way to increase the specificity, sensitivity, and yield of the multiplex RT-PCR-linkage process, is by performing an additional molecular amplification of the linked nucleotide sequences obtained from the multiplex RT-PCR followed by linkage by ligation or recombination or linkage using the multiplex overlap-extension RT-PCR. This additional amplification is preferably performed with PCR amplification, utilizing a primer mix adapted for amplifying the linked nucleic acid sequences of interest. The primer mix utilized may be the outer primers of the multiplex primer mix or multiplex overlap-extension primer mix, meaning the primers which anneal to the outermost 5' end and 3' end of the sense strand of the linked variable region encoding sequences, thereby enabling the amplification of the entire linked product. The outer primers can also be described as the primers of the multiplex overlap-extension primer mixture that do not contain overlap extension tails. Alternatively, a nested or semi-nested primer set can be used for the additional amplification of the linked nucleotide sequences. Such a nested PCR especially serves to increase the specificity of the method as well as to increase the amount of linked product. For the present invention, semi-nested PCR (as described in the section entitled Primer Mixtures and Design) is considered to function as well as the nested PCR. Thus, it is desired although not necessary for the present invention to perform an additional PCR amplification of the linked products from the multiplex overlap-extension RT-PCR or of the products linked by ligation or recombination, preferably using nested PCR or semi-nested PCR.

The additional amplification can either be performed directly using a fraction or the entire multiplex overlap-extension RT-PCR reaction product or ligation product or recombination product, or a fraction of any one of these products or using partially purified linked products from any one of these reactions, e.g. by performing an agarose gel electrophoresis of the linked products, and excising the fragment corresponding to the expected size of the linked variable region encoding sequences. For products linked by multiplex overlap-extension RT-PCR, the additional amplification is preferably performed directly on a fraction from the multiplex overlap-extension RT-PCR reaction, since this would assist linkage of the individual target sequences that were not linked in the first reaction.

Sequences of Interest

The nucleotide sequences of interest of the present invention can be selected from sequences that encode different subunits or domains, which when expressed, forms a protein or part of a protein. Such proteins that are composed of at least two non-identical subunits are known as heteromeric proteins. Heteromeric proteins are common in all kinds of species. Some of the classes to which such proteins belong are for example enzymes, inhibitors, structural proteins, toxins, channel proteins, G-proteins, receptor proteins, immunoglobulin superfamily proteins, transportation proteins etc. The nucleotide sequences encoding such heteromeric proteins are non-contiguous, meaning for example that they originate from different genes, or different mRNA molecules. However, non-contiguous as used in the present invention may also mean nucleotide sequences encoding domains of the same protein, where the domains are separated by nucleotide sequences which are not of interest.

In one embodiment of the present invention the nucleotide sequences of interest contain variable region encoding sequences from the immunoglobulin superfamily, such as immunoglobulins (antibodies), B cell receptors and T cell receptors (TcR's). Especially variable region encoding sequences from immunoglobulins are of interest. Such variable region encoding sequences comprise full-length antibodies as well as Fab's, Fv's, scFv's and combinations of fragments of the variable region encoding sequences, e.g. complementarity determining regions (CDR's), joining genes or V-genes or combinations of these. Generally the present invention can be applied with any combinations of variable region encoding sequences and fragments thereof. The present application exemplifies the linkage of the entire light chain with the variable domain of the heavy chain. However, the present invention also allow for the linkage of only the variable domains of the heavy and light chains generating Fv or scFv encoding sequences, or the linkage of the entire light chain with the heavy chain variable region+constant region domain $C_{H1}$+parts of the hinge region, generating Fab, Fab' or $F(ab)_2$. Further, it is possible to add any region of the heavy chain constant region domains to the variable heavy chain, thereby generating truncated antibody encoding sequences or full-length antibody encoding sequences.

In a further embodiment of the present invention variable region encoding sequences comprise one type of immunoglobulin light chain (kappa or lambda) encoding sequence and one immunoglobulin heavy chain variable region encoding sequence.

Variable region encoding sequences derived from T cell receptors (TcR's) are also of interest. Such TcR encoding sequences comprise encoding sequences for full-length alpha and beta chains or gamma and delta chains as well as soluble TcR's or only the variable domains of these chains or single chain fusion proteins thereof (e.g. single chain αβ or single chain γδ).

Template Sources

One feature of the present invention is the ability to link nucleotide sequences derived from an isolated single cell, a population of isogenic cells, or a genetically diverse population of cells which have not been separated into single vessels. The cells utilized in the present invention can for example be bacteria, yeast, fungi, insect cells, plant cells or mammalian cells or fractions of such cells. Blood cells derived from mammals are one example of a fraction of cells that can be utilized in the present invention.

A preferred feature of the present invention is the use of isolated single cells or a population of isogenic cells as template source, since scrambling of the nucleic acid sequences of interest, in particular variable region encoding sequences is avoided. This is of importance if one wishes to obtain an original pair of for example variable region encoding sequences.

Another preferred feature of the present invention, is obtaining a single cell or population of single cells from a cell fraction comprising lymphocytes, such as B lymphocytes, T lymphocytes, plasma cells and/or various developmental stages of these cell lineages. Other populations of cells that express binding proteins from the immunoglobulin superfamily might also be used to obtain single cells. Cell lines such as hybridoma cells, cell lines of B lymphocyte or T lymphocyte lineage or virus immortalized cell lines or donor derived cells participating in the immune response are also applicable in the present invention. Donor derived lymphocyte-containing cell fractions may be obtained from natural tissue or fluid which is rich in such cells, e.g. blood, bone marrow, lymph nodes, spleen tissue, tonsil tissue or from infiltrations in and around tumors or inflammatory tissue infiltrations. Suitable cell donors for the present invention can be selected from vertebrates that all contain an acquired immune system. Donors can either be naïve or hyperimmune with respect to a desired target. For the isolation of antigen binding proteins with binding specificities toward a desired target, hyperimmune donors are preferred. Such hyperimmune donors can either be donors immunized with the target, or fragments of the target, or it can be convalescent patients, or non-healthy individuals which are running a natural immune response towards the target e.g. autoimmune patients, cancer patients, patients with infectious diseases e.g. HIV patients, Hepetitis A, B or C patients, SARS patients etc., or patients with chronic diseases.

When utilizing recombinant proteins for treatment, it is preferable that they are derived from sequences that have species identity with the individual to be treated (e.g. human sequences for treatment of humans). Firstly, because recombinant proteins derived from a foreign sequence (i.e. non-human) will be recognized by the immune system leading to an immune response implicating polyclonal anti-protein antibodies. These anti-protein antibodies can block the drug action by occupying the active site, they will accelerate drug clearance and they could potentially induce adverse reactions such as hypersensitivity reactions upon repeated exposure.

Immunogenicity may however, also be seen in cases where the recombinant protein is derived from a sequence that have species identity. Such immunogenicity can for example be induced by post-translational modifications that might differ from those seen in vivo. Combinatorial libraries of variable region encoding sequences might also give rise to immunogenicity, since they consist of random pairs of variable region encoding sequences created in vitro. The rules that govern formation of antibody heavy and light chain encoding sequence pairs (or T cell receptors) in vivo are not completely understood. Hence, it follows that some of the in vitro formed pairs could be recognized as foreign by the immune system, even though both sequences constituting the pair are perfectly human. Binding proteins obtained from cognate libraries do on the other hand not create said abnormal combinations and they are consequently of lesser potential immunogenicity than binding proteins from combinatorial libraries. This does not mean that products from combinatorial libraries are unsuitable for treatment, they just require a larger degree of monitoring with respect to the above mentioned side effects.

For use in the present invention, cell donors should preferably be of the same species as the species to be treated with the products obtainable from the linked nucleotide sequences of the present invention. Preferably, a cell donor is a domestic animal, a pet, a human or a transgenic animal. Transgenic animals carrying human immunoglobulin loci are described in U.S. Pat. No. 6,111,166 and Kuroiwa, Y. et al. Nature Biotechnology; 2002; 20: 889-893. Such transgenic animals are capable of producing human immunoglobulins. Thus, fully human antibodies against a specific target can be raised by usual immunization techniques of such transgenic animals. This allows for generation of libraries encoding for binding proteins with specificities towards more difficult targets such as human antigens to which no or limited natural human antibody response exist. Such transgenic animals can likewise be developed to produce human T cell receptors.

In a further embodiment of the present invention, the lymphocyte-containing cell fraction is constituted of whole blood, bone marrow, mononuclear cells, or white blood cells obtained from a donor. Mononuclear cells can be isolated from blood, bone marrow, lymph nodes, spleen, infiltrations around cancer cells and inflammatory infiltrations. Mononuclear cells can be isolated by density centrifugation techniques, e.g. Ficoll gradients. If the mononuclear cells are isolated from samples composed of tissue, the tissue is disintegrated before the gradient centrifugation is performed. Disintegration can be performed, for example, by mechanical methods such as grinding, electroporation and/or by chemical methods such as enzymatic treatments. The isolation of white blood cells can be performed directly from donors using leukopheresis. Raw preparations of for example bone marrow or tissue, which contain lymphocytes, can also be used in the present invention. Such preparations will need to be disintegrated, for example as described above, in order to facilitate single cell distribution.

A further feature of the present invention is enrichment of the lymphocyte-containing cell fraction e.g. whole blood, mononuclear cells, white blood cells or bone marrow, with respect to a particular lymphocyte population, such as cells from the B lymphocyte or T lymphocyte lineage. Enrichment of B lymphocytes can for example be performed, using magnetic bead cell sorting or fluorescence activated cell sorting (FACS) taking advantage of lineage-specific cell surface marker proteins such as CD19 or other B cell lineage-specific markers. Enrichment of T lymphocytes can for example be performed, utilizing a cell surface marker such as CD3 or other T cell lineage-specific markers.

A preferred feature of the present invention is to sort the enriched B lymphocytes further in order to acquire plasma cells, before distributing the cells individually among a plurality of vessels. Isolation of plasma cells is generally performed by FACS sorting, utilizing surface markers such as CD38 possibly in combination with CD45. Other plasma cell-specific surface markers or combinations thereof can be utilized as well, for example CD138, CD20, CD21, CD40, CD9, HLA-DR or CD62L, the exact choice of marker depends on the plasma cell source, e.g. tonsils, blood or bone marrow. Plasma cells can also be obtained from a non-enriched lymphocyte-containing cell population obtained from any of these sources. The plasma cells isolated from blood are sometimes called early plasma cells or plasmablasts. In the present invention these cells are also termed plasma cells although they are CD19 positive in contrast to plasma cells residing in the bone marrow. Plasma cells are desired for the isolation of cognate pairs of immunoglobulin encoding sequences because a higher frequency of these cells produces antigen-specific antibodies that reflect the acquired immunity toward the desired antigen and most of the cells have undergone somatic hypermutation and therefore encode for high-affinity antibodies. Further, the mRNA levels in plasma cells are elevated compared to the remaining B lymphocyte population, thus the reverse transcription procedure is more efficient when using single plasma cells. As an alternative to plasma cell isolation, memory B cells may be isolated from a lymphocyte containing cell fraction utilizing a cell surface marker such as CD22.

An alternative feature of the present invention, is selecting the enriched B lymphocytes for antigen specificity before distributing the cells among a plurality of vessels. Isolation of antigen-specific B lymphocytes is performed by contacting the enriched B lymphocytes with the desired antigen or antigens enabling binding of antigen to surface exposed immunoglobulin, followed by isolation of binders. This can be done, for example, by coating magnetic beads with the desired antigen or antigens followed by magnetic bead cell sorting, by FACS, by coating a column with the antigens followed by affinity chromatography, by filter screening assays or other methods known in the art. Plasma cells as well as B lymphocytes, non-enriched mononuclear cells, white blood cells, whole blood, bone marrow or tissue preparations can be subjected to isolation with respect to antigen specificity if this is desired.

Another feature of the present invention, is to sort enriched T lymphocytes (e.g. CD3 positive cells) using surface markers CD45R0 and/or CD27 to obtain a fraction of memory T cells. T lymphocytes can also be selected for MHC-antigen specificity using MHC-peptide complexes (e.g. Callan, M. F. et al. 1998. J. Exp. Med. 187, 1395-1402; Novak, E. J. et al. 1999. J. Clin. Invest 104, R63-R67).

A further feature of the present invention is immortalization of any of the isolated cell fractions described in the above (e.g. B lymphocytes, plasma cells, memory cells or T lymphocytes). Immortalization may for example be performed with Epstein-Barr virus (Traggiai, E., et al., 2004. Nat Med 10, 871-875) prior to cell distribution. Alternatively, isolated single cells may be immortalized and expanded prior to reverse transcription. Traggiai et al., Nat. Med. 2004 August; 10(8):871-5.

A further feature of the present invention, is the distribution of a population of desired cells (e.g. hybridoma cells, cell lines of B lymphocyte or T lymphocyte lineage, whole blood cells, bone marrow cells, mononuclear cells, white blood cells, B lymphocytes, plasma cells, antigen-specific B lymphocytes, memory B cells, T lymphocytes, antigen/MHC-specific T lymphocytes, or memory T cells) individually, into a plurality of vessels, in order to obtain a population of isolated single cells. This isolation of single cells refers to the physical separation of cells from a population of cells in such a way that a single vessel contains a single cell, or a micro array, chip or gelmatrix is loaded in a manner that produce single cells. The cells may be distributed directly into multitudes of vessels such as arrays of single vessels by limiting dilution. The single vessels utilized in the present invention are preferably those applicable in PCR (e.g. PCR tubes and 96 well or 384 well PCR plates or larger arrays of vessels). However other vessels may also be used. When distributing single cells into a large number of single vessels (e.g. 384 well plates), a population of single cells is obtained. Such a distribution may be performed, for example, by dispensing a volume into a single vessel that on average encompasses a cell concentration of one, 0.5 or 0.3 cell, thereby obtaining vessels that on average contain a single cell or less. Since distribution of cells by limiting dilution is a statistical event, a fraction of the vessels will be empty, a major fraction will contain a single cell, and a minor fraction will contain two or more cells. Where two or more cells are present in a vessel some scrambling of the variable region encoding sequences may occur among the cells present in the vessel. However, since it is a minor event it will not affect the overall utility of the present invention. Additionally, combinations of variable region encoding sequences which do not posses the desired binding affinity and specificity will most likely not be selected and hence eliminated during a screening process. Therefore, minor events of scrambling will not significantly affect the final library of the present invention.

There are alternatives to cell distribution by limiting dilution using, for example, cell sorters such as FACS machines or robots that can be programmed to accurately dispense single cells into single vessels. These alternatives are preferable, since they are less laborious and are more efficient in uniformly obtaining a distribution of single cells into single vessels.

The enrichment, sorting and isolation procedures described in the above, are performed such that the majority of the cells are kept intact. Rupture of cells during enrichment and sorting might result in scrambling of the variable region encoding sequences. However, this is not expected to be a problem since the frequency of rupture is expected to be low. Washing and possible RNAse treatment of the cells prior to distribution into single vessels will remove any RNA that has leaked during the process.

Further, when considering the above descriptions of how to distribute cells in order to obtain a population of single cells in a population of single vessels, it is not to be interpreted as an absolutely required feature that every vessel must contain a single cell. Rather, it indicates that a majority of the vessels contain single cells, e.g. the number of vessels with two or more cells is below 25% of the total amount of cells distributed, or even better it is below 10%.

A further feature of the present invention is the performance of a reverse transcription using template derived from cells distributed individually among a plurality of vessels.

For the purpose of reverse transcription (RT), in accordance with the present invention, the nucleic acids within a single cell that is to serve as template source for the RT, are considered to be derived from a single cell although they have not necessarily been separated from the remaining contents of that single cell.

When the final distribution of the single cells to their single vessels has been performed, the single cells may be expanded in order to obtain a population of isogenic cells prior to reverse transcription. This process yields more mRNA to be used as template, which might be important if a rare target is to be amplified and linked. However, the cells should remain genetically identical with respect to the target gene during the expansion. The isolated cells or the population of isogenic cells can either be kept intact or lysed, as long as the template for the reverse transcription is not degraded. Preferentially, the cells are lysed in order to ease the following reverse transcription and PCR amplification.

In a different embodiment of the present invention, the disclosed multiplex overlap-extension RT-PCR method or multiplex RT-PCR followed by linkage by ligation or recombination may also be utilized on template derived from a genetically diverse population of cells which have not been separated into single vessels, but all remain together as a pool of cells. This method may be used for the generation of combinatorial libraries. Such an approach will not require the distribution of single cells. However, the cells which may be used in this approach are the same as those described for the single cell approach, for example a population (pool) of sorted B lymphocytes or T lymphocytes. When performing the single-step multiplex overlap-extension RT-PCR or single-step multiplex RT-PCR followed by linkage by ligation or recombination on such a population of cells, it is preferable to lyse the cells prior to the reaction and if desired total RNA or mRNA may be isolated from the lysate.

The sensitivity of the single-step multiplex overlap-extension RT-PCR of the present invention enables the use of a very low amount of template. As shown in Example 2 and 3, single-step multiplex overlap-extension RT-PCR may be carried out on an amount of template corresponding to the lysate of a single cell.

Primer Mixtures and Design

The primer mixtures of the present invention comprise at least four primers that form primer sets two by two, which are capable of amplifying at least two different target sequences of interest. Mixtures of two or more of such primer sets constitute a multiplex primer mix. Preferably, a multiplex mix comprise at least 3, 4, 5, 6, 7, 8, 9, 10, 11, 12, 13, 14, 15, 16, 17, 18, 19 or 20, 30, 40, 50, 60, 70, 80, 90 100, 110, 120, 130, 140 or 150 primer sets (primer pairs). In particular for the amplification of variable region encoding sequences, may an individual primer set within the multiplex primer mix constitute several more than two primers. Preferably, an individual primer set comprise at least 3, 4, 5, 6, 7, 8, 9, 10, 11, 12, 13, 14, 15, 20, 25, 30, 35, 45, 50, 60, 70, 80, 90, 100, 110, 120, 130, 140, 150, 160, 170, 180, 190, 200, 220, 240, 260, 280 or 300 primers. Preferably the total number of primers in a multiplex primer mix is at least 5, 6, 7, 8, 9, 10, 11, 12, 13, 14, 15, 20, 25, 30, 35, 45, 50, 60, 70, 80, 90, 100, 125, 150 or 200 and at the most 225, 250, 275, 300, 325, 350, 375 or 400 primers.

All the primers of the present invention comprise a gene-specific region, and preferably all primers are additionally equipped with a primer tail at the 5' end of the primer, i.e. 5' non-coding sequences which are fused to the 3' end of the gene-specific primer part. Such a primer tail is approximately from 6 to 50 nucleotides long, but it may also be longer if desired. Upon amplification the primer tails are added to the target sequences.

Primer tails of the present invention are for example, cloning tails and linkage tails such as, tails adapted for linkage by ligation, tails adapted for linkage by recombination or overlap-extension tails.

Cloning tails may be from 6 to 20 nucleotides long or longer and comprise restriction sites and/or recombination sites, which are useful for the insertion of the linked product into an appropriate vector.

To enable linkage by ligation, the primer sets of the multiplex primer mix are designed such that one part (forward or reverse primer(s)) of the first primer set is equipped with a linkage-tail containing a restriction site that upon cleavage will be compatible with a restriction site located in the linkage tail of one part of the second primer set. For linkage of more than two target sequences, the second part of the second primer set is equipped with a restriction site that upon cleavage will be compatible with a restriction site located in one part of the third primer set. This second restriction site located in the second primer set should be non-compatible with that of the first primer set. A considerable number of target sequences can be linked by designing primer sets this way. Restriction sites with a low frequency or no occurrence, in the target sequences should be chosen. Further, it is preferable that compatible restriction sites are not identical, such that the site of ligation becomes cleavage-resistant for the particular restriction enzymes used. This will drive the reaction towards linkage of target sequence one with target sequence two, since linkage between identical target sequences will be cleavable by the restriction enzymes. Suitable pairs of restriction sites are for example, SpeI with XbaI (alternatively NheI or AvrII can substitute one or both of these), NcoI with BspHI, EcoRI with MfeI or PstI with NsiI. For linkage, SpeI can for example be located in target sequence one, XbaI can be located in target sequence two, NcoI can be located at the other end of target sequence two and BspHI in target sequence three and so forth. To simplify the process further, it is an advantage if the restriction enzymes function in the same buffer.

To enable linkage by recombination the primer sets of the multiplex primer mix can for example be designed as exemplified in the article by Chapal (1997 BioTechniques 23, 518-524), which is hereby incorporated by reference.

To enable the linkage of the nucleotide sequences of interest in the same step as the multiplex PCR amplification, tails adapted for overlap-extension PCR are added to at least one primer of each primer set of the multiplex primer mix, thereby generating a multiplex overlap-extension primer mixture.

The overlap-extension tails are typically longer, ranging from 8 to 75 nucleotides in length and may contain restriction sites or recombination sites which allow for subsequent insertion of regulatory elements such as promoters, ribosomal binding sites, termination sequences, or linker sequences such as in a scFv. The overlap-extension tail may also contain a stop codon if that is desired. Generally there are three types of overlap-extension tails, as illustrated in FIG. 1. In type I the overlap-extension tails of two primer sets solely overlap with each other. Not necessarily all of the nucleotides of two overlap-extension tails are complementary to each other. In one aspect of the present invention the complementary nucleotides represent between 60 to 85% of the overlap-extension tail. In type II overlap-extension tails, 4 to 6 of the 5' nucleotides are complementary to the gene-specific region of the adjacent target sequence. In type III overlap-extension tails, the entire overlap is complementary to the adjacent target sequence. The type I and II overlap-extension tails are preferred when regulatory elements and the like are later to be inserted between the linked target sequences. Type II overlap-extension tails are preferred if the target sequences are to be linked by a defined linker as seen with scFv. Type III overlap-extension tails are preferred if the target sequences are to be linked in-frame to each other.

Design of overlap-extension tails is dependent on sequence features such as length, relative GC content (GC %), presence of restriction sites, palindromes, melting temperature, the gene-specific part to which they are coupled etc. The length of the overlap-extension tails should be between 8 and 75 nucleotides long, preferably they are from 15 to 40 nucleotides long. Even more preferred they are from 22 to 28 nucleotides long. The use of very long overlap-extension tails (50 to 75 nucleotides) could favor the linkage of the products produced by each primer set. However, the proportion between the length of the overlap-extension tail and the gene-specific region probably will need to be adjusted when using very long overlap-extension tails. The GC % preference is dependent on the length of the overlap-extension tail. Since shorter tails have a shorter area where they are complementary they need a higher GC % to strengthen the interaction than longer tails. Other principles of primer design should likewise be observed, e.g. primer dimerization and hairpin formation should be minimized. Neither shall they engage in false priming. Further, it is known that Taq DNA polymerase often adds an adenosine (A) at the 3' end of the newly synthesized DNA strand, and this can be accommodated for in overlap-extension tail design by enabling overlap-extension tails to accommodate 3' non-template A addition.

The choice of primers that carry the linkage tail, e.g. the overlap-extension tail, tail adapted for linkage by ligation or tail adapted for linkage by recombination, defines the order and direction of linkage of the target sequences. It is not essential to the invention whether it is the forward primer(s) or reverse primer(s) of a primer set or possibly both forward and reverse primers that are equipped with the linkage tail. However, some consideration should be given to this anyway since the order and direction of the target sequences in the final product might be of relevance e.g. for the insertion of regulatory elements such as promoters and termination sequences or for the in-frame linkage of the individual target sequences.

Figure 3:
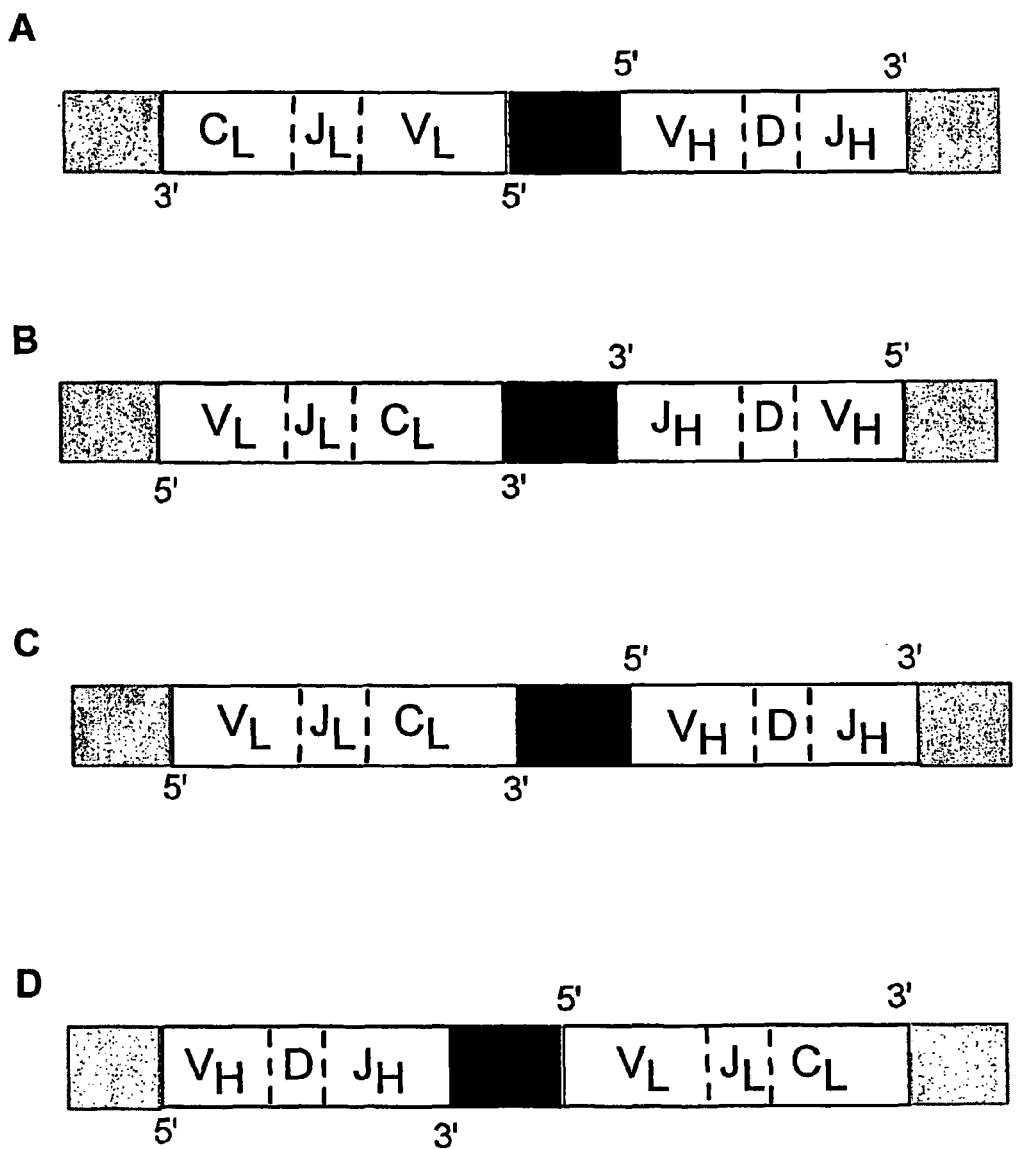
FIG. 3 is a series of diagrams illustrating the different linking direction of the products that can be obtained depending on which primers are equipped with the linkage tail. Solid black illustrates the overlap region. 5' and 3' indicates the direction of the open reading frame.

For the linkage of two nucleotide sequences of interest the linkage tail may be added either to the reverse primer(s) or forward primer(s) of each primer set used for the PCR amplification of each target sequence. The present invention exemplifies addition of overlap-extension tails and tails adapted for linkage by ligation, to the $V_H$ and $V_L$ forward primers of each set (e.g. FIG. 2 and example 9, respectively). This results in a linking direction of the products that is 5' to 5' (head-to-head and bi-directional). However, linkage tails might as well be added to the reverse primer(s) of each set (e.g. $C_\kappa$ and/or $C_\lambda$ in the first set and $C_H$ or $J_H$ in the second set). This results in a linking direction of the product that is 3' to 3' (tail-to-tail and bi-directional). A third option is adding the linkage tails to the reverse primer(s) of the first primer set (e.g. $C_\kappa$ and/or $C_\lambda$ primers) and the forward primer(s) of the second primer set (e.g. $V_H$ primer(s)) or visa versa. This results in a 3' to 5' orientation (head-to-tail and unidirectional). FIG. 3 illustrates the possible directions that can be generated depending on which primer of each primer set that is equipped with the linkage tail.

When linking more than two nucleotide sequences of interest some of the primer sets need to have linkage tails on both the forward and reverse primers, such that one tail is complementary to a tail of the preceding primer set and the other tail is complementary to one of the primers of the subsequent primer set. This principle holds for all the primer sets that amplify target sequences that are to be linked between two other target sequences.

The design of the gene-specific primer part generally should observe known primer design rules such as minimizing primer dimerization, hairpin formation and non-specific annealing. Further, multiple G or C nucleotides as the 3' bases are to be avoided when possible. The melting temperature (Tm) of the gene-specific regions in a primer set should preferably be equal to each other plus/minus 5° C. In the present invention Tm values between 45° C. and 75° C. are desirable and Tm values of about 60° C. are optimal for most applications. Advantageously, the initial primer design can be aided by computer programs developed for this task. However, primer designs generally need laboratory testing and routine optimization. This may be done, for example, by analyzing size, restriction fragment length polymorphism (RFLP) and sequencing of the amplification products obtained using the primer sets. The use of degenerate positions within primers is a useful approach when amplifying sequences with variable regions or when searching for new family members belonging to a specified class of proteins. The numbers of degenerate positions may also require optimization.

The present invention encompasses improved primer sets that can be used together in a highly multiplexed format. The primer set described by de Haard (de Haard, H. J. et al. 1999. J. Biol. Chem. 274, 18218-18230) were used as starting point, and was modified by trimming the 3' ends of the primers to reduce non-specific interactions and adding overlap-extension tails or tails adapted for linkage by ligation.

One feature of the present invention, are primer mixes composed of at least two primer sets that are able to prime amplification and promote linkage of at least two nucleotide sequences of interest. The primer mixes of the present invention are capable of priming the amplification of at least two subunits or domains from heteromeric proteins, e.g. belonging to the class of enzymes, inhibitors, structural proteins, toxins, channel proteins, G-proteins, receptor proteins, immunoglobulin superfamily proteins, transportation proteins etc.

A further feature of the present invention is a multiplex overlap-extension primer mix comprising primer sets wherein at least one primer set member of each primer set comprises an overlap-extension tail capable of hybridizing to the overlap-extension tail of a primer set member of a second primer set.

The overlap-extension tails enables the immediate linkage of the nucleotides of interest during the multiplex overlap-extension PCR amplification by equipping each individual product arising from the primer sets with a tail that is complementary to an adjoining product. This however does not mean that the linkage necessarily occur during this first PCR amplification. Depending on the reaction setup, the majority of the actual linkage may be performed during an additional amplification with the outer primers of the first PCR amplification (multiplex PCR amplification).

A further feature of the present invention, is a primer set designed to amplify a family of nucleotide sequences containing variable region encoding sequences. Examples of such families are kappa light chains (e.g. VKI-VI in humans), lambda light chains (e.g. VL1-10 in humans) and variable heavy chains (e.g. VH1-7 in humans and VH1-15 in mice) from immunoglobulins, and α, β, γ or δ TcR variable regions. A primer set for the amplification of a family of nucleotide sequences containing variable region encoding sequences often comprise a plurality of primers where several primers can be degenerate primers. Amplification of families of immunoglobulin light chain variable region encoding sequences is for example performed using a primer set comprised of a plurality of primers complementary to the 5' end of the variable region of the kappa chain ($V_{L\kappa}$ primer(s)) or the kappa leader sequence ($V_{L\kappa L}$ primer(s)) and/or the lambda chain ($V_{L\lambda}$ primer(s)) or the lambda leader sequence ($V_{L\lambda L}$ primer(s)) (forward primers) together with constant region kappa ($C_{\kappa}$ primer(s)) and/or lambda primers ($C_{\lambda}$ primer(s)) (reverse primers) or a plurality of such primers. Alternatively, light chain joining region primers ($J_{L\kappa}$ and/or $J_{L\lambda}$ primer(s)) may be used as reverse primers instead of the constant region primers. Alternatively, forward primers anneal in the UTR region preceding the leader sequence of the variable light chain. Equally, families of immunoglobulin heavy chain variable region encoding sequences can be amplified with one primer set utilizing various primer combinations. For example, a plurality of primers complementary to the 5' end of the heavy chain variable region ($V_H$ primer(s)) or the leader sequence of this region ($V_{HL}$ primer(s)) (forward primers) together with a plurality of heavy chain joining region primers ($J_H$ primer(s)) or heavy chain constant region primer(s) (reverse primers). The $C_H$ primer may be isotype-specific and in principle any $C_H$ primer can be utilized (e.g. $C_{H1}, C_{H2}, C_{H3},$ or $C_{H4}$), also one that would result in a full-length heavy chain. Alternatively, forward primers anneal in the UTR region preceding the leader sequence of the variable heavy chain.

The use of forward primers annealing in the leader sequence instead of the 5' end of the variable region is particular useful if cross-hybridization is observed for the variable region primers. Since mutations due to cross-hybridization will be eliminated from the final protein because leader sequences are cleaved off during protein processing within the cell. Example 9 describes the design of antibody variable heavy chain and kappa light chain leader primers. The aspect that the site of priming is located in the 3' end of the leader encoding sequence (C-terminal) is an advantage over previous antibody leader primers, since this allows for shuttling of the amplified sequences between bacterial and eukaryotic expression vectors in a way that allow functional leader sequences in both system. The design system described in Example 9 can easily be applied to antibody lambda light chains, TcR α, β, γ or δ chains as well.

One feature of the present invention are primers which anneal in the 3' end of the leader encoding sequence preceding a variable region encoding sequence, and their use for amplification of variable region encoding sequences.

A preferred feature of the present invention is the application of primers with at least 90% sequence identity (preferably at least 95% identity) with the gene-specific region of SEQ ID NO 86 to 92, which correspond to primers annealing in the C-terminal of heavy chain leader encoding sequences ($V_{HL}$ primers). The gene-specific sequence of these SEQ ID NO's correspond to base number 18 to the 3' end of the sequences (see also table 11).

Another preferred feature of the present invention is the application of primers with at least 90% sequence identity (preferably at least 95% identity) with the gene-specific region of SEQ ID NO 93 to 98, which correspond to primers annealing in the C-terminal of kappa light chain leader encoding sequences ($V_{L\kappa L}$ primers). The gene-specific sequence of these SEQ ID NO's correspond to base number 25 to the 3' end of the sequences (see also table 11).

In one embodiment of the present invention, the multiplex overlap-extension primer mix utilized for the multiplex overlap-extension PCR and possibly for the reverse transcription step as well comprises a) at least one $C_L$ or $J_L$ primer complementary to the sense strand of an immunoglobulin light chain region encoding sequence; b) at least one $V_L$ 5' primer or $V_L$ leader primer complementary to the antisense strand of an immunoglobulin light chain variable region encoding sequence and capable of forming a primer set with the primer(s) in a); c) at least one $C_H$ or $J_H$ primer complementary to the sense strand of an immunoglobulin constant heavy chain domain encoding sequence or the heavy chain joining region and d) at least one $V_H$ 5' primer or $V_H$ leader primer complementary to the antisense strand of an immunoglobulin heavy chain variable region encoding sequence, and capable of forming a primer set with the primer(s) in c).

Primer sets of the present invention can for example be $V_{L\kappa}+C_{\kappa}$, $V_{L\lambda}+C_{\lambda}$, $V_{L\kappa}+J_{L\kappa}$, $V_{L\lambda}+J_{L\lambda}$, $V_{L\kappa L}+C_{\kappa}$, $V_{L\lambda L}+C_{\lambda}$, $V_{L\kappa L}+J_{L\kappa}$, $V_{L\lambda L}+J_{L\lambda}$, $V_H+J_H$, $V_H+C_H$, $V_{HL}+J_H$ or $V_{HL}+C_H$ or combinations of these, capable of amplifying a variable region encoding target sequence.

In a further embodiment are the $C_L$ ($J_L$) primer(s) and $V_L$ ($V_{LL}$) primer(s) adapted for amplifying sequences comprising kappa light chain variable regions or lambda light chain variable regions.

In a preferred embodiment of the present invention the are the $C_L$ ($J_L$) primer(s) and $V_L$ ($V_{LL}$) primer(s) adapted for amplifying both kappa and lambda light chain variable region encoding sequences.

In an even more preferred embodiment of the present invention, are the forward primers for light chain amplification $V_{LL}$ primers with at least 90% sequence identity (preferably at least 95% identity) with the gene-specific region of SEQ ID 93 to 98, and the forward primers for heavy chain amplification are $V_{HL}$ primers with at least 90% identity (preferably at least 95%) with the gene-specific region of SEQ ID 86 to 92.

In a further embodiment of the present invention, carries the immunoglobulin $V_L/V_{LL}$ and $V_H/V_{HL}$ primers linkage tails, preferably in the form of complementary overlap-extension tails. This generates variable region encoding sequences that are linked in a head-to-head fashion. For the linkage of variable region encoding sequences in a head-to-tail fashion, either the $C_L/J_L$ and $V_H/V_{HL}$ primers contain linkage tails or the $V_L/V_{LL}$ and $C_H/J_H$ primers contain linkage tails, preferably in the form of complementary overlap-extension tails. For the linkage of variable region encoding sequences in a tail-to-tail fashion, the $C_L/J_L$ and $C_H/J_H$ primers contain linkage tails, preferably in the form of complementary overlap-extension tails (FIG. 3).

Preferentially, the multiplex primer mixes, including multiplex overlap-extension primer mixes, of the present invention comprise two primer sets. Thus, a multiplex primer mix comprises at least four different primers. In a further aspect of the present invention a multiplex primer mix comprises more than four different primers. A multiplex primer mix of the present invention is used for the amplification of target sequences in a single vessel. For example are kappa, lambda and heavy chain variable regions all amplified in the same vessel. One multiplex primer mix of the present invention was comprised of 16 different degenerate primers distributed as follows: eight $V_H$ primers, one $C_{H1}$ primer, six $V_{L\kappa}$ primers, and one $C_\kappa$ primer (FIG. 2). Another set was comprised of 19 degenerate primers distributed as follows: eight $V_H$ primers, four $J_H$ primers, six $V_{L\kappa}$ primers, and one $C_\kappa$ primer. A third set was comprised of 22 degenerate primers distributed as follows: eight $V_H$ primers, one $C_{H1}$ primer, eleven $V_{L\lambda}$ primers, and two $C_\lambda$ primers. A fourth set was comprised of 27 degenerate primers distributed as follows: eight $V_H$ primers, one $C_{H1}$ primer, six $V_{L\kappa}$ primers, one $C_\kappa$ primer, eleven $V_{L\lambda}$ primers, and two $C_\lambda$ primers.

The present invention also encompasses primers for an additional PCR amplification of the linked products obtained by multiplex RT-PCR followed by linkage by ligation or recombination or by multiplex overlap-extension RT-PCR. This additional PCR amplification can be performed using a primer mix adapted for amplifying the linked target sequences. Such a primer mix may comprise the outer primers of the multiplex primer mix or multiplex overlap-extension primer mix, meaning the primers that anneals to the outermost 5' end and 3' end of the sense strand of the linked nucleotide sequences, thereby enabling the amplification of the entire linked product. One example of primers that can be utilized as outer in the present invention are the $C_\kappa/J_\kappa$ and/or $C_\lambda/J_\lambda$ primers forming a primer set with the $J_H$ or $C_H$ primers. This process generally serves to increase the amount of linked product obtained from the multiplex RT-PCR followed by linkage by ligation or recombination or from the multiplex overlap-extension RT-PCR.

Alternatively, a primer set which is nested compared to the outer primers used in the primary multiplex RT-PCR or multiplex overlap-extension RT-PCR reaction can be used for the additional amplification of the linked nucleotide sequences. In the present invention such a primer set is termed a nested primer set. The design of nested primers generally observes the same design rules as for the gene-specific primers previously described, except that they prime 3' to the annealing position of the outer primers used in the multiplex RT-PCR or multiplex overlap-extension RT-PCR. The product resulting from a nested PCR is therefore shorter than the linked product obtained by the multiplex RT-PCR followed by linkage by ligation or recombination or by multiplex overlap-extension RT-PCR. In addition to increase the amount of linked product, the nested PCR further serves to increase the overall specificity, especially of the multiplex overlap-extension RT-PCR technology. However, it should be noted that not all multiplex primer mixes/multiplex overlap-extension primer mixes that have been described previously are suitable for combination with a nested primer set when performing the additional amplification. In such cases the outer primers of the multiplex primer mix/multiplex overlap-extension primer mix can be used for the additional amplification or a semi-nested PCR can be applied as described later.

In one embodiment of the present invention, a mixture of $J_L$ and $J_H$ primers is used as nested primers for the additional amplification of the linked immunoglobulin variable region encoding sequences.

Nested primer sets of the present invention can also be comprised of a reverse (or forward) outer primer(s) from the first multiplex primer mix/multiplex overlap-extension primer mix and a second nested primer that prime 3' to the annealing position of the forward (or reverse) outer primer(s) of the first multiplex primer mix/multiplex overlap-extension primer mix. The use of such a primer set for an additional PCR amplification is generally known as a semi-nested PCR. Semi-nested PCR can for example be applied if it is difficult to design a nested primer in one specific region e.g. for the variable region sequences (V and J primers), because such a primer would have to anneal in the complementarity determining regions (CDRs). Further, semi-nested PCR can be used when it is desirable to keep one end of the linked sequences intact e.g. for cloning purposes.

One feature of the present invention keeps the constant light chain encoding sequence kept intact during the additional amplification reaction. The $C_L$ (reverse) primer(s) used for the additional amplification is only slightly modified compared to the outer primer(s) used for the primary reaction (the multiplex RT-PCR or multiplex overlap-extension RT-PCR reaction). The modification comprises the addition of a few bases to the 3' end of the $C_L$ primer(s) used for the primary amplification. Further, a different cloning tail might be added to the nested $C_L$ primer(s). The forward primer(s) used in the additional amplification is completely nested compared to the constant heavy chain-specific outer primer(s) used in the primary reaction. The combined use of the outer primer(s) in the primary reaction and the slightly modified nested $C_L$ primer(s) together with the completely nested forward primer(s) in the additional amplification results in an increase in specificity that is comparable to what is achievable with a nested PCR using a completely nested primer set.

In a preferred embodiment of the present invention, the nested PCR is performed with $J_H$ primer(s) and modified $C_L$ primer(s) where between 2 and 10 gene-specific base pairs have been added at the 3'end compared to the first $C_L$ primer(s) of the multiplex primer mix/multiplex overlap-extension primer mix.

Optimization of Multiplex Overlap-Extension PCR

The parameters of the multiplex overlap-extension PCR step of both the two-step and the single-step procedure can be optimized on several parameters (see, for example, Henegariu, O. et al. 1997. BioTechniques 23, 504-511; Markoulatos, P. et al. 2002. J. Clin. Lab. Anal. 16, 47-51). Generally the same optimization parameters apply for multiplex RT-PCR, although the ratio between outer and inner primers is less important for such a reaction.

a. Primer Concentration

The concentration of the primers carrying the overlap-extension tail (for example the $V_H$ and $V_L$ primers) is preferably lower than the concentration of the outer primers without overlap-extension tail (for example $J_H$ and kappa primers).

If one of the target sequences amplifies with a lower efficiency than the others, for example, as a result of a higher GC %, it may be possible to equalize the amplification efficacy. This may be done by using a higher concentration of the primer set which mediates amplification with low efficiency, or lowering the concentration of the other primer set. For example, sequences encoding for heavy chain variable regions tend to have a higher GC % and hence lower amplification efficiency than light chain variable regions. This points towards using $V_L$ primers at a lower concentration than the $V_H$ primers.

Further, when using a large number of primers the total primer concentration might be an issue. The upper limit is determined experimentally by titration experiments. For the "AmpliTaq Gold" PCR system from Applied Biosystems the upper limit was found to be 1.1 µM total oligonucleotide concentration, for other systems it may however be as high as 2.4 µM. Such an upper limit of total oligonucleotide concentration influences the maximal concentration of individual primers. If the individual primer concentration is too low it is likely to cause a poor PCR sensitivity.

The quality of the oligonucleotide primers have also been found to be important for the multiplex overlap-extension PCR. HPLC-purified oligonucleotides, have produced the best results.

b. PCR Cycling Conditions:

Preferentially the cycling conditions are as follows:

| Denaturation: | 10-30 s | 94° C. | |
|---|---|---|---|
| Annealing: | 30-60 s | 50-70° C. | Approximately 5° C. below Tm of primers. |
| Extension: | 1 min × EPL | 65-72° C. | EPL is Expected Product Length in kb. |
| Cycle number: | 30-80 | | |
| Final extension: | 10 min | 65-72° C. | |

For the single-step multiplex overlap-extension RT-PCR the following steps were built into the cycling program prior to the amplification cycling outlined above:

| Reverse transcription: | 30 min | 42-60° C. | These conditions are also used where separate reverse transcription is performed. |
|---|---|---|---|
| Polymerase activation: | 10-15 min | 95° C. | Hot-start polymerases are favorable in single-step RT-PCR. Activation according to manufacturer. |

It is possible to optimize on all these parameters. Especially the annealing temperature is important. Thus, initially all the individual primer sets that are to constitute the final primer mix should be tested separately in order to identify optimal annealing temperature and time, as well as elongation and denaturing times. This will give a good idea about the window within which these parameters can be optimized for the multiplex overlap-extension primer mix.

Problems with poor PCR sensitivity, for example due to low primer concentration or template concentration can be overcome by using a high number of thermal cycles. A high number of thermal circles constitute between 35 and 80 cycles, preferably around 40 cycles.

Further, longer extension times can improve the multiplex overlap-extension PCR process. Long extension times constitute 1.5-4 min×EPL compared to the normal 1 min extension.

c. Use of Adjuvants

Multiplex PCR reactions can be significantly improved by using a PCR additive, such as DMSO, glycerol, formamide, or betaine, which relax DNA, thus making template denaturation easier.

d. dNTP and $MgCl_2$

Deoxynucleoside triphosphate (dNTP) quality and concentration is important for the multiplex overlap-extension PCR. The best dNTP concentration is between 200 and 400 µM of each dNTP (dATP, dCTP, dGTP and dTTP), above which the amplification is rapidly inhibited. Lower dNTP concentrations (100 µM of each dNTP) suffice to achieve PCR amplification. dNTP stocks are sensitive to thawing/freezing cycles. After three to five such cycles, multiplex PCR often do not work well. To avoid such problems, small aliquots of dNTP can be made and kept frozen at −20° C.

Optimization of $Mg^{2+}$ concentration is critical since most DNA polymerases are magnesium-dependent enzymes. In addition to the DNA polymerase, the template DNA primers and dNTP's bind $Mg^{2+}$. Therefore, the optimal $Mg^{2+}$ concentration will depend on the dNTP concentration, template DNA, and sample buffer composition. If primers and/or template DNA buffers contain chelators such as EDTA or EGTA, the apparent $Mg^{2+}$ optimum may be altered. Excessive $Mg^{2+}$ concentration stabilizes the DNA double strand and prevents complete denaturation of DNA, which reduces yield. Excessive $Mg^{2+}$ can also stabilize spurious annealing of primer to incorrect template sites, thereby decreasing specificity. On the other hand, an inadequate $Mg^{2+}$ concentration reduces the amount of product.

A good balance between dNTP and $MgCl_2$ is approximately 200 to 400 µM dNTP (of each) to 1.5 to 3 mM $MgCl_2$.

e. PCR Buffer Concentration

Generally KCl based buffers suffice for multiplex overlap-extension PCR; however, buffers based on other components such as $(NH_4)_2SO_4$, $MgSO_4$, Tris-HCl, or combinations thereof may also be optimized to function with the multiplex overlap-extension PCR. Primer pairs involved in the amplification of longer products work better at lower salt concentrations (e.g. 20 to 50 mM KCl), whereas primer pairs involved in the amplification of short products work better at higher salt concentrations (e.g. 80 to 100 mM KCl). Raising the buffer concentration to 2× instead of 1× may improve the efficiency of the multiplex reaction.

f. DNA Polymerase

The present invention is exemplified with Taq polymerase. Alternatively, other types of heat-resistant DNA polymerases including, for example, Pfu, Phusion, Pwo, Tgo, Tth, Vent, Deep-vent may be used. Polymerases without or with 3' to 5'exonuclease activity may either be used alone or in combination with each other.

Vectors and Libraries

The linkage of nucleotide sequences of interest according to the present invention produces a nucleotide segment comprising the linked nucleotide sequences of interest. Further, libraries of such linked nucleic acid sequences of interest are produced by the methods of the present invention, in particular libraries of variable region encoding sequences.

One feature of the present invention is the insertion of a segment containing linked nucleotide sequences of interest or a library of linked nucleotide sequences of interest, generated by a method of the present invention, into suitable vectors. The libraries may be combinatorial libraries or libraries of cognate pairs of variable region encoding sequences. The restriction sites generated by the outer primers, nested primers or semi-nested primers are preferably designed to match appropriate restriction sites of the vector of choice. The linked nucleic acid sequences of interest can also be inserted into vectors by recombination, if one of the semi-nested, nested primers or outer primers were equipped with a suitable recombination site and the vector of choice contains one as well.

Basically there are no limitations to the vectors that can be used as carriers of the products generated by one of the multiplex RT-PCR-linkage methods of the present invention. Vectors of choice may be those suitable for amplification and expression in cells including, for example, bacteria, yeast, other fungi, insect cells, plant cells, or mammalian cells. Such vectors may be used to facilitate further cloning steps, shuttling between vector systems, display of the product inserted into the vector, expression of the inserted product and/or integrate into the genome of a host cell.

Cloning and shuttle vectors are preferably bacterial vectors. However, the other types of vectors may also be applied in cloning and shuttle procedures.

Display vectors can for example be phage vectors or phagemid vectors originating from the class of fd, M13, or f1 filamentous bacteriophages. Such vectors are capable of facilitating the display of a protein including, for example, a binding protein or a fragment thereof, on the surface of a filamentous bacteriophage. Display vectors suitable for display on ribosomes, DNA, yeast cells or mammalian cells are also known in the art. These comprise for example viral vectors or vectors encoding for chimeric proteins.

Expression vectors exist for all the mentioned species and the one to be chosen completely depend on the protein to be expressed. Some expression vectors are additionally capable of integrating into the genome of a host cell either by random integration, or by site-specific integration, utilizing appropriate recombination sites. Expression vectors may be designed to provide additional encoding sequences that, when the linked product is inserted in-frame to these sequences, enable the expression of a larger protein, e.g. a full-length monoclonal antibody, when introduced into an appropriate host cell. This in-frame insertion may also facilitate the expression of chimeric proteins that facilitate the display on the surface of a filamentous bacteriophage or cell. In a bacteriophage display system, the linked nucleotide sequences of interest may be inserted in-frame to a sequence encoding a coat protein such as pIII or pVIII (Barbas, C. F. et al. 1991. Proc. Natl. Acad. Sci. USA 88, 7978-7982; Kang, A. S. et al. 1991. Proc. Natl. Acad. Sci. USA 88, 4363-4366).

In one embodiment of the present invention, the individual segments of linked nucleotide sequences of interest is comprised of an immunoglobulin heavy chain variable region encoding sequence associated with a light chain variable region encoding sequence. Preferably, these linked sequences are inserted into a vector that contains sequences encoding one or more immunoglobulin constant domains. The insertion is engineered such that the linked heavy chain variable region and/or light chain variable region encoding sequences are inserted in-frame to the constant region encoding sequences. Such an insertion can for example generate a Fab expression vector, a full-length antibody expression vector or an expression vector encoding a fragment of a full-length antibody. Preferentially such a vector is an expression vector suitable for screening (e.g. *E. coli*, phagemid, or mammalian vectors) and the constant region heavy chain encoding sequences are chosen from the human immunoglobulin classes IgG1, IgG2, IgG3, IgG4, IgM, IgA1, IgA2, IgD, or IgE, thereby enabling the expression of a Fab or full-length recombinant antibody. In addition to the constant heavy chain encoding sequences the vector may also contain a constant light chain encoding sequence chosen from human lambda or kappa chains. This is appropriate when the linked nucleotide sequences only encode the immunoglobulin variable region encoding sequences (Fv's).

In another embodiment of the present invention, the individual segments of the linked nucleotide sequences is comprised of a TcR α chain variable region encoding sequence associated with a β chain variable region encoding sequence or a γ chain variable region encoding sequence associated with a δ chain variable region encoding sequence. Preferably, these linked sequences are inserted into a vector that contains sequences encoding one or more TcR constant domains. The insertion is engineered such that the inserted linked variable region encoding sequences are in-frame to the corresponding TcR constant region encoding sequences. In a further embodiment, such a vector is a chimeric expression vector comprising sequences that encode a leucine zipper in-frame to the TcR constant regions. It has been shown that such constructs increase stability of soluble TcR's (Willcox, B. E. et al. 1999. Protein Sci 8, 2418-2423).

Figure 12:
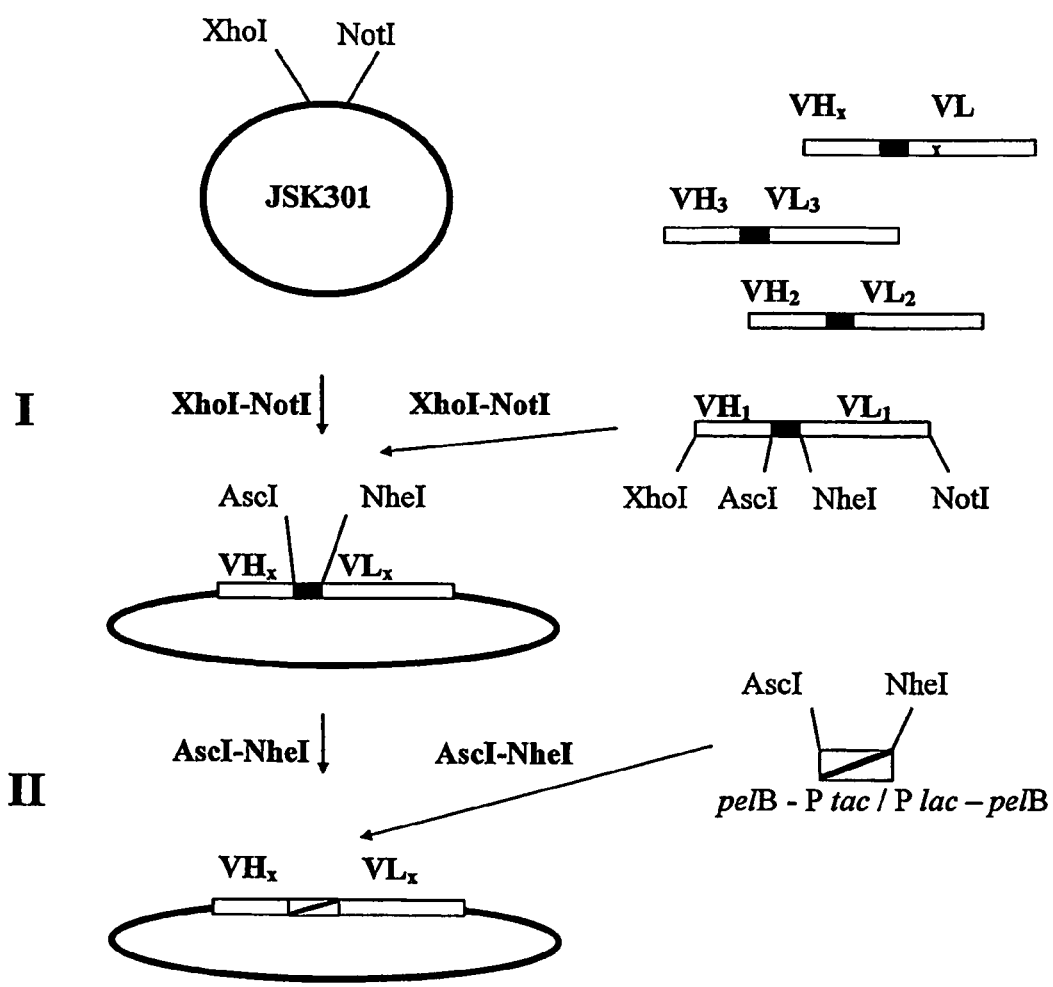
FIG. 12 is a schematic diagram illustrating the generation of a library of cognate Fab expression vectors. Step I illustrates the insertion of cognate pairs of variable region encoding sequences ($VH_1$-$VL_1$ to VHx-VLx) into *E. coli* vector JSK301 by XhoI-NotI digestion. Step II illustrates the insertion of a bacterial promoter and leader cassette (pelB leader-P tac-promoter driving the expression of VHx and P lac promoter-pelB leader driving the expression of VLx) by AscI-NheI digestion.

Libraries of cognate pairs of the present invention may be introduced into vectors by two different approaches. In the first approach, the single cognate pairs are inserted individually into a suitable vector. This library of vectors may then either be kept separate or be pooled. In the second approach, all the cognate pairs are pooled prior to vector insertion, followed by in-mass insertion into suitable vectors generating a pooled library of vectors (illustrated in FIG. 12). Such a library of vectors comprises a large diversity of pairs of variable region encoding sequences.

One aspect of the present invention is a library of cognate pairs of linked variable region encoding sequences. Preferably the individual cognate pairs of the library comprise an immunoglobulin light chain variable region encoding sequence associated with a heavy chain variable region encoding sequence.

Another preferred library of cognate pairs comprise linked TcR region encoding sequences, where each individual TcR region encoding sequences comprise an alpha chain variable region encoding sequence associated with a beta chain variable region encoding sequence and/or a TcR gamma chain variable region encoding sequence associated with a delta chain variable region encoding sequence.

An embodiment of the present invention is a sub-library of cognate pairs of linked variable region encoding sequences which encode for desired binding specificities directed against a particular target. Preferably these cognate pairs comprise linked immunoglobulin light chain variable region and heavy chain variable region encoding sequences, TcR alpha chain variable region and beta chain variable region encoding sequences and/or TcR gamma chain variable region and delta chain variable region encoding sequences.

A further embodiment is a sub-library selected from a parent library of cognate pairs of variable region encoding sequences as described throughout the invention.

A preferred embodiment of the present invention is a library or sub-library encoding for cognate pairs of full-length immunoglobulins selected from human immunoglobulin classes IgA1, IgA2, IgD, IgE, IgG1, IgG2, IgG3, IgG4, or IgM.

Another preferred feature of the present invention is a library or sub-library encoding for soluble and stable cognate pairs of TcRs.

A feature of the present invention is the diversity of said libraries, which are comprised of at least 5, 10, 20, 50, 100, 1000, $10^4$, $10^5$ or $10^6$ different cognate pairs.

In a further embodiment of the present invention, said libraries of cognate pairs of linked variable region encoding sequences are obtainable by a method comprising the steps described herein. This library is also termed the parent library.

Screening and Selection

The parent library of pairs of linked variable region encoding sequences isolated from a donor, utilizing one of the methods of the present invention, is expected to represent a diversity of binding proteins of which some will be irrelevant, i.e. not binding to a desired target, in particular for combinatorial libraries. Therefore, the present invention encompasses enrichment and screening, for a sublibrary encoding a subset of diversities of binding specificities directed against a particular target.

For libraries of cognate pairs the diversity of the library is expected to represent the diversity present in the donor material, with only a minor number of randomly linked variable regions. Thus, an enrichment step may not be necessary prior to the screening for target-specific binding affinities in a library composed of cognate pairs.

In a further embodiment of the present invention, the method of generating a library of pairs of linked variable region encoding sequences, further comprises creating a sub-library by selecting a subset of pairs of linked variable region sequences that encode binding proteins with a desired target specificity. Such a selection of linked variable region encoding sequences, is also termed a library of target-specific cognate pairs.

In a preferred embodiment of the present invention, is the library of target-specific cognate pairs of variable region encoding sequences transferred to a mammalian expression vector.

Figure 10:
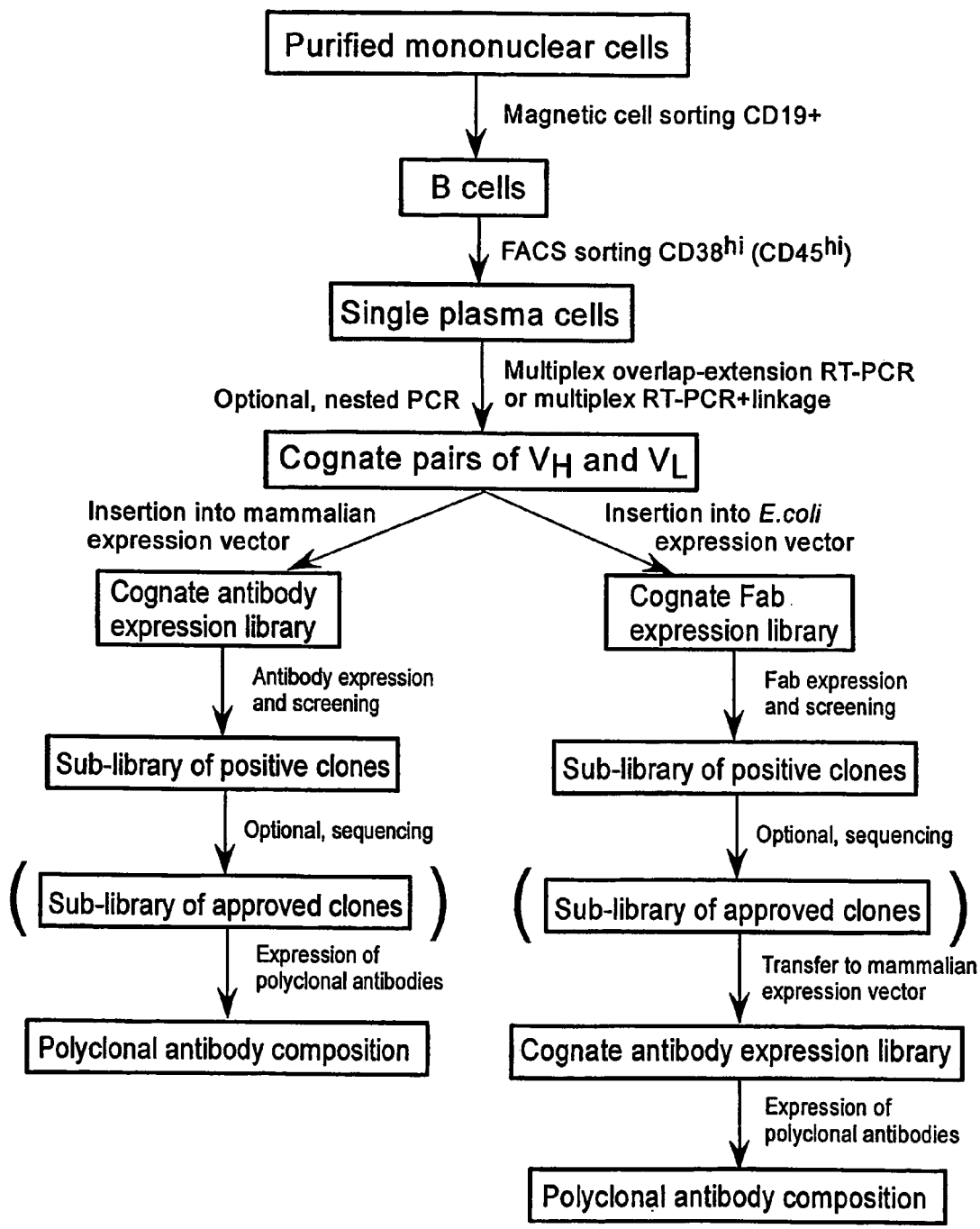
FIG. 10 is a flow chart showing the steps applied in order to generate a cognate antibody expression library from which polyclonal or monoclonal antibodies can be expressed.

Immunological assays are generally suitable for the selection of target-specific immunoglobulin variable region encoding sequences. Such assays are well know in the art and constitute for example ELISPOTS, ELISA, membrane assays (e.g. Western blots), arrays on filters, or FACS. The assays can either be performed in a direct manner, utilizing the polypeptides produced from the immunoglobulin variable region encoding sequences. Alternatively, the immunoassays can be performed in combination with or following enrichment methods such as phage display, ribosome display, bacterial surface display, yeast display, eukaryotic virus display, RNA display or covalent display (reviewed in FitzGerald, K., 2000. Drug Discov. Today 5, 253-258). As illustrated in FIG. 10, both cognate Fab expression libraries and cognate full-length antibody expression libraries can be subjected to screening, thereby generating a sub-library of positive clones. Such screening assays and enrichment procedures are also suitable for Fv or scFv fragments or combinatorial libraries of linked variable regions.

In a preferred embodiment of the present invention, the selection of a sub-library of target-specific cognate pairs or combinatorial pairs of variable region encoding sequences is performed by using a high-throughput screening assay. High-throughput screening assays could be, but are not restricted to, ELISA assays performed with semi-automated or fully automated equipment. It could also be a membrane assays in which bacteria are robotically picked and gridded onto an appropriate membrane on top of agar plates generating arrays of colonies expressing antigen-binding molecules. The molecules are secreted through the membrane onto a second underlying antigen-coated membrane which can be developed separately and used to identify clones that secrete antigen binding molecules towards the desired target (de Wildt, R. M., et al. 2000. Nat. Biotechnol. 18, 989-994).

When a sub-library of cognate pairs or combinatorial pairs of antigen-binding clones has been selected by an appropriate technology it is possible to perform an additional analysis by DNA sequencing of the linked immunoglobulin light chain variable region and heavy chain variable region encoding sequences. First of all such a DNA sequencing will provide information about the library diversity such as germline origin, family distribution and maturation within the CDR regions. Such an analysis will enable the selection of clones which represent a broad diversity, and leaving out repeated clones. Secondly, DNA sequencing will reveal mutations introduced during the isolation process.

When analyzing variable region encoding sequences there are three types of mutations to consider when assessing whether a mutation is acceptable: i) The most frequent type of mutations result from intra-family cross-priming, where V gene primers prime to the wrong subset within one particular V gene family. The changes introduced are mainly substitutions of naturally occurring codons at one particular position. Due to the high degree of sequence homology within a V gene family these changes usually can be regarded as conservative and acceptable changes; ii) Less frequent mutations are induced by inter-family cross-priming (e.g., a VH3 family primer primes a VH1 family encoding sequence) and induces more significant structural changes, sometimes with no natural counterpart. Such changes could potentially affect the immunogenicity of the variable region by creating new epitopes. Such changes can easily be identified and subsequently repaired using standard molecular biological techniques or the clones can be excluded from the library; iii) Errors created by the Taq DNA polymerase are most easily identified in the constant region encoding sequences and can easily be eliminated. However, Taq induced mutations will of course also be present in the variable region encoding sequences where they are indistinguishable from the naturally occurring somatic mutations, which are also the result of random mutations in the variable region encoding sequences. Considering that the mutations are non-systematic and only affect particular pairs in distinct ways, it appears reasonable to disregard such changes.

Further the sequence analysis can be used to identify the degree of scrambling in a cognate pair library, as illustrated in table 20 for VH group H4.

As described in Example 9 the presence of the mutations described in i) and ii) can be circumvented in the expression library, when utilizing primers that anneal in the leader sequence of the variable region encoding sequences instead of primers that anneal in the 5' region of the variable regions.

In a further embodiment of the present invention, the sub-library of target-specific and possibly sequence analysed pairs of linked immunoglobulin light chain variable region and heavy chain variable region encoding sequences are transferred to a mammalian expression vector. Such a transfer can be performed into any of the vectors described in the previous section, enabling the expression of a full-length recombinant antibody. If the screening is performed with a mammalian cognate full-length antibody expression library such a transfer may not be needed.

In another embodiment of the present invention, the parent library is generated from a lymphocyte-containing cell fraction which is enriched for T lymphocytes. The pairs of linked variable region encoding sequences constituting the parent library, may be selected for encoding a subset of pairs of linked variable region sequences, composed of alpha and beta and/or gamma and delta chains that encode binding proteins with a desired target specificity, generating a sub-library of cognate pairs or combinatorial pairs. Antigen-specific T cell receptors can subsequently be identified from a pool of transfected cells using standard methodology such as staining with tetrameric MHC-peptide complexes (e.g., Callan, M. F. et al. 1998. J. Exp. Med. 187, 1395-1402; Novak, E. J. et al. 1999. J. Clin. Invest 104, R63-R67), by measuring cellular responses in the form of IL-2 release or by more sophisticated means such as yeast or retroviral display techniques.

Host Cells and Expression

The libraries of the present invention can be transferred to vectors suitable for expression and production of proteins encoded from the linked nucleic acid sequences of interest, in particular variable region containing binding proteins or fragments thereof. Such vectors are described in the Vectors and Libraries section, and provide for the expression of for example full-length antibodies, Fab fragments, Fv fragments, scFv, membrane bound or soluble TcRs or TcR fragments of a species of choice.

One feature of the present invention is the introduction into a host cell of a library or a sub-library of vectors of cognate pairs of linked variable region encoding sequences or a single clone encoding a cognate pair of linked variable region encoding sequences, for amplification and/or expression. Host cells can be chosen from bacteria, yeast, other fungi, insect cells, plant cells, or mammalian cells. For expression purposes mammalian cells, such as Chinese hamster ovary (CHO) cells, COS cells, BHK cells, myeloma cells (e.g., Sp2/0 cells, NS0), NIH 3T3, fibroblast or immortalized human cells such as HeLa cells, HEK 293 cells, or PER.C6 are preferred.

The introduction of vectors into host cells may be accomplished by a number of transformation or transfection methods known to those skilled in the art, including calcium phosphate precipitation, electroporation, microinjection, liposome fusion, RBC ghost fusion, protoplast fusion, viral infection and the like. The production of monoclonal full-length antibodies, Fab fragments, Fv fragments and scFv fragments is well known.

The production of recombinant polyclonal antibodies to be used for treatment is a quite new area. A recombinant polyclonal manufacturing technology has been described in PCT application WO 2004/061104. In brief, this technology involves the generation of a collection of cells, suitable as a manufacturing cell line. The following description of the technique is made for a library of cognate pairs, it is however just as applicable for a combinatorial library. The individual cells in the collection of cells are capable of expressing a distinct member of the recombinant polyclonal binding protein for example from a library of cognate pairs. In order to ensure that the individual cells express a single cognate pair and not several cognate pairs of the polyclonal binding protein, the nucleic acid sequences encoding the cognate pairs are introduced into a single site-specific site in the genome of each individual cell. This is an important feature of the collection of cells, since this prevent scrambling of the heavy and light chains expressed from each cell, but also because it generates cells that are virtually identical to one another, except for the small differences in the variable regions of the individual cognate pairs. This trait will enable an unbiased growth of the collection of cells over the period of time necessary for the production. To ensure single site-specific integration, a host cell line with only one integration site should be used, these are commercially available e.g. Invitrogen's CHO Flp-In cells containing a single FRT site. Appropriate vectors for this cell line contain a corresponding FRT site and are introduced into the genome using the Flp recombinase. There are several other known recombinases e.g. Cre, beta-recombinase, Gin, Pin, PinB, PinD, R/RS, lambda integrase, or phage ΦC31 integrase that can be used in combination with their corresponding recombination sites. Further, appropriate vectors contain a selection marker that enables the selection of site-specific integrants.

The generation of a polyclonal manufacturing cell line and the production of a recombinant polyclonal protein from such a cell line can be obtained by several different transfection and manufacturing strategies.

One way, is to use a library of vectors mixed together into a single composition, for the transfection of a host cell line with a single integration site per cell. This method is termed bulk transfection or transfection in bulk. Generally, the vector and host cell design previously described will ensure that a polyclonal cell line capable of unbiased growth will be obtained upon appropriate selection. A frozen stock of the polyclonal cell line will be generated before initiation of the recombinant polyclonal protein manufacturing.

Another way, is to use a library of vectors split into fractions, containing approximately 5 to 50 individual vectors of the library in a composition, for transfection. Preferably, a fraction of the library constitutes 10 to 20 individual vectors. Each composition is then transfected into an aliquot of host cells. This method is termed semi-bulk transfection. The number of aliquots transfected will depend on the size of the library and the number of individual vectors in each fraction. If the library for example constitutes 100 distinct cognate pairs, which are split into fractions containing 20 distinct members in a composition, 5 aliquots of host cells would need to be transfected with a library composition constituting a distinct fraction of the original library. The aliquots of host cells are selected for site-specific integration. Preferably, the distinct aliquots are selected separately. However, they can also be pooled before selection. The aliquots can be analyzed for their clonal diversity and only those with sufficient diversity will be used to generate a polyclonal cognate pair library stock. To obtain the desired polyclonal cell line for manufacturing, the aliquots can be mixed before generating the freezing stock, immediately after they have been retrieved from the stock or after a short proliferation and adaptation time. Optionally, the aliquots of cells are kept separate throughout production, and the polyclonal protein composition is assembled by combining the products of each aliquot rather than the aliquots of cells before production.

A third way, is a high throughput method in which host cells are transfected separately using the individual vectors constituting the library of cognate pairs. This method is termed individual transfection. The individually transfected host cells are preferably selected for site specific integration separately. The individual cell clones generated upon selection may be analyzed with respect to proliferation time and preferably, those with similar growth rates are used to generate a polyclonal cognate pair library stock. The individual cell clones can be mixed to obtain the desired polyclonal cell line before generating the stock, immediately after they have been retrieved from the stock, or after a short proliferation and adaptation time. This approach may eliminate any possible residual sequence bias during transfection, integration and selection. Alternatively the individually transfected host cells are mixed before selection is performed, this will enable control of sequence bias due to transfection.

A shared feature in the manufacturing strategies outlined in the above is that all the individual cognate pairs constituting the recombinant polyclonal protein can be produced in one, or a limited number of bioreactors. The only difference is the stage at which one chooses to generate the collection of cells that constitutes the polyclonal manufacturing cell line.

One embodiment of the present invention, is a population of host cells comprising a cognate library or sub-library of linked pairs of variable region encoding sequences.

In a further embodiment, a population of host cells comprises a library obtained from a population of isolated single cells constituting lymphocytes, utilizing the multiplex RT-PCR amplification followed by linkage by ligation or recombination or the multiplex overlap-extension RT-PCR technology of the present invention, to link the cognate pairs.

Another embodiment of the present invention, is a population of host cells comprising a combinatorial library or sub-library of linked pairs of variable region encoding sequences.

A population of host cells according to the present invention, will encompass a diverse population of cells corresponding to the diversity of the library the cells have been transformed/transfected with. Preferably, each cell of the population of cells only constitutes one cognate pair of the entire library of cognate pairs, and no individual member of the library of cognate pairs exceeds more than 50%, more preferred 25%, or most preferred 10%, of the total number of individual members expressed from the population of host cells.

In a preferred embodiment of the present invention, the population of host cells is mammalian cells.

A population of host cells as described in the above can be utilized for the expression of a recombinant polyclonal binding protein, since individual cells of the population constitute variable region encoding sequences of different diversity.

One embodiment of the present invention, is a recombinant polyclonal protein expressed from a population of host cells comprising a library of vectors encoding diverse cognate pairs of linked variable region encoding sequences, where such a library is obtainable by the method of the present invention. Typically, a recombinant polyclonal protein of the present invention is comprised of at least 2, 5, 10, 20, 50, 100, 1000, $10^4$, $10^5$ or $10^6$ proteins composed of different cognate pairs.

A preferred embodiment of the present invention, is a recombinant polyclonal immunoglobulin expressed from a population of host cells comprising a library of vectors encoding diverse cognate pairs of heavy chain variable region and light chain variable region encoding sequences.

Another preferred embodiment of the present invention, is a recombinant polyclonal TcR expressed from a population of host cells comprising a library of vectors encoding diverse cognate pairs of TcR alpha chain variable region linked with beta chain variable region encoding sequences and/or TcR gamma chain variable region linked with delta chain variable region encoding sequences.

Another embodiment of the present invention is a host cell suitable for production of a monoclonal protein. In particular a monoclonal antibody comprised of a cognate pair of a light chain variable region with a heavy chain variable region or a monoclonal TcR comprised of a cognate pair of an alpha variable region with a beta variable region or a delta variable region with a gamma variable region. Preferably such a monoclonal production cell line is not a hybridoma cell line.

Such a monoclonal antibody or TcR can be generated by adding the following steps to the method of linking a plurality of non-contiguous nucleotide sequences of interest a) inserting said linked nucleic acid sequences into a vector; b) introducing said vector into a host cell; c) cultivating said host cells under conditions suitable for expression; and d) obtaining the protein product expressed from the vector inserted into said host cell. Preferably, the vector introduced into the host cell encodes an individual cognate pair of variable region encoding sequences.

Applications of the Invention

One of the major applications of the present invention is the linkage of cognate pairs of variable region encoding sequences, especially immunoglobulin heavy and light chain variable region encoding sequences or TcR alpha and beta chain or gamma and delta chain variable region encoding sequences, by a high-throughput method for the generation of libraries of cognate pairs. In addition to the generation of cognate pair libraries, the multiplex RT-PCR followed by linkage by ligation or recombination or the multiplex overlap-extension RT-PCR techniques of the present invention may be utilized in the generation of combinatorial libraries by performing the technique on a population of genetically diverse cells, cell lysates from such a population of cells, or on RNA purified from such a population of cells. The libraries, sub-libraries, or single clones from one of these libraries facilitate the expression of polyclonal or monoclonal proteins. Especially monoclonal or polyclonal antibodies may be obtained from the libraries of the present invention.

The use of recombinant monoclonal antibodies in diagnostics, treatment, and prophylaxis is well known. Recombinant monoclonal and polyclonal antibodies generated by the present invention will have the same applications as antibody products generated by existing technologies. In particular, a pharmaceutical composition comprising a polyclonal recombinant immunoglobulin as active ingredient, combined with at least one pharmaceutically acceptable excipient, can be produced by means of the present invention. More preferred are pharmaceutical compositions where the polyclonal recombinant immunoglobulin is comprised of cognate pairs of variable region encoding sequences. Such pharmaceutical compositions of polyclonal recombinant immunoglobulins can be used as medicaments. The polyclonal recombinant immunoglobulin of the composition can be specific for or reactive against a predetermined disease target, and the composition can thus be used for the treatment, amelioration or prevention of diseases such as cancer, infections, inflammatory diseases, allergy, asthma and other respiratory diseases, autoimmune diseases, immunological malfunctions, cardiovascular diseases, diseases in the central nervous system, metabolic and endocrine diseases, transplant rejection, or undesired pregnancy, in a mammal such as a human, a domestic animal, or a pet.

The present invention has a further application which cannot be obtained with conventional monoclonal combinatorial antibody techniques. In situations where protective antigens are either poorly characterized or completely unknown, such as in emerging infectious diseases, it is impossible to screen for a monoclonal antibody that will provide protection against the disease.

However, with the present invention it will be possible to obtain antibody-expressing cells directly from donors with an established protective antibody response, e.g. convalescent patients, and use the starting material from these individuals to generate a library of cognate pairs of immunoglobulin heavy and light chain variable region encoding sequences.

In situations where for example the virus is known, but the protective antigens are unknown, it will be possible to generate a sub-library of cognate antibody gene pairs with broad reactivity towards antigenic structures on the virus. If a recombinant polyclonal antibody is produced from such a sub-library, it will likely contain protective antibodies.

In situations where antigens are completely unknown, a recombinant polyclonal antibody generated from a cognate pair library from e.g. convalescent patients can be used in the same way as hyperimmune immunoglobulins are being used today. The reason for this is the cognate pairing which ensures that the recombinant polyclonal antibody produced closely resemble the antibody immune response of the convalescent patient.

Another application of the techniques for linking cognate pairs of variable regions, described in the present invention, is for diagnostic and analytical purposes. When administering a medicament to a patient, the possibility of an immune response directed towards the medicament always exists. This immunogenecity can be assessed by conventional techniques, such as medicament-specific binding assays with serum or plasma derived from the individual treated with the medicament. Alternatively, the methods of the present invention can be used to mirror the patients' immune response shortly after administration of the medicament, by isolating cognate pairs of variable heavy chain and light chain encoding sequences. Antibodies expressed from such a library can then be screened for reactivity towards the medicament or components of the medicament. This method is particular useful if the presence of the medicament in plasma or serum would interfere with the conventional method. Such medicaments are for example antibodies. With conventional methods, identification of an anti-medicament immune response (e.g. an anti-idiotypic, anti-framework or anti-Fc immune response) in relation to treatment with an antibody cannot be performed until the antibody used for treatment has been cleared completely from the blood. With the present invention sequences encoding such anti-medicament antibodies can be isolated and analyzed from the individual treated with the medicament within a couple of weeks. Thus, it would be an alternative method for assessing whether drugs in general and in particular antibody-based drugs are immunogenic.

A further application of the present invention is in the validation and comparison of vaccines and immunization programmes. This is particular useful during vaccine development, since it will be possible to assess and compare the sequence diversity of antibody responses generated in response to novel candidate vaccines, in addition to the current comparisons of antibody binding affinities and serum titer. Further, the present invention can be used to analyze, monitor and compare antibody responses in surveillance of vaccine efficacy in populations.

The present invention also finds applications outside the field of variable region containing binding proteins. It is merely a matter of optimization for one skilled in the art to adapt the technique disclosed in the present invention to link two or more transcribed nucleotide sequences encoding a heteromeric protein other that a binding protein. Such a linkage of sequences encoding for domains or subunits from a heteromeric protein may be an advantage in the isolation of these protein encoding sequences since it would reduce the number of steps considerably. Further, it is possible to isolate for example splice variants, mutations or new family members of such proteins by using only one multiplex primer mix/multiplex overlap-extension primer mix.

The linkage of sequences which encode distant domains of a single protein is also a possibility. Such a technique would ease the research in relation to the importance of certain domains in a multidomain protein, since it would ease the deletion of intermediate domains.

The generation of chimeric or coupled proteins is also an area where the present invention may be applied. Even if the proteins to be linked are of different origin, e.g. a chimera between a human and a mouse protein, the present invention may be utilized by mixing the cells prior to reverse transcription. Such a cell mixture may constitute either a population of cells from each species or a single cell from each species.

EXAMPLES

Example 1

Two-Step Multiplex Overlap-Extension RT-PCR

In this example, reverse transcription (RT) was performed using a template derived from an isolated single cell and the cDNA produced was used as template for more than one multiplex overlap-extension PCR.

a. Cells

An IgG1-kappa expressing Chinese hamster ovary (CHO) cell line was generated using the Flp-In technology (Invitrogen, Carlsbad, Calif., USA).

Figure 4:
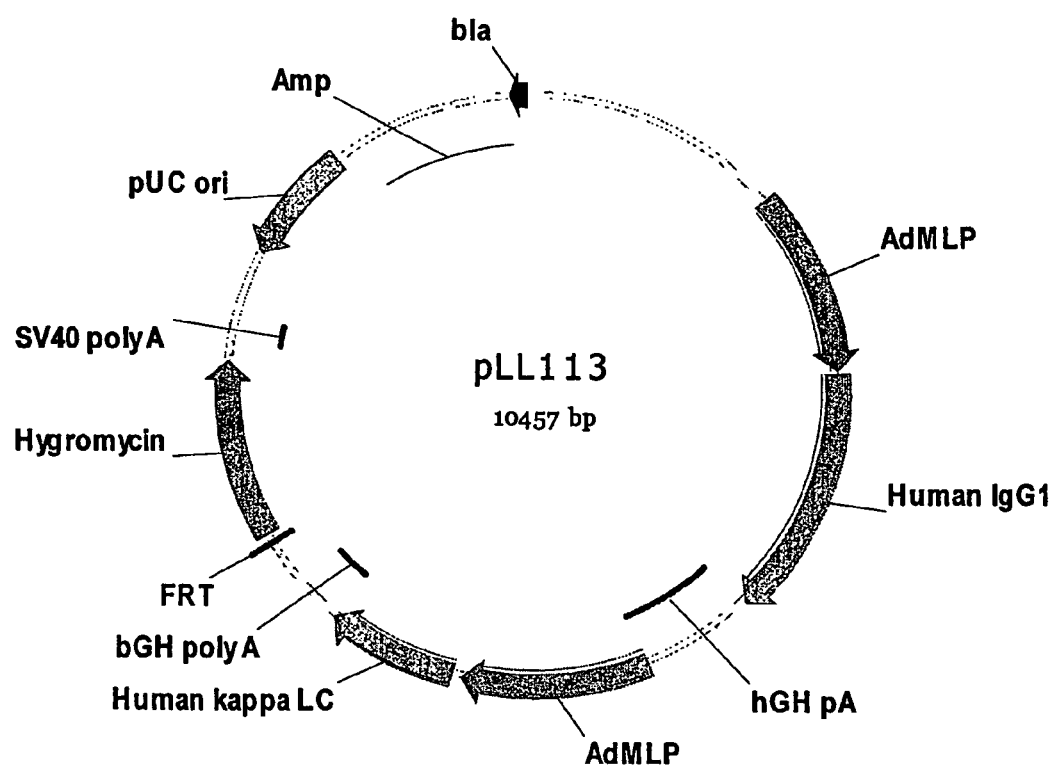
FIG. 4 is a schematic diagram of the immunoglobulin expression vector pLL113, where the encoding sequences are in a head-to-tail orientation. The vector comprises the following elements: bla=promoter allowing expression of the ampicillin resistance gene. Amp=gene encoding for ampicillin resistance. pUC ori=pUC origin of replication. AdMLP=Adenovirus major late promoter. Human IgG1=Sequence encoding for immunoglobulin isotype G1 heavy chain. hGH pA=Human growth hormone poly A signal sequence. bGH polyA=Bovine Growth Hormone poly A sequence. Human kappa LC=Sequence encoding immunoglobulin kappa light chain. FRT=A Flp recognition target site. Hygromycin=gene encoding hygromycin resistance. SV40 poly A=Simian virus 40 poly A signal sequence.

An IgG-kappa mammalian expressing plasmid vector pLL113 (FIG. 4) was constructed based on the Flp-In expression vector, pcDNA5/FRT. CHO-Flp-In cells were co-transfected, using Lipofectamin2000 (Invitrogen, Carlsbad, Calif., USA) according to the manufacturer's instructions, with pLL113 containing the antibody encoding genes and pOG44 conferring transient expression of the Flp recombinase. Transformants were selected and verified for production of IgG-kappa by immunoassays. The selected cell line was named CHO Flp-In pLL113, and maintained in Ham's F-12 medium, supplemented with 2 mM L-glutamine, 10% FCS and 900 Hygromycin B (maintenance media).

CHO Flp-In pLL113 cells were harvested using trypsin and washed 3× in maintenance media After the final wash the cells were re-suspended in the original volume of maintenance media The cell concentration was determined using a Casy-1 System (Schärfe System GmbH, Reutlingen, Germany) and diluted in maintenance media to a concentration of 1 cell/5 µl.

b. Reverse Transcription

CHO Flp-In pLL113 cell suspension, on average containing one cell, was dispensed into single wells of a 96-well PCR plate (Thermo-Fast 96, skirted AB-0800, ABgene, Epsom, Surrey, UK).

The cDNA was synthesized from the distributed cells by utilizing the reverse transcriptase (RT) step in the Qiagen One-Step RT-PCR protocol (Qiagen OneStep RT-PCR Kit, Cat#210210, Hilden, Germany).

Each well contained the following reagents in a total volume of 20 µl:

1× One Step RT-PCR buffer,
dNTP's in a final concentration of 1 mM of each,
5 pmol Oligo poly-dT (18),
26 U RNase inhibitor (RNasin, Promega, Madison USA, cat. No N2111),
2 µl One Step RT-PCR enzyme mix, and
5 µl CHO Flp-In pLL113 cell suspension.

The RT reaction was performed by incubating the reaction mixes at 55° C. for 30 min. Subsequently the reverse transcriptase was inactivated by incubating the reaction mixture at 94° C. for 10 min.

c. Multiplex Overlap-Extension PCR

A fraction of the cDNA products generated in step b) was used as template for multiplex overlap-extension PCR. The reactions were performed in 96-well plates.

Each well contained, in a total volume of 40 µl, the following reagents:

1× One Step RT-PCR buffer,
dNTP's in a final concentration of 500 µM of each,
Multiplex overlap-extension primer mix in the concentrations as indicated in Table 1,
26 U RNase inhibitor (RNasin, Promega, Madison USA, cat. No N2111),
2 µl One Step RT-PCR enzyme mix, and
1 µl cDNA template (derived from a single cell (step b)).

The multiplex overlap-extension primer mix used comprised the primers shown in table 1.

TABLE 1

| Primer name | Conc. | SEQ ID NO | primer sequence in 5' to 3' direction |
|---|---|---|---|
| $V_H$ | 20 nM of each | 1 | agcctatactattgattaggcgcgccCAGRTGCAGCTGGTGCART |
| | | 2 | agcctatactattgattaggcgcgccSAGGTCCAGCTGGTRCAGT |
| | | 3 | agcctatactattgattaggcgcgccCAGRTCACCTTGAAGGAGT |
| | | 4 | agcctatactattgattaggcgcgccSAGGTGCAGCTGGTGGAG |
| | | 5 | agcctatactattgattaggcgcgccCAGGTGCAGCTACAGCAGT |
| | | 6 | agcctatactattgattaggcgcgccCAGSTGCAGCTGCAGGAGT |
| | | 7 | agcctatactattgattaggcgcgccGARGTGCAGCTGGTGCAGT |
| | | 8 | agcctatactattgattaggcgcgccCAGGTACAGCTGCAGCAGTC |
| $C_H$ | 100 nM | 9 | GACSGATGGGCCCTTGGTGG |
| $V_L$ | 20 nM of each | 10 | cgcctaatcaatagtataggctagccGACATCCAGWTGACCCAGTCT |
| | | 11 | cgcctaatcaatagtataggctagccGATGTTGTGATGACTCAGTCT |
| | | 12 | cgcctaatcaatagtataggctagccGAAATTGTGWTGACRCAGTCT |
| | | 13 | cgcctaatcaatagtataggctagccGATATTGTGATGACCCACACT |
| | | 14 | cgcctaatcaatagtataggctagccGAAACGACACTCACGCAGT |
| | | 15 | cgcctaatcaatagtataggctagccGAAATTGTGCTGACTCAGTCT |
| $C_{L\kappa}$ | 100 nM | 16 | atatatgcggccgcttaTTAACACTCTCCCCTGTTG |

W = A/T, S = G/C, R = A/G. Capitalized sequences correspond to the gene-specific region.

The reactions were performed with a 96-well MWG Primus HT thermocycler (MWG Biotech AG, Ebersberg, Germany) with the following cycling conditions:

| Denature | 30 sec | 95° C. | }  |
| Anneal | 30 sec | 50° C. | } 50 cycles |
| Extend | 5 min | 72° C. | } |
| Final extension | 10 min | 72° C. | | d. Nested PCR

Nested PCR was performed using the multiplex overlap-extension products as template. The reactions were performed in 96-well plates.

Each well contained, in a total volume of 50 µl, the following reagents:

1× BioTaq buffer, dNTP's in a final concentration of 400 µM of each, 2 mM MgCl$_2$, Nested PCR primer mix, 1.25 U BIOTAQ DNA Polymerase (Cat. No BIO-21040, Bioline, UK.), and 1 µl Multiplex overlap-extension PCR product (step c).

The primers used are shown in table 2.

TABLE 2

| Primer name | Conc. | SEQ ID NO | primer sequence in 5' to 3' direction |
|---|---|---|---|
| $J_H$ | 100 nM of each | 17 | atattctcGAGACGGTGACCAGGGTG |
| | | 18 | atattctcGAGACGGTGACCATTGT |
| | | 19 | atattctcGAGACGGTGACCAGGGTTC |
| | | 20 | atattctcGAGACGGTGACCGTGGT |
| $C_{L\kappa}$ | 100 nM | 21 | accgcctccaccggcggccgcttaTTAACACTCTCCCCTGTTGAAGCTCTT |

Capitalized sequences correspond to the gene-specific region.

The reactions were performed with a 96-well MWG Primus HT thermocycler (MWG Biotech AG, Ebersberg, Germany) with the following cycling conditions:

| Denature | 30 sec | 95° C. | } |
| Anneal | 30 sec | 50° C. | } 25 cycles |
| Extend | 90 sec | 72° C. | } |
| Final extension | 10 min | 72° C. | |

The nested PCR products were analyzed by 1% agarose gel electrophoresis using ethidium bromide for detection (FIG. 5). The expected size of the overlap-extension product was 1076 bp. Such a product can be observed in lanes 1, 5, 6, 7, 8 and 12 indicated by the arrows (FIG. 5A). In the experiment shown, the negative control is contaminated and a similar contamination is also present in the samples. FIG. 5B illustrates the fragments of FIG. 5A, which are relevant to the present experiment.

The present experiment illustrates one way to perform two-step multiplex overlap-extension PCR, utilizing template derived from a single cell. Further, it was shown that it is possible to perform approximately twenty multiplex overlap-extension PCR's using cDNA generated from an isolated single cell.

Example 2

Single-Step Multiplex Overlap-Extension RT-PCR

In this example reverse transcription and multiplex overlap-extension PCR was performed in a single step using template from lysed cells, in concentrations corresponding to 100, 10, or 1 cells.

a. Cells

The human hybridoma cell line HB-8501 producing an anti-tetanus IgG1-kappa antibody was acquired from American Type Culture Collection and cultured in Iscove's Modified Dulbecco's Medium (Vitacell, Kiev, Ukraine, cat. No 30-2005) containing 10% fetal bovine serum. Before multiplex overlap-extension RT-PCR was performed, the cells were harvested, counted and frozen at −80° C. in culture medium in a concentration of 200 cells/µl.

b. Single-Step Multiplex Overlap-Extension RT-PCR

The Qiagen One-Step RT-PCR kit (Qiagen cat. No 210212, Hilden, Germany) was used for the multiplex overlap-extension RT-PCR essentially according to the manufacturer's recommendation. Before addition to the PCR tubes cell lysates were thawed and diluted in H$_2$O to yield a lysate concentration corresponding to 100, 10, and 1 cells per 5 µl.

Each PCR tube contained the following reagents in a total volume of 50 µl:
1× One-Step RT-PCR buffer,
dNTP's in a final concentration of 400 µM of each,
Multiplex overlap-extension primer mix in the concentrations as indicated in table 3,
2 µl One-step RT-PCR enzyme mix,
50 U RNase inhibitor (RNasin, Promega, Madison USA, cat. No N2515), and
5 µl diluted cell lysate The multiplex overlap-extension primer mix used comprised the primers shown in table 3.

TABLE 3

| Primer name | Conc. | SEQ ID NO | primer sequence in 5' to 3' direction |
|---|---|---|---|
| $V_H$ | 40 nM of each | 22 | gctagcattattattaccatggccCAGRTGCAGC TGGTGCART |
| | | 23 | gctagcattattattaccatggccSAGGTCCAGC TGGTRCAGT |
| | | 24 | gctagcattattattaccatggccCAGRTCACCT TGAAGGAGT |
| | | 25 | gctagcattattattaccatggccSAGGTGCAGC TGGTGGAG |
| | | 26 | tattggcgcgccatggccsaggtgCAGCTGGTGG AG |
| | | 27 | gctagcattattattaccatggccCAGGTGCAGC TACAGCAGT |
| | | 28 | gctagcattattattaccatggccCAGSTGCAGC TGCAGGAGT |
| | | 29 | gctagcattattattaccatggccGARGTGCAGC TGGTGCAGT |
| | | 30 | gctagcattattattaccatggccCAGGTACAGC TGCAGCAGTC |
| $J_H$ | 200 nM of each | 31 | atattctcGAGACGGTGACCAGGGTG |
| | | 32 | atattctcGAGACGGTGACCATTGTCC |
| | | 33 | atattctcGAGACGGTGACCAGGGTTC |
| | | 34 | atattctcGAGACGGTGACCGTGGTCC |
| $V_L$ | 40 nM of each | 35 | cctggtaataataatgctagccGACATCCAGWTG ACCCAGTCT |
| | | 36 | ccatggtaataataatgctagccGATGTTGTGAT GACTCAGTCT |
| | | 37 | ccatggtaataataatgctagccGAAATTGTGWT GACRCAGTCT |
| | | 38 | ccatggtaataataatgctagccGATATTGTGAT GACCCACACT |
| | | 39 | cctggtaataataatgctagccGAAACGACACTC ACGCAGT |
| | | 40 | ccatggtaataataatgctagccGAAATTGTGCT GACTCAGTCT |
| $C_{L\kappa}$ | 200 nM | 16 | atatatatgcggccgcttaTTAACACTCTCCCCT GTTG |

W = A/T, S = G/C, R = A/G. Capitalized sequences correspond to the gene-specific region.

The reactions were performed using the following cycling conditions:

| Reverse transcription: | 30 min | 55° C. | |
| Polymerase activation: | 15 min | 95° C. | inactivating reverse transcriptase and activating Taq polymerase. |

PCR reaction:

| Denature | 30 sec | 94° C. | } 50 cycles |
| Anneal | 30 sec | 44° C. | |

| -continued | | |
|---|---|---|
| Extend | 3 min | 72° C. |
| Final extension | 10 min | 72° C. |

Figure 6:
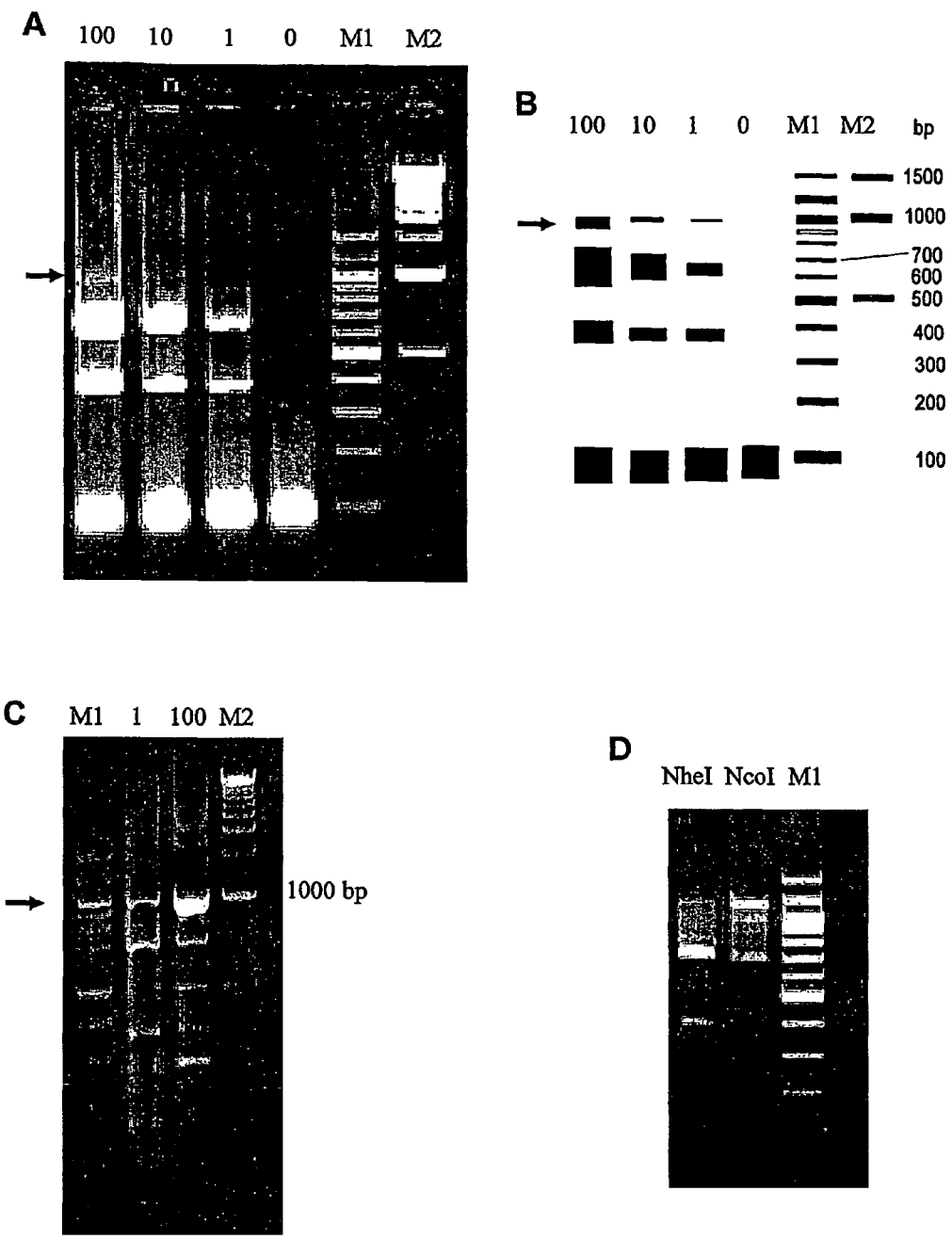
FIG. 6 is a series of photographs and a graphical representation of electrophoretic gels showing the results from a single-step multiplex overlap-extension RT-PCR reaction without additional PCR amplification. In each panel, M1 is a 100 bp ladder and M2 is a 500 bp ladder.

Ten microliters of the reaction products were analyzed by 1.5% agarose gel electrophoresis using ethidium bromide for detection (FIG. 6A).

Expected size of the fragments (the exact size depends upon the lengths of the variable regions):
$V_H$: 410 bp
LC: 680 bp
Overlap-extension fragment: 1070 bp Discrete DNA fragments with mobilities corresponding to the heavy chain variable region ($V_H$) and the light chain variable and constant region (LC) lengths are seen for all dilutions of cell lysate. A less intense fragment with mobility corresponding to the putative overlap-extension fragment is seen in lysates from 100 and 10 cells. The overlap-extension fragment of the one cell lysate sample, is difficult to recognize, although it can be seen on the original gel (see arrow in photo shown in FIG. 6A and sketch shown in FIG. 6B).

c. Identification of the Overlap-Extension Fragment

From an experiment reproduced as the one described above the presence of the overlap-extension band was verified. Regions in the agarose gel around 1070 bp from a lane corresponding to 1 cell and from a lane corresponding to 100 cells were excised and the DNA purified using Qiaex II (Qiagen cat. No 20051, Hilden, Germany) and eluted in 20 µl of water.

One microliter of the eluate was subjected to PCR (Biotaq kit, Bioline, UK cat. No BIO-21040) according to the manufacturers instructions with primers flanking the putative overlap-extension fragment ($J_H$ primers corresponding to SEQ ID NO 32 to 35 and $C_{L\kappa}$ primer corresponding to SEQ ID NO: 17, each primer at a concentration of 0.5 µM). Cycling parameters were:

| Denature | 30 sec | 95° C. | } 30 cycles |
| Anneal | 30 sec | 55° C. | |
| Extend | 1 min | 72° C. | |

Ten microliters of each reaction product was analyzed by 1% agarose gel electrophoresis using ethidium bromide for detection. Several fragments can be seen including, both from 1 and 100 cells, a fragment with mobility of the expected overlap-extension fragment (arrow in FIG. 6C). The 1 kb fragment from the gel lane corresponding to one cell was cut out of the gel and purified using Qiaex II as described above. The purified fragment was digested with the restriction enzymes NheI and NcoI (separately) and the reaction products were analyzed by 1% agarose gel electrophoresis using ethidium bromide for detection (FIG. 6D). These restriction sites are present in the overlap between VH and LC and the expected sizes after digestion are approximately 410 and 680 bp long, respectively (FIG. 2). The NheI digestion was partial since a large fraction is still present at the original size.

Example 3

Combined Single-Step Multiplex Overlap-Extension RT-PCR and Nested PCR

In this example, reverse transcription and multiplex overlap-extension PCR reactions were performed in a single step followed by a semi-nested PCR amplification, using template from lysed cells, in concentrations corresponding to 100, 10 or 1 cells.

a. Single-Step Multiplex Overlap-Extension RT-PCR

Multiplex overlap-extension RT-PCR using HB-8501 cell lysate was performed as described in Example 2 utilizing a multiplex overlap-extension primer mix comprising the primers shown in table 4.

TABLE 4

| Primer name | Conc. | SEQ ID NO | primer sequence in 5' to 3' direction |
|---|---|---|---|
| $V_H$ | 40 nM of each | 41 | tattggcgcgccatggccCAGRTGCAGCTGGTGC ART |
| | | 42 | tattggcgcgccatggccSAGGTCCAGCTGGTRC AGT |
| | | 43 | tattggcgcgccatggccCAGRTCACCTTGAAGG AGT |
| | | 44 | tattggcgcgccatggccSAGGTGCAGCTGGTGG AG |
| | | 45 | tattggcgcgccatggccCAGGTGCAGCTACAGC AG |
| | | 46 | tattggcgcgccatggccCAGSTGCAGCTGCAGG AGT |
| | | 47 | tattggcgcgccatggccGARGTGCAGCTGGTGC AGT |
| | | 48 | tattggcgcgccatggccCAGGTACAGCTGCAGC AGTC |
| $C_{H1-5}$ | 200 nM of one of these primers | 49 | AAGTAGTCCTTGACCAGGCAGCC |
| | | 50 | TGAGTTCCACGACACCGTCA |
| | | 51 | AGAGGTGCTCTTGGAGGAGG |
| | | 52 | AGTTTTGTCACAAGATTTGGG |
| | | 53 | GTTGCAGATGTAGGTCTGGGTGC |
| $V_L$ | 20 nM of each | 54 | gccattgcgcgccaatagctagccGACATCCAGW TGACCCAGTCT |
| | | 55 | gccatggcgcgccaatagctagccGATGTTGTGA TGACTCAGTCT |
| | | 56 | gccatggcgcgccaatagctagccGAAATTGTGW TGACTCAGTCT |
| | | 57 | gccatggcgcgccaatagctagccGATATTGTGA TGACCCACACT |
| | | 58 | gccatggcgcgccaatagctagccGAAACGACAC TCACGCAGT |
| | | 59 | gccatggcgcgccaatagctagccGAAATTGTGC TGACTCAGTCT |
| $C_{Lk}$ | 200 nM | 60 | atatatatgcggccgcttaTTAACACTCTCCCCT GTTGAA |

W = A/T, S = G/C, R = A/G. Capitalized sequences correspond to the gene-specific region.

It should however be noted that for each multiplex overlap-extension primer mix only one of the $C_{H1-5}$ primers were used, resulting in five different multiplex overlap-extension primer mixes.

Remaining parameters were as described for the multiplex overlap-extension RT-PCR reaction in Examples 2, only with a change in annealing temperature to 50° C. A reaction was performed for each heavy chain constant region reverse primer ($C_{H1}$, $C_{H2}$, $C_{H3}$, $C_{H4}$, $C_{H5}$ corresponding to SEQ ID NOs: 49 to 53, respectively) utilizing lysates corresponding to 100, 10, 1 and 0 cells.

b. Semi-Nested PCR

One microliter of the multiplex overlap-extension RT-PCR reaction product was subjected to semi-nested PCR (Biotaq kit, Bioline, UK cat. No BIO-21040), essentially as proposed by the manufacturer. The total volume of the reactions were 50 μl. The primers used are shown in table 5.

TABLE 5

| Primer name | Conc. | SEQ ID NO | primer sequence in 5' to 3' direction |
|---|---|---|---|
| $J_H$ | 200 nM of each | 61 | ggaggcgctcGAGACGGTGACCAGGGTGCC |
| | | 62 | ggaggcgctcGAGACGGTGACCATTGTCCC |
| | | 63 | ggaggcgctcGAGACGGTGACCAGGGTTCC |
| | | 64 | ggaggcgctcGAGACGGTGACCGTGGTCCC |
| $C_{Lk}$ | 200 nM | 21 | accgcctccaccggcggccgcttaTTAACACTCT CCCCTGTTGAAGCTCTT |

Capitalized sequences correspond to the gene-specific region.

Cycling conditions were as follows:

| Denature | 30 sec | 95° C. | } 25 cycles |
|---|---|---|---|
| Anneal | 30 sec | 65 50° C. | |
| Extend | 1.5 min | 72° C. | |
| Final extension | 5 min | 72° C. | |

Figure 7:
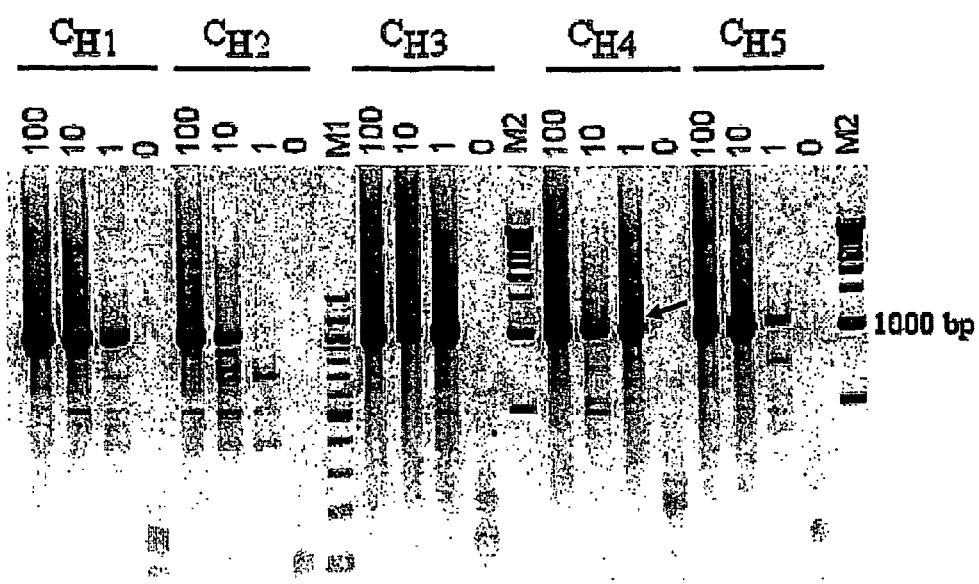
FIG. 7 is an electrophoretic gel showing the results from a single-step multiplex overlap-extension RT-PCR followed by a semi-nested PCR amplification. M1 is a 100 bp ladder and M2 is a 500 bp ladder. Results from multiplex overlap-extension primer mixtures containing either $C_{H1}$, $C_{H2}$, $C_{H3}$, $C_{H4}$ or $C_{H5}$ as the outer primer in the multiplex overlap-extension RT-PCR reaction. The reactions were performed on cell lysates corresponding to 100, 10, 1 or 0 cells. The size of the overlap-extension product is indicated with an arrow.

Ten microliters of each reaction was analyzed by 1.5% agarose gel electrophoresis using ethidium bromide for detection (FIG. 7).

The putative overlap-extension fragment from the semi-nested PCR corresponding to lysate from one cell and where the $C_{H4}$ primer was used in the first reaction (see arrow in FIG. 7), was excised from the agarose gel, purified using a Qiaex II kit (Qiagen cat. No. 20051, Hilden, Germany) and inserted into pCR2.1-TOPO using an Invitrogen TOPO TA cloning kit (Invitrogen cat. No 45-0641, Carlsbad, Calif., USA). Inserts of eight clones were sequenced and seven of these appeared to consist of a heavy chain variable region linked to a light chain variable and constant region, by the expected overlap region.

In summary, the sensitivity of the combined multiplex overlap-extension RT-PCR and the semi-nested PCR reaction was very satisfactory, with 4 out of 5 constant region primers capable of amplifying significant amounts of overlap-extension products from lysate corresponding to a single cell.

Example 4

Combined Single-Step Multiplex Overlap-Extension RT-PCR and Nested PCR Using Enriched Human B Lymphocytes as Template Source In this example, reverse transcription and multiplex overlap-extension PCR reactions were performed in a single step followed by a semi-nested amplification PCR, using isolated single human B lymphocytes as template source.

a. B-Cell Isolation

A human male donor was immunized with Tetanus toxoid. A blood sample of 120 ml was collected from the donor 6 days post immunization and peripheral blood mononuclear cells (PBMC's) were isolated using Lymphoprep (Axis-Shield, Oslo Norway, prod. No 1001967) according to the manufacturer's instructions. The CD19-positive cell population was enriched utilizing magnetic bead cell sorting. The PBMC's were stained with FITC-conjugated anti-CD19 antibody (Becton Dickinson, N.J., USA, cat. No 345776). Magnetic bead cell sorting using anti-FITC-conjugated magnetic microbeads and column purification was performed according to manufactures instructions (Miltenyi Biotec, Gladbach, Germany, cat. No 130-042401). The cells were diluted to a concentration of 200 cells per ml in PBS containing 2 nM EDTA and 0.5% BSA. Five microliters of the diluted cells was distributed to PCR tubes obtaining approximately a single cell pr. tube. The tubes were stored at −80° C. until use.

b. Multiplex Overlap-Extension RT-PCR and Semi-Nested PCR

Conditions for multiplex overlap-extension RT-PCR and semi-nested PCR were as described in Example 3. However, the reactions were only performed with the multiplex overlap-extension primer mix constituting primer $C_{H3}$ corresponding to SEQ ID NO: 51. Sixteen samples from the combined multiplex overlap-extension RT-PCR and semi-nested PCR reactions were analyzed by subjecting 10 µl from each semi-nested PCR reaction to 1% agarose gel electrophoresis using ethidium bromide for detection (FIG. 8).

Figure 8:
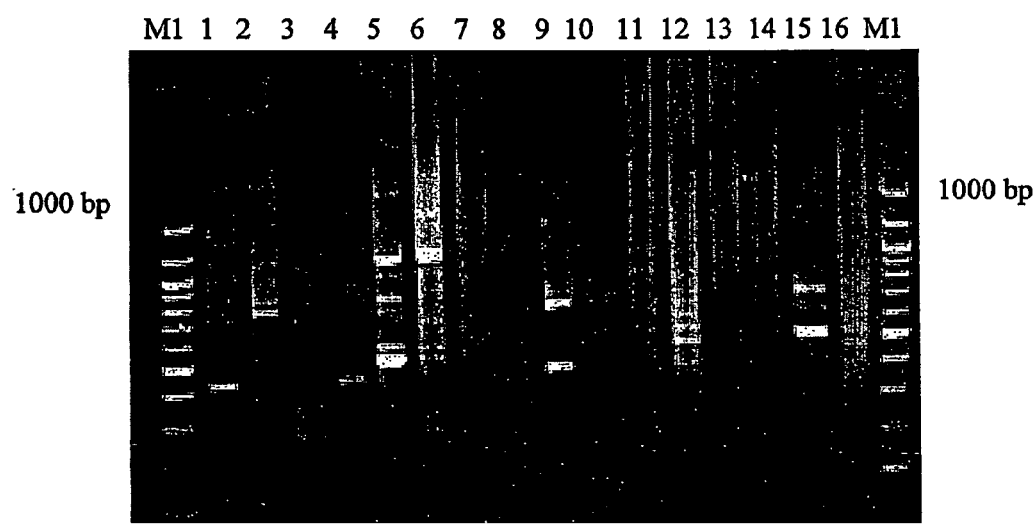
FIG. 8 is an electrophoretic gel showing the results from a single-step multiplex overlap-extension RT-PCR followed by a semi-nested PCR amplification using enriched human B lymphocytes as template. M1 is a 100 bp ladder. Lane 5 and 6 show bands of the size expected for the overlap-extension product.

As can be seen in FIG. 8, 2 out of 16 lanes (lanes 5 and 6) contained fragments of the expected mobility (around 1 kb). Further, lane 2 contained a less intense fragment at the expected mobility. The 1 kb fragments of lane 5 and 6 were excised from the agarose gel, purified using a Qiaex II kit (Qiagen cat. No 20051) and inserted into pCR2.1-TOPO using the Invitrogen TOPO TA cloning kit (Invitrogen cat. No 45-0641, Carlsbad, Calif., USA). Two clones from each isolated fragment had inserts of the correct size. Restriction enzyme digestion (NcoI and NheI, separately) showed fragments of the expected sizes (410 and 680 bp) indicating a correct linkage between the heavy chain variable region and the light chain variable and constant region encoding sequences.

The two clones originating from the fragment in lane 5 were sequenced and shown to be identical, indicating that the linked $V_H$ and LC were cognate pairs.

Example 5

Combined Single-Step Multiplex Overlap-Extension RT-PCR and Nested PCR Using $V_\lambda$-Specific Primers In this example, reverse transcription and multiplex overlap-extension PCR reactions were performed in a single step using $V_\lambda$-specific primers, followed by a semi nested PCR reaction. Total RNA purified from two different cell lines expressing lambda gene families 1b and 1e in combination with the same heavy chain variable region were used as templates.

a. Cells

Two IgG1-lambda expressing Chinese hamster ovary (CHO) cell lines were generated using the Flp-In technology (Invitrogen, Carlsbad, Calif., USA).

Figure 9:
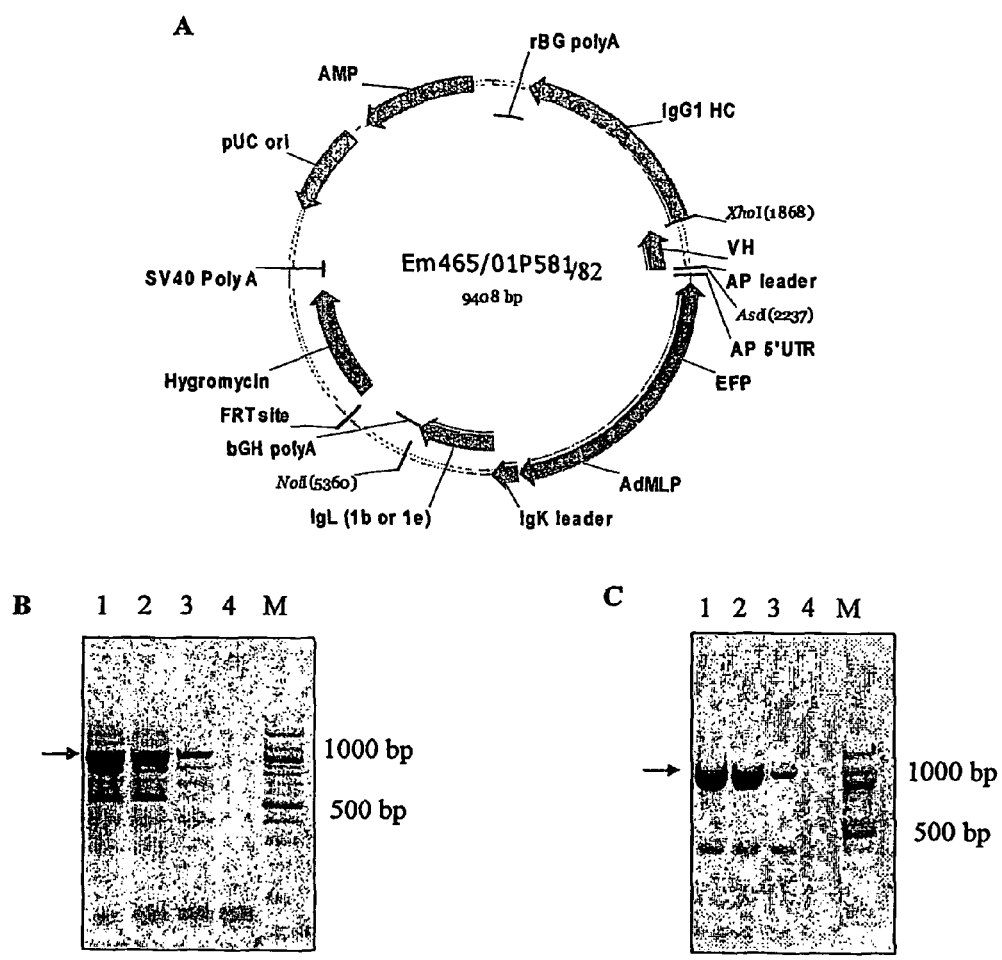
FIG. 9A is a schematic diagram of the mammalian expression vectors (Em465/01P582/Em465/01P581) used for generation of IgG1-lambda expressing cell lines, where the encoding sequences are in a head-to-head orientation. The vectors comprise the following elements: Amp=gene encoding for ampicillin resistance. pUC ori=pUC origin of replication. AdMLP=Adenovirus major late promoter. EFP=Elongation factor promoter. AP leader=alkaline phosphatase leader sequence. $V_H$=heavy chain variable region encoding sequence. IgG1 HC=Sequence encoding for immunoglobulin isotype G1 heavy chain constant region. rBG polyA=Rabbit beta-globin poly A signal sequence. bGH polyA=Bovine Growth Hormone poly A sequence. IgK leader=sequence encoding for murine kappa leader. IgL (1b or 1c)=Sequence encoding immunoglobulin lambda light chain family 1b or 1c. FRT=A Flp recognition target site. Hygromycin=gene encoding hygromycin resistance. SV40 polyA=Simian virus 40polyA signal sequence.
FIGS. 9B and 9C are ethidium bromide stained agarose gels loaded with PCR products isolated form cell line CHO Flp-In/Em464/01P581 and CHO Flp-In/Em464/01P582, respectively. Lanes 1 to 4 correspond to total RNA template concentrations of 50 pg, 5 pg, 0.5 pg or 0 pg used for the multiplex overlap-extension RT-PCR reaction. M is a 100 bp ladder (New England Biolabs, New England, USA). The arrows indicate the overlap-extension PCR product.

IgG1-lamda mammalian expressing vectors pEm465/01P581 and pEm465/01P582 (FIG. 9A) representing two lambda gene families were constructed based on the Flp-In expression vector, pcDNA5/FRT. CHO-Flp-In cells were co-transfected, using Fugene 6 (Roche, Mannheim, Germany) according to the manufacturer's instructions, with the above mentioned plasmids containing the antibody encoding genes and pOG44 conferring transient expression of the Flp recombinase. Transformants were selected for insertions. The selected cell lines were named CHO Flp-In/Em464/01P581 & CHO Flp-In/Em464/01P582, and maintained in Ham's F-12 medium, supplemented with 2 mM L-glutamine, 10% FCS and 900 µg/ml Hygromycin B (maintenance media).

The cell lines were harvested using trypsin and washed 3× in maintenance media. Approximately $10^7$ cells were used for Total RNA purification using Nucleo Spin L kit (Macherey-Nagel, Düren, Germany) according to the manufacturer's description. The final RNA concentrations were determined by $OD_{260}$ measurements.

b. Single-Step Multiplex Overlap-Extension RT-PCR

Multiplex overlap-extension RT-PCR using 50 pg, 5 pg, or 0.5 pg total RNA as template was essentially performed as described in Example 3 utilizing a multiplex overlap-extension primer mix comprising the primers shown in Table 6 and the cycling conditions specified below.

| Reverse transcription: | 30 min | 55° C. | |
|---|---|---|---|
| Polymerase activation: | 15 min | 95° C. | inactivating reverse transcriptase and activating Taq polymerase. |

PCR reaction:

| Denature | 30 sec | 95° C. | |
|---|---|---|---|
| Anneal | 30 sec | 50° C. | 35 cycles |
| Extend | 5 min | 72° C. | |
| Final extension | 10 min | 72° C. | |

TABLE 6

| Primer name | Conc. | SEQ ID NO | primer sequence in 5' to 3' direction |
|---|---|---|---|
| $V_H$ | 40 nM of each | 1 | agcctatactattgattaggcgcgccCAGRTG CAGCTGGTGCART |
| | | 2 | agcctatactattgattaggcgcgccSAGGTC CAGCTGGTRCAGT |
| | | 3 | agcctatactattgattaggcgcgccCAGRTC ACCTTGAAGGAGT |
| | | 4 | agcctatactattgattaggcgcgccSAGGTG CAGCTGGTGGAG |
| | | 5 | agcctatactattgattaggcggcgccCAGGT GCAGCTACAGCAGT |
| | | 6 | agcctatactattgattaggcgcgccCAGSTG CAGCTGCAGGAGT |
| | | 7 | agcctatactattgattaggcgcgccGARGTG CAGCTGGTGCAGT |
| | | 8 | agcctatactattgattaggcgcgccCAGGTA CAGCTGCAGCAGTC |
| $C_H$ | 100 nM | 9 | GACSGATGGGCCCTTGGTGG |
| $V_\lambda$ | 100 nM of each | 65 | cgcctaatcaatagtataggctagccCAGTCT GTGCTGACTCAGCCA |
| | | 66 | cgcctaatcaatagtataggctagccCAGTCT GTGYTGACGCAGC |
| | | 67 | cgcctaatcaatagtataggctagccCAGTCT GTCGTGACGCAGC |
| | | 68 | cgcctaatcaatagtataggctagccCARTCT GCCCTGACTCAGCCT |
| | | 69 | cgcctaatcaatagtataggctagccTCCTAT GWGCTGACTCAGCCA |
| | | 70 | cgcctaatcaatagtataggctagccTCTTCT GAGCTGACTCAGGAC |
| | | 71 | cgcctaatcaatagtataggctagccCACGTT ATACTGACTCAACCG |
| | | 72 | cgcctaatcaatagtataggctagccCAGGCT GTGCTGACTCAGC |
| | | 73 | cgcctaatcaatagtataggctagccAATTTT ATGCTGACTCAGCCCCA |
| | | 74 | cgcctaatcaatagtataggctagccCAGRCT GTGGTGACYCAGGA |
| | | 75 | cgcctaatcaatagtataggctagccCWGCCT GTGCTGACTCAGC |

TABLE 6-continued

| Primer name | Conc. | SEQ ID NO | primer sequence in 5' to 3' direction |
|---|---|---|---|
| $C_{\lambda 2/C\lambda 7}$ | 100 nM | 76 | gccgcttattaTGAACATTCTGTAGGGGCCA |
| | | 77 | gccgcttattaAGAGCATTCTGCAGGGGCCA |

Y = C/T, W = A/T, S = G/C, R = A/G. Capitalized sequences correspond to the gene-specific region.

c. Semi-Nested PCR

One microliter of the multiplex overlap-extension RT-PCR reaction product was subjected to semi-nested PCR (Biotaq kit, Bioline, UK cat. No BIO-21040), essentially as proposed by the manufacturer. The total volumes of the reactions were 20 µl. The primers used are shown in table 7.

TABLE 7

| Primer name | Conc. | SEQ ID NO | primer sequence in 5' to 3' direction |
|---|---|---|---|
| $J_H$ | 200 nM of each | 61 | ggaggcgctcGAGACGGTGACCAGGGTGCC |
| | | 62 | ggaggcgctcGAGACGGTGACCATTGTCCC |
| | | 63 | ggaggcgctcGAGACGGTGACCAGGGTTCC |
| | | 64 | ggaggcgctcGAGACGGTGACCGTGGTCCC |
| $C_{L\lambda}$ | 200 nM | 78 | atatatatgcggccgcttattaTGAACATTCTGTAGGGGCCACTG |
| | | 79 | atatatatgcggccgcttattaAGAGCATTCTGCAGGGGCCACTG |

Capitalized sequences correspond to the gene-specific region.

Cycling conditions were as follows:

| Denature | 30 sec | 95° C. | ⎫ | |
| Anneal | 30 sec | 50° C. | ⎬ | 25 cycles |
| Extend | 1.5 min | 72° C. | ⎭ | |
| Final extension | 5 min | 72° C. | | |

Ten microliters of the nested products were analyzed by 1.5% agarose gel electrophoresis using ethidium bromide for detection (FIGS. 9B and 9C). The arrows indicate overlap-extension products with the expected migration properties of approximately 1 kb.

The present experiment illustrates that the lambda multiplex overlap-extension primer mix shown in Table 6 is applicable in single-step multiplex overlap-extension RT-PCR independent on the template used. Further, specific overlap-extension PCR products were produced at 0.5 pg total RNA. This sensitivity suggest that cognate linked heavy chain variable region and light chain variable region encoding sequences can be amplified from a single cell.

Example 6

Generation of a Sub-Library of Tetanus-Specific Cognate Pairs of Antibody Encoding Sequences In the present example the steps outlined in the flow chart illustrated in FIG. 10, are exemplified using Tetanus Toxoid (TT) as target antigen.

a. Donors

Donors which previously have been immunized with the Tetanus vaccine are boosted with Tetanus vaccine (Statens Serum Institut, Denmark). Six days post the Tetanus vaccine boost a blood sample of approximately 200 ml is drawn from the donors into a tube containing anticoagulant.

It is required that the donors generally are healthy with no silent or chronic infections. They should not suffer from autoimmune diseases or receive any immunosuppressive medication, and they should not have had any vaccinations within the last 3 months. Also, at the time of the TT-vaccine boost, the donors must not have had any serious infections within the last month.

b. Preparation of Peripheral Blood Mononuclear Cells (PBMC)

PBMC are isolated from the blood samples using Lymphoprep (Axis-Shield PoC AS, Norway, prod. No 1001967) according to the manufactures recommendations. Briefly, the blood is diluted 1:1 in PBS and this suspension is layered over Lymphoprep in a 2:1 ratio. Vials are centrifuged for 20 min, 25° C. at 800 g and the white inter phase band is collected. Cells are washed in PBS containing 2 mM EDTA.

c. Enrichment of B Cells

The B-cell lineage (CD19+ cells) of the PBMC's is enriched by magnetic bead cell sorting using the following procedure.

The isolated PBMC are stained with anti-CD19-FITC (Becton Dickenson, N.J., USA, cat. No 345776). All steps are performed at 4° C. in the dark. Staining is performed with 10 µl anti-CD19-FITC pr. $1 \times 10^6$ cells in a volume of 100 µl per $1 \times 10^6$ cells using M-buffer (PBS, pH 7.2, 0.5% BSA, 2 mM EDTA). This will stain the B-cell lineage of the PBMCs. Cells are incubated for 20 min followed by two washing steps with M-buffer. The anti-CD19-FITC stained cells are magnetically labeled with anti-FITC conjugated microbeads, using 10 µl of anti-FITC magnetic beads (Miltenyi Biotec, Gladbach, Germany, cat. No 130-042-401) per $1 \times 10^6$ cells in a volume of 100 µl M-buffer per $1 \times 10^6$ cells. Incubation is performed for 15 min followed by a single washing step with M-buffer. The cells are resuspended in degassed M-buffer.

A MACS LS column (Miltenyi Biotec, Gladbach, Germany, cat. No 130-042-401) is pretreated with degassed M-buffer according to the manufactures prescriptions. The suspension of cells stained with anti-CD19-FITC and labeled with anti-FITC-magnetic beads are applied to the column and allowed to run through. Stained and labeled cells (CD19+) will be retained in the magnetic field surrounding the column while unstained cells (CD19−) will pass through the column. The column is washed with degassed M-buffer. The magnetic field is removed and the CD19+ cells are collected.

d. Sorting of Plasma Cells

The eluate from the MACS column is centrifuged and resuspended in FACS buffer (PBS, pH 7.2, 2% BSA) in a concentration of $1 \times 10^6$ cells/60 µl FACS buffer. Anti-CD19-FITC (Becton Dickenson, N.J., USA, cat. No 345776) (10 µl/$10^6$ cells), anti-CD38-PE (Becton Dickenson, N.J., USA, cat. No 555460) (10 µl/$10^6$ cells) and anti-CD45-PerCP (Becton Dickenson, N.J., USA, cat. No 345809) (20 µl/$10^6$ cells) are added. Incubation is performed at 4° C. for 20 min in the dark, followed by two times washing and resuspension in FACS buffer.

The cells are sorted by fluorescence activated cell sorting (FACS) using the following gating parameters:
 1. Forward scatter and side scatter in order to retain lymphocytes and monocytes including plasma blasters and plasma cells and to avoid dead cells and cells with very high side scatter which may be aggregates or granulocytes.
 2. Cells that are CD19 positive and express increased levels of CD38 ($CD38^{hi}$). This is basically only a gate on CD38 since the PBMCs have been enriched on a MACS column for CD19 expression, but this will disclose any contaminants.

3. CD45 positive cells. All lymphocytes express CD45. However, plasma cells down regulate their CD45 expression compared to earlier lymphocyte differentiation stages. Therefore a discrete population of cells corresponding to plasma cells can be obtained when gating on CD45.

FACS sorted cells are collected as single cells directly in single wells of 96 well plates containing 5 µl PBS buffer supplemented with 5 U RNase inhibitor (RNasin, Promega, Madison USA, cat. No N2515) per well. At this point the cells may be frozen for later RT-PCR or the cells may proceed immediately for RT-PCR.

e. Linkage of Cognate Pairs of Immunoglobulin Variable Region Encoding Sequences The multiplex overlap-extension RT-PCR technology is applied to the single cells, thereby achieving cognate linkage of transcribed anti-Tetanus Toxoid heavy chain variable region and light chain variable region encoding sequences.

e-1. Single-Step Multiplex Overlap-Extension RT-PCR

The Qiagen One-Step RT-PCR kit (Qiagen cat. No 210212, Hilden, Germany) is used for the multiplex overlap-extension RT-PCR essentially according to the manufacturer's recommendation. Frozen 96-well plates containing a single cell per well are removed from the freezer and when the wells are free of ice crystals 15 µl RT-PCR reaction mixture is added immediately to each sample (single cell).

The RT-PCR reaction mixture contains, in a total volume of 20 µl, the following reagents:

1× One-Step RT-PCR buffer,
dNTP's in a final concentration of 400 µM of each,
Multiplex overlap-extension primer mix in the concentrations as indicated in table 8,
0.8 µl One-step RT-PCR enzyme mix, and
20 U RNase inhibitor (RNasin, Promega, Madison USA, cat. No N2515).

The composition of the multiplex overlap-extension primer mix is shown in table 8.

TABLE 8

| Primer name | Conc. | SEQ ID NO | primer sequence in 5' to 3' direction |
|---|---|---|---|
| $V_H$ | 40 nM of each | 41 | tattggcgcgccatggccCAGRTG CAGCTGGTGCART |
| | | 42 | tattggcgcgccatggccSAGGTCCAGCTGGT RCAGT |
| | | 43 | tattggcgcgccatggccCAGRTCACCTTGAA GGAGT |
| | | 44 | tattggcgcgccatggccSAGGTGCAGCTGGT GGAG |
| | | 45 | tattggcgcgccatggccCAGGTGCAGCTACA GCAG |
| | | 46 | tattggcgcgccatggccCAGSTGCAGCTGCA GGAGT |
| | | 47 | tattggcgcgccatggccGARGTGCAGCTGGT GCAGT |
| | | 48 | tattggcgcgccatggccCAGGTACAGCTGCA GCAGTC |
| $C_{H(IgG)}$ | 200 nM | 9 | GACSGATGGGCCCTTGGTGG |
| $V_L$ | 40 nM of each | 54 | gccatggcgcgccaatagctagccGA CATCCAGWTGACCCAGTCT |
| | | 55 | gccatggcgcgccaatagctagccGATGTTGT GATGACTCAGTCT |
| | | 56 | gccatggcgcgccaatagctagccGAAATTGT |

TABLE 8-continued

| Primer name | Conc. | SEQ ID NO | primer sequence in 5' to 3' direction |
|---|---|---|---|
| | | | GWTGACRCAGTCT |
| | | 57 | gccatggcgcgccaatagctagccGATATTGT GATGACCCACACT |
| | | 58 | gccatggcgcgccaatagctagccGAAACGAC ACTCACGCAGT |
| | | 59 | gccatggcgcgccaatagctagccGAAATTGT GCTGACTCAGTCT |
| $C_{L\kappa}$ | 200 nM | 60 | atatatatgcggccgcttaTTAACACTCTCCC CTGTTGAA |

W = A/T, S = G/C, R = A/G. Capitalized sequences correspond to the gene specific region.

Cycling conditions are as follows:

| Reverse transcription: | 30 min | 55° C. | |
| Polymerase activation: | 15 min | 95° C. | inactivates reverse transcriptase and activates Taq polymerase. |

PCR reaction:

| Denature | 30 sec | 94° C. | ⎫ |
| Anneal | 30 sec | 52° C. | ⎬ 35 cycles |
| Extend | 5 min | 72° C. | ⎭ |
| Final extension | 10 min | 72° C. | | e-2. Additional Amplification

One microliter of the multiplex overlap-extension RT-PCR reaction product, from each sample, is subjected to semi-nested PCR (Biotaq kit, Bioline, UK cat. No BIO-21040), essentially as proposed by the manufacturer utilizing 96 well plates. The total volume of each reaction is 50 µl, containing a final concentration of 1× Biotaq buffer, 200 µM dNTP's (of each), 2 mM $MgCl_2$, 1.25 U Bio Taq polymerase and the primers shown in Table 9.

Cycling conditions are as follows:

| Denature | 30 sec | 95° C. | ⎫ |
| Anneal | 30 sec | 55° C. | ⎬ 30 cycles |
| Extend | 1.5 min | 72° C. | ⎭ |
| Final extension | 5 min | 72° C. | |

TABLE 9

| Primer name | Conc. | SEQ ID NO | primer sequence in 5' to 3' direction |
|---|---|---|---|
| $J_H$ | 200 nM of each | 61 | ggaggcgctcGAGACGGTGACCAGGGTGCC |
| | | 62 | ggaggcgctcGAGACGGTGACCATTGTCCC |
| | | 63 | ggaggcgctcGAGACGGTGACCAGGGTTCC |
| | | 64 | ggaggcgctcGAGACGGTGACCGTGGTCCC |
| $C_{L\kappa}$ | 200 nM | 21 | accgcctccaccggcggccgcttaTTAACACTCT CCCCTGTTGAAGCTCTT |

Capitalized sequences correspond to the gene specific region.

Ten microliters of a limited set of samples are analyzed by 1.5% agarose gel electrophoresis using ethidium bromide for visualization, in order to verify that the multiplex overlap-extension RT-PCR has been successful.

Expected size of the fragments (the exact size depends upon the lengths of the variable regions):

$V_H$: ~410 bp

LC: ~680 bp

Overlap-extension fragment: ~1070 bp

Two microliters from all the samples, run in the 96 well plates, originating from the same donor, are combined in a single tube. The pooled samples are digested with XhoI and NotI. The digested overlap-extension fragments are purified by preparative 1% agarose gel electrophoresis; the overlap-extension fragments are excised from the agarose gel and purified using a Qiaex II kit (Qiagen cat. No 20051, Hilden, Germany). It is not necessary to pool the cognate pairs at this stage if this is not desired. In that case each individual reaction will be subjected to restriction cleavage and the products are cloned individually into the vector described below.

f. Cognate Fab Expression Library

A library of Fab vectors is generated by inserting the pool of XhoI/NotI digested overlap-extension fragments into *E. coli* vector JSK301 (FIG. 11) by ligation. *E. coli* (TOP10) is transformed by electroporation with the library of Fab vectors and the transformants are selected on 2×YT agar containing 100 µg/ml carbenicillin. Plasmid DNA is prepared from colonies directly off the agar plates. The plasmid preparation is derived from a minimum number of colonies per donor, corresponding to 3× the total number of single plasma cells originally sorted, in order to maintain diversity. An Fab expression library is generated by inserting a prokaryotic promoter and leader cassette derived from phh3 (Den, W. et al. 1999. J. Immunol. Methods 222, 45-57) into the resulting plasmid preparation by digesting the plasmid preparation with AscI and NheI and subsequent ligation. The library generation process is outlined in FIG. 12. *E. coli* (TG1) is transformed by electroporation with the resulting Fab expression library and the transformants are selected on 2×YT agar containing 100 µg/ml carbenicillin. The individual donors are kept separate during the described procedure in Den et al, J Immunol Methods. 1999 Jan. 1; 222(1-2):45-57. They can, however, be combined at any stage where this might be desired.

g. Screening of Clones

Fab expressing clones are screened for TT antigen-binding by antigen-specific ELISA assays.

g-1. Master Plate Generation and Fab Expression

Individual selected colonies of the TG1 cells, each harbouring a cognate Fab expression vector from the library generated in step (f) are picked into single wells of 96 well plates containing 2×YT/100 µg/mL Amp/1% glucose. The colonies are grown overnight at 37° C. with gentle shaking. These plates are referred to as master plates, which are stored at −80° C. upon addition of glycerol to a final concentration of 15%.

Before the master plates are stored, they are used for inoculation of one or more 384 well plates containing 2×YT/100 µg/mL Amp 0.1% glucose using a 96 pin replicator. The plates are sealed and shaken for 2-3 h at 37° C.

Fab expression is induced by adding an equal volume of 2×YT/100 µg/mL Amp/0.2 mM IPTG, obtaining a final IPTG concentration of 0.1 mM. The plates are sealed and shaken overnight at 30° C. The following day, the Fab containing supernatants are analyzed for TT antigen-binding specificity by ELISA.

g-2. ELISA Analysis

Three hundred and eighty four (384) well ELISA plates (Nunc, Roskilde, Denmark, cat. No 265196) are coated overnight at 4° C. with tetanus toxoid (TT) antigen, diluted to a final concentration of 1 µg/ml in PBS in a volume of 25 µl per well. Excess binding sites of the wells are blocked for 1 h at RT by adding 2% M-PBS-T (2% skim milk powder in PBS, 0.05% Tween 20). The wells are washed 2 times with PBS-T (PBS, 0.05% Tween 20).

The Fab containing bacterial supernatants from g-1. are diluted 1:2 in 2% M-PBS-T, and transferred to the ELISA wells in duplicate. Incubation is performed for 1 h at RT. The wells are washed 4 times with PBS-T. Goat-anti-human Fab/HRP (Sigma, St. Louis, Mo., USA, cat. No A0293) 1:10.000 dilution in 2% M-PBS-T is added to the wells. Incubation is performed for 1 h at RT. The wells are washed 4 times with PBS-T. TMB Plus (KemEnTec, Copenhagen, Denmark, cat. No 4390L) substrate is added and incubation is performed for 5-15 minutes. The reactions are stopped by adding an equal volume of 1 M $H_2SO_4$. The extents of the reactions are read at 450 nm in an ELISA reader (Multiscan Ascent, Labsystems, Franklin, USA).

The original bacterial clones corresponding to TT antigen-binding clones are subsequently retrieved from the original master plates. Plasmid DNA is prepared from the isolated antigen positive Fab clones, generating a cognate Fab expression sub-library of TT antigen-binding clones.

The clones may also be analyzed by an anti-light chain ELISA assay, in order to get a correlation between the number of antigen-binding clones and the number of Fab expressing clones. Further, such an analysis provides information of kappa and lambda light chain representation in the clones.

h. Cognate Antibody Expression Library

In order to facilitate the expression of full-length human antibodies the cognate variable regions from the bacterial Fab expression vector must be transferred to a mammalian expression vector containing the constant domains from one of the human immunoglobulin isotypes. Such a transfer can either be performed clone by clone or in mass. Below it is described how to perform the mass transfer.

The mass transfer is performed in two steps. First, the plasmid preparations of the individually isolated antigen-binding Fab clones are pooled. The prokaryotic promoter and leader containing cassette is exchanged with a mammalian promoter and leader cassette consisting of human alkaline phosphatase leader sequence (AP Leader), human elongation factor 1-alpha promoter (EFP), adenovirus major late promoter (AdMLP), IgK leader sequence by digesting the pooled Fab expression sub-library with AscI and NheI followed by insertion of a mammalian promoter and leader cassette by a subsequent ligation. *E. coli* (TOP10) is transformed by electroporation with the resulting promoter exchanged Fab expression library and the transformants are selected on 2×YT agar containing 100 µg/ml carbenicillin. Plasmid DNA is prepared from colonies directly off the agar plates. The plasmid preparation is derived from a minimum number of colonies per donor, corresponding to approximately 3× the total number of clones in the original library, in order to maintain diversity.

Second, the cognate variable regions from the promoter exchanged Fab expression vector are isolated by digesting the plasmid preparation with XhoI and NotI. The isolated fragment is inserted by ligation into a mammalian expression vector resulting in a cognate antibody expression library. The vector used is essentially the same as in FIG. 9A, except that IgL in this case corresponds to the kappa light chain encoding sequence. The mammalian expression vector used above is based on the site-specific Flp-In system (Invitrogen Corporation, Carlsbad, Calif., USA, Cat No K6010-01). *E. coli* (TOP10) is transformed by electroporation with the resulting cognate antibody expression library and the transformants are selected on 2×YT agar containing 100 µg/ml carbenicillin. Plasmid DNA is prepared from colonies directly off the agar plates. The plasmid preparation is again derived from a minimum number of colonies per donor, corresponding to approximately 3× the total number of clones in the original library, in order to maintain diversity. The resulting plasmid preparation of the cognate antibody expression library can be used to transfect a mammalian host cell, e.g. the CHO cells from Invitrogen's Flp-In system (Invitrogen Corporation, Carlsbad, Calif., USA, Cat No K6010-01) in order to generate a stable mammalian expression cell lines by Flp recombinase-mediated integration. Such a cell line can be used in the production of recombinant polyclonal antibodies.

Example 7

Screening by High Density Membrane Assay

The Fab expressing clones from Example 6 f are screened by a high density membrane assay.

a. Master Plate Generation

Master plates are generated as described in step (g-1) of Example 6.

b. PVDF Membrane Preparation

PVDF membranes (Amersham, Uppsala, Sweden, cat. NoRPN2020F) are coated according to the manufacturer's instructions overnight at 4° C. with TT antigen diluted to a final concentration of 1 µg/ml in PBS. Excess binding sites on the membranes are blocked for 1 h in 2% M-PBS (2% skim milk powder in PBS). The membranes are rinsed 3 times in PBS. The membranes are soaked in 2×YT for a few minutes.

c. Clone Consolidation

Consolidation of clones into 384 well plates is performed by transferring clones from the master plates into one or more 384 well plates containing 20 µl 2×YT/well, using a 96 pin replicator.

Using a 384 pin replicator the bacteria are transferred to one or more nylon membranes in duplicate (Amersham, Uppsala, Sweden, cat. No RPN2020B) placed on 2×YT/Carb/1% glucose agar plates. The plates are incubated 4-6 h at 37° C.

d. Fab Induction

The PVDF membranes prepared in step b, are placed on a 2×YT/Carb/0.1 mM IPTG agar plates. The nylon membranes with the growing bacterial colonies are placed on top of the PVDF membranes (one nylon membrane per PVDF membrane) on the IPTG-containing agar plate. The IPTG-containing agar plate is incubated at 30° C. overnight to facilitate IPTG induced Fab expression from the colonies. The Fab molecules diffuse through the nylon membrane onto the PVDF membrane, where TT-antigen binding Fab's will be retained on the membrane.

e. Detection

The nylon membranes are removed and the PVDF membranes are washed 2×5 minutes with PBS-T (PBS, 0.05% Tween 20). The membranes are incubated for 30 minutes with 2% M-PBS. The PVDF membranes are washed 2×5 minutes with PBS-T, followed by incubation for 1 h with goat-anti-human IgG/HRP (Sigma, St. Louis, Mo., USA, cat No A0293), 1:10.000 diluted in 2% M-PBS. The PVDF membranes are washed 3×5 minutes with PBS-T. Finally, the PVDF membranes are incubated for 5 minutes with Super-Signal West Femto chemiluminiscent substrate (Pierce, Rockford, Ill., USA, cat. No 34095) according to the manufactures instructions. Excess substrate is removed and the PVDF membranes are placed under a CCD camera for detection of the chemiluminescent signal generated at positions on the PVDF membrane where a Fab fragment binds the TT-antigen.

Positive TT-antigen binding clones will appear as dots on the image. The original bacterial clone is subsequently retrieved from the original master plates. Plasmid DNA is prepared from the isolated antigen positive Fab clones, generating a cognate Fab expression sub-library of TT-antigen binding clones.

f. Correlation Between Antigen Binding Clones and Fab Expressing Clones

The nylon membranes removed in step e. are placed on a second series of PVDF membranes coated with anti-light chain antibody or anti-Fab antibody according to the procedure in step b. Step d. and e. are then repeated.

Fab positive clones will then appear as dots on the image and a correlation between the number of TT-antigen binding clones and the number of Fab expressing clones can be made.

Example 8

Figure 13:
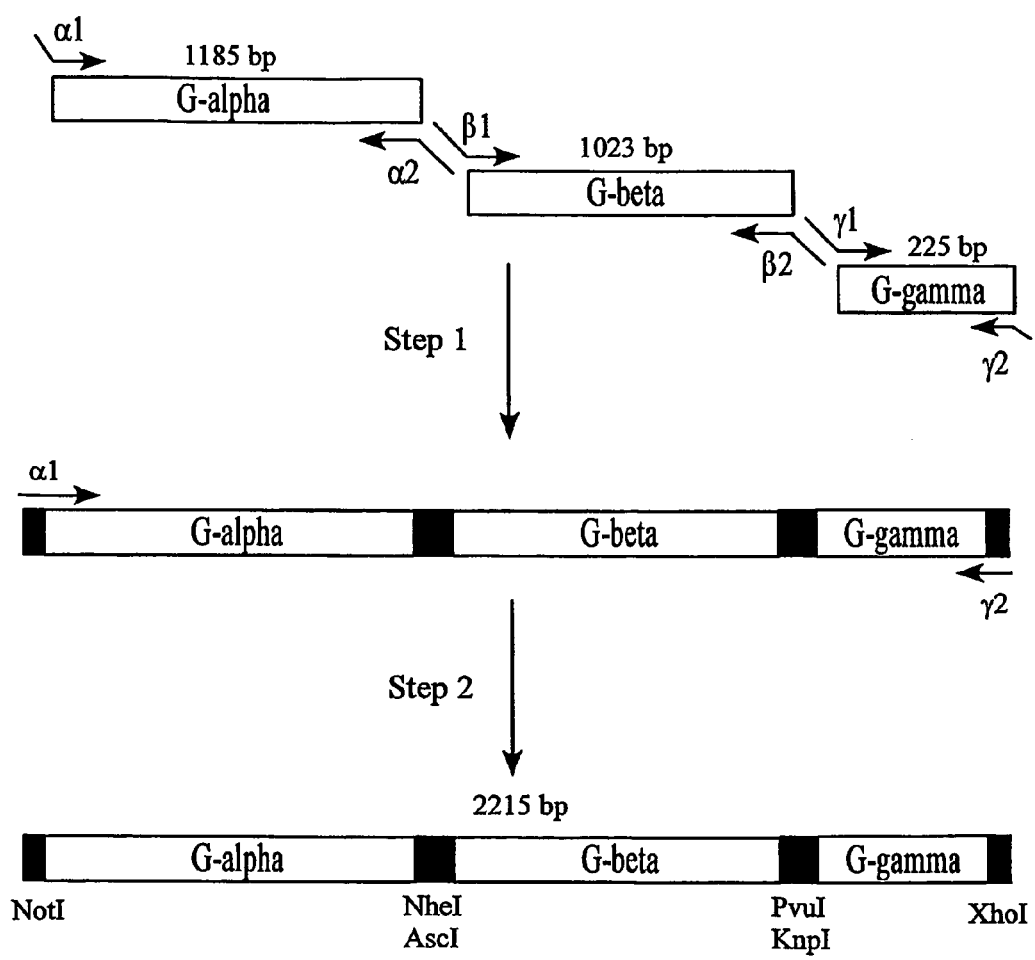
FIG. 13 illustrate the linkage of α-, β- and γ-subunits constituting a G-protein, utilizing single-step multiplex overlap-extension RT-PCR followed by an additional PCR amplification. The sizes of the individual coding regions are given as well as the size of the linked product. Restriction sites introduced by the primer tails during amplification are indicated for the final product.

Illustrative Example Describing the Isolation of Sequences Encoding a Heteromeric Protein The present example illustrates how a trimeric guanine nucleotide binding protein (G-protein) can be isolated in a single step utilizing the multiplex overlap-extension RT-PCR technique of the present invention. The family of G-protein subunits is large, alone in humans there are approximately 16 different alpha subunits, 5 beta subunits and 12 gamma subunits. For the present example subunit GαS (GenBank accession No X04408), subunit Gβ1 (GenBank accession No AF501822) and subunit Gγ1 (GenBank accession No BC029367) were chosen. The linkage procedure is illustrated in FIG. 13, where step 1 is the multiplex overlap-extension RT-PCR step and step 2 is the additional amplification of the linked product.

a. Cells

A population of human liver cells is obtained from surgical discharge samples. The liver cells are disintegrated and lysed, total RNA is isolated from the lysate using RNA L kit (Macherey—Nagel, Düren, Germany, cat No 740 962.20) according to the manufactures instructions.

b. Multiplex Overlap-Extension RT-PCR

The Qiagen One-Step RT-PCR kit (Qiagen cat. No 210212, Hilden, Germany) is used for the multiplex overlap-extension RT-PCR essentially according to the manufacturer's recommendation.

Each PCR tube contains, in a total volume of 50 µl, the following reagents:

1× One Step RT-PCR buffer, dNTP's in a final concentration of 400 µM of each,

Multiplex overlap-extension primer mix in the concentrations as indicated in table 10, 2 µl One step RT-PCR enzyme mix, 1 U/µl RNase inhibitor (RNasin, Promega, Madison USA, cat. No N2515), and 50 ng total RNA.

The multiplex overlap-extension primer mix used comprises the primers shown in table 10.

TABLE 10

| Primer name | Conc. | SEQ ID NO | primer sequence in 5' to 3' direction |
|---|---|---|---|
| α1 | 400 nM | 80 | atatatatgcggccgcttaATGGGCTGCCTCGGGAA |
| α2 | 80 nM | 81 | gccatggcgcgccaatagctagccTTAGAGCAGCTCGTACTGACGAA |
| β1 | 80 nM | 82 | tattggcgcgccatggccATGAGTGAGCTTGACCAGTACG |
| β2 | 80 nM | 83 | ggtacctaataataatcgatcgcTTAGTTCCAGATCTTGAGGAAGCT |
| γ1 | 80 nM | 84 | cgatcgattattattaggtaccccATGCCAGTAATCAATATTGAGGAC |
| γ2 | 400 nM | 85 | ggaggcgctcgagTTATGAAATCACACAGCCTCCTTTG |

Capitalized sequences correspond to the gene-specific region.

The cycling conditions used are:

| Reverse transcription: | 30 min | 42° C. | |
|---|---|---|---|
| Polymerase activation: | 15 min | 95° C. | inactivating reverse transcriptase and activating Taq polymerase. |

PCR reaction:

| Denature | 30 sec | 94° C. | |
|---|---|---|---|
| Anneal | 30 sec | 49° C. | 45 cycles |
| Extend | 3 min | 72° C. | |
| Final extension | 10 min | 72° C. | | c. Amplification PCR

One microliter of the multiplex overlap-extension RT-PCR reaction product is subjected to an additional PCR amplification step (Biotaq kit, Bioline, UK cat. No BIO-21040) essentially as proposed by the manufacturer. The primers used are α1 and γ2 as shown in table 10 corresponding to SEQ ID NO 80 and 85. The total volume of the reaction is 50 µl.

Cycling conditions are as follows:

| Denature | 30 sec | 95° C. | |
|---|---|---|---|
| Anneal | 30 sec | 53° C. | 25 cycles |
| Extend | 3 min | 72° C. | |
| Final extension | 10 min | 72° C. | |

Five microliters of the reaction product is analyzed by 1% agarose gel electrophoresis using ethidium bromide for detection. The size of the product is expected to be 2215 bp. However, additional unlinked fragments of the subunits might be present. The expected sizes of these fragments are Gα: 1228 bp, Gβ: 1064 bp and Gγ: 262 bp.

d. Cloning

The remaining reaction product is subjected to 1% agarose gel electrophoresis using ethidium bromide for detection and the overlap-extension fragment of 2215 bp is excised from the agarose gel, purified using a Qiaex II kit (Qiagen, Hilden, Germany, cat. No 20051) and inserted into pCR2.1-TOPO using Invitrogen's TOPO TA cloning kit (Invitrogen cat. No 45-0641, Carlsbad, Calif., USA).

Furthermore, promoter sequences or ribosome binding sites might be inserted upstream of each subunit encoding sequence in order to facilitate their expression from the vector. The restriction sites present in the overlap-extension sequences are applicable for such insertion.

e. General Considerations

The linkage of sequences encoding subunits constituting a heteromeric protein, as described above, can be performed for most heteromeric proteins where the sequence of the individual subunits is known. Moreover, when utilizing a multiplex overlap-extension primer mixture capable of amplifying several members of a particular family, e.g. all the G-protein α-, β-, and γ-subunits, it is possible to identify and link any combination of subunits from a cell type without first having to analyze which family members are expressed by what cell type. For example, the above example can be performed utilizing template derived from isolated single liver cells employing a multiplex overlap-extension primer mix capable of amplifying and linking all 16 Gα subunits with the 5 Gβ subunits and 12 Gγ subunits, thereby identifying which combination of subunits are expressed in each cell and simultaneously isolating the encoding sequences responsible for that combination of subunits. In addition, the use of degenerate primers might even serve to identify new members of a particular family.

When linking subunits of a heteromeric protein using the multiplex overlap-extension RT-PCR technique of the present invention, the overall size of the linked product should be considered, since there are limits to the number of base pairs a DNA polymerase can amplify. The Deep Vent polymerase from New England Biolabs, MA, USA is one DNA polymerase capable of generating very long primer extensions, of up to 14,000 bp in length. Theoretically, 14,000 bp can encode a protein with an average weight of 510 kDa. Thus, it should be possible to isolate encoding sequences for very large heteromeric proteins utilizing the method of the present invention. The extension capability could possibly be increased even further by utilizing mixtures of DNA polymerases.

Example 9

Design of Leader Primers

In this example, a multiplex set of primers in which the site of priming is kept in the sequence encoding the leader region of the human antibody heavy chain and kappa light chain families was designed.

When using primers annealing to the N-terminal encoding sequences of the variable region families, some degree of cross-hybridization may be observed. Primers of one particular gene family sequence can hybridize to the cDNA of another gene family, which in many cases cause creation of novel sequences. Proteins produced from such sequences are potentially immunogenic when used in treatment. Generally, these novel sequences can be corrected by PCR, or eliminated from the library.

An alternative solution, is to position the site of priming in the sequence encoding the leader peptide region of the antibody variable region. Hybrid sequences, generated as a result of cross-priming, will be eliminated during intra-cellular processing of the antibody, in which the peptide leader containing the potential immunogenic sequences will be cleaved off, and hence will not be present in the secreted antibody product. Previous sets of leader primers for antibody cloning, have been located in the 5' end of the leader encoding sequence, allowing for direct eukaryotic expression (Campbell M. J. et al. 1992 Mol Immunol. 29, 193-203). Unfortunately, eukaryotic leader peptides are poorly suited for prokaryotic processing.

The ease by which nucleic acid sequences are manipulated in bacteria makes it attractive to develop cloning systems in which sequence shuttling between bacterial vectors and vectors for other host organisms is possible. Therefore, a multiplex primer set, in which the site of priming is kept at a position in the leader region encoding sequence, that allow for functional expression of antibodies or antibody fragments in both eukaryotic and prokaryotic expression systems, was designed in the present example.

The sequence requirement for signal peptidase cleavage at the C-terminal region of any leader peptide seems very similar for prokaryote and eukaryote systems (Nielsen H. et al. 1997 Protein Eng. 10, 1-6). Further, it follows that mutations in the C-terminal region of the leader peptide is likely to have little effect on the conformation of the N-terminal region and vice versa Thus, it is expected that C-terminal sequences could be transferable among species without loss of function.

The basic concept of the primer design in the present example, was to place the site of priming at the last six codons of the C-terminal region of the leader peptide. The remaining part of the leader encoding sequence, up-stream of the site of priming (approximately 50 nucleotides) should be supplied by the appropriate expression vector matching the host species. For example, vectors suitable for expression in gram negative bacteria can be designed with a partial or full-length PelB leader sequence. For expression of antibodies in eukaryotes, a vector with a partial native antibody heavy chain leader encoding sequence and a partial variable kappa chain leader encoding sequence will be suitable. Regardless of expression system, the last six amino acids of the leader, will originate from the endogenous antibody leader encoding sequence contained in the nucleic acid segment inserted into the vector.

The following primer sequences were designed for use in the multiplex overlap-extension RT-PCR (table 11). However, the overlapping tails (lowercase letters) can easily be redesigned to function in the linkage by ligation or recombination procedures.

TABLE 11

| Primer name | SEQ ID NO | primer sequence in 5' to 3' direction |
|---|---|---|
| $V_{HL}$ | 86 | tattcccagcggccgccGCCACAGGTGCCCACTC |
|  | 87 | tattcccagcggccgccCCTTCMTGGGTCTTGTC |
|  | 88 | tattcccagcggccgccTTARAAGGTGTCCAGTGT |
|  | 89 | tattcccagcggccgccCCCAGATGGGTCCTG |
|  | 90 | tattcccagcggccgccCTCCAAGGAGTCTGTTC |
|  | 91 | tattcccagcggccgccCCATGGGTGTCCTGTCA |
|  | 92 | tattcccagcggccgccGCAACAGGTGCCCACT |
| $C_{H(IgG)}$ | 9 | GACSGATGGGCCCTTGGTGG |
| $V_{L\kappa L}$ | 93 | ggcggccgctgggaatagctagcgYTCCCAGGTGCCAGATG |
|  | 94 | ggcggccgctgggaatagctagcgCTCCCTGGATCCAGTG |
|  | 95 | ggcggccgctgggaatagctagcgCTCCCAGATACCACCGGA |
|  | 96 | ggcggccgctgggaatagctagcgATCTCTGGTGCCTAC |
|  | 97 | ggcggccgctgggaatagctagcgATCTCTGATACCAGGGCA |

TABLE 11-continued

| Primer name | SEQ ID NO | primer sequence in 5' to 3' direction |
|---|---|---|
|  | 98 | ggcggccgctgggaatagctagcgGTTCCAGCCTCCAGGGGT |
| $C_{L\kappa}$ | 99 | atatatatggcgcgccTTAACACTCTCCCCTGTTGAA |

M = A/T, R = A/G, Y = C/T, S = G/C. Capitalized sequences correspond to the gene-specific region.

It should be noted that the restriction sites in this primer design were slightly modified compared to the primers described in the previous examples. Thus, the overlap sequence between the heavy chain and light chain variable region encoding sequences comprised a NotI and a NheI restriction site, and in the constant kappa primer ($C_{L\kappa}$), the previous NotI site has been exchanged with an AscI site. The later modification should of course be observed when designing the primers for the additional PCR amplification. Further, the NotI site in the cloning vector, shown in FIG. 11, should be changed to a AscI site, and the AscI site in the promoter unit should be changed to a NotI site.

The functionality with respect to leader cleavage has been tested in silico using SignalP provided by CBS at the Danish Technical University.

The chimeric leader peptides tested for the variable heavy chain, were encoded by nucleic acid sequences composed of a truncated PelB sequence, a C-terminal NotI site (SEQ ID NO 100: ATG AAA TAT CTT CTA CCA ACA GCG GCA GCT GGA TTA TTG GCG GCC GCC), and in association with the NotI site the gene specific part of one of SEQ ID NO 86 to 92, encoding the six C-terminal amino acids from native $V_{HL}$ family members. All seven sequences showed signal peptide cleavage in gram negative bacteria, using the SignalP program.

The chimeric leader peptides tested for the variable light chain, were encoded by nucleic acid sequences composed of a truncated PelB sequence, a C-terminal NheI site (SEQ ID NO 101: ATG AAA TAT TTG CTA CCA ACA GCG GCA GCT GGA TTA TTG TTA CTA GCG), and in association with the NheI site the gene specific part of one of SEQ ID NO 93 to 98, encoding the six C-terminal amino acids from native $V_{L\kappa L}$ family members. All six sequences showed signal peptide cleavage in gram negative bacteria, using the SignalP program.

Figure 11:
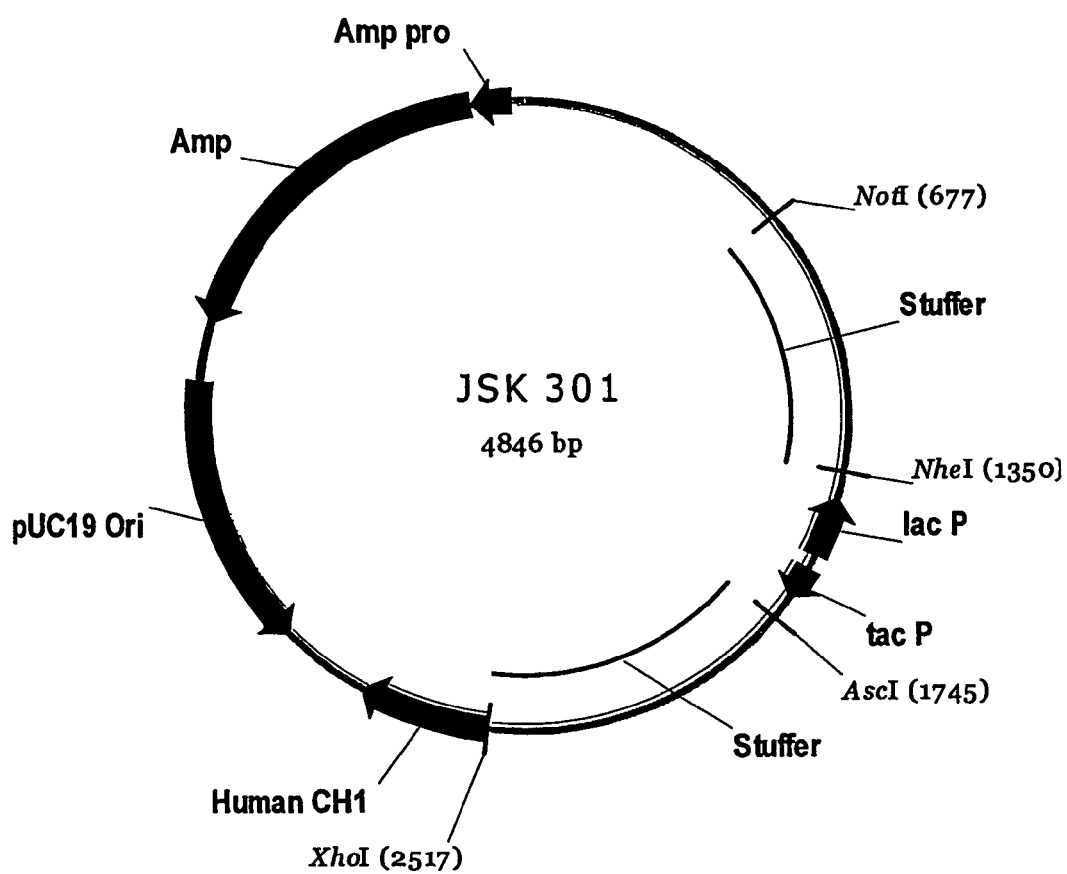
FIG. 11 is a schematic diagram of JSK301, an *E. coli* vector used to generate a library of Fab vectors by inserting the overlap-extension fragments comprising the cognate variable region encoding sequences into the vector at the indicated NotI/XhoI restriction sites. The vector comprises the following elements: Amp and Amp pro=ampicillin resistance gene and its promoter. pUC19 Ori=origin of replication. Human CH1=sequence encoding human immunoglobulin gamma 1 heavy chain domain 1. Stuffer=an irrelevant sequence insert which is cut out upon insertion of the overlap-extension fragments. tac P and lac Z=bacterial promoters which can be excised at the NheI and AscI restriction sites.

The sequences of SEQ ID NO 100 and 101 are suitable for the construction of a bacterial expression vector similar to the one illustrated in FIG. 11, in that the AscI site illustrated in FIG. 11 is substituted with SEQ ID NO 100 and the NheI site is substituted with SEQ ID NO 101. Further, the NotI site illustrated in FIG. 11 needs to be substituted for a AscI site.

The mammalian expression vector (FIG. 9) can likewise be re-designed to enable expression in mammalian cells following transfer of the variable region encoding segments from the bacterial vector just described.

Example 10

One Tube Multiplex RT-PCR and Linkage by Ligation

The present example illustrates how a cognate pair comprising linked heavy chain variable region and light chain variable region encoding sequences can be generated in a single tube reaction using ligation instead of overlap-extension PCR, to obtain linkage.

a. Multiplex RT-PCR

An in-house produced cell line expressing Fab molecules with specificity towards Tetanus Toxoid are distributed by limiting dilution to obtain a single cell in a single PCR tube.

In addition to the single cell, each PCR tube contains the following reagents in a total volume of 20 µl:
1× Phusion HF buffer
dNTP's in a final concentration of 200 µM each
Multiplex primer mix in the concentrations as indicated in table 12
0.8 U Phusion polymerase (FinnZymes Cat. No F-530-L)
1 µl Sensiscript reverse transcriptase (Qiagen Cat. No 205213
20 U Rnase inhibitor

TABLE 12

| Primer name | Conc. | SEQ ID NO | primer sequence in 5' to 3' direction |
|---|---|---|---|
| $V_H$ | 200 nM of each | 102 | tgttgttctagatgaaggcgcgccCAGRTGCAGC TGGTGCART |
| | | 103 | tgttgttctagatgaaggcgcgccSAGGTCCAGC TGGTRCAGT |
| | | 104 | tgttgttctagatgaaggcgcgccCAGRTCACCT TGAAGGAGT |
| | | 105 | tgttgttctagatgaaggcgcgccSAGGTGCAGC TGGTGGAG |
| | | 106 | tgttgttctagatgaaggcgcgccCAGGTGCAGC TACACAGT |
| | | 107 | tgttgttctagatgaaggcgcgccCAGSTGCAGC TGCAGGAGT |
| | | 108 | tgttgttctagatgaaggcgcgccGARGTGCAGC TGGTGCAGT |
| | | 109 | tgttgttctagatgaaggcgcgccCAGGTACAGC TGCAGCAGTC |
| $J_H$ | 200 nM of each | 61 | ggaggcgctcGAGACGGTGACCAGGGTGCC |
| | | 62 | ggaggcgctcGAGACGGTGACCATTGTCCC |
| | | 63 | ggaggcgctcGAGACGGTGACCAGGGTTCC |
| | | 64 | ggaggcgctcGAGACGGTGACCGTGGTCCC |
| $V_L$ | 200 nM of each | 110 | aacaacactagtgataggctagccGACATCCAGW TGACCCAGTCT |
| | | 111 | aacaacactagtgataggctagccGATGTTGTGA TGACTCAGTCT |
| | | 112 | aacaacactagtgataggctagccGAAATTGTGW TGACRCAGTCT |
| | | 113 | aacaacactagtgataggctagccGATATTGTGA TGACCCACACT |
| | | 114 | aacaacactagtgataggctagccGAAACGACAC TCACGCAGT |
| | | 115 | aacaacactagtgataggctagccGAAATTGTGC TGACTCAGTCT |
| $C_{L\kappa}$ | 200 nM | 16 | atatatatgcggccgcttaTTAACACTCTCCCCT GTTG |

W = A/T, R = A/G, S = G/C. Capitalized sequences correspond to the gene-specific region The cycling conditions are:

| Reverse transcription | 30 min | 37° C. | |
|---|---|---|---|
| Denature | 30 sec | 98° C. | |
| Denature | 10 sec | 98° C. | ⎫ |
| Anneal | 30 sec | 55° C. | ⎬ 40 cycles |
| Extend | 30 sec | 72° C. | ⎭ |
| Final extension | 5 min | 72° C. | | b. Linkage by Linkage

To perform the linkage by ligation, restriction enzymes and ligase are added directly to the multiplex RT-PCR reaction products. Alternatively, the multiplex RT-PCR can be purified prior to this addition in order to free the mixture from the polymerase.

The following reagents are added to each tube in a total volume of 40 µl:
1×NEBII buffer
1 mM ATP
50 U XbaI (New England Biolabs Cat. No R0145L)
25 U SpeI (New England Biolabs Cat. No R0133S)
100 µg/ml BSA
400 U T4 DNA ligase (New England Biolabs Cat. No M0202S)

The reaction is incubated at 16° C. over night.

The linked heavy chain and light chain variable region encoding sequences are purified from the reaction by gel electrophoresis and excision of the band of approximately 1000 bp.

In an alternatively version of this method, the multiplex RT-PCR reaction is performed with a $C_H$ primer instead of the $J_H$ primers in the multiplex primer set. This primer may either be equipped with a cloning tail that allows in-frame insertion of the heavy chain variable region into an expression vector, or a semi nested PCR may be performed with the primers of table 5.

Example 11

Generation of a Recombinant Polyclonal Immunoglobulin with Specificity Towards Tetanus Toxoid In the present example results from a single donor (TT03) immunized with Tetanus Toxoid (TT) is used to illustrate the steps outlined in the flow chart in FIG. 10.

a. Donors

Eight Donors which previously have been immunized with the Tetanus vaccine were boosted with Tetanus vaccine (Statens Serum Institut, Denmark). The donors were assigned with numbers TT01 to TT08. Six days after the Tetanus vaccine boost a blood sample of approximately 200 ml was drawn from the donors into a tube containing anticoagulant.

The donors were healthy without chronic infections, autoimmune disease, or immunosuppressive medication, and they had not had any vaccinations within the last 3 months.

a-1. Monitoring Donor Quality

Pre-bleedings of the donors were taken at the time of immunization. Fourteen days later additional bleedings were taken to determine the serum titer. All donors responded with an increase in the TT-titer. An ELISPOT assay was also set up to measure the frequency of TT-specific plasma cells. Different cell fractions can be used for the ELISPOT, e.g. the major bleed from day 6, the PBMC fraction, the magnetic sorted fraction, or the FACS sorted fraction. ELISPOT can be used to evaluate the donor material and to identify the best responders, which then may proceed through the sorting step and multiplex overlap-extension RT-PCR. For donor TT03 an ELISPOT was performed using the CD19+ cell fraction (see section c). The ELISPOT assay was performed as described by Lakew (Lakew, M. et al. 1997. J. Immunol. Methods 203, 193-198) with minor modifications. The frequency of TT specific plasma cells in the PBMC fraction was calculated to 0.021% b. Preparation of Peripheral Blood Mononuclear Cells (PBMC)

PBMC's were isolated from the blood sample using Lymphoprep (Axis-Shield PoC AS, Norway, prod. No 1001967) according to the manufactures recommendations. Briefly, the blood was diluted 1:1 in PBS and this suspension was layered over Lymphoprep in a 2:1 ratio. Vials were centrifuged for 20 min, 25° C. at 800 g and the white inter phase band was collected. Cells were washed in PBS containing 2 mM EDTA.

From the 200 ml full blood drawn from donor TT03 approximately $2 \times 10^8$ PBMC's were obtained.

c. Enrichment of B Cells

The B-cell lineage (CD19+ cells) of the PBMC's was enriched by magnetic bead cell sorting using the following procedure.

The isolated PBMC's were stained with anti-CD19-FITC (Becton Dickenson, N.J., USA, cat. No 345776). All steps were performed at 4° C. in the dark. Staining was performed with 10 µl anti-CD19-FITC pr. $1 \times 10^6$ cells in a volume of 100 µl per $1 \times 10^6$ cells using M-buffer (PBS, pH 7.2, 0.5% BSA, 2 mM EDTA). This will stain the B-cell lineage of the PBMC's. Cells were incubated for 20 min followed by two washing steps with M-buffer. The anti-CD19-FITC stained cells were magnetically labeled with anti-FITC-conjugated microbeads, using 10 µl of anti-FITC magnetic beads (Miltenyi Biotec, Gladbach, Germany, cat. No 130-042-401) per $1 \times 10^6$ cells in a volume of 100 µl M-buffer per $1 \times 10^6$ cells. Incubation was performed for 15 min followed by a single washing step with M-buffer. The cells were resuspended in degassed M-buffer.

A MACS LS column (Miltenyi Biotec, Gladbach, Germany, cat. No 130-042-401) was pretreated with degassed M-buffer according to the manufacturers descriptions. The suspension of cells stained with anti-CD19-FITC and labeled with anti-FITC-magnetic beads were applied to the column and allowed to run through. Stained and labeled cells (CD19+) were retained in the magnetic field surrounding the column while unstained cells (CD19+) passed through the column. The column was washed with degassed M-buffer. The magnetic field was removed and the CD19+ cells were collected.

Figure 14:
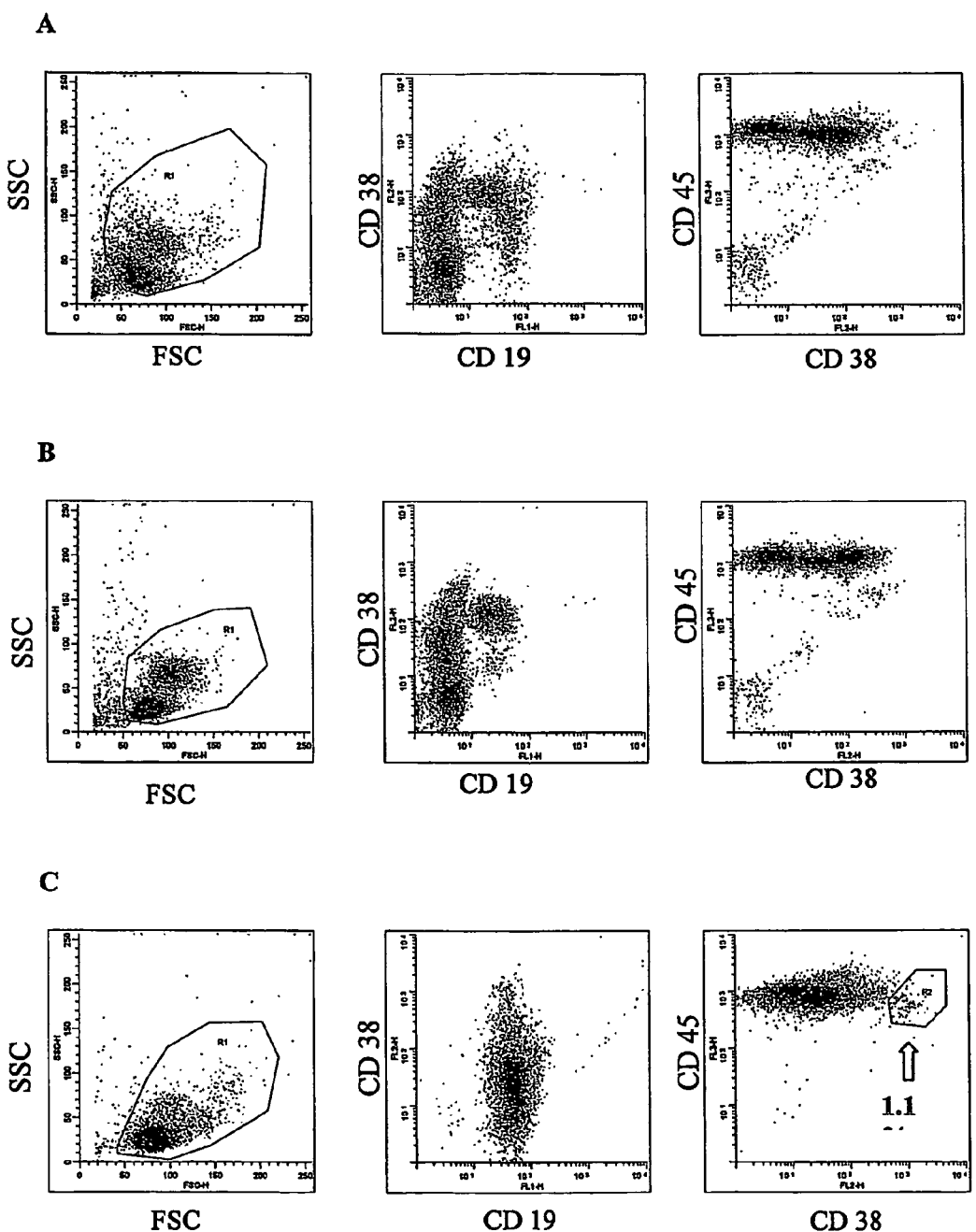
FIG. 14 shows dot plots of an analytic FACS staining of (A) PBMC purified from donor blood; (B) the magnetically sorted non-labelled CD19 negative cell fraction and (C) magnetically sorted CD19+ cells fraction. A scatter plot, a CD19/CD38 plot, and a CD38/CD45 plot is shown for each fraction.

An analytic staining of the starting material (PBMC), the unlabelled fraction and the CD19 labelled fraction from TT03, using anti-CD19-FITC, anti-CD38-PE, and anti-CD45-PerCP was performed (FIG. 14). This shows that the Magnetic cell sorting results in two distinct fractions compared to the PBMC fraction. The CD19 negative cells shown in panel B and the CD19 positive cells shown in panel C. Of the PBMC fraction 11% of the cells were CD19+, the extent of CD19 positive cell purification was 99.5% of R1 (the scatter gate in FIG. 14C) for TT03.

As seen in FIG. 14C, the anti-CD38/anti-CD45 plot showed a distinct population of CD38hi, CD45 in cells (R2) corresponding to 1.1% of R1. This population contained the plasma cells and was collected during the later sorting step. This indicated that in the PBMC is fraction 0.12% of the cells corresponded to plasma cells.

Figure 15:
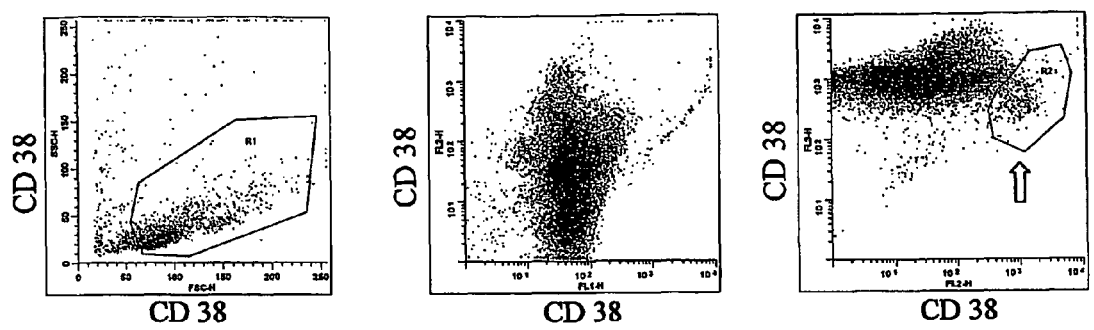
FIG. 15 shows the CD19+ fraction from FIG. 9C, which had been stored in liquid nitrogen, thawed and stained with anti-CD19, anti-CD38 and anti-CD45. Dot plots corresponding to FIG. 9C are shown.

The CD19 positive cell fraction was frozen in FCS (Invitrogen, Cat. No. 16000-044) +10% DMSO (Sigma, Cat. No. D2650) for later sorting. An analysis like the one seen in FIG. 14 was made on the MACS purified cells that had been frozen to make sure that the cells were intact (FIG. 15). The staining patterns seen in FIG. 15 were the same as seen in FIG. 14C although a slightly broader staining intensity were observed. The cells that were collected by sorting is the subset of R1 and R2. This corresponds to approx. 1.1% of the MACS purified cells.

d. Sorting of Plasma Cells

The frozen eluate from the MACS column was thawed, centrifuged and resuspended in FACS buffer (PBS, pH 7.2, 2% BSA) in a concentration of $1 \times 10^6$ cells/60 µl FACS buffer. Anti-CD19-FITC (Becton Dickenson, N.J., USA, cat. No 345776) (10 µl/$10^6$ cells), anti-CD38-PE (Becton Dickenson, N.J., USA, cat. No 555460) (10 µl/$10^6$ cells) and anti-CD45-PerCP (Becton Dickenson, N.J., USA, cat. No 345809) (20 µl/$10^6$ cells) were added, and the mixture was incubated at 4° C. for 20 min in the dark, followed by two times washing and resuspension in FACS buffer.

The cells were sorted by fluorescence activated cell sorting (FACS) using the following gating parameters:
  1. Forward scatter and side scatter in order to retain lymphocytes and monocytes including plasma blasters and plasma cells and to avoid dead cells and cells with very high side scatter which may be aggregates or granulocytes.
  2. Cells that are CD19 positive and express increased levels of CD38 (CD38hi) This is basically only a gate on CD38 since the PBMC's have been enriched on a MACS column for CD19 expression, but this will disclose any contaminants.
  3. CD45 intermediate positive cells. All lymphocytes express CD45. However, plasma cells down regulate their CD45 expression compared to earlier lymphocyte differentiation stages. Therefore, a discrete population of cells corresponding to plasma cells can be obtained when gating on CD45.

Figure 16:
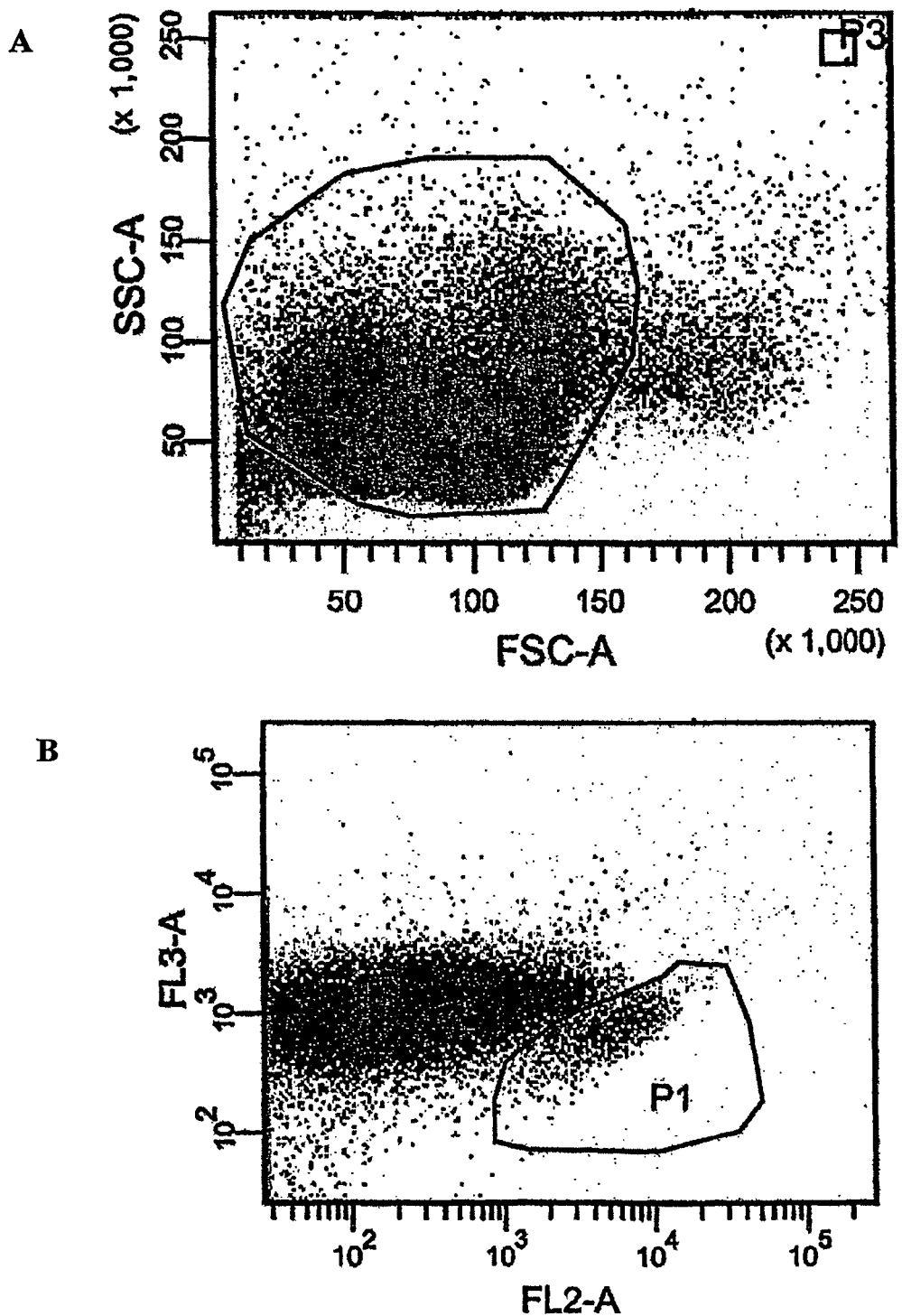
FIG. 16 shows gates used for sorting on the CD19+ cell fraction. A scatter gate and a fluorescence gate based on CD38 and CD45 were used for isolating the CD38high (CD38hi), CD45intermediate (CD45in) cells.

FACS sorted cells from donor TT03 were collected as the subset of the two gates P2 and P1 (FIGS. 16A and 16B, respectively). The cells were CD38hi (FL2-A), CD45 in (FL3-A) and CD19+, the latter due to the MACS purification. Briefly, the cells were collected in bulk, counted and diluted in RPMI (Invitrogen, Cat No. 21875-034) containing 10% FCS (Invitrogen Cat. No. 16000-044), 100 units/ml Penicillin-streptomycin (Invitrogen, cat. No. 15140-122), 2 mM L-glutamine (cat No. 25030-024). Cells were then dispensed into fifty 96 well PCR plates (ABgene, cat. No. AB-0800) with one cell per well in 5 µL medium. The plates were sealed and frozen immediately, and stored for later RT-PCR analysis.

e. Linkage of Cognate Pairs of Immunoglobulin Variable Region Encoding Sequences The multiplex overlap-extension RT-PCR technology was applied to the single cells obtained from donor TT03, thereby achieving cognate linkage of transcribed anti-Tetanus Toxoid heavy chain variable region and light chain variable region encoding sequences.

e-1. Single-Step Multiplex Overlap-Extension RT-PCR

The Qiagen One-Step RT-PCR kit (Qiagen cat. No 210212, Hilden, Germany) was used for the multiplex overlap-extension RT-PCR essentially according to the manufacturer's recommendation. Fifty frozen 96-well PCR plates containing approximately a single cell per well were removed from the freezer and when the wells were free of ice crystals, 15 µl RT-PCR reaction mixture was added immediately to each well.

The RT-PCR reaction mixture contained, in a total volume of 20 µl, the following reagents:
  1× One Step RT-PCR buffer
  dNTP's in a final concentration of 400 µM of each
  Multiplex overlap-extension primer mix in the concentrations as indicated in table 13
  0.8 µl One-step RT-PCR enzyme mix
  20 U RNase inhibitor (RNasin, Promega, Madison USA, cat. No N2515)

The composition of the multiplex overlap-extension primer mix is shown in table 13.

TABLE 13

| Primer name | Conc. | SEQ ID NO | primer sequence in 5' to 3' direction |
|---|---|---|---|
| $V_H$ | 40 nM of each | 116 | tattcccatggcgcgccCAGRTGCAGCTGGTGCART |
| | | 117 | tattcccatggcgcgccSAGGTCCAGCTGGTRCAGT |
| | | 118 | tattcccatggcgcgccCAGRTCACCTTGAAGGAGT |
| | | 119 | tattcccatggcgcgccSAGGTGCAGCTGGTGGAG |
| | | 120 | tattcccatggcgcgccCAGGTGCAGCTACAGCAGT |
| | | 121 | tattcccatggcgcgccCAGSTGCAGCTGCAGGAGT |
| | | 122 | tattcccatggcgcgccGARGTGCAGCTGGTGCAGT |
| | | 123 | tattcccatggcgcgccCAGGTACAGCTGCAGCAGTC |
| $C_{H (IgG)}$ | 200 nM | 9 | GACSGATGGGCCCTTGGTGG |
| $V_L$ | 40 nM of each | 124 | ggcgcgccatgggaatagctagccGACATCCAGWTGACCCAGTCT |
| | | 125 | ggcgcgccatgggaatagctagccGATGTTGTGATGACTCAGTCT |
| | | 126 | ggcgcgccatgggaatagctagccGAAATTGTGWTGACRCAGTCT |
| | | 127 | ggcgcgccatgggaatagctagccGATATTGTGATGACCCACACT |
| | | 128 | ggcgcgccatgggaatagctagccGAAACGACACTCACGCAGT |
| | | 129 | ggcgcgccatgggaatagctagccGAAATTGTGCTGACTCAGTCT |
| $C_{L\kappa}$ | 200 nM | 130 | atatatatgcggccgcTTAACACTCTCCCCTGTTGAA |

W = A/T, S = G/C, R = A/G. Capitalized sequences correspond to the gene-specific region Cycling conditions were as follows:

| Reverse transcription: | 30 min | 55° C. | |
|---|---|---|---|
| Polymerase activation: | 15 min | 95° C. | inactivates reverse transcriptase and activates Taq polymerase. |

PCR reaction:

| Denature | 30 sec | 94° C. | |
|---|---|---|---|
| Anneal | 30 sec | 52° C. | } 35 cycles |
| Extend | 5 min | 72° C. | |
| Final extension | 10 min | 72° C. | | e2. Additional Amplification

One microliter of the multiplex overlap-extension RT-PCR reaction product, from each sample, was subjected to semi-nested PCR (Biotaq kit, Bioline, UK cat. No BIO-21040), essentially as proposed by the manufacturer utilizing 96 well PCR plates (ABgene, cat No. AB-0800). The total volume of each reaction was 50 µl, containing a final concentration of 1× Biotaq buffer, 200 µM dNTP's (of each), 2 mM MgCl$_2$, 1.25 U Bio Taq polymerase and the primers shown in table 14.

TABLE 14

| Primer name | Conc. | SEQ ID NO | primer sequence in 5' to 3' direction |
|---|---|---|---|
| $J_H$ | 200 nM of each | 61 | ggaggcgctcGAGACGGTGACCAGGGTGCC |
| | | 62 | ggaggcgctcGAGACGGTGACCATTGTCCC |
| | | 63 | ggaggcgctcGAGACGGTGACCAGGGTTCC |
| | | 64 | ggaggcgctcGAGACGGTGACCGTGGTCCC |
| $C_{L\kappa}$ | 200 nM | 21 | accgcctccaccggcggccgcttaTTAACACTCTCCCCTGTTGAAGCTCTT |

Capitalized sequences correspond to the gene-specific region.

Cycling conditions were as follows:

| Denature | 30 sec | 95° C. | |
|---|---|---|---|
| Anneal | 30 sec | 55° C. | } 30 cycles |
| Extend | 1.5 min | 72° C. | |
| Final extension | 5 min | 72° C. | |

Figure 17:
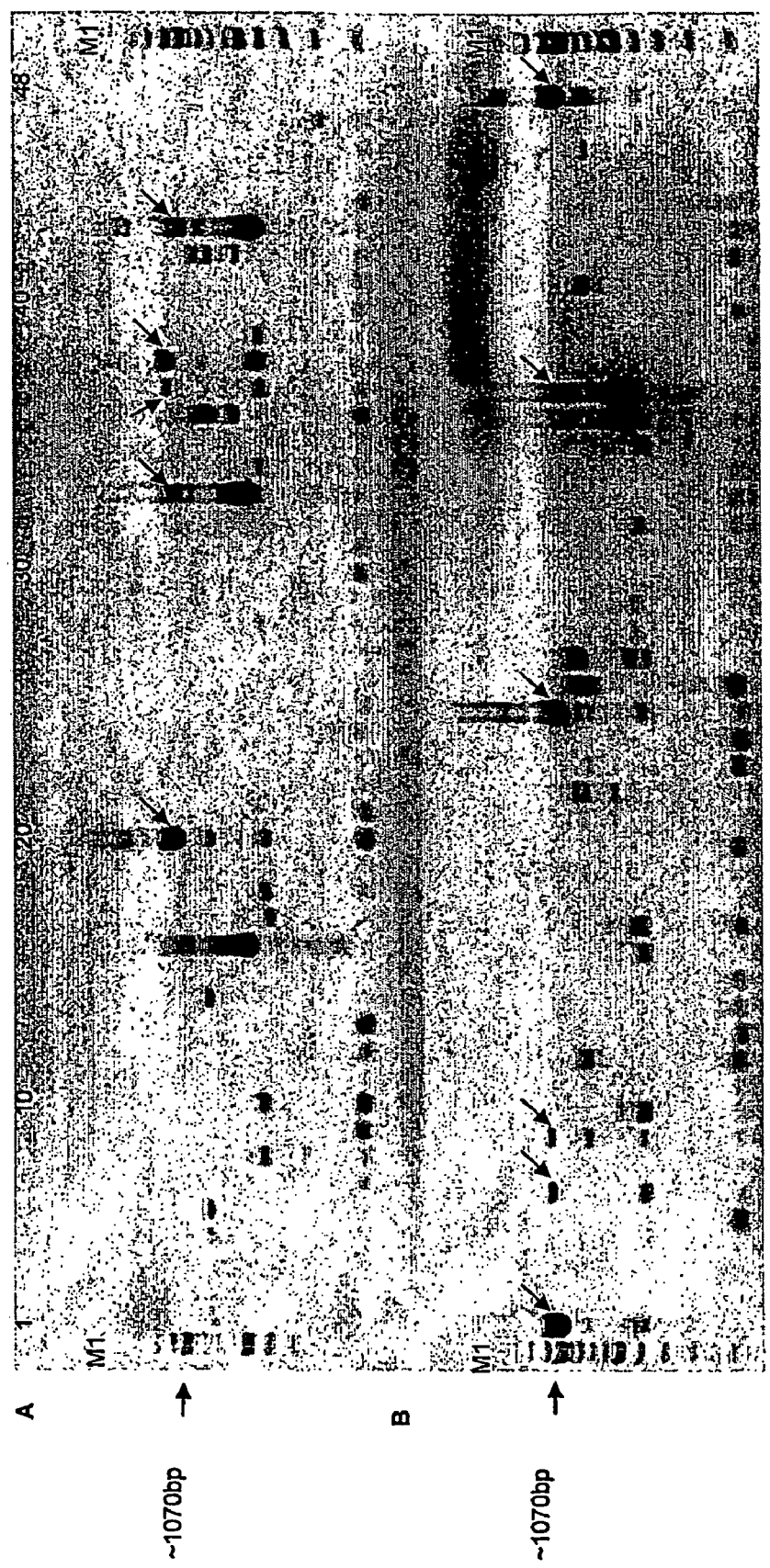
FIG. 17 is an electrophoretic gel showing the successful multiplex overlap-extension RT-PCR reaction on donor TT03 (row A, well 1-12 from eight 96 well plates). The samples have been applied to the agarose gel in two rows (A and B) with 48 samples in each. The expected size of the overlap-extension fragment was approximately 1070 bp. The putative overlap-extension fragments are marked with arrows.

Ten microliters of samples from row A, well 1-12 from each plate were analyzed by 1.5% agarose gel electrophoresis using ethidium bromide for visualization, in order to verify that the multiplex overlap-extension RT-PCR was successful. The expected size of the overlap-extension fragment was approximately 1070 bp (the exact size depends upon the lengths of the variable regions). FIG. 17 shows samples from eight 96 well plates. The average number of successful overlap-extension RT-PCR fragments from fifty 96 well plates, was estimated to eight per plate. Thus, the total number of successful overlap-extension RT-PCR fragments were estimated to approximately 400.

Ten microliters from all the performed reactions, run in the 96 well plates, originating from the same donor, were consolidated in a single tube. An aliquot consisting of 200 µl of the pooled PCR products were subsequently purified using QIAquick PCR purification kit according to the manufactures procedure (Qiagen cat. No. 28106, Hilden, Germany) using 60 microliters buffer EB for elution. The purified pool of overlap PCR products was digested with XhoI and NotI and subsequently purified by preparative 1% agarose gel electrophoresis; the overlap-extension fragments are excised from the agarose gel and purified using a Qiaex II kit (Qiagen cat. No 20051, Hilden, Germany).

f. Cognate Fab Expression Library

A Fab expression library was generated by a two-step ligation procedure. Initially the pool of digested overlap-extension fragments described above was ligated into the XhoI/NotI digested E. coli vector JSK301 (FIG. 11). The ligation reaction was subsequently transformed into electrocompetent E. coli cells (XL1-Blue electroporation competent, Stratagen, cat. No. 200228, La Jolla, USA), according to manufactures instructions. The transformed E. coli cells were plated onto 2×YT agar containing 100 µg/ml carbenicillin. Biomass corresponding to approximately $10^{10}$-$10^{11}$ cells originating from a number of independent colonies that exceeded at least 5 times the total number of overlap PCR products was used as starting material for plasmid preparation using Qiagen Plasmid preparation Maxi kit (Qiagen cat. No. 12163, Hilden, Germany). To enable Fab expression of the cloned cognate linked VH and VL encoding sequences, a prokaryotic promoter and leader cassette was inserted in a second ligation step. The used bi-directional promoter fragment (SEQ ID NO 321) was extracted from the parental JSK301 by AscI/NheI digestion. The purified pool of plasmids was likewise digested with AscI/NheI restriction endonucleases and gel purified as previously described. The purified fragments were subsequently ligated and transformed into electrocompetent E. coli cells (TG1, Stratagene, cat. No. 200123, La Jolla, USA) and plated on 2×YT agar containing 1100 g/ml carbenicillin, and 1% glycose. The Fab expression library generation process is outlined in FIG. 12.

g. Screening of Clones

Fab expressing clones were screened for TT antigen-binding by antigen-specific ELISA assays.

g-1. Master Plate Generation and Fab Expression

Individual selected colonies of the TG1 cells, each harbouring a cognate Fab expression vector from the library generated as described in section (f) were picked into single wells of 96 well plates containing 2×YT/100 µg/ml Carb/1% glucose. The plates were incubated overnight at 37° C. with gentle shaking. Four 96 well plates were consolidated into the wells of one 384 well plate, containing 2×YT/100 µg/ml Carb/1% glucose, using 96 pin replicators. The 384 well plates were incubated overday at 37° C. These plates are referred to as master plates, and they were stored at −80° C. after addition of glycerol to a final concentration of 15%.

The masterplates were used for inoculation of 384 Deep-Well plates containing 2×YT/100 µg/ml Carb 0.1% glucose using a 96 pin replicator. The plates were sealed and incubated for 2-3 h at 37° C. with shaking.

Fab expression was induced by adding an equal volume of 2×YT/100 µg/ml Carb/0.2 mM IPTG, obtaining a final IPTG concentration of 0.1 mM. The plates were sealed and incubated overnight at 30° C. with shaking. The following day, the Fab-containing supernatants were analyzed for TT antigen-binding specificity by ELISA.

g-2. ELISA Analysis

Three hundred and eighty four (384) well ELISA plates (Corning Inc., Corning, N.Y., USA, cat. No 3700) were coated overnight at 4° C. with Tetanus Toxoid (TT) antigen, diluted to a final concentration of 1 µg/ml in PBS in a volume of 25 µl per well. Excess binding sites as of the wells were blocked for 1 h at room temperature (RI) by adding 2% M-PBS-T (2% skim milk powder in PBS, 0.05% Tween 20). The wells were washed 2 times with PBS-T (PBS, 0.05% Tween 20).

The Fab-containing bacterial supernatants from section (g-1) were diluted 1:2 in 2% M-PBS-T, and transferred to the ELISA wells in duplicate. Incubation was performed for 1 h at RT. The wells were washed 4 times with PBS-T. Goat-anti-human Fab/HRP (Sigma, St. Louis, Mo., USA, cat. No A0293) 1:10.000 dilution in 2% M-PBS-T was added to the wells. Incubation was performed for 1 h at RT. The wells were washed 4 times with PBS-T. TMB Plus (KemEnTec, Copenhagen, Denmark, cat. No 4390L) substrate was added and incubation was performed for 5-15 minutes. The reactions were stopped by adding an equal volume of 1 M $H_2SO_4$, and analyzed using a spectrophotometer at 450 nm (Multiscan Ascent, Labsystems, Franklin, USA).

The original bacterial clones corresponding to TT antigen-binding clones may subsequently be retrieved from the original master plates. Plasmid DNA can be prepared from the isolated antigen positive Fab clones, generating a cognate Fab expression sub-library of TT antigen-binding clones.

A subset of the clones were further analyzed by an anti-kappa ELISA assay, in order to get a correlation between the number of antigen-binding clones and the number of Fab expressing clones. The anti-kappa assay was generally performed as the TT-assay, except that the wells were coated with a 1:1000 dilution of goat anti-human kappa antibody (Caltag, Calif., USA, Cat. No H16000), using a carbonate buffer, pH 9.6.

g-3. Screening Results

Clones from four 384 well plates were screened for reactivity with anti-kappa Ab and TT using ELISA assays according to the procedure described in g-2. The results obtained results are summarized in the tables 15 through 19. The anti-kappa ELISA results inform about the expression of Fab fragments in a given clone, the TT ELISA results inform about the functionality of the Fab fragments.

TABLE 15

ELISA screening, anti-kappa coat (1440 clones in total)

| Plate # | 2 × background | 3 × background | 4 × background |
|---|---|---|---|
| G050 | 105 | 79 | 73 |
| G051 | 93 | 79 | 68 |
| G052 | 120 | 96 | 73 |
| G053 | 164 | 141 | 125 |
| Sum | 482 | 395 | 339 |
| % Fab pos. clones | 34% | 27% | 24% |

Of 1440 single clones analyzed, 482 clones or 34% exhibited anti-Kappa reactivity at a level exceeding 2× background reactivity. 395 clones or 27% of the clones showed reactivity above 3× background, etc.

The same clones were analyzed for TT-antigen reactivity by ELISA, and results are given in table 16 below:

TABLE 16

ELISA screening, TT coat (1440 clones in total)

| Plate # | 2 × background | 3 × background | 4 × background |
|---|---|---|---|
| G050 | 26 | 19 | 17 |
| G051 | 24 | 18 | 15 |
| G052 | 34 | 31 | 24 |
| G053 | 46 | 36 | 30 |
| Sum | 130 | 104 | 86 |
| % TT pos. clones | 9.0% | 7.2% | 6.1% |

From this table it is seen that 9.0% clones showed reactivity with TT at 2× background (defined as the signal obtained by the reactivity of a Fab fragment with a irrelevant specificity). 104 clones reacted at 3× background (7.2%) etc.

Of the Fab-positive clones (482 clones in total), approximately 27% of the clones (130/482) exhibited reactivity with TT at the 2× background level. This level does not change significantly at the other background levels.

Six 384 well plates were screened for clones with TT reactivity. The number of clones giving rise to reactivity with the antigen are shown in the table 17. Anti-kappa ELISA was not carried out with these plates.

TABLE 17

ELISA screening, TT coat (2160 clones in total)

| Plate # | 2 × background | 3 × background | 4 × background |
|---|---|---|---|
| G054 | 82 | 65 | 52 |
| G055 | 30 | 24 | 21 |
| G056 | 25 | 23 | 21 |
| G057 | 30 | 28 | 26 |

TABLE 17-continued

ELISA screening, TT coat (2160 clones in total)

| Plate # | 2 × background | 3 × background | 4 × background |
|---|---|---|---|
| G058 | 24 | 21 | 19 |
| G059 | 18 | 14 | 13 |
| Sum | 209 | 175 | 151 |
| % TT pos. clones | 9.7% | 8.1% | 7.0% |

The percentage of TT positive clones in plates G054-G059 was comparable to what was found in plates G050-G053 (table 16).

The results from all the clones screened against TT (table 16 and 17) are summarized in table 18.

TABLE 18

All clones screened, TT reactive clones

| Plates | 2 × background | 3 × background | 4 × background |
|---|---|---|---|
| G050-G053 | 130 | 104 | 86 |
| G054-G059 | 209 | 175 | 151 |
| Sum | 339 | 279 | 237 |
| % of total (3600) | 9.4% | 7.8% | 6.6% |

In summary, a total of 339 clones showed reactivity with TT at least at 2× background levels (table 18). This corresponds to 9.4% of all clones screened.

Figure 18:
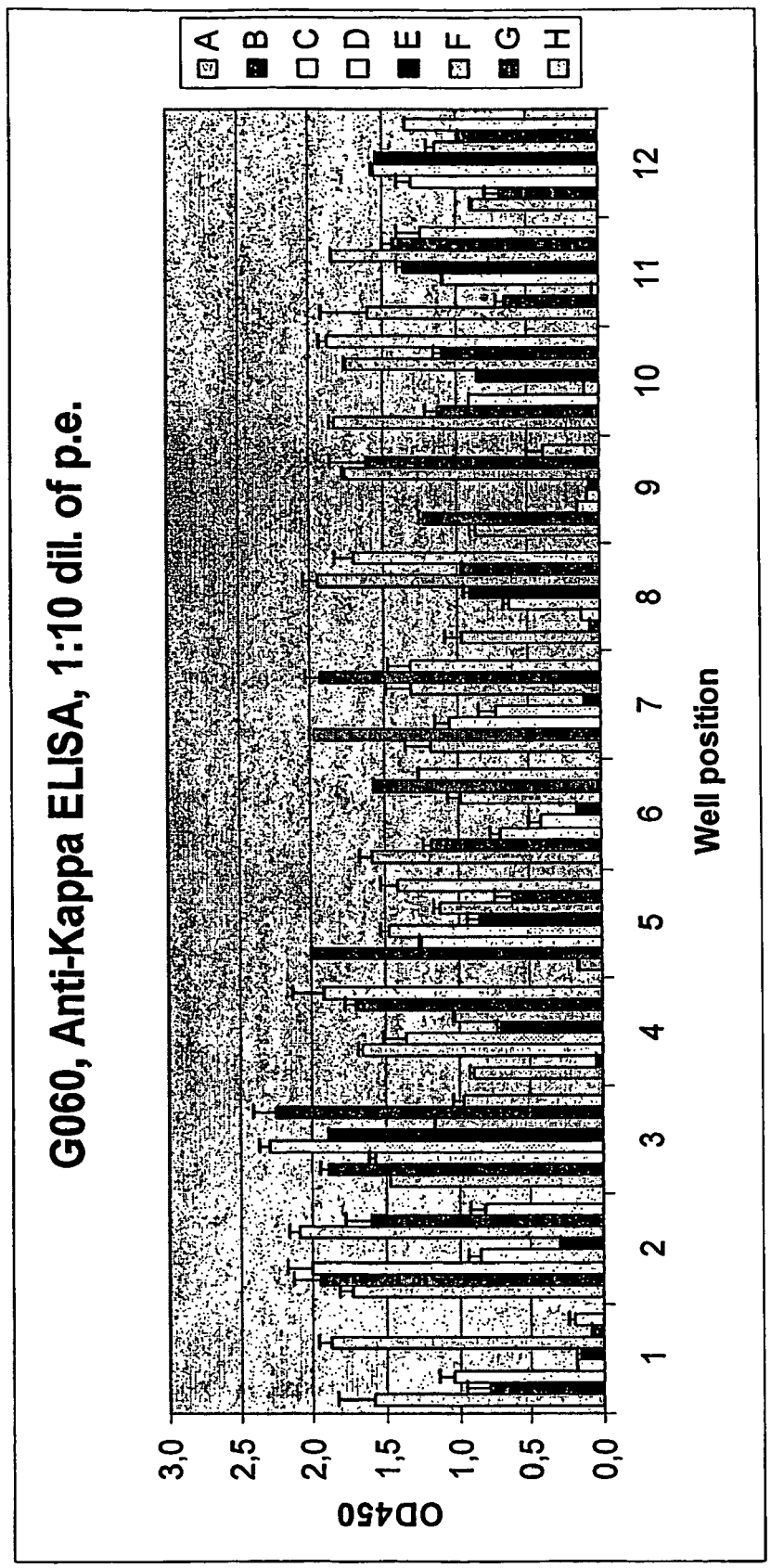
FIG. 18 shows ELISA analysis of periplasmic extracts from plate G060. The ELISA plate was coated with goat (gt)-anti-human Kappa, and captured Fab fragments were detected with a HRP-conjugated gt-anti-human Fab-specific antibody.
Figure 20:
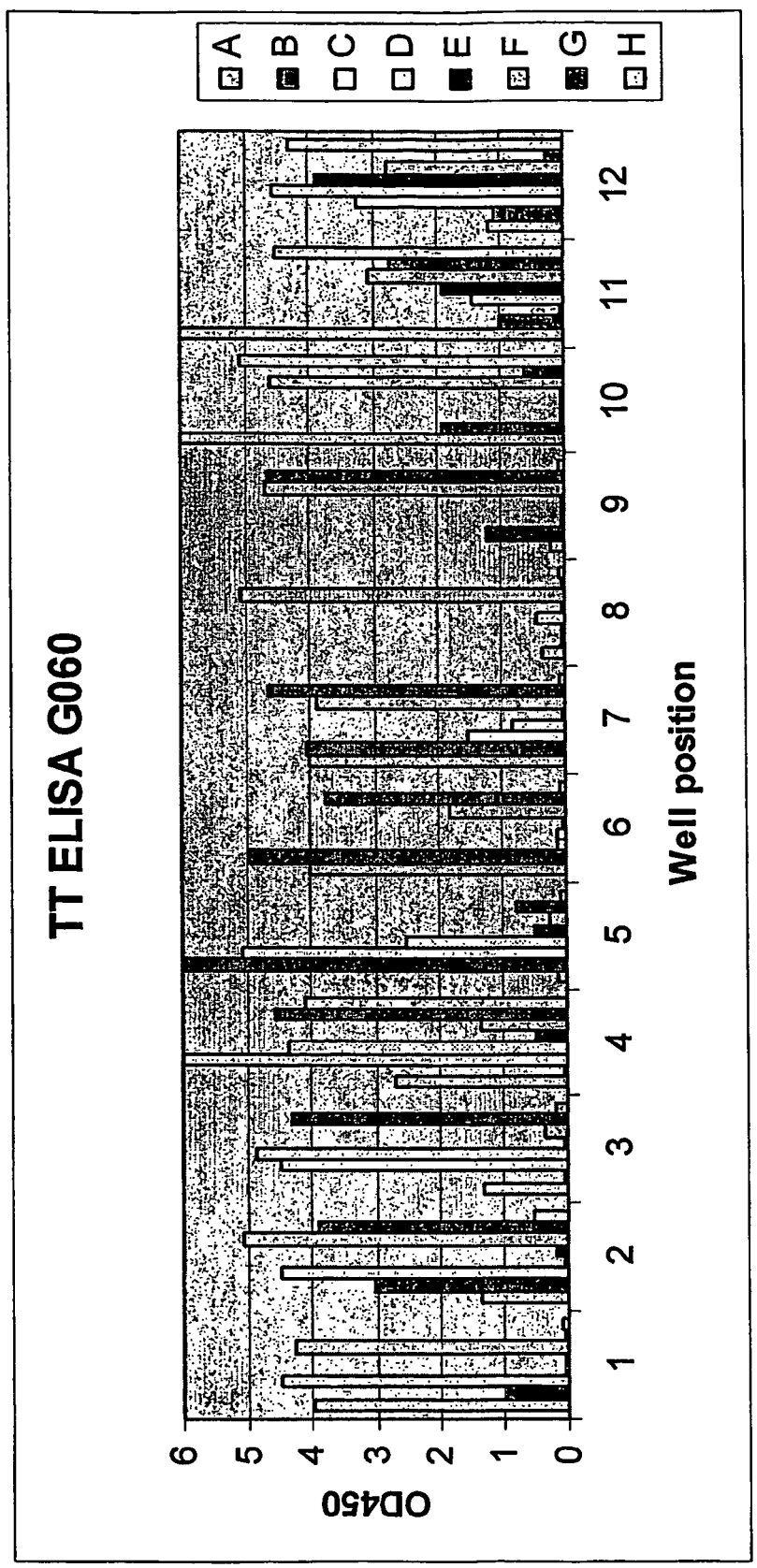
FIG. 20 shows ELISA analysis of periplasmic extracts from plate G060. The ELISA plate was coated with Tetanus Toxoid, and captured Fab fragments were detected with a HRP-conjugated gt-anti-human Fab-specific antibody.
Figure 21:
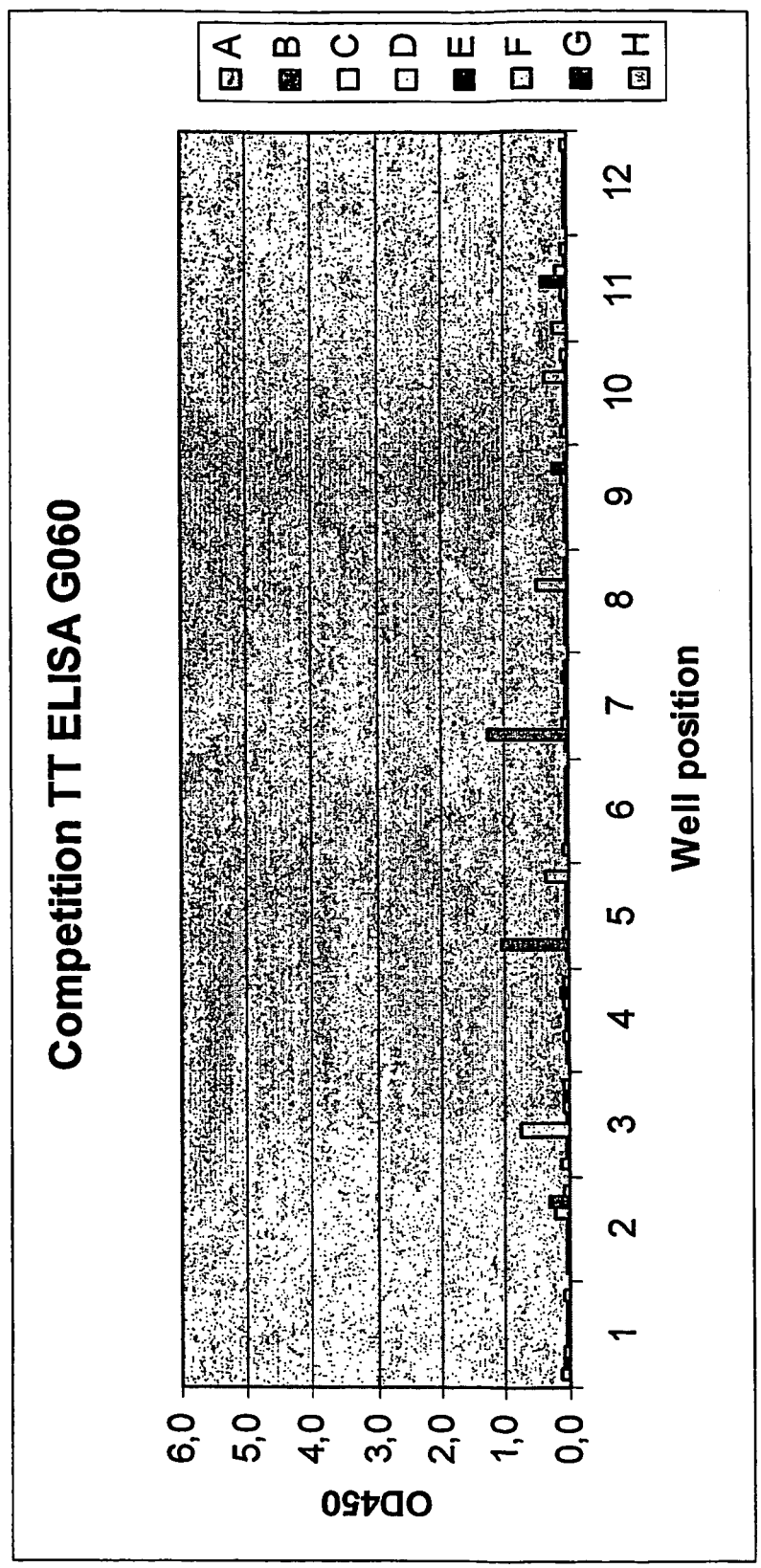
FIG. 21 shows a one step competition ELISA analysis of periplasmic extracts from plate G060. The ELISA plate was coated with Tetanus Toxoid (TT), and soluble TT was added to each well at $10^{-7}$ M in order to compete for the binding of Fab fragments from the bacterial supernatants, to immobilized TT. Captured Fab fragments were detected with a HRP-conjugated gt-anti-human Fab-specific antibody.

All positive clones exhibiting reactivity with TT at 2× background was inoculated into 96 well plates as previously described, from the master plate. The next day, the bacteria was collected by centrifugation at 4000 rpm for 15 minutes, and the pellet was resuspended in 0.8 mM EDTA, 0.4×PBS, 0.8 M NaCl, and incubated on ice for 15 minutes. The periplasmic extract was collected by centrifugation, and the reactivity of the clones was further analyzed. Here we show results from one such plate (G060) for reactivity with anti-Kappa (FIG. 18), Ovalbumin (unrelated antigen) (FIG. 19), TT (FIG. 20), and a one-step competitive assay using $10^{-7}$ M concentration of TT-antigen in solution (FIG. 21). These ELISA assays were performed on the same periplasmic extract, at the same dilution.

Figure 19:
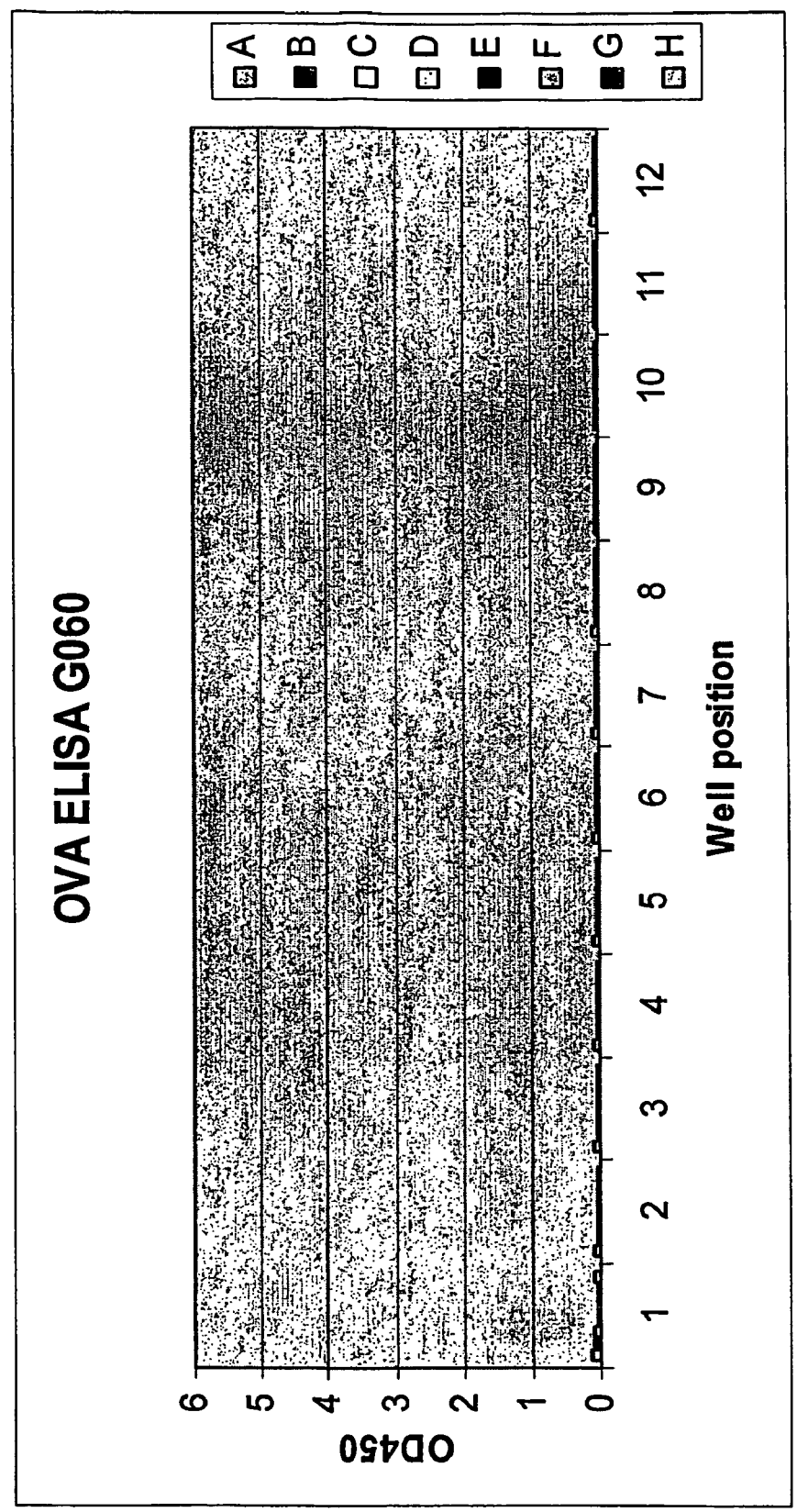
FIG. 19 shows ELISA analysis of periplasmic extracts from plate G060. The ELISA plate was coated with 10 µg/ml Ovalbumin (Sigma A-5503), and captured Fab fragments were detected with a HRP-conjugated gt-anti-human Fab-specific antibody.

Most of the clones expressed Fab fragments (90/96) (FIG. 13), and no clones reacted with Ovalbumin (FIG. 19). The reactivity with immobilized TT was reduced or completely inhibited by TT in solution (FIG. 21), indicating that the clones react specifically with TT. The reactivity of the clones in plate G060 is summarized in table 19.

TABLE 19

Summary of G060 plate (96 clones in total)

| Background level | Anti-Kappa positive | TT positive |
|---|---|---|
| 2× | 94% (90/96) | 74% (71/96) |
| 3× | 91% (87/96) | 72% (69/96) |
| 4× | 84% (81/96) | 69% (66/96) | h. Diversity Analysis and Clone Approval

Plasmid isolated from 47 clones (from plate G060) from the cognate TT antigen-binding Fab expression sub-library were subjected to sequence analysis. The variable heavy chain encoding sequences were sequenced using primer LSN-HCP: AGGAAACAGGAGATATACAT (SEQ ID NO131), annealing to the P tac promoter, and the light chain encoding sequences were sequenced using primer LSN-LCP: TCGCCAAGGAGACAGTCATA (SEQ ID NO132), annealing to the P lac promoter. The sequence data was analysed using the Vector NTI software (Informax, Frederick, Md., USA). The resulting sequence data of the heavy chain was trimmed to one base pair 5' of the upstream AscI restriction site and immediately 3' of the downstream XhoI restriction site. The light chain sequence data was trimmed to the second 5' base pair of the upstream NheI restriction site and 3' of the last codon "AAA" encoding the variable chain C-terminal lysine. The trimming was performed in order to facilitate further analysis such as translation of each DNA sequence.

The variable heavy and light chain encoding sequences were analyzed for germline gene usage by comparing the sequences to the V-base germline variable region sequence database (MRC Centre for Protein Engineering, Cambridge, UK). The closest related germline allele was thus determined for each sequence showing a V-gene repertoire originating from 12 different variable heavy chain germline alleles belonging to VH-family VH1 through VH5 and 8 different variable kappa light chain germline alleles belonging to VKI, VKIII and VKIV (Table 20).

Furthermore, the variable gene sequences were translated into protein sequences which were aligned using the AlignX software (Informax, Frederick, Md., USA) as depicted in FIG. 22 and FIG. 23. Based on the protein sequence alignments, the variable chain sequences could be categorized into groups according to V(D)J rearrangement events, designated with H for the variable heavy chain sequence and L for the variable kappa chain sequence followed by a unique number. In each rearrangement group, the sequences were categorized according to the maturation genotype (M-type in table 20) within the CDR1, 2 and 3 regions, represented by a lower case letter in alphabetical order. Seven of the clones had premature stop codons, Whereof 6 clones were an amber mutation (TAG) (clone IDs g060:b12, d08, f06, c12, f03, c04) and 1 clone was an opal mutation (TGA) (clone ID g060: h12). These codons were most likely suppressed by *E. coli* resulting in functional Fab fragments. Four of these clones were members of groups containing similar clones making them redundant. Additional clones would have to be analyzed in order to replace the remaining 3 clones with premature stop codons as they were single members of their groups. Alternatively, the sequences could be corrected by standard molecular biology techniques such as PCR, replacing the stop codon with an appropriate codon.

The 47 analyzed V-region sequences could be divided into 20 unique V(D)J rearrangement groups (designated "groups" in table 20) both for the variable heavy and variable kappa gene. Four of the rearrangement groups could further be divided into 1 to 4 maturation types (a through d), resulting in 27 unique antibody encoding sequences (Table 12). Generally, specific heavy chain rearrangement groups combine with specific light chain rearrangement groups (e.g. H1 with L1, H12 with L24 and so forth). Further, the maturation type match among pairs of variable heavy chain and the variable light encoding sequences (e.g. H4c match with L13c). Such stringency in paring among rearrangement groups and maturation types indicating cognate paring of the variable region encoding sequences.

However, heavy chain rearrangement group H4 is an exception. H4 pairs with two different light chains L28 and L13. L13 was unique to H4, comprising maturation types a, b and c that matches with L13 maturations types. L28, on the other hand, was also found paired with the single member in heavy chain group H2. Two out of seven H4a heavy chain sequences pair with heavy chain L13a and five out of seven H4a heavy chain sequences pair with L28a In summary, these observations suggested a multiplex overlap-extension RT-PCR event where two TT-specific antibody producing plasma cells, with the genotype combinations H2-L28 and H4a-L13a, were present in a single well. Rare scrambling events of the light chain and heavy chain gene pairing, such as for H2 and H4a with L28, was expected as the experiment was based on limiting dilution of plasma cells.

The sequence identity among individual cognate pairs of the variable heavy chain and variable light chain encoding sequences from the same group and maturation type is at least 90% and preferably at least 95%. Take for example g060g03 and g060a01 from group H1 maturation type a Clone g060g03 correspond to nucl. SEQ ID pair 168:215, where the variable heavy chain encoding sequence correspond to SEQ ID NO 168 and the variable light chain encoding sequences correspond SEQ ID NO 215. Clone g060a01 correspond to nucl. SEQ ID pair 133:180. When SEQ ID NO 168 is aligned with SEQ ID NO 133 (the variable heavy chains) 4/369 bases are not identical and for the variable lights chains (SEQ ID NOs 215 and 180) 8/327 bases are not identical, this correspond to a sequence identity of 98.3% between these two cognate pairs (g060g03 and g060a01). However, when looking at sequence identity among different groups it is not expected that the sequence identity will be high, since it is a polyclonal sub-library and diversity is desired. In this particular example the lowest identity among the cognate pairs is approximately 40% (e.g. g060b11 and g060h11 have a sequence identity of 39.5%).

One embodiment of the present invention is a sub-library of cognate pairs of immunoglobulin heavy chain variable region and light chain variable region encoding sequences, where the immunoglobulins obtainable from said library are capable of reacting with or binding to Tetanus Toxin.

A further embodiment of the present invention is such a sub-library of cognate pairs of immunoglobulin heavy chain variable region and light chain variable region encoding sequences, comprising individual cognate pairs with at least 90% sequence identity with one individual SEQ ID pair, selected from the group consisting of SEQ ID pairs 135:182, 168:215, 146:193, 151:198, 173:220, 152:199, 164:211, 148: 195, 137:184, 169:216, 138:185, 143:190, 161:208, 166:213, 157:204, 139:186, 134:181, 150:197, 156:203, 158:205, 170: 217, 178:225, 141:188 or 144:191.

TABLE 20

| Clone ID | Group | M-type | Family | Germ-line | Seq nucl. | Seq prot. | Group | M-type | Family | Germ-line | Seq nucl. | Seq prot. |
|---|---|---|---|---|---|---|---|---|---|---|---|---|
| | | | VH | | | | | | Vkappa | | | |
| g060a03 | H1 | b | VH1 | DP-14 | 135 | 229 | L1 | b | VKI | DPK9 | 182 | 276 |
| g060g03 | H1 | a | VH1 | DP-14 | 168 | 262 | L1 | a | VKI | DPK9 | 215 | 309 |
| g060a01 | H1 | a | VH1 | DP-14 | 133 | 227 | L1 | a | VKI | DPK9 | 180 | 274 |
| g060b12 | H11 | a | VH3 | DP-77 | 145 | 239 | L10 | a | VKIII | DPK22 | 192 | 286 |
| g060c03 | H11 | a | VH3 | DP-77 | 146 | 240 | L10 | a | VKIII | DPK22 | 193 | 287 |
| g060d08 | H11 | a | VH3 | DP-77 | 154 | 248 | L10 | a | VKIII | DPK22 | 201 | 295 |
| g060f06 | H11 | a | VH3 | DP-77 | 162 | 256 | L10 | a | VKIII | DPK22 | 209 | 303 |
| g060d04 | H12 | a | VH1 | DP-10 | 151 | 245 | L24 | a | VKI | DPK4 | 198 | 292 |
| g060h02 | H12 | a | VH1 | DP-10 | 175 | 269 | L24 | a | VKI | DPK4 | 222 | 316 |
| g060h10 | H12 | a | VH1 | DP-10 | 177 | 271 | L24 | a | VKI | DPK4 | 224 | 318 |
| g060g11 | H12 | b | VH1 | DP-10 | 173 | 267 | L24 | b | VKI | DPK4 | 220 | 314 |
| g060d05 | H12 | c | VH1 | DP-10 | 152 | 246 | L24 | c | VKI | DPK4 | 199 | 293 |
| g060f09 | H12 | d | VH1 | DP-10 | 164 | 258 | L24 | d | VKI | DPK4 | 211 | 305 |
| g060c07 | H15 | a | VH5 | DP-73 | 148 | 242 | L16 | a | VKIII | DPK22 | 195 | 289 |
| g060d11 | H15 | a | VH5 | DP-73 | 155 | 249 | L16 | a | VKIII | DPK22 | 202 | 296 |
| g060g02 | H15 | a | VH5 | DP-73 | 167 | 261 | L16 | a | VKIII | DPK22 | 214 | 308 |
| g060a09 | H16 | — | VH1 | DP-73 | 44137 | 231 | L4 | — | VKI | DPK9 | 184 | 278 |
| g060g04 | H17 | a | VH4 | DP-66 | 169 | 263 | L3 | a | VKI | DPK9 | 216 | 310 |
| g060h04 | H17 | a | VH4 | DP-66 | 176 | 270 | L3 | a | VKI | DPK9 | 223 | 317 |
| g060a10 | H18 | a | VH2 | VII-5 | 138 | 232 | L21 | a | VKI | L12a | 185 | 279 |
| g060h12 | H18 | a | VH2 | VII-5 | 179 | 273 | L21 | a | VKI | L12a | 226 | 320 |
| g060b09 | H19 | a | VH2 | VII-5 | 143 | 237 | L23 | a | VKI | DPK8 | 190 | 284 |
| g060f10 | H19 | a | VH2 | VII-5 | 165 | 259 | L23 | a | VKI | DPK8 | 212 | 306 |
| g060f05 | H2* | — | VH1 | DP-88 | 161 | 255 | L28* | a | VKIV | DPK24 | 208 | 302 |
| g060f11 | H21 | a | VH3 | DP-32 | 166 | 260 | L31 | a | VKI | DPK9 | 213 | 307 |
| g060g12 | H21 | a | VH3 | DP-32 | 174 | 268 | L31 | a | VKI | DPK9 | 221 | 315 |
| g060f01 | H10 | — | VH3 | COS-8 | 157 | 251 | L7 | — | VKI | DPK8 | 204 | 298 |
| g060a11 | H23 | a | VH3 | DP-77 | 139 | 233 | L5 | a | VKI | DPK9 | 186 | 280 |
| g060c12 | H23 | b | VH3 | DP-77 | 149 | 243 | L5 | b | VKI | DPK9 | 196 | 290 |
| g060f03 | H24 | — | VH3 | DP-38 | 159 | 253 | L20 | — | VKI | DPK8 | 206 | 300 |
| g060a02 | H3 | — | VH3 | DP-77 | 134 | 228 | L9 | — | VKI | O16 | 181 | 275 |
| g060d03 | H4 | a | VH1 | DP-88 | 150 | 244 | L13 | a | VKIII | DPK22 | 197 | 291 |
| g060f08 | H4 | a | VH1 | DP-88 | 163 | 257 | L13 | a | VKIII | DPK22 | 210 | 304 |
| g060b05 | H4* | a | VH1 | DP-88 | 140 | 234 | L28* | a | VKIV | DPK24 | 187 | 281 |
| g060b07 | H4* | a | VH1 | DP-88 | 142 | 236 | L28* | a | VKIV | DPK24 | 189 | 283 |
| g060f04 | H4* | a | VH1 | DP-88 | 160 | 254 | L28* | a | VKIV | DPK24 | 207 | 301 |
| g060g10 | H4* | a | VH1 | DP-88 | 172 | 266 | L28* | a | VKIV | DPK24 | 219 | 313 |
| g060d07 | H4* | a | VH1 | DP-88 | 153 | 247 | L28* | a | VKIV | DPK24 | 200 | 294 |
| g060e05 | H4 | c | VH1 | DP-88 | 156 | 250 | L13 | c | VKIII | DPK22 | 203 | 297 |
| g060f02 | H4 | b | VH1 | DP-88 | 158 | 252 | L13 | b | VKIII | DPK22 | 205 | 299 |
| g060g09 | H4 | c | VH1 | DP-88 | 171 | 265 | L13 | c | VKIII | DPK22 | 218 | 312 |
| g060c04 | H6 | — | VH1 | DP-88 | 147 | 241 | L12 | — | VKIII | DPK22 | 194 | 288 |
| g060g07 | H20 | — | VH4 | DP-71 | 170 | 264 | L8 | a | VKI | DPK9 | 217 | 311 |

TABLE 20-continued

| | | | VH | | | | | | Vkappa | | | Seq |
|---|---|---|---|---|---|---|---|---|---|---|---|---|
| Clone ID | Group | M-type | Family | Germ-line | Seq nucl. | Seq prot. | Group | M-type | Family | Germ-line | Seq nucl. | prot. |
| g060h11 | H7 | — | VH2 | VII-5 | 178 | 272 | L18 | — | VKI | L12a | 225 | 319 |
| g060b06 | H8 | a | VH3 | DP-46 | 141 | 235 | L17 | a | VKI | DPK1 | 188 | 282 |
| g060a04 | H8 | a | VH3 | DP-46 | 136 | 230 | L17 | a | VKI | DPK1 | 183 | 277 |
| g060b10 | H9 | — | VH1 | DP-14 | 144 | 238 | L30 | — | VKI | DPK1 | 191 | 285 |

Asterisk indicates V encoding sequences implicated in scrambling.
Seq prot. indicates SEQ ID numbers from the sequence list corresponding to the protein sequences and
Seq nucl. indicate SEQ ID numbers corresponding to the nucleic acid sequence in the sequence list i. Apparent Affinities A competition assay was set up in order to determine the apparent affinity or $IC_{50}$ of selected clones from plate G060.

Briefly, Fab fragments were expressed in 50 ml cultures as follows: 50 ml 2×YT/100 µg/ml Carb/0.1% glucose was added 0.5 ml overnight culture, and shaken for approximately 2 h at 37° C. IPTG was added to a final concentration of 0.1 mM, and shaking was continued overnight at 30° C. The next day, the bacteria were collected by centrifugation at 4000 rpm for 15 minutes, and the pellet was resuspended in 1 ml 0.8 mM EDTA, 0.4×PBS, 0.8 M NaCl, and incubated on ice for 15 minutes. The periplasmic extract was collected by centrifugation, and stored at −20° C.

Figure 24:
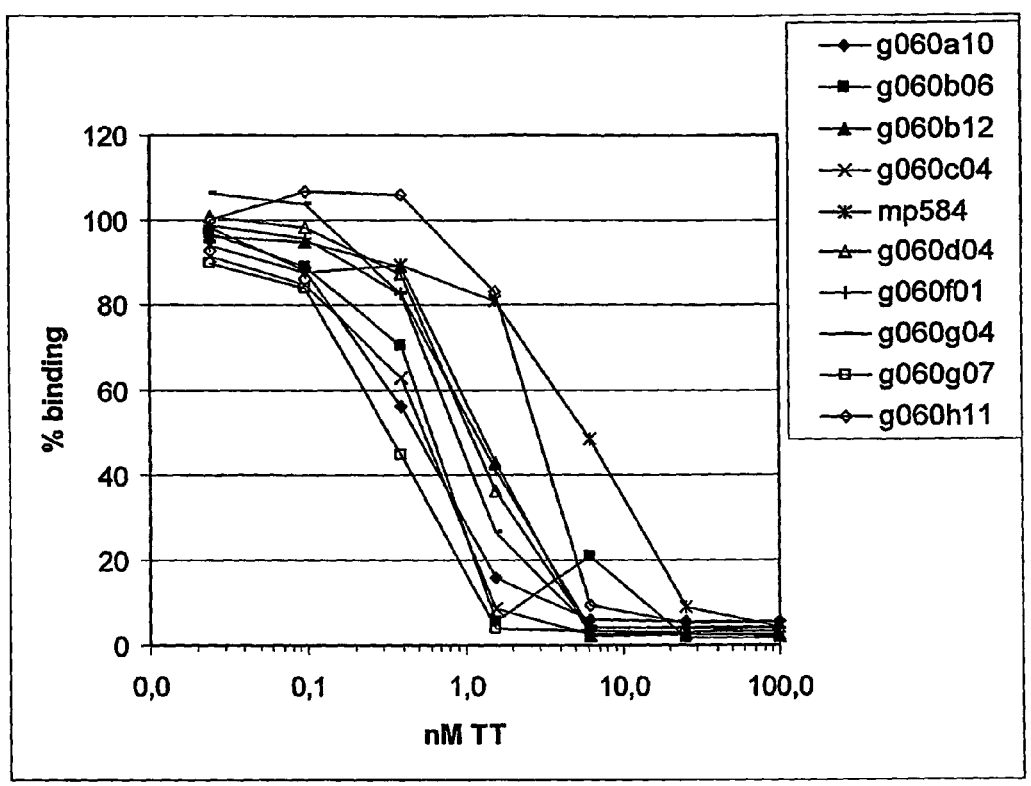
FIG. 24 shows a competition ELISA assay for determination of apparent affinities of selected clones from plate G060. Soluble TT dilutions in concentrations from 100 nM to 25 pM (four-fold dilutions) were added to the Fab fragments, thereby competing out the binding of the Fab-fragments to immobilized TT. The extents of the reactions are given as the ratio of the observed binding at a given soluble TT concentration to the binding found when no soluble TT was added to the reactions.

The competition assay was performed as follows: the periplasmic extracts in appropriate dilutions estimated by titration were added to a series of tubes. As a positive control the phage display derived Fab fragment mp584, derived from the human hybridoma cell line HB8501 expressing an anti-TT antibody was used. Soluble TT was added to the first tube at 100 nM concentration, and subsequently diluted at four-fold steps in the following tubes, making a total of seven dilutions of TT (from 100 nM to 25 pM). The reactions were incubated for approximately 45 minutes at room temperature. The samples were transferred to ELISA plates coated with TT at 1 µg/ml, and blocked as previously described. The plates were incubated for 1 h at room temperature, followed by 4× wash with PBS-T, goat-anti-human Fab/HRP was added at a 1:10.000 dilution, and incubated for 1 h. TMB Plus substrate (KemEnTech, Denmark, cat. No. 4390A) was added, incubation was performed for approximately 10 minutes, and the reactions were stopped with 1 M $H_2SO_4$. The plates were read at 450 nm. The data are plotted in FIG. 24.

The apparent affinities of the analyzed clones are given in the table 21:

TABLE 21

| Clone | Apparent affinity |
|---|---|
| g060a10 | 0.50 nM |
| g060b06 | 0.60 nM |
| g060b12 | 1.2 nM |
| g060c04 | 0.55 nM |
| g060d04 | 1.1 nM |
| g060f01 | 1.2 nM |
| g060g04 | 0.9 nM |
| g060g07 | 0.35 nM |
| g060h11 | 3.0 nM |
| mp584 (pos. cont.) | 6.0 nM |

As seen in table 21, the Fab fragments have apparent affinities in the lower nano-molar or upper pico-molar range. Furthermore, all cognate paired Fab fragments exhibit a higher apparent affinity than that of the phage display derived Fab fragment.

j. Summary

In donor TT03 the frequency of TT specific plasma cells in the peripheral blood monocyte cell fraction was calculated to 0.022%. Approximately 400 cognate pairs were generated from TT03. 3600 clones from the cells transformed with the cognate pair library were screened using ELISA, of these 339 clones showed TT reactivity in the ELISA screening. 47 of these clones have been analysed with respect to their clonal diversity. Of these 47 clones, 27 proved to resemble unique non-scrambled variable region encoding sequences. Three of these clones contained a premature stop codon that will need correction before transfer to a mammalian expression vector. The transfer to mammalian expression vectors was described in example 1 section h. The apparent affinities were measured on selected clones, ranging from the lower nano-molar to upper pico-molar range.

k. Prospects

The Tetanus Toxin is one of the most toxic substances known with a lethal dose of a few nanogram. The toxin is produced by *Clostridium tetani*, a soil bacteria also present in the digestive tract of up to 25% of humans. The tetanus immunization program has effectively abolished the disease in the western world, although 100-200 cases are still observed in the major western countries annually, with a case-fatality ratio of 50%. In the developing world the number of cases is significantly greater. Bacterial growth in contaminated penetrating wounds may lead to toxin release, ultimately leading to rigidity, spasms, respiratory arrest and death.

Hyperimmune immunoglobulin products isolated from human blood donors with a high titer of antibody response against Tetanus Toxoid may be used to prevent tetanus or if instituted early to treat established tetanus, also in conjunction with active immunization. However, due to shortage of human product, equine hyperimmune anti-Tetanus Toxoid is used in the developing world. Recombinant monoclonal or polyclonal antibodies against Tetanus Toxoid have potential to substitute hyperimmune globulin products for therapeutic and/or prophylactic use. Recombinant monoclonal antibodies originating from the conventional hybridoma technology has been described to be effective against TT (Chin, J. et al. 2003. Biologicals 31, 45-53). Interestingly, a synergistic effect was observed when mixing two monoclonal antibodies. Thus, a recombinant polyclonal anti-Tetanus Toxoid antibody capable of reacting with or binding to Tetanus Toxin could potentially be very effective in treatment or prophylaxis protection of patients at risk of developing tetanus.

One embodiment of the present invention is a recombinant polyclonal immunoglobulin or fragments thereof capable of reacting with or binding to Tetanus Toxin.

A preferred embodiment of the present invention is a recombinant polyclonal immunoglobulin capable of reacting with or binding to Tetanus Toxin comprised of cognate pairs of immunoglobulin heavy chain variable region and light chain variable region.

A further embodiment of the present invention is a recombinant polyclonal immunoglobulin capable of reacting with or binding to Tetanus Toxin obtained by the method according to the present invention.

A further embodiment of the present invention is a recombinant polyclonal immunoglobulin capable of reacting with or binding to Tetanus Toxin comprising individual cognate pairs of immunoglobulin heavy chain variable region and light chain variable region with at least 90% sequence identity with one individual SEQ ID pair, selected among SEQ ID pairs 229:276, 262:309, 240:287, 245:292, 267:314, 246:293, 258:305, 242:289, 231:278, 263:310, 232:279, 237:284, 255:302, 260:307, 251:298, 233:280, 228:275, 244:291, 250:297, 252:299, 264:311, 272:319, 235:282 or 238:285.

Another embodiment of the invention, is a pharmaceutical composition comprising a recombinant polyclonal antibody capable of reacting with or binding to Tetanus Toxin as active ingredient intended for the treatment or prevention of a tetanus. Preferably, the recombinant polyclonal antibody is combined with a pharmaceutically acceptable excipient.

A further embodiment of the present invention is the use of a recombinant polyclonal immunoglobulin capable of reacting with or binding to Tetanus Toxin as a medicament for the treatment or prophylactic protection of a patient at risk of developing tetanus.

An additional embodiment is a method of preventing or treating a patient at risk of developing tetanus by administering to a patient in need thereof a composition comprising a recombinant polyclonal antibody capable of reacting with or binding to Tetanus Toxin.

Example 12

Comparing Results Obtained from Two Donors

In the following example results obtained from donor TT08 are compared with the results obtained from donor TT03 in Example 11. The results are summarized in table 22.

TABLE 22

| | TT03 | TT08 |
|---|---|---|
| TT specific plasma cells in PBMC fraction (ELISPOT) | 0.021% | 0.011% |
| CD 19+ cells in PBMC fraction (FACS) | 11% | 5% |
| Plasma cells in PBMC fraction (FACS CD38hi, CD45in) | 0.12% | 0.08% |
| Estimated number of linked $V_H$ and $V_L$ sequences | 400 | 400 |
| Number of clones screened for Fab expression | 1400 | 2000 |
| Number of Fab positive clones (2 × background) | 482 | 558 |
| Number of clones screened for TT-specificity | 3600 | 3400 |
| Number of TT-specific clones (2 × background) | 339 | 188 |
| Number of sequences analyzed from TT-specific clones | 47 | 102 |
| VH germline alleles | 12 (VH1-5) | NA |
| VL germline alleles | 8 (VKI, III, IV) | NA |
| Number of unique cognate pairs | 27 | 40 |
| Apparent affinity range | 0.35-3.0 nM | NA |

NA = not analyzed

This clearly illustrated that libraries of similar quality could be isolated from two different donors immunized with TT.

The reason for the higher number of unique cognate pairs in the library obtained from donor TT08 is most likely due to the larger number of sequences analyzed.

Example 13

Comparing the Library of Cognate Pairs from Example 11 with a Combinatorial Phage Display Library Generated from the Same Donor In the present example a combinatorial phage display library was prepared from the same donor previously used to prepare the library of cognate pairs, in order to compare library diversity, affinity and specificity between libraries of cognate pairs and combinatorial libraries.

a. Combinatorial Phage Library Construction

A phage display library was generated from the CD19+ fraction of cells from donor TT03 (identical to the cell fraction obtained in Example 11c).

Total RNA was prepared from app. 5×10⁶ CD19+ cells using NucleoSpin RNA L kit (Machery-Nagel cat. no. 740 962.20). cDNA was subsequently synthesized in an oligo (dT)-primed reaction using ThermoScript reverse transcriptase (Invitrogen cat. no. 11146-016).

The $V_H$ and Kappa chains were PCR amplified using HotMasterTaq DNA polymerase (Eppendorf cat. no. 0032 002.692) and primers essentially as described by de Haard et al. (J. Biol. Chem. 274, 18218-18230; 1999), only modified with respect to restriction enzyme recognition sequences in the 5'-end.

The combinatorial phage display library was generated by successive insertion of Kappa and $V_H$ PCR products into Em351 phage display vector (modified from phh3 described in Den, W. et al. 1999 J. Immunol. Methods 222, 45-57).

The final library was electroporated into TG1 E. coli strain (Stratagene). The size of the combinatorial library contained 3×10⁶ independent clones with a high insert frequency.

b. Panning of the Combinatorial Library

Fab displaying phage particles were prepared according to standard procedures (e.g. Antibody Engineering, A Practical Approach 1996, ed. McCafferty, Hoogenboom and Chiswell).

Panning was performed on tetanus toxoid (TT; SSI batch no. 89-2) diluted to 1 μg/mL in PBS, and immobilized in MaxiSorp immunotubes (Nunc cat. no. 444202). Following a one hour incubation period and several washing steps, bound phage particles were eluted using 100 mM TEA (Triethylamine).

The phage particle eluate was neutralized, and used to infect exponentially growing TG1 cells, from which Fab displaying phage particles enriched for TT specificity were obtained. A second round of panning using the eluted phages was performed following the general procedure outlined above.

In parallel, three panning rounds were performed on the C-fragment of the tetanus toxin molecule (Sigma cat. no. T3694), following the procedure outlined above.

Single colonies were screened for binding to tetanus toxoid and the C-fragment from the unselected library, and after each panning round, from both sets of panning described above.

c. Comparing Specificity and Affinity of Combinatorial Phage Particle Clones and Cognate Pair Clones Single colonies were picked from the unselected library and after each round of panning (on intact tetanus toxin (TT)

and the tetanus toxoid C-fragment, respectively). Fab displaying phage particles were analyzed for reactivity by ELISA assays. The number of Fab-positive clones exhibiting TT and/or C-fragment reactivity of at least 2× background reactivity and at least 4× background reactivity are given in table 23 to 25 below. All the results are shown as number of specific clones/number of Fab positive clones.

TABLE 23

Clones selected on TT and analyzed by TT-specific ELISA

| Enrichment | 2 × background | 4 × background |
|---|---|---|
| Unselected clones | — | 13/app. 5000 |
| After 1 round of panning | 61/99 | 59/93 |
| After 2 rounds of panning | 165/169 | 163/166 |

TABLE 24

Clones selected on TT and analyzed by C-fragment-specific ELISA

| Enrichment | 2 × background | 4 × background |
|---|---|---|
| Unselected clones | 0/13 | 0/13 |
| After 1 round of panning | 0/85 | 0/85 |
| After 2 rounds of panning | 0/85 | 0/85 |

TABLE 25

Clones selected on C-fragment, analyzed by C-fragment-specific ELISA

| Enrichment | 2 x background | 4 x background |
|---|---|---|
| After 1 round of panning | 1/35 | 0/35 |
| After 2 rounds of panning | 12/47 | 9/47 |
| After 3 rounds of panning | 64/126 | 26/126 |

Panning of the phage display library against TT revealed an increasing number of TT specific clones when increasing the number of panning rounds, and only a few clones were identified in the unselected library. No clones were found to be reactive with the tetanus toxoid C-fragment from the unselected library or after two rounds of panning of the library against TT. To obtain Fab fragments with C-fragment specificity from the combinatorial phage display library, this library had to be panned against the C-fragment specifically.

For comparison, thirteen TT-specific clones from Example 11 were subjected to C-fragment-specific ELISA, of these seven showed reactivity above 2× background. Thus, Fab fragments with specificity towards the tetanus toxin C-fragment could be expressed from a library of cognate pairs obtained from a TT-immunized individual.

This clearly illustrates the disadvantage of using panning to identify clones with specificity towards a particular antigen. If important antigen fragments or epitopes are unknown, they may be discharged during panning, thereby resulting in a less efficient product in the end.

Further, apparent affinities of the combinatorial clones were measured as described in the assay of Example 11i. Ten of the combinatorial clones obtained after two rounds of panning on TT were analyzed, revealing apparent binding affinities between 1 and 15 nM.

For comparison four of the nine clones analyzed from the library of cognate pairs (table 21), showed affinities in the pico-molar range.

Figure 25:
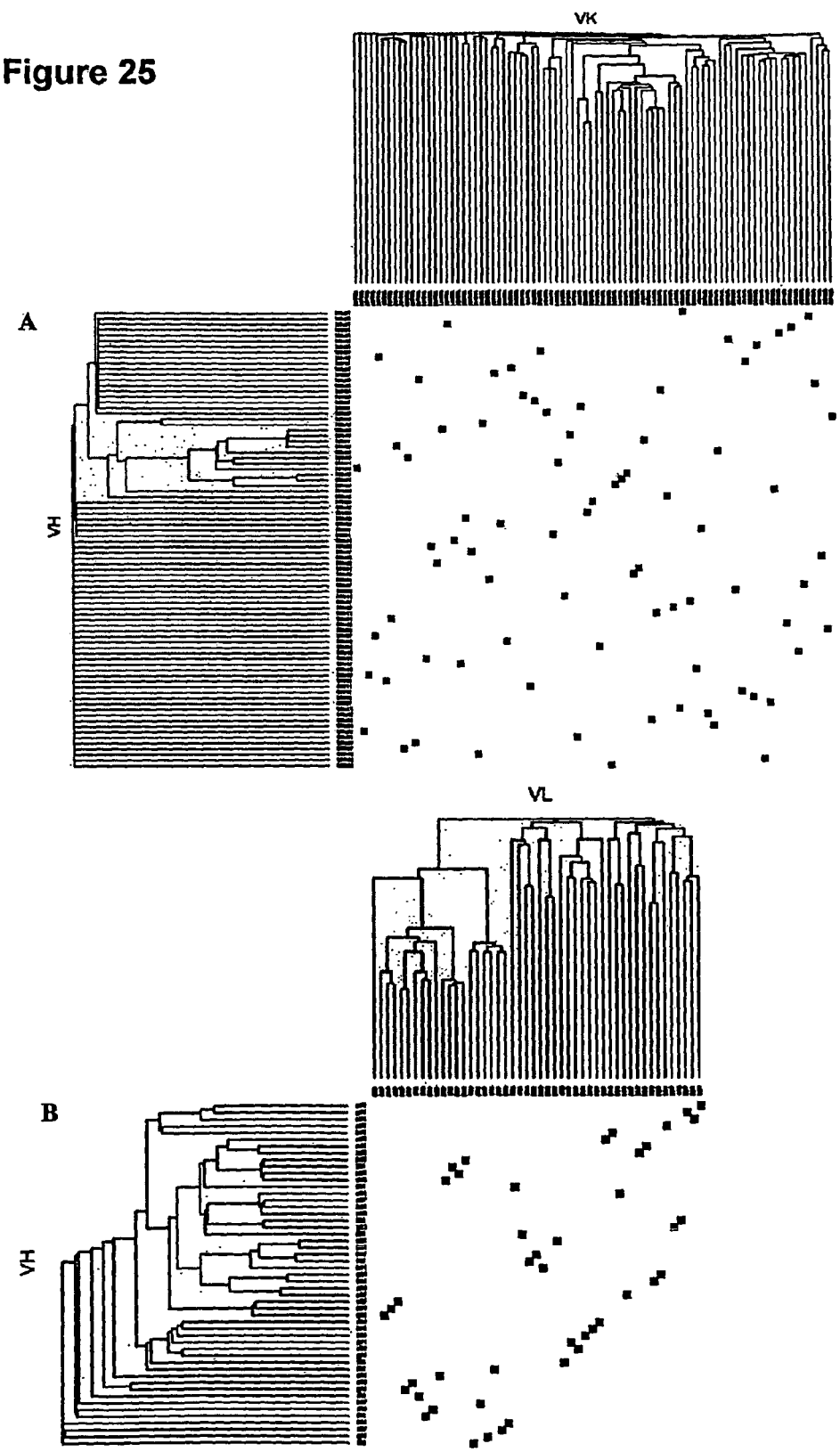
FIG. 25 shows a double phylogenetic dot matrix plot showing the intra- and intergenetic relationship between antibody heavy and light chain variable domain sequences. Phylogenetic threes of $V_H$ and $V_L$ sequences are paired in a dot matrix in order to indicate actual pairing of particular V genes. A) TT binding clones obtained from a combinatorial library using phage display. B) TT binding clones obtained from a library of cognate pairs using the present invention.

This indicates that the pairing of variable regions as originally selected for by the donors immune system, in combination with the somatic hyper-mutations the pairs have been subjected to as a pair, potentially results in higher apparent binding affinities than random combinations of such variable regions.

d. Comparing Sequences of TT Specific Combinatorial Phage Particle Clones and Cognate Pair Clones The large amount of sequence data generated from the two libraries precludes direct comparisons of raw sequences. In order to visualize the difference between $V_H$ and $V_L$ sequence pairs in the phage display library an in the library of cognate pairs, phylogenetic threes were generated for the $V_H$ and $V_L$ sequences, and pairs were illustrated in a dot matrix. The pairing of phylogenetic information in a dot matrix (FIG. 25) revealed very different distribution profiles of $V_H$ and $V_L$ sequence pairs in the two libraries. The scattered appearance of the $V_H$ and $V_L$ sequence pairs in the phage display library (FIG. 25A) indicated little phylogenetic relation between $V_H$ and $V_L$ genes in agreement with the random paring of the V genes in this library. In contrast, $V_H$ and $V_L$ sequence pairs from the library of cognate pairs (FIG. 25B) show a clustered appearance indicating co-evolution of V genes as expected for cognate pairs. Also, the genetic diversity is much greater for the V-genes in the library of cognate pairs compared to the V-genes from the combinatorial library, indicating that the method of isolating cognate paired V-genes is less biased.

Example 14

Combined Single-Step Multiplex Overlap-Extension RT-PCR and Nested PCR Using T-Cells as Template Source In this example, it is described how a single-step multiplex overlap-extension RT-PCR can be performed on T lymphocytes derived from a human donor.

a. Obtaining a Lymphocyte Containing Cell Fraction

A blood sample is obtained from human donors who have been subjected to the desired antigen, for example by immunization, natural infection, malignancy, through an autoimmune reaction, or other diseases. The peripheral blood mononuclear cells (PBMC's) are isolated using Lymphoprep (Axis-Shield, Oslo Norway, prod. No 1001967) according to the manufacturer's instructions.

In the present example antigen-specific T cells are generated by further stimulation of the PBMC fraction. However, the multiplex overlap-extension RT-PCR can also be performed directly on single cells from the PBMC fraction or on a cell fraction enriched for T cells (e.g. by FACS-sorting for CD3-positive cells).

b. Generating Antigen-Specific T Cells

The PBMC cell fraction is re-suspended in an appropriate culture medium containing relevant cytokines such as IL2. Further, the desired antigen is added to the culture, where it will be presented to the T lymphocytes by antigen presenting cells (APC) present in the PBMC fraction. Alternatively, APC feeder cells treated in beforehand such that they are presenting the desired antigen may be added to the PBMC fraction. Such APC feeder cells can be APC exposed to the desired antigen in the form of for example peptide, protein or other molecular form, or microbially infected APC or cells transfected to express and present the antigen, or APC co-cultured with other antigenic cells, e.g. such as cancer cell in the form of primary tissue or cell lines. Many different types of APC feeder cell are known from the literature, including transformed cell lines, B cell lines, dendritic cells, etc.

The PBMC fraction is cultivated for approximately 3 to 5 weeks, during which fresh antigen presenting cells are added together with cytokines, e.g. on a weekly basis. This results in T lymphocyte proliferation, activation and maturation. At the end of the cultivation period the cell culture will be dominated by antigen-specific T cells. Whether these cells are CD4+ or CD8+ depends on the disease, the antigen, the APC cells, and the cytokine mixtures used during the stimulation period.

The antigen specificity can for example be tested with a CTL assay, proliferation assays and MHC tetramers loaded with the desired antigen (Altman, J. D., et al. 1996. Science 274, 94-96).

The antigen-specific T cells are distributed to PCR tubes, either by limiting dilution or using a FACS in order to obtain a single cell pr. vessel. The vessel can be stored at −80° C. until use.

b. Single-Step Multiplex Overlap-Extension RT-PCR

The Qiagen One-Step RT-PCR kit (Qiagen cat. No 210212, Hilden, Germany) is used for the multiplex overlap-extension RT-PCR essentially according to the manufacturer's recommendation. Before addition of PCR reaction mixture to the PCR tubes, the cells are thawed.

PCR reaction mixtures and cycling conditions are initially set up as described in Example 11 e-1. However, a certain amount of optimization may be expected for a new set of primers.

The multiplex overlap-extension primer mix used comprise the primers shown in table 26.

TABLE 26

| Primer name | Conc. | SEQ ID NO | primer sequence in 5' to 3' direction |
|---|---|---|---|
| Vα | 10 nM of each | 322 | tattggcgcgccatggccGCCCAGTCTGTGACCCAGC |
| | | 323 | tattggcgcgccatggccGCCCAGAAGATAACTCAA |
| | | 324 | tattggcgcgccatggccGATGCTAAGACCACCCAG |
| | | 325 | tattggcgcgccatggccGCCCAGACAGTCACTCAG |
| | | 326 | tattggcgcgccatggccAAACAGGAGGTGACACAGA |
| | | 327 | tattggcgcgccatggccGGAGACTCGGTTACCCAGA |
| | | 328 | tattggcgcgccatggccGGAGATTCAGTGACCCAGA |
| | | 329 | tattggcgcgccatggccAGCAATTCAGTCAAGCAGA |
| | | 330 | tattggcgcgccatggccGGACAAAACATTGACCAG |
| | | 331 | tattggcgcgccatggccAAAAATGAAGTGGAGCAGA |
| | | 332 | tattggcgcgccatggccGAAGACCAGGTGACGCAGA |
| | | 333 | tattggcgcgccatggccGGAATACAAGTGGAGCAGA |
| | | 334 | tattggcgcgccatggccCTACATACACTGGAGCAGA |
| | | 335 | tattggcgcgccatggccGAAGCAAGGTGGTACAAA |
| | | 336 | tattggcgcgccatggccGAAAACCAGGTGGAGCACA |
| | | 337 | tattggcgcgccatggccCAGGAGAATGTGGAGCAG |
| | | 338 | tattggcgcgccatggccGGAGAGAGTGTGGGCTG |
| | | 339 | tattggcgcgccatggccGGAGAGGATGTGGAGCAGA |
| | | 340 | tattggcgcgccatggccAGCCAAAAGATAGAACAGA |
| | | 341 | tattggcgcgccatggccAGTCAACAGGGAGAAGAG |
| | | 342 | tattggcgcgccatggccCAACAACCAGTGCAGAGT |
| | | 343 | tattggcgcgccatggccAGCCAAGAACTGGAGCAGA |
| | | 344 | tattggcgcgccatggccGGTCAACAGCTGAATCAGA |
| | | 345 | tattggcgcgccatggccACCCAGCTGCTGGAGGAGA |
| | | 346 | tattggcgcgccatggccCAGCAGCAGGTGAAACAA |
| | | 347 | tattggcgcgccatggccATACTGAACGTGGAACAA |
| | | 348 | tattggcgcgccatggccGACCAGCAAGTTAAGCAA |
| | | 349 | tattggcgcgccatggccGGACAACAGGTAATGCAA |
| | | 350 | tattggcgcgccatggccAAGGACCAAGTGTTTCAG |
| Cα | 200 nM | 351 | TAGGCAGACAGACTTGTCACT |
| Vβ | 10 nM of each | 352 | gccatggcgcgccaatagctagccGGTGAAGAAGTCGCCCAGA |
| | | 353 | gccatggcgcgccaatagctagccGATGCCATGGTCATCCAGA |
| | | 354 | gccatggcgcgccgctagccGAAGCCCAAGTGACCCAGA |
| | | 355 | gccatggcgcgccaatagctagccCATGCCAAAGTCACACAGA |
| | | 356 | gccatggcgcgccaatagctagccGACACAGCCGTTTCCCAGA |
| | | 357 | gccatggcgcgccaatagctagccGAAACGGGAGTTACGCAGA |
| | | 358 | gccatggcgcgccaatagctagccGAACCTGAAGTCACCCAGA |
| | | 359 | gccatggcgcgccaatagctagccGAAGCTGACATCTACCAGA |
| | | 360 | gccatggcgcgccaatagctagccATATCTGGAGTCTCCCACA |
| | | 361 | gccatggcgcgccaatagctagccGATGCTGGAATCACCCAGA |
| | | 362 | gccatggcgcgccaatagctagccAATGCTGGTGTCACTCAGA |
| | | 363 | gccatggcgcgccaatagctagccAGTGCTGTCGTCTCTCAA |
| | | 364 | gccatggcgcgccaatagctagccGACGCTGGAGTCACACAA |
| | | 365 | gccatggcgcgccaatagctagccGATGGTGGAATCACTCAGT |
| | | 366 | gccatggcgcgccaatagctagccACTGCTGGGATCACCCAG |
| | | 367 | gccatggcgcgccaatagctagccGAAGCTGGAGTTGCCCAGT |
| | | 368 | gccatggcgcgccaatagctagccGAAGCTGGAGTGGTTCAGT |
| | | 369 | gccatggcgcgccaatagctagccGAAGCTGGAGTTACTCAGT |
| | | 370 | gccatggcgcgccaatagctagccGATGCTGTAGTTACACAA |
| | | 371 | gccatggcgcgccaatagctagccGATGCTGGAGTTATCCAGT |
| | | 372 | gccatggcgcgccaatagctagccGGTGCTGGAGTCTCCCAG |
| | | 373 | gccatggcgcgccaatagctagccGATGCTGATGTTACCCAGA |
| | | 374 | gccatggcgcgccaatagctagccTCTCAGACTATTCATCAAT |
| Cβ | 200 nM | 375 | CAGGCACACCAGTGTGGCCTT | c. Semi-Nested PCR

Semi-nested PCR is likewise proposed to be performed as described in Example 11 e-2, and some optimization may be expected.

The primers used are shown in table 27.

TABLE 27

| Primer name | Conc. | SEQ ID NO | primer sequence in 5' to 3' direction |
|---|---|---|---|
| Cα | 200 nM | 376 | caccttagagctcTTAGAGTCTCTCAGCTGGTAC AC |
| Cβ | 200 nM | 377 | gacattatgCAtGATCTCTGCTTCTGATGGCTC |

Capitalized sequences correspond to the gene-specific region.

In order to verify that the multiplex overlap-extension RT-PCR is successful a proportion of the samples from the semi-nested PCR reactions are analyzed by subjecting 10 μl from each semi-nested PCR reaction to 1% agarose gel electrophoresis using ethidium bromide for detection. The expected size of the overlap-extension fragment is approximately 850 bp (the exact size depends upon the lengths of the variable regions).

Approximately ten microliters from all the performed reactions originating from the same donor, are consolidated in a single tube. An aliquot of the pooled PCR products is subsequently purified using QIAquick PCR purification kit according to the manufactures procedure (Qiagen cat. No. 28106, Hilden, Germany. The purified pool of overlap PCR products can be digested with appropriate restriction enzymes and subsequently purified and inserted into a suitable vector.

In the present experiment constant region primers (SEQ ID NO 376 and 377) used in the semi-nested PCR are designed for sub-cloning of semi-nested PCR product into a suitable vector. The design of the Cβ primer relies on changing a SER to Met at pos. 21 in the β chain constant region peptide, whereby a NsiI site can be introduced into the nucleic acid sequence:

```
                             NsiI
    tcc cac      ->       atg cat
    SER HIS               MET HIS
```

This transition should be relative safe since SER 21 is exposed on the β chain constant region in a loop structure at the membrane proximal end of the domain. This relative conservative change is therefore not likely to disturb the overall domain structure.

The design of the Cα primer relies on changing nucleotides corresponding to pos. 15-17 in the α chain constant region peptide, whereby a SacI site can be introduced into the nucleic acid sequence:

```
                             SacI
    aaa tcc agt    ->     aag agc tct
    LYS SER SER           LYS SER SER
```

Suitable vectors will therefore contain the remaining parts of the constant regions of the TcR α and β chains and will contain appropriate modification in terms of restriction sites. These changes can be performed using standard PCR and sub-cloning techniques.

e. Additional Considerations

The large amount of variable region primers may potentially interact in an inhibitory manner during the multiplex overlap-extension PCR amplification. To avoid this, variable region primers may be divided into sub-sets and used separately in proper combinations.

Other Embodiments

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of linking a plurality of non-contiguous nucleotide sequences of interest, said method comprising:
   (a) distributing cells from a lymphocyte-containing cell fraction from a donor individually into a plurality of vessels to obtain isolated single cells;
   (b) amplifying, in a multiplex molecular amplification procedure, nucleotide sequences of interest using templates derived from said isolated single cells; and
   (c) effecting linkage of the nucleotide sequences of interest amplified in step (b), wherein the nucleotide sequences of interest comprise variable region encoding sequences and the linkage generates a cognate pair of variable region encoding sequences.

2. The method according to claim 1, wherein the nucleotide sequences of interest comprise immunoglobulin variable region encoding sequences and the linkage generates a cognate pair of a light chain variable region encoding sequence associated with a heavy chain variable region encoding sequence.

3. The method according to claim 1, wherein the nucleotide sequences of interest comprise T cell receptor variable region encoding sequences and the linkage generates a cognate pair constituted of an alpha chain variable region encoding sequence associated with a beta chain variable region encoding sequence or a gamma chain variable region encoding sequence associated with a delta chain variable region encoding sequence.

4. The method according to claim 1, wherein said multiplex molecular amplification procedure is a multiplex RT-PCR amplification.

5. The method according to claim 4, wherein said multiplex RT-PCR amplification is a two step process comprising a separate reverse transcription (RT) step prior to the multiplex PCR amplification.

6. The method according to claim 4, wherein said multiplex RT-PCR amplification is performed in a single step comprising initially adding all the components necessary to perform both reverse transcription (RT) and multiplex PCR amplification into a single vessel.

7. The method according to claim 1, wherein said isolated single cells are expanded in order to obtain populations of isogenic cells prior to the reverse transcription step of the multiplex molecular amplification procedure.

8. The method according to claim 1, wherein said linkage of the nucleotide sequences of interest is performed in the same vessel as the multiplex molecular amplification.

9. The method according to claim 4, wherein said linkage of the nucleotide sequences of interest is effected in association with the multiplex RT-PCR amplification, utilizing a multiplex overlap-extension primer mix.

10. The method according to claim 4, wherein said linkage of the nucleotide sequences of interest is effected by ligation.

11. The method according to claim 1, wherein an additional molecular amplification, utilizing a primer mix adapted for amplifying the linked nucleic acid sequences of interest, is performed.

12. The method according to claim 9, wherein the multiplex overlap-extension primer mix comprises primer sets wherein at least one primer set member of each primer set comprises an overlap-extension tail capable of hybridizing to the overlap-extension tail of a primer set member of a second primer set.

13. The method according to claim 9, wherein the multiplex overlap-extension primer mix comprises:
   (a) at least one $C_L$ or $J_L$ primer complementary to the sense strand of an immunoglobulin light chain region encoding sequence;
   (b) at least one $V_L$ 5' primer or $V_{LL}$ primer complementary to the antisense strand of an immunoglobulin light chain variable region encoding sequence or light chain variable region leader sequence, and capable of forming a primer set with the primer(s) in step (a);
   (c) at least one $C_H$ or $J_H$ primer complementary to the sense strand of an immunoglobulin constant heavy chain domain encoding sequence or a heavy chain joining region encoding sequence; and
   (d) at least one $V_H$ 5' primer or $V_{HL}$ primer complementary to the antisense strand of an immunoglobulin heavy chain variable region encoding sequence or heavy chain variable region leader sequence, and capable of forming a primer set with the primer(s) in step (c).

14. The method according to claim 13, wherein the primers of step b) are $V_{LL}$ primers comprising the gene-specific region of SEQ ID 93 to 98, and the primers of step d) are $V_{HL}$ primers comprising the gene-specific region of SEQ ID 86 to 92.

15. The method according to claim 1, further comprising inserting the linked nucleotide sequences into a vector.

16. The method according to claim 15, wherein said vector is selected from the group consisting of cloning vectors, shuttle vectors, display vectors or expression vectors.

17. The method according to claim 15, wherein the linked nucleotide sequences comprise an immunoglobulin heavy chain variable region encoding sequence associated with a light chain variable region encoding sequence and said sequences are inserted in-frame into a vector already containing sequences encoding one or more immunoglobulin constant domains or fragments thereof.

18. The method according to claim 15, wherein the linked nucleotide sequences comprise a T cell receptor α chain variable region encoding sequence associated with a β chain variable region encoding sequence and said sequences are inserted in-frame into a vector already containing sequences encoding one or more T cell receptor constant domains or fragments thereof.

19. The method according to claim 17, wherein said vector is a mammalian expression vector.

20. The method according to claim 19, wherein the mammalian expression vector encodes one or more constant region domains selected from human immunoglobulin classes IgA1, IgA2, IgD, IgE, IgG1, IgG2, IgG3, IgG4, IgM, kappa light chain or lambda light chain or from human T cell receptor alpha, beta, delta and/or gamma chains.

21. The method according to claim 15, further comprising the steps:
   (a) introducing the vector encoding a segment of linked nucleotide sequences into a host cell;
   (b) cultivating said host cell under conditions adapted for expression; and
   (c) obtaining the protein product expressed from the vector inserted into said host cell.

22. The method according to claim 21 wherein said protein product is a monoclonal antibody comprising a cognate pair of a light chain variable region associated with a heavy chain variable region.

23. The method according to claim 21, wherein said protein product is a monoclonal T cell receptor comprising a cognate pair of an alpha chain variable region associated with a beta chain variable region.

24. The method according to claim 1, wherein said isolated single cells are B lymphocytes obtained by enrichment of said lymphocyte-containing cell fraction.

25. The method according to claim 24, wherein enrichment is performed using a B cell lineage-specific marker.

26. The method according to claim 24, wherein enrichment is performed by magnetic bead cell sorting or fluorescence activated cell sorting.

27. The method of claim 1, wherein the nucleotide sequences of interest originate from different genes or different mRNA molecules.

28. The method of claim 27, wherein the nucleotide sequences of interest are oriented head-to-head.

29. The method of claim 27, wherein the nucleotide sequences of interest are oriented tail-to-tail.

* * * * *

SEQUENCE LISTING

```
<160> NUMBER OF SEQ ID NOS: 377

<210> SEQ ID NO 1
<211> LENGTH: 45
<212> TYPE: DNA
<213> ORGANISM: Artificial
<220> FEATURE:
<223> OTHER INFORMATION: Primer sequence

<400> SEQUENCE: 1
agcctatact attgattagg cgcgcccagr tgcagctggt gcart          45

<210> SEQ ID NO 2
<211> LENGTH: 45
<212> TYPE: DNA
<213> ORGANISM: Artificial
<220> FEATURE:
<223> OTHER INFORMATION: Primer sequence

<400> SEQUENCE: 2
```

```
agcctatact attgattagg cgcgccsagg tccagctggt rcagt          45

<210> SEQ ID NO 3
<211> LENGTH: 45
<212> TYPE: DNA
<213> ORGANISM: Artificial
<220> FEATURE:
<223> OTHER INFORMATION: Primer sequence

<400> SEQUENCE: 3
agcctatact attgattagg cgcgcccagr tcaccttgaa ggagt          45

<210> SEQ ID NO 4
<211> LENGTH: 44
<212> TYPE: DNA
<213> ORGANISM: Artificial
<220> FEATURE:
<223> OTHER INFORMATION: Primer sequence

<400> SEQUENCE: 4
agcctatact attgattagg cgcgccsagg tgcagctggt ggag           44

<210> SEQ ID NO 5
<211> LENGTH: 45
<212> TYPE: DNA
<213> ORGANISM: Artificial
<220> FEATURE:
<223> OTHER INFORMATION: Primer sequence

<400> SEQUENCE: 5
agcctatact attgattagg cgcgcccagg tgcagctaca gcagt          45

<210> SEQ ID NO 6
<211> LENGTH: 45
<212> TYPE: DNA
<213> ORGANISM: Artificial
<220> FEATURE:
<223> OTHER INFORMATION: Primer sequence

<400> SEQUENCE: 6
agcctatact attgattagg cgcgcccags tgcagctgca ggagt          45

<210> SEQ ID NO 7
<211> LENGTH: 45
<212> TYPE: DNA
<213> ORGANISM: Artificial
<220> FEATURE:
<223> OTHER INFORMATION: Primer sequence

<400> SEQUENCE: 7
agcctatact attgattagg cgcgccgarg tgcagctggt gcagt          45

<210> SEQ ID NO 8
<211> LENGTH: 46
<212> TYPE: DNA
<213> ORGANISM: Artificial
<220> FEATURE:
<223> OTHER INFORMATION: Primer sequence

<400> SEQUENCE: 8
agcctatact attgattagg cgcgcccagg tacagctgca gcagtc         46

<210> SEQ ID NO 9
<211> LENGTH: 20
<212> TYPE: DNA
<213> ORGANISM: Artificial
```

```
<220> FEATURE:
<223> OTHER INFORMATION: Primer sequence

<400> SEQUENCE: 9
gacsgatggg cccttggtgg                                              20

<210> SEQ ID NO 10
<211> LENGTH: 47
<212> TYPE: DNA
<213> ORGANISM: Artificial
<220> FEATURE:
<223> OTHER INFORMATION: Primer sequence

<400> SEQUENCE: 10
cgcctaatca atagtatagg ctagccgaca tccagwtgac ccagtct                47

<210> SEQ ID NO 11
<211> LENGTH: 47
<212> TYPE: DNA
<213> ORGANISM: Artificial
<220> FEATURE:
<223> OTHER INFORMATION: Primer sequence

<400> SEQUENCE: 11
cgcctaatca atagtatagg ctagccgatg ttgtgatgac tcagtct                47

<210> SEQ ID NO 12
<211> LENGTH: 47
<212> TYPE: DNA
<213> ORGANISM: Artificial
<220> FEATURE:
<223> OTHER INFORMATION: Primer sequence

<400> SEQUENCE: 12
cgcctaatca atagtatagg ctagccgaaa ttgtgwtgac rcagtct                47

<210> SEQ ID NO 13
<211> LENGTH: 47
<212> TYPE: DNA
<213> ORGANISM: Artificial
<220> FEATURE:
<223> OTHER INFORMATION: Primer sequence

<400> SEQUENCE: 13
cgcctaatca atagtatagg ctagccgata ttgtgatgac ccacact                47

<210> SEQ ID NO 14
<211> LENGTH: 45
<212> TYPE: DNA
<213> ORGANISM: Artificial
<220> FEATURE:
<223> OTHER INFORMATION: Primer sequence

<400> SEQUENCE: 14
cgcctaatca atagtatagg ctagccgaaa cgacactcac gcagt                  45

<210> SEQ ID NO 15
<211> LENGTH: 47
<212> TYPE: DNA
<213> ORGANISM: Artificial
<220> FEATURE:
<223> OTHER INFORMATION: Primer sequence

<400> SEQUENCE: 15
cgcctaatca atagtatagg ctagccgaaa ttgtgctgac tcagtct                47
```

```
<210> SEQ ID NO 16
<211> LENGTH: 38
<212> TYPE: DNA
<213> ORGANISM: Artificial
<220> FEATURE:
<223> OTHER INFORMATION: Primer sequence

<400> SEQUENCE: 16
atatatatgc ggccgcttat taacactctc ccctgttg                              38

<210> SEQ ID NO 17
<211> LENGTH: 26
<212> TYPE: DNA
<213> ORGANISM: Artificial
<220> FEATURE:
<223> OTHER INFORMATION: Primer sequence

<400> SEQUENCE: 17
atattctcga gacggtgacc agggtg                                           26

<210> SEQ ID NO 18
<211> LENGTH: 25
<212> TYPE: DNA
<213> ORGANISM: Artificial
<220> FEATURE:
<223> OTHER INFORMATION: Primer sequence

<400> SEQUENCE: 18
atattctcga gacggtgacc attgt                                            25

<210> SEQ ID NO 19
<211> LENGTH: 27
<212> TYPE: DNA
<213> ORGANISM: Artificial
<220> FEATURE:
<223> OTHER INFORMATION: Primer sequence

<400> SEQUENCE: 19
atattctcga gacggtgacc agggttc                                          27

<210> SEQ ID NO 20
<211> LENGTH: 25
<212> TYPE: DNA
<213> ORGANISM: Artificial
<220> FEATURE:
<223> OTHER INFORMATION: Primer sequence

<400> SEQUENCE: 20
atattctcga gacggtgacc gtggt                                            25

<210> SEQ ID NO 21
<211> LENGTH: 51
<212> TYPE: DNA
<213> ORGANISM: Artificial
<220> FEATURE:
<223> OTHER INFORMATION: Primer sequence

<400> SEQUENCE: 21
accgcctcca ccggcggccg cttattaaca ctctcccctg ttgaagctct t               51

<210> SEQ ID NO 22
<211> LENGTH: 43
<212> TYPE: DNA
<213> ORGANISM: Artificial
<220> FEATURE:
<223> OTHER INFORMATION: primer sequence
```

```
<400> SEQUENCE: 22
gctagcatta ttattaccat ggcccagrtg cagctggtgc art                43

<210> SEQ ID NO 23
<211> LENGTH: 43
<212> TYPE: DNA
<213> ORGANISM: Artificial
<220> FEATURE:
<223> OTHER INFORMATION: Primer sequence

<400> SEQUENCE: 23
gctagcatta ttattaccat ggccsaggtc cagctggtrc agt                43

<210> SEQ ID NO 24
<211> LENGTH: 43
<212> TYPE: DNA
<213> ORGANISM: Artificial
<220> FEATURE:
<223> OTHER INFORMATION: Primer sequence

<400> SEQUENCE: 24
gctagcatta ttattaccat ggcccagrtc accttgaagg agt                43

<210> SEQ ID NO 25
<211> LENGTH: 42
<212> TYPE: DNA
<213> ORGANISM: Artificial
<220> FEATURE:
<223> OTHER INFORMATION: Primer sequence

<400> SEQUENCE: 25
gctagcatta ttattaccat ggccsaggtg cagctggtgg ag                 42

<210> SEQ ID NO 26
<211> LENGTH: 36
<212> TYPE: DNA
<213> ORGANISM: Artificial
<220> FEATURE:
<223> OTHER INFORMATION: Primer sequence

<400> SEQUENCE: 26
tattggcgcg ccatggccsa ggtgcagctg gtggag                        36

<210> SEQ ID NO 27
<211> LENGTH: 43
<212> TYPE: DNA
<213> ORGANISM: Artificial
<220> FEATURE:
<223> OTHER INFORMATION: Primer sequence

<400> SEQUENCE: 27
gctagcatta ttattaccat ggcccaggtg cagctacagc agt                43

<210> SEQ ID NO 28
<211> LENGTH: 43
<212> TYPE: DNA
<213> ORGANISM: Artificial
<220> FEATURE:
<223> OTHER INFORMATION: Primer sequence

<400> SEQUENCE: 28
gctagcatta ttattaccat ggcccagstg cagctgcagg agt                43

<210> SEQ ID NO 29
```

-continued

```
<211> LENGTH: 43
<212> TYPE: DNA
<213> ORGANISM: Artificial
<220> FEATURE:
<223> OTHER INFORMATION: Primer sequence

<400> SEQUENCE: 29
gctagcatta ttattaccat ggccgargtg cagctggtgc agt                43

<210> SEQ ID NO 30
<211> LENGTH: 44
<212> TYPE: DNA
<213> ORGANISM: Artificial
<220> FEATURE:
<223> OTHER INFORMATION: Primer sequence

<400> SEQUENCE: 30
gctagcatta ttattaccat ggcccaggta cagctgcagc agtc               44

<210> SEQ ID NO 31
<211> LENGTH: 26
<212> TYPE: DNA
<213> ORGANISM: Artificial
<220> FEATURE:
<223> OTHER INFORMATION: Primer sequence

<400> SEQUENCE: 31
atattctcga gacggtgacc agggtg                                   26

<210> SEQ ID NO 32
<211> LENGTH: 27
<212> TYPE: DNA
<213> ORGANISM: Artificial
<220> FEATURE:
<223> OTHER INFORMATION: Primer sequence

<400> SEQUENCE: 32
atattctcga gacggtgacc attgtcc                                  27

<210> SEQ ID NO 33
<211> LENGTH: 27
<212> TYPE: DNA
<213> ORGANISM: Artificial
<220> FEATURE:
<223> OTHER INFORMATION: Primer sequence

<400> SEQUENCE: 33
atattctcga gacggtgacc agggttc                                  27

<210> SEQ ID NO 34
<211> LENGTH: 27
<212> TYPE: DNA
<213> ORGANISM: Artificial
<220> FEATURE:
<223> OTHER INFORMATION: Primer sequence

<400> SEQUENCE: 34
atattctcga gacggtgacc gtggtcc                                  27

<210> SEQ ID NO 35
<211> LENGTH: 44
<212> TYPE: DNA
<213> ORGANISM: Artificial
<220> FEATURE:
<223> OTHER INFORMATION: Primer sequence

<400> SEQUENCE: 35
```

-continued ccatggtaat aataatgcta gccgacatcc agwtgaccca gtct                44

<210> SEQ ID NO 36
<211> LENGTH: 44
<212> TYPE: DNA
<213> ORGANISM: Artificial
<220> FEATURE:
<223> OTHER INFORMATION: Primer sequence

<400> SEQUENCE: 36
ccatggtaat aataatgcta gccgatgttg tgatgactca gtct                44

<210> SEQ ID NO 37
<211> LENGTH: 44
<212> TYPE: DNA
<213> ORGANISM: Artificial
<220> FEATURE:
<223> OTHER INFORMATION: Primer sequence

<400> SEQUENCE: 37
ccatggtaat aataatgcta gccgaaattg tgwtgacrca gtct                44

<210> SEQ ID NO 38
<211> LENGTH: 44
<212> TYPE: DNA
<213> ORGANISM: Artificial
<220> FEATURE:
<223> OTHER INFORMATION: Primer sequence

<400> SEQUENCE: 38
ccatggtaat aataatgcta gccgatattg tgatgaccca cact                44

<210> SEQ ID NO 39
<211> LENGTH: 42
<212> TYPE: DNA
<213> ORGANISM: Artificial
<220> FEATURE:
<223> OTHER INFORMATION: Primer sequence

<400> SEQUENCE: 39
ccatggtaat aataatgcta gccgaaacga cactcacgca gt                  42

<210> SEQ ID NO 40
<211> LENGTH: 44
<212> TYPE: DNA
<213> ORGANISM: Artificial
<220> FEATURE:
<223> OTHER INFORMATION: Primer sequence

<400> SEQUENCE: 40
ccatggtaat aataatgcta gccgaaattg tgctgactca gtct                44

<210> SEQ ID NO 41
<211> LENGTH: 37
<212> TYPE: DNA
<213> ORGANISM: Artificial
<220> FEATURE:
<223> OTHER INFORMATION: Primer sequence

<400> SEQUENCE: 41
tattggcgcg ccatggccca grtgcagctg gtgcart                         37

<210> SEQ ID NO 42
<211> LENGTH: 37
<212> TYPE: DNA

```
<213> ORGANISM: Artificial
<220> FEATURE:
<223> OTHER INFORMATION: Primer sequence

<400> SEQUENCE: 42
tattggcgcg ccatggccsa ggtccagctg gtrcagt                              37

<210> SEQ ID NO 43
<211> LENGTH: 37
<212> TYPE: DNA
<213> ORGANISM: Artificial
<220> FEATURE:
<223> OTHER INFORMATION: Primer sequence

<400> SEQUENCE: 43
tattggcgcg ccatggccca grtcaccttg aaggagt                              37

<210> SEQ ID NO 44
<211> LENGTH: 36
<212> TYPE: DNA
<213> ORGANISM: Artificial
<220> FEATURE:
<223> OTHER INFORMATION: Primer sequence

<400> SEQUENCE: 44
tattggcgcg ccatggccsa ggtgcagctg gtggag                               36

<210> SEQ ID NO 45
<211> LENGTH: 36
<212> TYPE: DNA
<213> ORGANISM: Artificial
<220> FEATURE:
<223> OTHER INFORMATION: Primer sequence

<400> SEQUENCE: 45
tattggcgcg ccatggccca ggtgcagcta cagcag                               36

<210> SEQ ID NO 46
<211> LENGTH: 37
<212> TYPE: DNA
<213> ORGANISM: Artificial
<220> FEATURE:
<223> OTHER INFORMATION: Primer sequence

<400> SEQUENCE: 46
tattggcgcg ccatggccca gstgcagctg caggagt                              37

<210> SEQ ID NO 47
<211> LENGTH: 37
<212> TYPE: DNA
<213> ORGANISM: Artificial
<220> FEATURE:
<223> OTHER INFORMATION: Primer sequence

<400> SEQUENCE: 47
tattggcgcg ccatggccga rgtgcagctg gtgcagt                              37

<210> SEQ ID NO 48
<211> LENGTH: 38
<212> TYPE: DNA
<213> ORGANISM: Artificial
<220> FEATURE:
<223> OTHER INFORMATION: Primer sequence

<400> SEQUENCE: 48
tattggcgcg ccatggccca ggtacagctg cagcagtc                             38
```

<210> SEQ ID NO 49
<211> LENGTH: 23
<212> TYPE: DNA
<213> ORGANISM: Artificial
<220> FEATURE:
<223> OTHER INFORMATION: Primer sequence

<400> SEQUENCE: 49
aagtagtcct tgaccaggca gcc                                              23

<210> SEQ ID NO 50
<211> LENGTH: 20
<212> TYPE: DNA
<213> ORGANISM: Artificial
<220> FEATURE:
<223> OTHER INFORMATION: Primer sequence

<400> SEQUENCE: 50
tgagttccac gacaccgtca                                                  20

<210> SEQ ID NO 51
<211> LENGTH: 20
<212> TYPE: DNA
<213> ORGANISM: Artificial
<220> FEATURE:
<223> OTHER INFORMATION: Primer sequence

<400> SEQUENCE: 51
agaggtgctc ttggaggagg                                                  20

<210> SEQ ID NO 52
<211> LENGTH: 21
<212> TYPE: DNA
<213> ORGANISM: Artificial
<220> FEATURE:
<223> OTHER INFORMATION: Primer sequence

<400> SEQUENCE: 52
agttttgtca caagatttgg g                                                21

<210> SEQ ID NO 53
<211> LENGTH: 23
<212> TYPE: DNA
<213> ORGANISM: Artificial
<220> FEATURE:
<223> OTHER INFORMATION: Primer sequence

<400> SEQUENCE: 53
gttgcagatg taggtctggg tgc                                              23

<210> SEQ ID NO 54
<211> LENGTH: 45
<212> TYPE: DNA
<213> ORGANISM: Artificial
<220> FEATURE:
<223> OTHER INFORMATION: Primer sequence

<400> SEQUENCE: 54
gccatggcgc gccaatagct agccgacatc cagwtgaccc agtct                      45

<210> SEQ ID NO 55
<211> LENGTH: 45
<212> TYPE: DNA
<213> ORGANISM: Artificial
<220> FEATURE:

-continued

<223> OTHER INFORMATION: Primer sequence

<400> SEQUENCE: 55
gccatggcgc gccaatagct agccgatgtt gtgatgactc agtct        45

<210> SEQ ID NO 56
<211> LENGTH: 45
<212> TYPE: DNA
<213> ORGANISM: Artificial
<220> FEATURE:
<223> OTHER INFORMATION: Primer sequence

<400> SEQUENCE: 56
gccatggcgc gccaatagct agccgaaatt gtgwtgacrc agtct        45

<210> SEQ ID NO 57
<211> LENGTH: 45
<212> TYPE: DNA
<213> ORGANISM: Artificial
<220> FEATURE:
<223> OTHER INFORMATION: Primer sequence

<400> SEQUENCE: 57
gccatggcgc gccaatagct agccgatatt gtgatgaccc acact        45

<210> SEQ ID NO 58
<211> LENGTH: 43
<212> TYPE: DNA
<213> ORGANISM: Artificial
<220> FEATURE:
<223> OTHER INFORMATION: Primer sequence

<400> SEQUENCE: 58
gccatggcgc gccaatagct agccgaaacg acactcacgc agt          43

<210> SEQ ID NO 59
<211> LENGTH: 45
<212> TYPE: DNA
<213> ORGANISM: Artificial
<220> FEATURE:
<223> OTHER INFORMATION: Primer sequence

<400> SEQUENCE: 59
gccatggcgc gccaatagct agccgaaatt gtgctgactc agtct        45

<210> SEQ ID NO 60
<211> LENGTH: 40
<212> TYPE: DNA
<213> ORGANISM: Artificial
<220> FEATURE:
<223> OTHER INFORMATION: Primer sequence

<400> SEQUENCE: 60
atatatatgc ggccgcttat taacactctc ccctgttgaa              40

<210> SEQ ID NO 61
<211> LENGTH: 30
<212> TYPE: DNA
<213> ORGANISM: Artificial
<220> FEATURE:
<223> OTHER INFORMATION: Primer sequence

<400> SEQUENCE: 61
ggaggcgctc gagacggtga ccagggtgcc                         30

```
<210> SEQ ID NO 62
<211> LENGTH: 30
<212> TYPE: DNA
<213> ORGANISM: Artificial
<220> FEATURE:
<223> OTHER INFORMATION: Primer sequence

<400> SEQUENCE: 62
ggaggcgctc gagacggtga ccattgtccc                              30

<210> SEQ ID NO 63
<211> LENGTH: 30
<212> TYPE: DNA
<213> ORGANISM: Artificial
<220> FEATURE:
<223> OTHER INFORMATION: Primer sequence

<400> SEQUENCE: 63
ggaggcgctc gagacggtga ccagggttcc                              30

<210> SEQ ID NO 64
<211> LENGTH: 30
<212> TYPE: DNA
<213> ORGANISM: Artificial
<220> FEATURE:
<223> OTHER INFORMATION: Primer sequence

<400> SEQUENCE: 64
ggaggcgctc gagacggtga ccgtggtccc                              30

<210> SEQ ID NO 65
<211> LENGTH: 47
<212> TYPE: DNA
<213> ORGANISM: Artificial
<220> FEATURE:
<223> OTHER INFORMATION: Primer sequence

<400> SEQUENCE: 65
cgcctaatca atagtatagg ctagcccagt ctgtgctgac tcagcca           47

<210> SEQ ID NO 66
<211> LENGTH: 45
<212> TYPE: DNA
<213> ORGANISM: Artificial
<220> FEATURE:
<223> OTHER INFORMATION: Primer sequence

<400> SEQUENCE: 66
cgcctaatca atagtatagg ctagcccagt ctgtgytgac gcagc             45

<210> SEQ ID NO 67
<211> LENGTH: 45
<212> TYPE: DNA
<213> ORGANISM: Artificial
<220> FEATURE:
<223> OTHER INFORMATION: Primer sequence

<400> SEQUENCE: 67
cgcctaatca atagtatagg ctagcccagt ctgtcgtgac gcagc             45

<210> SEQ ID NO 68
<211> LENGTH: 47
<212> TYPE: DNA
<213> ORGANISM: Artificial
<220> FEATURE:
<223> OTHER INFORMATION: Primer sequence
```

<400> SEQUENCE: 68
cgcctaatca atagtatagg ctagcccart ctgccctgac tcagcct                47

<210> SEQ ID NO 69
<211> LENGTH: 47
<212> TYPE: DNA
<213> ORGANISM: Artificial
<220> FEATURE:
<223> OTHER INFORMATION: Primer sequence

<400> SEQUENCE: 69
cgcctaatca atagtatagg ctagcctcct atgwgctgac tcagcca                47

<210> SEQ ID NO 70
<211> LENGTH: 47
<212> TYPE: DNA
<213> ORGANISM: Artificial
<220> FEATURE:
<223> OTHER INFORMATION: Primer sequence

<400> SEQUENCE: 70
cgcctaatca atagtatagg ctagcctctt ctgagctgac tcaggac                47

<210> SEQ ID NO 71
<211> LENGTH: 47
<212> TYPE: DNA
<213> ORGANISM: Artificial
<220> FEATURE:
<223> OTHER INFORMATION: Primer sequence

<400> SEQUENCE: 71
cgcctaatca atagtatagg ctagcccacg ttatactgac tcaaccg                47

<210> SEQ ID NO 72
<211> LENGTH: 45
<212> TYPE: DNA
<213> ORGANISM: Artificial
<220> FEATURE:
<223> OTHER INFORMATION: Primer sequence

<400> SEQUENCE: 72
cgcctaatca atagtatagg ctagcccagg ctgtgctgac tcagc                  45

<210> SEQ ID NO 73
<211> LENGTH: 49
<212> TYPE: DNA
<213> ORGANISM: Artificial
<220> FEATURE:
<223> OTHER INFORMATION: Primer sequence

<400> SEQUENCE: 73
cgcctaatca atagtatagg ctagccaatt ttatgctgac tcagccca              49

<210> SEQ ID NO 74
<211> LENGTH: 46
<212> TYPE: DNA
<213> ORGANISM: Artificial
<220> FEATURE:
<223> OTHER INFORMATION: Primer sequence

<400> SEQUENCE: 74
cgcctaatca atagtatagg ctagcccagr ctgtggtgac ycagga                 46

<210> SEQ ID NO 75
<211> LENGTH: 45

```
<212> TYPE: DNA
<213> ORGANISM: Artificial
<220> FEATURE:
<223> OTHER INFORMATION: Primer sequence

<400> SEQUENCE: 75
cgcctaatca atagtatagg ctagcccwgc ctgtgctgac tcagc              45

<210> SEQ ID NO 76
<211> LENGTH: 31
<212> TYPE: DNA
<213> ORGANISM: Artificial
<220> FEATURE:
<223> OTHER INFORMATION: Primer sequence

<400> SEQUENCE: 76
gccgcttatt atgaacattc tgtaggggcc a                             31

<210> SEQ ID NO 77
<211> LENGTH: 31
<212> TYPE: DNA
<213> ORGANISM: Artificial
<220> FEATURE:
<223> OTHER INFORMATION: Primer sequence

<400> SEQUENCE: 77
gccgcttatt aagagcattc tgcaggggcc a                             31

<210> SEQ ID NO 78
<211> LENGTH: 45
<212> TYPE: DNA
<213> ORGANISM: Artificial
<220> FEATURE:
<223> OTHER INFORMATION: Primer sequence

<400> SEQUENCE: 78
atatatatgc ggccgcttat tatgaacatt ctgtaggggc cactg              45

<210> SEQ ID NO 79
<211> LENGTH: 45
<212> TYPE: DNA
<213> ORGANISM: Artificial
<220> FEATURE:
<223> OTHER INFORMATION: Primer sequence

<400> SEQUENCE: 79
atatatatgc ggccgcttat taagagcatt ctgcaggggc cactg              45

<210> SEQ ID NO 80
<211> LENGTH: 36
<212> TYPE: DNA
<213> ORGANISM: Artificial
<220> FEATURE:
<223> OTHER INFORMATION: Primer sequence

<400> SEQUENCE: 80
atatatatgc ggccgcttaa tgggctgcct cgggaa                        36

<210> SEQ ID NO 81
<211> LENGTH: 47
<212> TYPE: DNA
<213> ORGANISM: Artificial
<220> FEATURE:
<223> OTHER INFORMATION: Primer sequence

<400> SEQUENCE: 81
```

```
gccatggcgc gccaatagct agccttagag cagctcgtac tgacgaa         47
```

<210> SEQ ID NO 82
<211> LENGTH: 41
<212> TYPE: DNA
<213> ORGANISM: Artificial
<220> FEATURE:
<223> OTHER INFORMATION: Primer sequence

<400> SEQUENCE: 82

```
tattggcgcg ccatggccat gagtgagctt gaccagttac g              41
```

<210> SEQ ID NO 83
<211> LENGTH: 47
<212> TYPE: DNA
<213> ORGANISM: Artificial
<220> FEATURE:
<223> OTHER INFORMATION: Primer sequence

<400> SEQUENCE: 83

```
ggtacctaat aataatcgat cgcttagttc cagatcttga ggaagct        47
```

<210> SEQ ID NO 84
<211> LENGTH: 48
<212> TYPE: DNA
<213> ORGANISM: Artificial
<220> FEATURE:
<223> OTHER INFORMATION: Primer sequence

<400> SEQUENCE: 84

```
cgatcgatta ttattaggta ccccatgcca gtaatcaata ttgaggac       48
```

<210> SEQ ID NO 85
<211> LENGTH: 38
<212> TYPE: DNA
<213> ORGANISM: Artificial
<220> FEATURE:
<223> OTHER INFORMATION: Primer sequence

<400> SEQUENCE: 85

```
ggaggcgctc gagttatgaa atcacacagc ctcctttg                  38
```

<210> SEQ ID NO 86
<211> LENGTH: 34
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (18)..(34)
<223> OTHER INFORMATION: gene-specific region

<400> SEQUENCE: 86

```
tattcccagc ggccgccgcc acaggtgccc actc                      34
```

<210> SEQ ID NO 87
<211> LENGTH: 34
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (18)..(34)
<223> OTHER INFORMATION: gene-specific region

<400> SEQUENCE: 87
tattcccagc ggccgccccct tcmtgggtct tgtc            34

<210> SEQ ID NO 88
<211> LENGTH: 35
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (18)..(35)
<223> OTHER INFORMATION: gene-specific region

<400> SEQUENCE: 88
tattcccagc ggccgcctta raaggtgtcc agtgt            35

<210> SEQ ID NO 89
<211> LENGTH: 32
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (18)..(32)
<223> OTHER INFORMATION: gene-specific region

<400> SEQUENCE: 89
tattcccagc ggccgccccc agatgggtcc tg               32

<210> SEQ ID NO 90
<211> LENGTH: 34
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (18)..(34)
<223> OTHER INFORMATION: gene-specific region

<400> SEQUENCE: 90
tattcccagc ggccgccctc caaggagtct gttc             34

<210> SEQ ID NO 91
<211> LENGTH: 35
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (18)..(35)
<223> OTHER INFORMATION: gene-specific region

<400> SEQUENCE: 91
tattcccagc ggccgcccca tggggtgtcc tgtca            35

<210> SEQ ID NO 92
<211> LENGTH: 33
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (18)..(33)
<223> OTHER INFORMATION: gene-specific region

```
<400> SEQUENCE: 92
tattcccagc ggccgccgca acaggtgccc act                                    33

<210> SEQ ID NO 93
<211> LENGTH: 41
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (25)..(41)
<223> OTHER INFORMATION: gene-specific region

<400> SEQUENCE: 93
ggcggccgct gggaatagct agcgytccca ggtgccagat g                           41

<210> SEQ ID NO 94
<211> LENGTH: 40
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (25)..(40)
<223> OTHER INFORMATION: gene-specific region

<400> SEQUENCE: 94
ggcggccgct gggaatagct agcggtccct ggatccagtg                             40

<210> SEQ ID NO 95
<211> LENGTH: 42
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (25)..(42)
<223> OTHER INFORMATION: gene-specific region

<400> SEQUENCE: 95
ggcggccgct gggaatagct agcgctccca gataccaccg ga                          42

<210> SEQ ID NO 96
<211> LENGTH: 39
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (25)..(39)
<223> OTHER INFORMATION: gene-specific region

<400> SEQUENCE: 96
ggcggccgct gggaatagct agcgatctct ggtgcctac                              39

<210> SEQ ID NO 97
<211> LENGTH: 42
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (25)..(42)
```

<400> SEQUENCE: 97
ggcggccgct gggaatagct agcgatctct gataccaggg ca              42

<210> SEQ ID NO 98
<211> LENGTH: 42
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (25)..(42)
<223> OTHER INFORMATION: gene-specific region

<400> SEQUENCE: 98
ggcggccgct gggaatagct agcggttcca gcctccaggg gt              42

<210> SEQ ID NO 99
<211> LENGTH: 37
<212> TYPE: DNA
<213> ORGANISM: Artificial
<220> FEATURE:
<223> OTHER INFORMATION: Primer sequence

<400> SEQUENCE: 99
atatatatgg cgcgccttaa cactctcccc tgttgaa                    37

<210> SEQ ID NO 100
<211> LENGTH: 48
<212> TYPE: DNA
<213> ORGANISM: Artificial
<220> FEATURE:
<223> OTHER INFORMATION: Vector sequence

<400> SEQUENCE: 100
atgaaatatc ttctaccaac agcggcagct ggattattgg cggccgcc        48

<210> SEQ ID NO 101
<211> LENGTH: 48
<212> TYPE: DNA
<213> ORGANISM: Artificial
<220> FEATURE:
<223> OTHER INFORMATION: Vector sequence

<400> SEQUENCE: 101
atgaaatatt tgctaccaac agcggcagct ggattattgt tactagcg        48

<210> SEQ ID NO 102
<211> LENGTH: 43
<212> TYPE: DNA
<213> ORGANISM: Artificial
<220> FEATURE:
<223> OTHER INFORMATION: Primer sequence

<400> SEQUENCE: 102
tgttgttcta gatgaaggcg cgcccagrtg cagctggtgc art             43

<210> SEQ ID NO 103
<211> LENGTH: 43
<212> TYPE: DNA
<213> ORGANISM: Artificial
<220> FEATURE:
<223> OTHER INFORMATION: Primer sequence

<400> SEQUENCE: 103
tgttgttcta gatgaaggcg cgccsaggtc cagctggtrc agt             43

<210> SEQ ID NO 104
<211> LENGTH: 43
<212> TYPE: DNA
<213> ORGANISM: Artificial
<220> FEATURE:
<223> OTHER INFORMATION: Primer sequence

<400> SEQUENCE: 104
tgttgttcta gatgaaggcg cgcccagrtc accttgaagg agt        43

<210> SEQ ID NO 105
<211> LENGTH: 42
<212> TYPE: DNA
<213> ORGANISM: Artificial
<220> FEATURE:
<223> OTHER INFORMATION: Primer sequence

<400> SEQUENCE: 105
tgttgttcta gatgaaggcg cgccsaggtg cagctggtgg ag        42

<210> SEQ ID NO 106
<211> LENGTH: 43
<212> TYPE: DNA
<213> ORGANISM: Artificial
<220> FEATURE:
<223> OTHER INFORMATION: Primer sequence

<400> SEQUENCE: 106
tgttgttcta gatgaaggcg cgcccaggtg cagctacagc agt        43

<210> SEQ ID NO 107
<211> LENGTH: 43
<212> TYPE: DNA
<213> ORGANISM: Artificial
<220> FEATURE:
<223> OTHER INFORMATION: Primer sequence

<400> SEQUENCE: 107
tgttgttcta gatgaaggcg cgcccagstg cagctgcagg agt        43

<210> SEQ ID NO 108
<211> LENGTH: 43
<212> TYPE: DNA
<213> ORGANISM: Artificial
<220> FEATURE:
<223> OTHER INFORMATION: Primer sequence

<400> SEQUENCE: 108
tgttgttcta gatgaaggcg cgccgargtg cagctggtgc agt        43

<210> SEQ ID NO 109
<211> LENGTH: 44
<212> TYPE: DNA
<213> ORGANISM: Artificial
<220> FEATURE:
<223> OTHER INFORMATION: Primer sequence

<400> SEQUENCE: 109
tgttgttcta gatgaaggcg cgcccaggta cagctgcagc agtc       44

<210> SEQ ID NO 110
<211> LENGTH: 45
<212> TYPE: DNA
<213> ORGANISM: Artificial
<220> FEATURE:

<223> OTHER INFORMATION: Primer sequence

<400> SEQUENCE: 110
aacaacacta gtgataggct agccgacatc cagwtgaccc agtct                45

<210> SEQ ID NO 111
<211> LENGTH: 45
<212> TYPE: DNA
<213> ORGANISM: Artificial
<220> FEATURE:
<223> OTHER INFORMATION: Primer sequence

<400> SEQUENCE: 111
aacaacacta gtgataggct agccgatgtt gtgatgactc agtct                45

<210> SEQ ID NO 112
<211> LENGTH: 45
<212> TYPE: DNA
<213> ORGANISM: Artificial
<220> FEATURE:
<223> OTHER INFORMATION: Primer sequence

<400> SEQUENCE: 112
aacaacacta gtgataggct agccgaaatt gtgwtgacrc agtct                45

<210> SEQ ID NO 113
<211> LENGTH: 45
<212> TYPE: DNA
<213> ORGANISM: Artificial
<220> FEATURE:
<223> OTHER INFORMATION: Primer sequence

<400> SEQUENCE: 113
aacaacacta gtgataggct agccgatatt gtgatgaccc acact                45

<210> SEQ ID NO 114
<211> LENGTH: 43
<212> TYPE: DNA
<213> ORGANISM: Artificial
<220> FEATURE:
<223> OTHER INFORMATION: Primer sequence

<400> SEQUENCE: 114
aacaacacta gtgataggct agccgaaacg acactcacgc agt                  43

<210> SEQ ID NO 115
<211> LENGTH: 45
<212> TYPE: DNA
<213> ORGANISM: Artificial
<220> FEATURE:
<223> OTHER INFORMATION: Primer sequence

<400> SEQUENCE: 115
aacaacacta gtgataggct agccgaaatt gtgctgactc agtct                45

<210> SEQ ID NO 116
<211> LENGTH: 36
<212> TYPE: DNA
<213> ORGANISM: Artificial
<220> FEATURE:
<223> OTHER INFORMATION: Primer sequence

<400> SEQUENCE: 116
tattcccatg gcgcgcccag rtgcagctgg tgcart                          36

```
<210> SEQ ID NO 117
<211> LENGTH: 36
<212> TYPE: DNA
<213> ORGANISM: Artificial
<220> FEATURE:
<223> OTHER INFORMATION: Primer sequence

<400> SEQUENCE: 117
tattcccatg gcgcgccsag gtccagctgg trcagt                             36

<210> SEQ ID NO 118
<211> LENGTH: 36
<212> TYPE: DNA
<213> ORGANISM: Artificial
<220> FEATURE:
<223> OTHER INFORMATION: Primer sequence

<400> SEQUENCE: 118
tattcccatg gcgcgcccag rtcaccttga aggagt                             36

<210> SEQ ID NO 119
<211> LENGTH: 35
<212> TYPE: DNA
<213> ORGANISM: Artificial
<220> FEATURE:
<223> OTHER INFORMATION: Primer sequence

<400> SEQUENCE: 119
tattcccatg gcgcgccsag gtgcagctgg tggag                              35

<210> SEQ ID NO 120
<211> LENGTH: 36
<212> TYPE: DNA
<213> ORGANISM: Artificial
<220> FEATURE:
<223> OTHER INFORMATION: Primer sequence

<400> SEQUENCE: 120
tattcccatg gcgcgcccag gtgcagctac agcagt                             36

<210> SEQ ID NO 121
<211> LENGTH: 36
<212> TYPE: DNA
<213> ORGANISM: Artificial
<220> FEATURE:
<223> OTHER INFORMATION: Primer sequence

<400> SEQUENCE: 121
tattcccatg gcgcgcccag stgcagctgc aggagt                             36

<210> SEQ ID NO 122
<211> LENGTH: 36
<212> TYPE: DNA
<213> ORGANISM: Artificial
<220> FEATURE:
<223> OTHER INFORMATION: Primer sequence

<400> SEQUENCE: 122
tattcccatg gcgcgccgar gtgcagctgg tgcagt                             36

<210> SEQ ID NO 123
<211> LENGTH: 37
<212> TYPE: DNA
<213> ORGANISM: Artificial
<220> FEATURE:
<223> OTHER INFORMATION: Primer sequence
```

```
<400> SEQUENCE: 123
tattcccatg gcgcgcccag gtacagctgc agcagtc                       37

<210> SEQ ID NO 124
<211> LENGTH: 45
<212> TYPE: DNA
<213> ORGANISM: Artificial
<220> FEATURE:
<223> OTHER INFORMATION: Primer sequence

<400> SEQUENCE: 124
ggcgcgccat gggaatagct agccgacatc cagwtgaccc agtct             45

<210> SEQ ID NO 125
<211> LENGTH: 45
<212> TYPE: DNA
<213> ORGANISM: Artificial
<220> FEATURE:
<223> OTHER INFORMATION: Primer sequence

<400> SEQUENCE: 125
ggcgcgccat gggaatagct agccgatgtt gtgatgactc agtct             45

<210> SEQ ID NO 126
<211> LENGTH: 45
<212> TYPE: DNA
<213> ORGANISM: Artificial
<220> FEATURE:
<223> OTHER INFORMATION: Primer sequence

<400> SEQUENCE: 126
ggcgcgccat gggaatagct agccgaaatt gtgwtgacrc agtct             45

<210> SEQ ID NO 127
<211> LENGTH: 45
<212> TYPE: DNA
<213> ORGANISM: Artificial
<220> FEATURE:
<223> OTHER INFORMATION: Primer sequence

<400> SEQUENCE: 127
ggcgcgccat gggaatagct agccgatatt gtgatgaccc acact             45

<210> SEQ ID NO 128
<211> LENGTH: 43
<212> TYPE: DNA
<213> ORGANISM: Artificial
<220> FEATURE:
<223> OTHER INFORMATION: Primer sequence

<400> SEQUENCE: 128
ggcgcgccat gggaatagct agccgaaacg acactcacgc agt               43

<210> SEQ ID NO 129
<211> LENGTH: 45
<212> TYPE: DNA
<213> ORGANISM: Artificial
<220> FEATURE:
<223> OTHER INFORMATION: Primer sequence

<400> SEQUENCE: 129
ggcgcgccat gggaatagct agccgaaatt gtgctgactc agtct             45

<210> SEQ ID NO 130
<211> LENGTH: 37
```

```
<212> TYPE: DNA
<213> ORGANISM: Artificial
<220> FEATURE:
<223> OTHER INFORMATION: Primer sequence

<400> SEQUENCE: 130
atatatatgc ggccgcttaa cactctcccc tgttgaa                              37

<210> SEQ ID NO 131
<211> LENGTH: 20
<212> TYPE: DNA
<213> ORGANISM: Artificial
<220> FEATURE:
<223> OTHER INFORMATION: Vector Sequence

<400> SEQUENCE: 131
aggaaacagg agatatacat                                                 20

<210> SEQ ID NO 132
<211> LENGTH: 20
<212> TYPE: DNA
<213> ORGANISM: Artificial
<220> FEATURE:
<223> OTHER INFORMATION: Vector sequence

<400> SEQUENCE: 132
tcgccaagga gacagtcata                                                 20

<210> SEQ ID NO 133
<211> LENGTH: 369
<212> TYPE: DNA
<213> ORGANISM: Homo Sapiens

<400> SEQUENCE: 133
gggcgcgccc aggtgcagct ggtgcaatct ggacctgaag tgaagaagcc tggggcctca     60
gtgagggtct cctgcaaggc ctctggttac tcctttaaga actatggtat ccactgggtg    120
cgacaggccc ctggacaggg gcttgagtgg atggggtgga tcagcgctga caatggtgac    180
acaaccactg cactgaacct ccggggcaga gtctccatga ccacagacac atccacaaac    240
acagtctaca tggaggtgaa gagcctaaga tctgacgaca cggccatata tttctgtgcg    300
cgagattttt atagtgggag ttaccggtcc tttgactgct ggggccaggg caccctggtc    360
accgtctcg                                                            369

<210> SEQ ID NO 134
<211> LENGTH: 378
<212> TYPE: DNA
<213> ORGANISM: Homo Sapiens

<400> SEQUENCE: 134
gggcgcgccc aggtgcagct acagcagtct gggggaggcc tggtcaagcc tgggggtcc     60 ctgagactct cctgtgcagc ctctggattc accttcagta gctatagcat gaactgggtc    120
cgccaggctc cagggaaggg gctggagtgg gtctcatcca ttagtagtag tagtagttac    180
atatactacg cagactcagt gaagggccga ttcaccatct ccagagacaa cgccaagaac    240
tcactgtatc tgcaaatgaa cagcctgaga gccgaggaca cggctgtgta ttactgtgcg    300
agacgccctg gttgggctgc tactcgggcg gcgggtgctt ttgatatctg gggccaaggg    360
acaatggtca ccgtctcg                                                  378

<210> SEQ ID NO 135
```

<210> SEQ ID NO 135
<211> LENGTH: 357
<212> TYPE: DNA
<213> ORGANISM: Homo Sapiens

<400> SEQUENCE: 135

| gggcgcgccc aggtgcagct ggtgcaatct ggacctgaac tgaagaagcc tggggcctca | 60 |
|---|---|
| gtgaggatct cctgcaaggc ctctgagaaa tgtgatatcc actgggtgcg acaggcccct | 120 |
| ggacaggggc ttgagtggat gggatggatc agcgctgacg atggtgggac aaccactgcg | 180 |
| ctgaacctcc gggcagagt ctccatgacc acagacagag ccacaaacac agtatacatg | 240 |
| gaactgaaga gcctaagatc tgacgacacg gccatttatt tctgtgcgcg agatttttat | 300 |
| agtgggactt accggtcctt tgactactgg ggccagggaa ccctggtcac cgtctcg | 357 |

<210> SEQ ID NO 136
<211> LENGTH: 396
<212> TYPE: DNA
<213> ORGANISM: Homo Sapiens

<400> SEQUENCE: 136

| gggcgcgcca aggtgcagct ggtggagtct gggggaggcg tggtccagcc tgggacgtcc | 60 |
|---|---|
| ctcagactct cctgtgtagt ctctggattc accttcagaa cctatggtat gaactgggtc | 120 |
| cgccaggctc caggcaaggg gctggagtgg ctggcatttc tatcatctga tgggagcgat | 180 |
| gaattctacg cggactccgt gaagggccga ttcaccgtct ccagggacaa ttccaagagc | 240 |
| actctctttc tgaaaatgaa cagtctgaga cctgatgaca cggctgtcta ttactgtgcg | 300 |
| agggatcgtg ggcccaaat tacacttttt ggagcccctc ttataaggcc ttcgtccttt | 360 |
| gactcctggg gccagggcac cctggtcacc gtctcg | 396 |

<210> SEQ ID NO 137
<211> LENGTH: 362
<212> TYPE: DNA
<213> ORGANISM: Homo Sapiens

<400> SEQUENCE: 137

| gggcgcgccc aggtgcagct gcaggagtct ggacctgagg tgaagaagcc tggggcctca | 60 |
|---|---|
| gtgaaggtgt cctgcaaggc ttctggctac acgtttaaca gttatggaat cgcctgggtg | 120 |
| cgacaggtcc ctggacaagg gcttgagtgg atgggatgga tcagcccta cagtggtcac | 180 |
| acaaactatg cagagaaggt ccagggcaga gtcaccatga ccacagacac cgccacgagc | 240 |
| acagcctgca tggagctgac gagcctgaga tctgacgaca cggccgttta tttctgtgcg | 300 |
| agagactaca gtagtccgta ccactttgac tactggggcc agggcacctg gtcaccgtct | 360 |
| cg | 362 |

<210> SEQ ID NO 138
<211> LENGTH: 366
<212> TYPE: DNA
<213> ORGANISM: Homo Sapiens

<400> SEQUENCE: 138

| gggcgcgccc agatcacctt gaaggagtct ggtcctacgc tggtgaaacc cacacagacc | 60 |
|---|---|
| ctcacgctga cctgcacctt gtctgggttc tcactctaca ctactggagt gggtgtgggc | 120 |
| tggatccgtc agccccccagg aaaggccctg gagtggctgg cacgcattta ttgggatgat | 180 |
| gatgagcgct acaacccgtc tctgaagagc aggctcacca tcaccaagga cgcctccaaa | 240 |
| aaccaggtgg tccttaaaat gaccaacatg gaccctgtgg acacagccac atattactgt | 300 |

```
gcccggacca tgggcgtcgt tcttccattt gactactggg gccagggaac cctggtcacc    360
gtctcg                                                                366
```

<210> SEQ ID NO 139
<211> LENGTH: 351
<212> TYPE: DNA
<213> ORGANISM: Homo Sapiens

<400> SEQUENCE: 139

```
gggcgcgcca aggtgcagct ggtggagtct gggggaggcc tggtcaagcc ggggggggtcc    60 ctgagactct cctgtgtagt ttctgggttc cccctcaata gatacaccat gaactgggtc   120
cgccaggctc cagggaaggg gctggagtgg ctctcgtcca ttagtagtac tagttcttac   180
atatactacg cagactcagt gaagggccga ttcaccatct ccagagacaa cgccaagaat   240
tctctgtttc tgcagatgaa cagcctgaga gccgacgaca cggctctcta tttctgtgcg   300
agtggcaata ctcatgacta ctggggccag ggaaccctgg tcaccgtctc g             351
```

<210> SEQ ID NO 140
<211> LENGTH: 378
<212> TYPE: DNA
<213> ORGANISM: Homo Sapiens

<400> SEQUENCE: 140

```
gggcgcgccc aggtgcagct ggtgcagtct ggggctgagg tgaagaagct tggga cgtca   60 gtgagggtct cctgcaagac tcctggaggc tatgttttca gctgggtgcg acaggcccct   120
ggacaagggc ctgagtggat gggagggatc atcaccaact ttgggacaac aaactacgca   180
cggaagttcc agggcagaat cacgttacc gcggacaaat ccacgaacac agtgtacatg    240
gatttgagca acctggcatc tgaggacacg gccgtgtatt actgtgcgag agccccccga   300
ggcacgtcga ctatagcagc tcgttttaat cgatatttct ttgactcctg gggccagggc   360
accctggtca ccgtctcg                                                   378
```

<210> SEQ ID NO 141
<211> LENGTH: 396
<212> TYPE: DNA
<213> ORGANISM: Homo Sapiens

<400> SEQUENCE: 141

```
gggcgcgccc aggtgcagct tcaggagtct gggggaggcg tggtccagcc tgggacgtcc    60
ctcagactct cctgtgtagt ctctggattc accttcagaa cctatggtat gaactgggtc   120
cgccaggctc caggcaaggt gctggagtgg ctggcatttg tatcatctga tgggagcgat   180
gaattctacg cggactccgt gaagggccga ttcaccgtct ccagggacaa ttccaagagc   240
actctctttc tgaaaatgaa cagtctgaga gctgatgaca cggctgtcta ttactgtgcg   300
agagatcgtg gggcccaaat tacactttt  ggagcccctc ttataaggcc ttcgtccttt   360
gactcctggg gccagggaac cctggtcacc gtctcg                              396
```

<210> SEQ ID NO 142
<211> LENGTH: 378
<212> TYPE: DNA
<213> ORGANISM: Homo Sapiens

<400> SEQUENCE: 142

```
gggcgcgccg aggtgcagct ggtggagtct ggggctgagg tgaagaagcc tgggacctca    60
```

```
gtgagggtct cctgcaagac ttctggaggc tatgttttca gctgggtgcg acaggcccct    120
ggacaagggc ctgagtggat gggagggatc atcaccagct ttgggacaac aagctacgca    180
cagaagttcc agggcagagt cacgattacc gcggacaaag ccacgaacac agtgtacatg    240
gatttgagcg acctgacatc tgaggacacg gccatatatt actgtgcgaa agccccccga    300
ggcacgtcga ctatagcagc tcgtttaat cgctatttct ttgactcctg ggccagggc     360 accctggtca ccgtctcg                                                   378

<210> SEQ ID NO 143
<211> LENGTH: 366
<212> TYPE: DNA
<213> ORGANISM: Homo Sapiens

<400> SEQUENCE: 143
gggcgcgccc aggtgcagct gcaggagtct ggtcctacgc tggtgaaacc cacacagacc     60
ctcacgctga cctgctcgtt ctctggtttc tcactcggca ctactggagt caatgtgggc    120
tggatccgtc agcccccggg aaaggccctg agtggcttg cactcatttc ttgggatggt    180
ggtaagcact acagcccatc tctgaactcc aggatcaccc tcactaagga cgcctccaga    240
gagcaggtgg tggtccctac aatgaccaac atggaccctg cggacacagg cagatattat    300
tgtgcacgta tagtggggac tcacggcttt gactactggg gccagggaac cctggtcacc    360
gtctcg                                                                366

<210> SEQ ID NO 144
<211> LENGTH: 393
<212> TYPE: DNA
<213> ORGANISM: Homo Sapiens

<400> SEQUENCE: 144
gggcgcgcca aggtgcagct ggtggagtct ggagctgagg tgaagaagcc tggggccaca     60
gtcagggtct cctgtaaggc ttctggttac aggtttaacg actattgtat cagctgggtg    120
cgacaggccc ctggacaagg gcttgagtgg atggggtgga tcaacggtaa caatgctgac    180
acattctatg caccgaagct ccagggcaga gtcaccatga gcacagacac atccacgagc    240
acagcctaca tggagctgag gaacttgaga tcggacgaca cggccgttta tttctgtgcg    300
cgagatcgag gacgtattac tcttttttggc gaagttattt aagggcggg atggttcgac    360 tcctggggcc agggcaccct ggtcaccgtc tcg                                  393

<210> SEQ ID NO 145
<211> LENGTH: 372
<212> TYPE: DNA
<213> ORGANISM: Homo Sapiens

<400> SEQUENCE: 145
gggcgcgccc aggtgcagct ggtgcagtct ggggaggcc tggtcaagcc ggggggggtcc      60 ctgagactct cctgtgcagc ctctggattc tcctttagta ataataacat gaattgggtc    120
cgccagactc caggaaaggg actggagtgg gtcgcatcta ttagttttgg aagtcattac    180
atatcctacg cagactcagt gaagggccga ttcaccatct ccagagacaa cgccaggaat    240
gcagtttatc tgcagatgaa cagcctgaga gtcgaggaca cggctgtcta ttactgcacg    300
agatgcaggg gcggaactcg tacctattat tacatggacg tctgggcaa aggcaccctg    360 gtcaccgtct cg                                                         372
```

<210> SEQ ID NO 146
<211> LENGTH: 372
<212> TYPE: DNA
<213> ORGANISM: Homo Sapiens

<400> SEQUENCE: 146

```
gggcgcgcca aggtgcagct ggtggagtct gggggaggcc tggtcaagcc agggggtcc     60 ctgagactct cctgtgcagc ctctggatcc tcctttagta ataataacat gaattgggtc    120
cgccagactc caggaaaggg actggagtgg gtcgcatcca ttagttttgg aagtcattac    180
atatcctacg cagactcagt gaagggccga ttcaccatct ccagagacaa cgccaggaat    240
gcagtttatc tgcagatgaa cagcctgaga gtcgaggaca cggctgtcta ttactgcacg    300
agatgcaggg gcggaactcg tacctattat tacatggacg tctggggcaa aggcaccctg    360
gtcaccgtct cg                                                        372
```

<210> SEQ ID NO 147
<211> LENGTH: 390
<212> TYPE: DNA
<213> ORGANISM: Homo Sapiens

<400> SEQUENCE: 147

```
gggcgcgccc agatgcagct ggtgcaatct ggggctgagg tgaagaagcc tgggtcctcg     60
gtgaaggtct cctgccagtc ttctggaggc ccccccaaaa gttatactct cagctgggtg    120
cggcaggccc ctggacaagg ccctgagtgg atgggcggaa tcattctaat ctttggccca    180
ccaaactacg cccagaagtt ccaggacaga ctcacgatca ccgcggacaa gtccaccaac    240
acagtctaca tggagttaag tagcctgaga tctgatgaca cggccatgta ctactgtgtg    300
acagcccccg acgacactgg cactatatta gctcgtcaca accgttacta ctttgactcc    360
tggggccagg gcaccctggt caccgtctcg                                     390
```

<210> SEQ ID NO 148
<211> LENGTH: 390
<212> TYPE: DNA
<213> ORGANISM: Homo Sapiens

<400> SEQUENCE: 148

```
gggcgcgcca aggtgcagct ggtgcagtct ggagcagagg tgaagaagcc cggggagtct     60
ctgaaaatct cctgtcaggc ttctggatac ggctttaccg tctactggat cggctgggtg    120
cgccagccgc ccgggaaagg cctggagtgg ctgggtatca tctatcctgg tgactctgat    180
accagataca atccgtcctt ccaaggccag gtcaccatct cagccgacaa gtccgtcagc    240
accacctacc tgcagtggag cagcctgaag gcctcggaca ccgccattta ctactgtgcg    300
agacatctgg actcatacga tgtttttcact ggttataatt tggggggcta catggacgtc    360
tggggcaagg gaaccctggt caccgtctcg                                     390
```

<210> SEQ ID NO 149
<211> LENGTH: 351
<212> TYPE: DNA
<213> ORGANISM: Homo Sapiens

<400> SEQUENCE: 149

```
gggcgcgcca aagtgtagct ggtgcagtct gggggaggcc tggtcaagcc tgggggtcc     60 ctgagactct cctgtgtagt ctctggattc cccctcaata gatacatcat gaactgggtc    120
cgccagactc cagggaaggg gctggagtgg ctctcgtcca ttagtagtac cagttcttac    180
```

| | |
|---|---|
| atatactacg cagactcagc gaagggccga ttcaccatct ccagagacaa cgccaagaat | 240 |
| tctctgtttc tgcagatgaa cagcctgaga gccgaggaca caggtctcta ttactgtgcg | 300 |
| agtggcaata tcatgactat tggggccag ggcaccctgg tcaccgtctc g | 351 |

<210> SEQ ID NO 150
<211> LENGTH: 378
<212> TYPE: DNA
<213> ORGANISM: Homo Sapiens

<400> SEQUENCE: 150

| | |
|---|---|
| gggcgcgccc agatgcagct ggtgcagtct ggggctgagg tgaagaagcc tgggacctca | 60 |
| gtgagggtct cctgcaagac ttctggaggc tatgttttca gctgggtgcg acaggcccct | 120 |
| ggacaagggc ctgagtggat gggagggatc atcaccaact ttgggacaac aaactacgca | 180 |
| cagaagttcc agggcagagt cacgattacc gcggacaaat ccacgaacac agtgtatatg | 240 |
| gatttgagca acctgacatc tgaggacacg gccgtgtatt actgtgcgag agcccccga | 300 |
| ggcacgtcga ctatagcagc tcgttttaat cggtatttct ttgactcctg gggccagggc | 360 |
| accctggtca ccgtctcg | 378 |

<210> SEQ ID NO 151
<211> LENGTH: 372
<212> TYPE: DNA
<213> ORGANISM: Homo Sapiens

<400> SEQUENCE: 151

| | |
|---|---|
| gggcgcgcca aggtgcagct ggtggagtct ggggctgagg tgaagaagcc tgggtcctcg | 60 |
| gtgaaggtct cctgcaaggc ctctggaggc agcttcagca cctatgctat cacctgggtg | 120 |
| cgccaggccc ctggacaggg gcttgaatgg atgggaggga tcatccctat ctttgcttca | 180 |
| agagactacg cacagaagtt tcagggcaga gtcacagtca ccgcggacga atccacgagg | 240 |
| acagtgtaca tggagctgag cagcctgaga tctgacgaca cggccgtgta ttactgtgca | 300 |
| agagtgctgg gaggtacaag gctctactac gctctgaacg tctggggcca agggacaatg | 360 |
| gtcaccgtct cg | 372 |

<210> SEQ ID NO 152
<211> LENGTH: 372
<212> TYPE: DNA
<213> ORGANISM: Homo Sapiens

<400> SEQUENCE: 152

| | |
|---|---|
| gggcgcgcca aggtgcagct ggtggagtct ggggctgagg tgaagaagcc tgggtcctcg | 60 |
| gtgaaggtct cctgcaagac atctggaggc agtttcagca catactctat cacctgggtg | 120 |
| cgccaggccc ctggacaggg gcttgagtgg atgggaggga tcaaccctat cttcgctaca | 180 |
| agagactacg cacagaagtt ccagggcaga gtcacgatca ccgcggacga atccacgagg | 240 |
| acagtctaca tggagttgag gaacttgaga tctgaggaca cggccgtgta ttattgtgca | 300 |
| agagtgttcg gaggaacaag actctactac gccctgaacg tctggggcca aggcaccctg | 360 |
| gtcaccgtct cg | 372 |

<210> SEQ ID NO 153
<211> LENGTH: 378
<212> TYPE: DNA
<213> ORGANISM: Homo Sapiens

<400> SEQUENCE: 153

```
gggcgcgccg aagtgcagct ggtgcagtct ggggctgagg tgaagaagcc tgggacgtca      60
gtgagggtct cctgcaagac tcctggaggc tatgttttca gctgggtgcg acaggcccct     120
ggacaagggc ctgagtggat gggagggatc atcaccaact tgggacaac aaaactacgca     180 cggaagttcc agggcagaat cacggttacc gcggacaaat ccacgaacac agtgtacatg     240
gatttgagca acctggcatc tgaggacacg gccgtgtatt actgtgcgag agccccccga     300
ggcacgtcga ctatagcagc tcgttttaat cgatatttct ttgactcctg gggccagggc     360
accctggtca ccgtctcg                                                   378

<210> SEQ ID NO 154
<211> LENGTH: 372
<212> TYPE: DNA
<213> ORGANISM: Homo Sapiens

<400> SEQUENCE: 154
gggcgcgcca aggtgcagct ggtggagtct ggggggaggcc tggtcaagcc ggggggggtcc    60 ctgagactct cctgtgcagc ctctggattc tcctttagta ataataacat gaattgggtc    120
cgccagaccc caggaaaggg actggagtgg gtcgcatcca ttagttttgg aagtcattac    180
atatcctacg cagactcagt gaagggccga ttcaccatct ccagagacaa cgccaggaat    240
gcagtttatc tgcagatgaa cagcctgaga gtcgaggaca cggctgtcta ttactgcacg    300
agatgcaggg gcggaactcg tacctattat tacatggacg tctggggcaa agggacaatg    360
gtcaccgtct cg                                                        372

<210> SEQ ID NO 155
<211> LENGTH: 390
<212> TYPE: DNA
<213> ORGANISM: Homo Sapiens

<400> SEQUENCE: 155
gggcgcgcca aggtgcagct ggtgcagtct ggagcagagg tgaagaagcc cggggagtct     60
ctgaaaatct cctgtcaggc ttctggatac ggctttaccg tctactggat cggctgggtg    120
cgccagccgc ccgggaaagg cctggagtgg ctgggtatca tctatcctgg tgactctgat    180
accagataca atccgtcctt ccaaggccag gtcaccatct cagccgacaa gtccgtcagc    240
accacctacc tgcagtggag cagcctgaag gcctcggaca ccgccattta ctactgtgcg    300
agacatctgg actcatacga tgttttcact ggttataatt ggggggcta catggacgtc     360 tggggcaagg gaaccctggt caccgtctcg                                     390

<210> SEQ ID NO 156
<211> LENGTH: 378
<212> TYPE: DNA
<213> ORGANISM: Homo Sapiens

<400> SEQUENCE: 156
gggcgcgccc aggtgcagct ggtggagtct ggggctgaag tgaagaagcc tgggtcctca     60
gtgaaggtct cctgcaagtc ttctggaggc tatgttttca gctgggtgcg acaggcccct    120
gggcaaggac tagagtggat gggagggatc atctccaact ttcgcacggc agagtacgca    180
cggaagttcc agggtagagt caccatgacc gcggacacat ccacgaacac aatctacatg    240
gagctgacca gcctgacatc tgaagacacg gccgtatatt tctgtgtgag cgccccccga    300
gacacgtcga ctatagcagc tcgttttaat cgatacttct ttgacacctg gggccagggc    360
```

```
accctggtca ccgtctcg                                                   378

<210> SEQ ID NO 157
<211> LENGTH: 378
<212> TYPE: DNA
<213> ORGANISM: Homo Sapiens

<400> SEQUENCE: 157
gggcgcgccc aggtgcagct acagcagtcg gggggaggcg tggtccagcc tgggaggtcc     60
ctgagactct cctgtgctgc ctctggattc gccttcagag actatgccat gcactgggtc    120
cgccaggccc caggcaaggg gctggagtgg atgggagtta tctcatttaa tggagatcag    180
atattttacg cagactccat gaagggccgc ttcaccatct ccagagagaa ctccaagaac    240
acgctgcatc tgcgcatgaa cagcctgaga cctgaggaca cggctgtcta ttactgtgcg    300
agagcccgac ttcttttttg tagcggtggt aggtgcgaca tggactcttg gggccaggga    360
accctggtca ccgtctcg                                                  378

<210> SEQ ID NO 158
<211> LENGTH: 378
<212> TYPE: DNA
<213> ORGANISM: Homo Sapiens

<400> SEQUENCE: 158
gggcgcgcca aagtgcagct ggtgcagtct ggggctgagg tgaagaagcc tgggacctca     60
gtgagggtct cctgcaagac ttctggaggc tatgttttca gttgggtgcg acaggcccct    120
ggacacgggc ctgaatggat gggagggatc atcaccaact ttgggacagc aacctacgca    180
cagaagttcc agggcagagt ctcgattacc gcggacacat ccacgaacac atttacatg    240 gatttgaaca atctgaaatc tgacgacacg gccgtttatt actgtgcgag cgcccccga    300 gacacgtcga ctatagcggc tcggtttaat cggtacttct ttgacttctg gggcccgggc    360
accctggtca ccgtctcg                                                  378

<210> SEQ ID NO 159
<211> LENGTH: 348
<212> TYPE: DNA
<213> ORGANISM: Homo Sapiens

<400> SEQUENCE: 159
gggcgcgcct aggtgcagct ggtgcagtct gggggaggct tggtaaaacc tgggggggtcc    60 cttagactct cctgtgcagc ctctggattc actttcagta acgcctggat gagctgggtc    120
cgccaggctc cagggaaggg gctggagtgg gttggccatg ttaaaagcat gactgatggt    180
gggacaacag actacgctgc acccgtgaaa ggcagattca ccatctcaag agatgattca    240
gaaaacacgc tgtatctgca aatgaacagc ctgaagaccg acgacacagc cgtgtattac    300
tgtaccactc atgactactg gggccagggc accctggtca ccgtctcg                 348

<210> SEQ ID NO 160
<211> LENGTH: 378
<212> TYPE: DNA
<213> ORGANISM: Homo Sapiens

<400> SEQUENCE: 160
gggcgcgcca aagtgcagct ggtgcagtct ggggctgagg tgaagaagcc tgggacgtca     60
gtgagggtct cctgcaagac tcctggaggc tatgttttca gctgggtgcg acaggcccct    120
ggacaagggc ctgagtggat gggagggatc atcaccaact ttgggacaac aaaactacgca   180
```

-continued

| | |
|---|---|
| cggaagttcc agggcagaat cacggttacc gcggacaaat ccacgaacac agtgtacatg | 240 |
| gatttgagca acctggcatc tgaggacacg gccgtgtatt actgtgcgag agccccccga | 300 |
| ggcacgtcga ctatagcagc tcgtttaat cgatatttct ttgactcctg gggccagggc | 360 |
| accctggtca ccgtctcg | 378 |

<210> SEQ ID NO 161
<211> LENGTH: 393
<212> TYPE: DNA
<213> ORGANISM: Homo Sapiens

<400> SEQUENCE: 161

| | |
|---|---|
| gggcgcgccc aggtgcagct ggtggagtct ggggctgaga tgaagaagcc tgggtcctcg | 60 |
| gtgaaggtct cctgccaggc ctctggaggc accttcagca actatggcat caattgggtg | 120 |
| cgacacgccc ctggacaagg gcttgagtgg atggggaggaa tcgtccctat ctatggtcca | 180 |
| ccgaagtacg cacagaagtt ccagggcaga gtcacgatta ctgcggacac gtccacgagc | 240 |
| acagcctaca tggagctgag cagcctgagc tctgatgaca cggccgtgta ttactgtgcg | 300 |
| cgactttccc ggactgtgtt tggctcgggg acttatcgtc cgggctacta ctacatggac | 360 |
| gtctggggca tagggaccac ggtcaccgtc tcg | 393 |

<210> SEQ ID NO 162
<211> LENGTH: 372
<212> TYPE: DNA
<213> ORGANISM: Homo Sapiens

<400> SEQUENCE: 162

| | |
|---|---|
| gggcgcgcct aggtgcagct acagcagtct ggggagggcc tggtcaagcc ggggggtcc | 60 |
| ctgagactct cctgtgcagc ctctggattc tcctttagta ataataacat gaattgggtc | 120 |
| cgccagactc caggaaaggg actggagtgg gtcgcatcca ttagttttgg aagtcattac | 180 |
| atatcctacg cagactcagt gaagggccga ttcaccatct ccagagacaa cgccaggaat | 240 |
| gcagtttatc tgcagatgaa cagcctgaga gtcgaggaca cggctgtcta ttactgcacg | 300 |
| agatgcaggg gcggaactcg tacctattat tacatggacg tctggggcaa aggcaccctg | 360 |
| gtcaccgtct cg | 372 |

<210> SEQ ID NO 163
<211> LENGTH: 378
<212> TYPE: DNA
<213> ORGANISM: Homo Sapiens

<400> SEQUENCE: 163

| | |
|---|---|
| gggcgcgcca aggtgcagct ggtgcagtct ggggctgagg tgaagaagcc tgggacctca | 60 |
| gtgagggtct cctgcaagac ttctggaggc tatgttttca gctgggtgcg acaggcccct | 120 |
| ggacaagggc ctgagtggat gggagggatc atcaccaact ttgggacaac aaactacgca | 180 |
| cagaagttcc agggcagagt cacgattacc gcggacaaat ccacgaacac agtgtacatg | 240 |
| gatttgagca acctgacatc tgaggacacg gccgtgtatt actgtgcgag agccccccga | 300 |
| ggcacgtcga ctatagcagc tcgtttaat cggtatttct ttgactcctg gggccagggc | 360 |
| accctggtca ccgtctcg | 378 |

<210> SEQ ID NO 164
<211> LENGTH: 372
<212> TYPE: DNA

<210> SEQ ID NO 164
<211> LENGTH: 372
<212> TYPE: DNA
<213> ORGANISM: Homo Sapiens

<400> SEQUENCE: 164

```
gggcgcgccg aagtgcagct ggtgcagtct ggggctgagg tgaagaagcc tgggtcctcg      60
gtgaaggtct cctgcaagac tgaaggaggc accttcagca cctatgttat cagttggatg     120
cgacaggccc ctggacaagg gcttgagtgg atgggaggga tcgtcccat ctttaacaca      180
ccaaactacg ctcagaaatt ccagggcaga gtcacaatta ccgcggacag atccacgagc     240
acagcctaca tggagctgag gagcctggga tctgaggaca cggccgtcta ttactgtgcg     300
agggtagtgg gaggtacaag gtcctactac gcttttgggct ctggggcca ggggaccacg     360
gtcaccgtct cg                                                         372
```

<210> SEQ ID NO 165
<211> LENGTH: 366
<212> TYPE: DNA
<213> ORGANISM: Homo Sapiens

<400> SEQUENCE: 165

```
gggcgcgccc aggtcacctt gaaggagtct ggtcctacgc tggtgaaacc cacacagacc      60
ctcacgctga cctgcacgtt ctctggtttc tcactcggca ctactggagt caatgtgggc     120
tggatccgtc agcccccagg aaaggccctg gagtggcttg cactcatttc ttggggtggt     180
ggtaagcact acagcccatc tctgaactcc aggatcaccc tcactaagga cgcctccaga     240
gagcaggtgg tggtccttac aatggccaac atggaccctg tggacacagg cagatattat     300
tgtgcacgta tagtggggac tcacggcttt gactactggg gccagggcac cctggtcacc     360
gtctcg                                                                366
```

<210> SEQ ID NO 166
<211> LENGTH: 372
<212> TYPE: DNA
<213> ORGANISM: Homo Sapiens

<400> SEQUENCE: 166

```
gggcgcgccg aggtccagct ggtgcagtct gggggaggtg tggtgcggcc tggggggtcc      60
ctgagactct cgtgtgcagg ctctggattc acctttgatg aatacgctat gagctgggtc     120
cgccaagctc cagggaaggg gctggagtgg gtcgctttta ttaattggaa tggtgatagc     180
acatattatg cagactctgt gaagggccga ttcaccgtct ccagaaccaa cgccaagaac     240
tccctgtatc tgcaaatgaa cagtctgaga gccgaggaca cggccttcta ttactgtgcg     300
agagaccccc gcactaaact ggggatgtcc tattttgact attggggcca gggcaccctg     360
gtcaccgtct cg                                                         372
```

<210> SEQ ID NO 167
<211> LENGTH: 390
<212> TYPE: DNA
<213> ORGANISM: Homo Sapiens

<400> SEQUENCE: 167

```
gggcgcgccg aagtgcagct ggtgcagtct ggagcagagg tgaagaagcc cggggagtct      60
ctgaaaatct cctgtcaggc ttctggatac ggctttaccg tctactggat cggctgggtg     120
cgccagctgc ccgggaaagg cctggagtgg ctgggtatca tctatcctgg tgactctgat     180
accagataca atccgtcctt ccaaggccag gtcaccatct cagccgacaa gtccgtcagc     240
accacctacc tgcagtggag cagcctgaag gcctcggaca ccgccattta ctactgtgcg     300
```

-continued agacatctgg actctatacga tgttttcact ggttataatt tgggggcta catggacgtc    360 tggggcaagg ggacaatggt caccgtctcg                                    390

<210> SEQ ID NO 168
<211> LENGTH: 369
<212> TYPE: DNA
<213> ORGANISM: Homo Sapiens

<400> SEQUENCE: 168
gggcgcgccg aggtgcagct ggtgcagtct ggacctgaag tgaagaagcc tggggcctca    60
gtgagggtct cctgcaaggc ctctggttac tcccttaaga actatggtat ccactgggtg   120
cgacaggccc ctggacaggg gcttgagtgg atggggtgga tcagcgctga caatggtgac   180
acaaccactg cactgaacct ccggggcaga gtctccatga ccacagacac atccacaaac   240
acagtctaca tggaggtgaa gagcctaaga tctgacgaca cggccatata tttctgtgcg   300
cgagattttt atagtgggag ttaccggtcc tttgactact ggggccaggg caccctggtc   360
accgtctcg                                                          369

<210> SEQ ID NO 169
<211> LENGTH: 378
<212> TYPE: DNA
<213> ORGANISM: Homo Sapiens

<400> SEQUENCE: 169
gggcgcgccg aagtgcagct ggtgcagtcg ggcccaggac tggtgaagcc ttcggagacc    60
ctgtccctca catgcgctgt ctctggtgcc tccgtcagcg gtggtgatta ctactggagc   120
tggatccggc agcccccagg gaaggcactg gagtggattg gtatatcta ttacataggg   180 agcaccaact acaatccctc tctcaagagt cgactctccc tatcagtaga cacggccaag   240
agccagttct ccctgaagtt gagctctgtg accgctgcgg acacggccat ttatttctgt   300
gcgagagcac gtcggacgta tagtggctac gactccgcct ttgactactg gggccaggga   360
accctggtca ccgtctcg                                                378

<210> SEQ ID NO 170
<211> LENGTH: 372
<212> TYPE: DNA
<213> ORGANISM: Homo Sapiens

<400> SEQUENCE: 170
gggcgcgccc aggtgcagct gcagcagtcg ggcccaggac tggtgaagcc ctcggagacc    60
ctgcccctca cctgcactgt ctctggtggc tccttcagta cctactactg gagctggatc   120
cggcagtccc cagagaaggg actggagtgg attggatata ccaaaacag tgtgaacacc   180 aactacaacc cctccctcaa gagtcgtgtc atcatttcag tggacacgtc caacaaccag   240
ttctccctga agctgaggtc tgtgaccgct gcggacacgg ccgtatatta ctgtgcgaga   300
gtaagcggct ggggcccaag gggaggcatc tactttgact actggggcca gggaaccctg   360
gtcaccgtct cg                                                      372

<210> SEQ ID NO 171
<211> LENGTH: 378
<212> TYPE: DNA
<213> ORGANISM: Homo Sapiens

<400> SEQUENCE: 171

```
gggcgcgcca aggtgcagct ggtgcagtct ggggctgaag tgaagaagcc tgggtcctca      60
gtgaaggtct cctgcaagtc ttctggaggc tatgttttca gctgggtgcg acaggcccct    120
gggcaaggac tagagtggat gggagggatc atctccaact ttcacacggc agagtacgca    180
cagaagttcc agggtagagt caccatgacc gcggacacat ccacgaacac aatctacatg    240
gagctgacca gcctgacatc tgaagacacg gccgtatatt tctgcgtgag cgcccccga     300 gacacgtcga ctatagcagc tcgttttaat cgatacttct ttgacacctg gggccagggc    360
accctggtca ccgtctcg                                                  378

<210> SEQ ID NO 172
<211> LENGTH: 378
<212> TYPE: DNA
<213> ORGANISM: Homo Sapiens

<400> SEQUENCE: 172
gggcgcgccg aggtgcagct ggtgcagtct ggggctgagg tgaagaagcc tgggacgtca     60
gtgagggtct cccgcaagac tcctggaggc tatgttttca gctgggtgcg acaggcccca   120
ggacaagggc ctgagtggat gggagggatc atcaccaact ttgggacaac aaactacgca   180
cggaagttcc agggcagaat cacggttacc gcggacaaat ccacgaacac agtgtacatg   240
gatttgagca acctggcatc tgaggacacg gccgtgtatt actgtgcgag agccccccga   300
ggcacgtcga ctatagcagc tcgttttaat cgatatttct ttgactcctg gagccagggc   360
accctggtca ccgtctcg                                                  378

<210> SEQ ID NO 173
<211> LENGTH: 372
<212> TYPE: DNA
<213> ORGANISM: Homo Sapiens

<400> SEQUENCE: 173
gggcgcgccg aggtgcagct ggtggagtct ggggctgagg tgaagaagcc tgggtcctcg     60
gtgaaggtct cctgcaaggc ctctggaggc agcttcagca cctatatttt cacctgggtg   120
cgccaggccc ctggacaggg gcttgagtgg atgggaggga tcaatcctat ctttgctaca   180
agagactacc caaagaagtt ccagggcaga gtcacgatca ccgcggacga atccacgagg   240
actgtctata tggagttgag cagcctcaca tctgaggaca cggccgtcta ttactgtgca   300
agagtgttgg gaggtacaag gctctactac gctctgaacg tctggggcca agggaccacg   360
gtcaccgtct cg                                                        372

<210> SEQ ID NO 174
<211> LENGTH: 372
<212> TYPE: DNA
<213> ORGANISM: Homo Sapiens

<400> SEQUENCE: 174
gggcgcgccg aagtgcagct ggtgcagtct gggggaggtg tggtgcggcc tgggggtcc     60 ctgagactct cgtgtgcagg ctctggattc acctttgatg aatacgccat gagctgggtc   120
cgccaagctc cagggaaggg gctgaagtgg gtcgctttta ttaattggaa tggtgatagc   180
acatattatg cagactctgt gaagggccga ttcaccgtct ccagatccaa cgccaagaac   240
tccctgtatc tgcaaatgaa cagtctgaga gccgaggaca cggccttcta ttgctgtgcg   300
agagaccccc gcactaaact ggggatgtcc tattttgact attggggcca gggcaccctg   360
gtcaccgtct cg                                                        372
```

<210> SEQ ID NO 175
<211> LENGTH: 372
<212> TYPE: DNA
<213> ORGANISM: Homo Sapiens

<400> SEQUENCE: 175

```
gggcgcgccg aggtgcagct ggtgcagtct ggggctgagg tgaagaagcc tgggtcctcg      60
gtgaaggtct cctgcaaggc ctctggaggc agcttcagca cctatgctat cacctgggtg     120
cgccaggccc ctggacaggg gcttgaatgg atgggaggga tcatccctat ctttgcttca     180
agagactacg cacagaagtt tcagggcaga gtcacaatca ccgcggacga atccacgagg     240
acagtgtaca tggagccgag gagcctgaga tctgaagaca cggccgtgta ttactgtgca     300
agagtgctgg gaggtacaag gctctactac gctctgaacg tctggggcca aggcaccctg     360
gtcaccgtct cg                                                         372
```

<210> SEQ ID NO 176
<211> LENGTH: 378
<212> TYPE: DNA
<213> ORGANISM: Homo Sapiens

<400> SEQUENCE: 176

```
gggcgcgccg aggtgcagct ggtgcagtcg ggcccaggac tggtgaagcc ttcggagacc      60
ctgtccctca catgcgctgt ctctggtgcc tccgtcagcg gtggtgatta ctactggagc     120
tggatccggc agcccccagg gaaggcactg gagtggattg gtatatctta ttacataggg     180
agcaccaact acaatccctc tctcaagagt cgactctccc tatcagtaga cacggccaag     240
agccagttct ccctgaagtt gagctctgtg accgctgcgg acacggccac ttatttctgt     300
gcgagagcac gtcggacgta tagtggctac gactccgcct ttgactactg ggccaggga     360
accctggtca ccgtctcg                                                   378
```

<210> SEQ ID NO 177
<211> LENGTH: 372
<212> TYPE: DNA
<213> ORGANISM: Homo Sapiens

<400> SEQUENCE: 177

```
gggcgcgccg aggtgcagct ggtggagtct ggggctgagg tgaagaagcc tgggtcctcg      60
gtgaaggtct cctgcaaggc ctctggaggc agcttcagca cctatgctat cacctgggtg     120
cgccaggccc ctggacaggg gcttgaatgg atgggaggga tcatccctat ctttgcttca     180
agagactacg cacagaagtt tcagggcaga gtcacaatca ccgcggacga atccacgagg     240
acagtgtaca tggagctgag cagcctgaga tctgacgaca cggccgtgta ttactgtgca     300
agagtgctgg gaggtacaag gctctactac gctctgaacg tctggggcca agggaccacg     360
gtcaccgtct cg                                                         372
```

<210> SEQ ID NO 178
<211> LENGTH: 369
<212> TYPE: DNA
<213> ORGANISM: Homo Sapiens

<400> SEQUENCE: 178

```
gggcgcgccc aggtcacctt gaaggagtct ggtcctacag tggtgaaacc cacacagacc      60
ctcacgctga cctgtagcct ctctgggttc gcactcggca ctaccggagt ggctgtgggc     120
```

```
tggatccgtc agcccccagg aaaggccctg aatggcttg gactcatcga ttggaatgat        180
gataggcgct acagaccctc tctgaagacc agactcacca tcacccagga catgtccagg      240
aaccaggtgg tccttagact gaccaacttg gacccactgg acacaggcac atatttttgt      300
gcacgttcag tagtgccggc gactagggcc tttgacttct ggggccaggg caccctggtc       360
accgtctcg                                                             369
```

<210> SEQ ID NO 179
<211> LENGTH: 366
<212> TYPE: DNA
<213> ORGANISM: Homo Sapiens

<400> SEQUENCE: 179

```
gggcgcgccc aggtcacctt gaaggagtct ggtcctacgc tggtgaaacc cacacagacc       60
ctcacgctga cctgcacctt gtctgggttc tcactctaca ctactggagt gggtgtgggc      120
tggatccgtc agcccccagg aaaggccctg gagtgactgg cacgcattta ttgggatgat      180
gatgagcgct acaacccgtc tctgaagagc aggctcacca tcaccaagga cgcctccaaa     240
aaccaggtgg tccttaaaat gaccaacatg gaccctgtgg acacagccac atattactgt      300
gcccggacca tgggcgtcgt tcttccatt gactactggg gccagggaac cctggtcacc      360
gtctcg                                                                366
```

<210> SEQ ID NO 180
<211> LENGTH: 327
<212> TYPE: DNA
<213> ORGANISM: Homo Sapiens

<400> SEQUENCE: 180

```
ctagccgaaa ttgtgctgac tcagtctcca tcctccctgt ctgcatctct aggagacaga       60
gtcaccatca cttgccgggc aagtcagcac attagcaatt atttaaattg gtatcagcag     120
aaacctggga agcccctaa actcctgatc tgtgctgcat ccagtttgca aagtggggtc      180
ccatcaaggt tcactggcag tggatctggg gcagattaca ccctcaccat cagcagtctg      240
caacctgaag attttgcaac ttactactgt caacagagtt acagtacctc gtggacgttc      300
ggccaaggga ccacggtgga aatcaaa                                          327
```

<210> SEQ ID NO 181
<211> LENGTH: 327
<212> TYPE: DNA
<213> ORGANISM: Homo Sapiens

<400> SEQUENCE: 181

```
ctagccgaaa ttgtgttgac acagtctcca tcctccctgt ctgcatctgt aggagacaga       60
gtcaccatca cttgccgggc gagtcagggc attagcaatt atttagcctg gtatcagcag     120
aaaccaggga aagttcctaa gctcctgatc tatgctgcat ccactttgca atcagggtc      180 ccatctcggt tcagtggcag tggatctggg acagatttca ctctcaccat cagcagcctg      240
cagcctgaag atgttgcaac ttattactgt caaaagtata acagtgcccc gtacactttt      300
ggccagggga ccaagctgga gatcaaa                                          327
```

<210> SEQ ID NO 182
<211> LENGTH: 327
<212> TYPE: DNA
<213> ORGANISM: Homo Sapiens

<400> SEQUENCE: 182

```
ctagccgatg ttgtgatgac tcagtctcca tcctccctgt ctgcatctct aggagacaga     60
gtcagcatca cttgccgggc aagtcaacat attagcaatt atataaattg gtatcagcag    120
aaacctggga aagcccctaa actcctgatc tatgctgctt ccactttgca aagtggggtc    180
ccatcaaggt tcactggcag tggatctggg gcagattaca ctctcaccat caccagtctg    240
caacctgaag attttgcaac ttactactgt caacagagtt acggtacctc gtggacgttc    300
ggccaaggga ccacggtgga aatcaaa                                        327
```

```
<210> SEQ ID NO 183
<211> LENGTH: 327
<212> TYPE: DNA
<213> ORGANISM: Homo Sapiens

<400> SEQUENCE: 183
ctagccgatg ttgtgatgac tcagtctcca tcctccctgt ctgcatctgt gggagacaga     60
gtcaccatca cttgccaggc gagtcaagac attaccaact atttaaattg gtatcagcag    120
aaaccaggga aagcccctaa gctcctgatc tacgatgcat ccaatttgca accaggggtc    180
ccatcaaggt tcagtggaag tggatctgtg acagatttta ctttcaccat cagcagcctg    240
cggcctgaag atattgcaac atattactgt caacagtatg atggtccagt gcttactttc    300
ggcggaggga ccaaggtaga gatcaaa                                        327
```

```
<210> SEQ ID NO 184
<211> LENGTH: 327
<212> TYPE: DNA
<213> ORGANISM: Homo Sapiens

<400> SEQUENCE: 184
ctagccgatg ttgtgatgac tcagtctcca tcctccctgt ctgcatctgt aggagacaga     60
gtcaccatct cttgccgggc aagtcagccc attagcacct atttaaattg gtatcagcag    120
aaaccaggga aagcccctaa gatcctgatc tttggtgcat ctcgtttgca aagtggtgtc    180
ccatcaaggt tcagcggcag tggatctggg acagatttca gtctcaccat caccagtctc    240
caacctgaag attttgcaac ttacatctgt caacaaagca gagtccccc gtacaatttt    300 ggccggggga ccaagctgga gatcaaa                                        327
```

```
<210> SEQ ID NO 185
<211> LENGTH: 330
<212> TYPE: DNA
<213> ORGANISM: Homo Sapiens

<400> SEQUENCE: 185
ctagccgaaa ttgtgttgac acagtctcct tccaccctgt ctgcatctgt aggcgacaga     60
gtcaccatca cttgccgggc cagtcagagt attggtagcg gttggcctg gtatcaacag    120 aaaccaggga aagcccctaa actcctgatc tataaggcgt ctactttaca aagtgagacc    180
ccttcaaggt tccgcggcag tggatctggg accgaattca ctctcaccat cagcagcctg    240
cagcctgatg attttgcaac ttactactgc caacagttta atagttttc tccgtggacg    300 ttcggccaag ggaccaaggt ggaattcaaa                                     330
```

```
<210> SEQ ID NO 186
<211> LENGTH: 327
<212> TYPE: DNA
<213> ORGANISM: Homo Sapiens
```

<400> SEQUENCE: 186

```
ctagccgatg ttgtgatgac tcagtctcca tcgtccctgt ctgcatctgt tggtgacaga      60
gtcaccatca cttgccgggc aagtcagagc attaacatta atttaaattg gtttcagcag     120
aaacccggga agcccctaa cctactgatc tattctgcat ccactttgca aactggggtc     180
ccctcaaggt tcagtggaag tggatctggg acagagttca ctctcaccat cagcagtcta     240
caacctgaag attttgcaac ttactactgt caacagattt acagtcatgt taggacgttc     300
ggccaaggga ccaaggtgga gatcaaa                                         327
```

<210> SEQ ID NO 187
<211> LENGTH: 345
<212> TYPE: DNA
<213> ORGANISM: Homo Sapiens

<400> SEQUENCE: 187

```
ctagccgatg ttgtgatgac tcagtctcca gactccctgg ctgtgtctct gggcgagagg      60
gccaccatca actgcaagtc cagccagagt cttttgtaca gctccaacaa taagaattac     120
ttagcttggt accagcagaa accaggacag cctcctaagt tgctcattta ctgggcatct     180
acccgggaat ccggggtccc tgaccgattc agtggcagcg ggtctgggac agatttcact     240
ctcaccatca gcagcctgca ggctgaagat gtggcagttt attactgtca gcaatattat     300
agtactcctc cgatgttcgg ccaagggacc aaggtggaaa tcaaa                     345
```

<210> SEQ ID NO 188
<211> LENGTH: 327
<212> TYPE: DNA
<213> ORGANISM: Homo Sapiens

<400> SEQUENCE: 188

```
ctagccgaaa ttgtgttgac acagtctcca tcctccctgt ctgcatctgt gggagacaga      60
atcaccatca cttgccaggc gagtcaagac attaccaact atttaaattg gtatcagcag     120
aaaccaggga aagcccctaa gctcctgatc tacgatgcat ccaatttgca accaggggtc     180
ccatcaaggt tcagtggaag tagatctggg acagatttta ctttcaccat cagcagcctg     240
cggcctgaag atattgcaac atattactgt caacagtatg atggtccagt gcttactttc     300
ggcggaggga ccaaggtaga gatcaaa                                         327
```

<210> SEQ ID NO 189
<211> LENGTH: 345
<212> TYPE: DNA
<213> ORGANISM: Homo Sapiens

<400> SEQUENCE: 189

```
ctagccgaaa ttgtgttgac acagtctcca gactccctgg ctgtgtctct gggcgagagg      60
gccaccatca actgcaagtc cagccagagt cttttatata gctccaacaa taagaactac     120
ttagcttggt accagcagaa accaggacag cctcctaagt tgctcattta ctgggcatct     180
acccgggaat ccggggtccc tgaccgattc agtggcagcg ggtctgggac agatttcacc     240
ctcaccatca gcagcctgca ggctgaagat gtggcagttt attactgtca gcaatattat     300
agtactcctc cgatgttcgg ccaagggacc aaggtggaaa tcaaa                     345
```

<210> SEQ ID NO 190
<211> LENGTH: 330
<212> TYPE: DNA
<213> ORGANISM: Homo Sapiens

<400> SEQUENCE: 190

```
ctagccgaaa ttgtgttgac acagtctcca tccttcctgt ctgcatctgt aggagacaga      60
gtcaccatca cttgccgggc cagtcagggc attgggaatt ttttagcctg gtatcagcaa     120
aaaccaggga aagcccctaa gctcctaatc tctggtgcat ccactttgca aagttgggtc     180
ccatcaaggt tcagcggccg tggatctggg accgaattca ccctcacaat cagcagcctg     240
cagcctgaag attttgcaac ttattactgt caacagctta atcgttaccc tccatacact     300
tttggccagg ggaccaagct ggagatcaaa                                      330
```

<210> SEQ ID NO 191
<211> LENGTH: 327
<212> TYPE: DNA
<213> ORGANISM: Homo Sapiens

<400> SEQUENCE: 191

```
ctagccgaaa ttgtgatgac gcagtctcca tcctccctgt ctgcatctgt gggagacaga      60
gtcaccatca cttgccaggc gagtcaggac attagcaaat atttaaattg gtatcagcag     120
aaaccaggga gagcccctaa actcctgatc tacgaagcat ccaatttgga cagggggtc     180
ccaccaaggt tcagtggaag tggatctggg acacatttta ctttcaccat caccggcctg     240
cagcctgaag atattgcaac atattactgt caacagtgtg atagtctgcc tccggtcttt     300
ggccagggga ccaagctgga agtcaaa                                          327
```

<210> SEQ ID NO 192
<211> LENGTH: 330
<212> TYPE: DNA
<213> ORGANISM: Homo Sapiens

<400> SEQUENCE: 192

```
ctagccgaaa ttgtgctgac tcagtctcca ggcaccctgg ctttgtctcc aggtgataga      60
gccaccctct cctgcggggc cagtcagagc gtgttcggcg acttcttagc ctggtaccaa     120
cacaagcctg gccaggctcc caggctcctc atctatggtg cttccaccag ggccactggc     180
atcccagaca ggttcagtgg cagtggagct gggacagact tcactctcac catcagcaga     240
ctggagcctg aggattttgc agtttatttc tgtcagtagt atggtgactc agtgttcacg     300
ttcggccaag ggaccaagtt gggaatcaaa                                      330
```

<210> SEQ ID NO 193
<211> LENGTH: 330
<212> TYPE: DNA
<213> ORGANISM: Homo Sapiens

<400> SEQUENCE: 193

```
ctagccgaaa ttgtgatgac acagtctcca ggcaccctgg ctttgtctcc aggtgataga      60
gccaccctct cctgcggggc cagtcagagc gtgttcggcg acttcttagc ctggtaccaa     120
cacaagcctg gccaggctcc caggctcctc atctatggtg cttccaccag ggccactggc     180
atcccagaca ggttcagtgg cagtggagct gggacagact tcactctcac catcagcaga     240
ctggagcctg aggattttgc agtttatttc tgtcagcagt atggtgactc agtgttcacg     300
ttcggccaag ggaccaagtt ggaaatcaaa                                      330
```

<210> SEQ ID NO 194
<211> LENGTH: 330
<212> TYPE: DNA

<213> ORGANISM: Homo Sapiens

<400> SEQUENCE: 194

| | | | | | |
|---|---|---|---|---|---|
| ctagccgaaa | ttgtgttgac | acagtctcca | ggcaccctgt | ctttgtctcc | agggcaaaga | 60 |
| gccaccctct | cctgcagggc | cagtcagagt | gttaacagag | actacctagc | ctggtaccag | 120 |
| cagaaacctg | gctaggctcc | caggctcctc | atctatggtg | catccagcag | ggccactggc | 180 |
| atcccagaca | ggttcagtgg | cagtgggtct | ggaacagact | tcactctcac | catcagcaga | 240 |
| ctggagcgag | acgattttgc | agtgtatttc | tgtcaccagt | atggtagctc | acctaacact | 300 |
| tttggccagg | ggaccaagct | ggagatcaaa | | | 330 |

<210> SEQ ID NO 195
<211> LENGTH: 330
<212> TYPE: DNA
<213> ORGANISM: Homo Sapiens

<400> SEQUENCE: 195

| | | | | | |
|---|---|---|---|---|---|
| ctagccgaaa | cgacactcac | gcagtctcca | ggcaccctgt | ctttgtctcc | aggggaaaga | 60 |
| gccaccctct | cctgcagggc | cagtcagagc | gttagcacca | actacttagc | ctggtaccga | 120 |
| cagaaacctg | gccaggctcc | caggctcctc | atccatggtg | catccagccg | ggccactggc | 180 |
| atcccagaca | ggttcagtgg | cagtgggtct | gggacagact | tcactctcac | catcagcaga | 240 |
| ctggagcctg | aagattttgc | agtgtatttc | tgtcagcagt | atggtagctc | acctcagacg | 300 |
| ttcggccaag | ggaccaggtt | ggaaatcaaa | | | 330 |

<210> SEQ ID NO 196
<211> LENGTH: 327
<212> TYPE: DNA
<213> ORGANISM: Homo Sapiens

<400> SEQUENCE: 196

| | | | | | |
|---|---|---|---|---|---|
| ctagccgaaa | ttgtgctgac | tcagtctcca | tcctccctgt | ctgcatctgt | tggtgacaga | 60 |
| gtcaccacca | cttgccggac | aagtcagagc | attttcatta | atttaaattg | gtttcagcag | 120 |
| aaacccggga | aagcccctaa | actcctgatc | tattctgcat | ccacttttgca | aactggggtc | 180 |
| ccctcaaggt | tcagtggcag | tggatctggg | acagagttca | ctctcaccat | cagcagtcta | 240 |
| caacctgaag | attttgcaac | ttactactgt | caacagattt | acagtcaggt | taggacgttc | 300 |
| ggccaaggga | ccaaggtgga | gatcaaa | | | 327 |

<210> SEQ ID NO 197
<211> LENGTH: 330
<212> TYPE: DNA
<213> ORGANISM: Homo Sapiens

<400> SEQUENCE: 197

| | | | | | |
|---|---|---|---|---|---|
| ctagccgaca | tccagatgac | ccagtctcca | ggcaccctgt | ctttgtctcc | aggggaaaga | 60 |
| gccaccctct | cctgcagggc | cagtcagagt | gttaacagcg | acaacttagc | ctggtaccag | 120 |
| cagaaacctg | gccaggctcc | caggctcctc | atgtctggtg | caaccagtag | ggccactgac | 180 |
| gtcccagaca | ggttcagtgg | cagtgggtct | gggacagact | tcactctcac | catcagcaga | 240 |
| ctggagcctg | aagattttgc | agtgtattac | tgtcaccagt | atggtagctc | agataacact | 300 |
| tttggccagg | ggaccaagct | ggagatcaaa | | | 330 |

<210> SEQ ID NO 198
<211> LENGTH: 330

```
<212> TYPE: DNA
<213> ORGANISM: Homo Sapiens

<400> SEQUENCE: 198
ctagccgatg ttgtgatgac tcagtttcct tcctctctgt ctgcatctgt gggagacaga      60
gtcaccatca cttgccgggc gagtcagggc attagcaatt ttttagcctg gtatcagcag     120
aaaccaggga agttcctga gctccttatc tatggtgcat ccactttgca atcagggtc       180 ccatctcggt tcagtggcag tggatctggg gcagagttca cactcaccat caacagcctg     240
cagcctgaag atgttgcgac ttattactgt caaaagtatg acagtggcct gagattcact     300
ttcggccctg ggaccaaagt ggatatcaaa                                     330

<210> SEQ ID NO 199
<211> LENGTH: 330
<212> TYPE: DNA
<213> ORGANISM: Homo Sapiens

<400> SEQUENCE: 199
ctagccgatg ttgtgatgac tcagtctcct tcctctctgt ctgcatctgt aggagacaga     60
gtcaccatca cttgccgggc gagtcagggc attagcaatt ttttagcctg gcatcagcag    120
aaaccagggc aagttcctaa actcctgatc tatggtgcat ccactttgca atcagggtc     180 ccatctcgct tcagtggcag tggatctggc acagatttca ctctcaccat caacggcctg    240
cagcctgaag atgttgcaac ttattactgt caaaagtatg acagtggcct gatattcact    300
ttcggccctg ggaccagagt ggagatcaaa                                    330

<210> SEQ ID NO 200
<211> LENGTH: 345
<212> TYPE: DNA
<213> ORGANISM: Homo Sapiens

<400> SEQUENCE: 200
ctagccgatg ttgtgatgac tcagtctcca gactccctgg ctgtgtctct gggcgagagg     60
gccaccatca actgcaagtc cagccagagt cttttataca gctccaacaa taagaactac    120
ttagcttggt accagcagaa accaggacag cctcctaagt tgctcattta ctgggcatct    180
acccgggaat ccggggtccc tgaccgattc agtggcagcg gtctgggac agatttcact     240 ctcaccatca gcagcctgca ggctgaagat gtggcagttt attactgtca gcaatattat    300
agtactcctc cgatgctcgg ccaagggacc aaggtggaaa tcaaa                    345

<210> SEQ ID NO 201
<211> LENGTH: 330
<212> TYPE: DNA
<213> ORGANISM: Homo Sapiens

<400> SEQUENCE: 201
ctagccgatg ttgtgatgac ttagtctcca ggcaccctgg ctttgtctcc aggtgataga     60
gccaccctct cctgcgggc cagtcagagc gtgttcggcg acttcttagc ctggtaccaa    120
cacaagcctg gccaggctcc caggctcctc atctatgttg cttccaccag gccactggc    180 atcccagaca ggttcagtgg cagtggagct gggacagact tcactctcac catcagcaga    240
ctggagcctg aggattttgc agtttatttc tgtcagcagt atggtgactc agtgttcacg    300
ttcggccaag ggaccaagtt ggaaatcaga                                    330

<210> SEQ ID NO 202
```

```
<211> LENGTH: 330
<212> TYPE: DNA
<213> ORGANISM: Homo Sapiens

<400> SEQUENCE: 202
ctagccgaaa cgacactcac gcagtctcca ggcaccctgt ctttgtctcc aggggaaaga      60
gccaccctct cctgcagggc cagtcagagc gttagcacca actacttagc ctggtaccga     120
cagaaacctg gccaggctcc caggctcctc atccatggtg catccagccg ggccactggc     180
atcccagaca ggttcagtgg cagtgggtct gggacagact tcactctcac catcagcaga     240
ctggagcctg aagattttgc agtgtatttc tgtcagcagt atggtagctc acctcagacg     300
ttcggccaag ggaccaggtt ggaaatcaaa                                      330

<210> SEQ ID NO 203
<211> LENGTH: 330
<212> TYPE: DNA
<213> ORGANISM: Homo Sapiens

<400> SEQUENCE: 203
ctagccgaaa ttgtgctgac tcagtctcca ggcaccctgt ctttgtctcc aggggaaaga      60
gccaccctct cctgcagggc cagtcggagt gtaaacagca caacttagc ctggtatcag     120
cagaaacctg accaggctcc caggctcctc atgtatggtg catccagtag gccactggc     180
atcccagaca ggttcactgg cagtgggtct gggacagact tcactctcac catcagcaga     240
ctggagcctg aagattttgc agtgtattac tgtcatcagt atggtgcctc agataacact     300
tttggccagg ggaccaagct ggagatcaag                                      330

<210> SEQ ID NO 204
<211> LENGTH: 327
<212> TYPE: DNA
<213> ORGANISM: Homo Sapiens

<400> SEQUENCE: 204
ctagccgaaa ttgtgatgac acagtctcca tccttcctgt ctgcatctgt aggagacaga      60
gtcaccatca cttgccgggc cagtcaggac attatcactt atttagcctg gtatcaacaa     120
aaaccaggga agcccctga ggtcctgatc tttggtgcgt ccactttgca aagtggggtc     180
ccatcaagat tcagcggcag tggatctggg accgaattca ctctcactat ctccagcctg     240
cagcctgaag attttgcaac ttattactgt caacagatta ttcgttaccc tcgcactttc     300
ggccaaggga ccagggtgga aatcaaa                                         327

<210> SEQ ID NO 205
<211> LENGTH: 330
<212> TYPE: DNA
<213> ORGANISM: Homo Sapiens

<400> SEQUENCE: 205
ctagccgatg ttgtgatgac tcagtctcca ggcaccctgt ctttgtctcc aggggaaaga      60
gccaccctct cctgccgggc cagtcagagt gttaacagca caacttagc ctggtaccag     120
cagaaacctg gccaggctcc caggctcctc gtctctggtg caaccaatag gccactgac     180
atcccagaca ggttcagtgg cagtgggtct gggacagact tcactctcac catcagcaga     240
ctggagcctg aagattttgc agtgtattac tgtcaccagt atggtagctc agagaacact     300
tttggccagg ggaccaagct ggagatcaga                                      330
```

<210> SEQ ID NO 206
<211> LENGTH: 327
<212> TYPE: DNA
<213> ORGANISM: Homo Sapiens

<400> SEQUENCE: 206

```
ctagccgaaa ttgtgatgac gcagtctcca cccttcctgt ctgcatctgt aggagacaga      60
gtcaccatca cttgccgggc cagtcagggc ttaagcactt atttagcctg gtatcaggta     120
aaaccaggga agcccctaa gctcctgatc tatgctgcat ccactttgca aagtggggtc     180
ccatcaaggt tcagcggcag tggatctggg acagaattca ctctcacaat caacagcctg     240
cagcctgaag attttgcaac ttattactgt caacaacttg atacttaccc tctcactctc     300
ggcggaggga ccaaggtgga gatcaaa                                          327
```

<210> SEQ ID NO 207
<211> LENGTH: 345
<212> TYPE: DNA
<213> ORGANISM: Homo Sapiens

<400> SEQUENCE: 207

```
ctagccgaaa ttgtgttgac acagtctcca gactccctgg ctgtgtctct gggcgagagg      60
gccaccatca actgcaagtc cagccagagt cttttataca gctccaacaa taagaactac     120
ttagcttggt accagcagaa accaggacag cctcctaagt tgctcattta ctgggcatct     180
acccgggaat ccggggtccc tgaccgattc agtggcagcg gtctgggac agatttcact      240
ctcaccatca gcagcctgca ggctgaagat gtggcagttt attactgtca gcaatattat     300
agtactcctc cgatgttcgg ccaagggacc aaggtggaaa tcaaa                      345
```

<210> SEQ ID NO 208
<211> LENGTH: 345
<212> TYPE: DNA
<213> ORGANISM: Homo Sapiens

<400> SEQUENCE: 208

```
ctagccgaca tccagatgac ccagtctcca gactccctgg ctgtgtctct gggcgagagg      60
gccaccatca actgcaagtc cagccagagt cttttataca gctccaacaa taagaactac     120
ttagcttggt accagcagaa accaggacag cctcctaagt tgctcattta ctgggcatct     180
acccgggaat ccggggtccc tgaccgattc agtggcagcg gtctgggac agatttcact      240
ctcaccatca gcagcctgca ggctgaagat gtggcagttt attactgtca gcaatattat     300
agtactcctc cgatgttcgg ccaagggacc agggtggaaa tcaaa                      345
```

<210> SEQ ID NO 209
<211> LENGTH: 330
<212> TYPE: DNA
<213> ORGANISM: Homo Sapiens

<400> SEQUENCE: 209

```
ctagccgaaa ttgtgatgac acagtctcca ggcaccctgg ctttgtctcc aggtgataga      60
gccaccctct cctgcggggc cagtcagagc gtgttcggcg acttcttagc ctggtaccaa     120
cacaagcctg gccaggctcc caggcccctc atctatggtg cttccaccag gccactggc     180
atcccagaca ggttcagtgg cagtggagct gggacagact tcactctcac catcagcaga     240
ctggagcctg aggattttgc agtttatttc tgtcagcagt atggtgactc agtgttcacg     300
ttcggccaag ggaccaagtt ggaaatcaaa                                       330
```

```
<210> SEQ ID NO 210
<211> LENGTH: 330
<212> TYPE: DNA
<213> ORGANISM: Homo Sapiens

<400> SEQUENCE: 210
ctagccgatg ttgtgatgac tcagtctcca ggcaccctgt ctttgtctcc aggggaaaga      60
gccaccctct cctgcagggc cagtcagagt gttaacagcg acaacttagc ctggtaccag     120
cagaaacctg gccaggctcc caggctcctc atgtctggtg caaccagtag ggccactgac     180
atcccagaca ggttcagtgg cagtgggtct gggacagact tcactctcac catcagcaga     240
ctggagcctg aagattttgc agtgtattac tgtcaccagt atggtagctc agataacact     300
tttggccagg ggaccaagct ggagatcaaa                                      330

<210> SEQ ID NO 211
<211> LENGTH: 330
<212> TYPE: DNA
<213> ORGANISM: Homo Sapiens

<400> SEQUENCE: 211
ctagccgaca tccagttgac ccagtctcca tcctccctgt ctgcatctgt tggagacagc      60
gtcaccatca cttgccgggc gagtcagggc attagcaatt ttttagcctg gtatcagaag     120
aaaccgggaa aagttcctag gctcctgatc tatggtgcat ccactttgca atcagggggtc    180 ccatctcggt tcagtggcag tggatctggg accgatttca ctctcaccat cagcagcctg     240
cagcctgaag atgttgcgac ttattactgt caggagtata gcaatgccct gatattcact     300
ttcggccctg ggaccaaagt tcatatcaaa                                      330

<210> SEQ ID NO 212
<211> LENGTH: 330
<212> TYPE: DNA
<213> ORGANISM: Homo Sapiens

<400> SEQUENCE: 212
ctagccgaaa ttgtgatgac acagtctcca tccttcctgt ctgcgtctgt aggagacaga      60
gtcaccatca cttgccgggc cagtcagggc attgggaatt ttttagcctg gtatcagcaa     120
aaaccaggga aagcccctaa gctcctgatc tctggtgcat ccactttgca aagttgggtc     180
ccatcaaggt tcagcggccg tggatctggg accgaattca ctctcacaat cagcagcctg     240
cagcctgaag attttgcaac ttattactgt caacagctta atcgttaccc tccatacact     300
tttggccagg ggaccaagct ggagatcaaa                                      330

<210> SEQ ID NO 213
<211> LENGTH: 327
<212> TYPE: DNA
<213> ORGANISM: Homo Sapiens

<400> SEQUENCE: 213
ctagccgaaa ttgtgatgac acagtctcca tcctccctgt ctgcatctgt aggagacaga      60
gtcaccatca cttgccgggc aagtcagacc attagcaacc atttaaattg gtatcagcag     120
aaaccaggga gagcccctaa gctcctgatc tatgttgggt ccagtctgca aagtggggtc     180
ccatcaaggt tcagtggcag tggatctggg acagatttca ctctcaccat cagtggtctg     240
caacctgaag attttgcaac ttactactgt caacagagtt acagtccctc gtacactttt     300
ggccagggga ccaaggtgga gatcaaa                                         327
```

<210> SEQ ID NO 214
<211> LENGTH: 330
<212> TYPE: DNA
<213> ORGANISM: Homo Sapiens

<400> SEQUENCE: 214

| ctagccgaca tccagttgac ccagtctcca ggcaccctgt ctttgtctcc aggggaaaga | 60 |
| gccaccctct cctgcagggc cagtcagagc gttagcacca actacttagc ctggtaccga | 120 |
| cagaaacctg gccaggctcc caggctcctc atccatggtg catccagccg ggccactggc | 180 |
| atcccagaca ggttcagtgg cagtgggtct gggacagact tcactctcac catcagcaga | 240 |
| ctggagcctg aagattttgc agtgtatttc tgtcagcagt atggtagctc acctcagacg | 300 |
| ttcggccaag ggaccaggtt ggaaatcaaa | 330 |

<210> SEQ ID NO 215
<211> LENGTH: 327
<212> TYPE: DNA
<213> ORGANISM: Homo Sapiens

<400> SEQUENCE: 215

| ctagccgatg ttgtgatgac tcagtctcca tcctccctgt ctgcatctct aggagacaga | 60 |
| gtcaccatca cttgccgggc aagtcagcat attagcaatt atttaaattg gtatcagcag | 120 |
| aaacctggga aagcccctaa actcctgatc tatgctgcat ccagtttgca aagtggggtc | 180 |
| ccatcaaggt tcactggcag tggatctggg cagattaca ctctcaccat cagcagtctg | 240 |
| caacctgaag attttgcaac ttactactgt caacagagtt acagcacctc gtggacgttc | 300 |
| ggccaaggga ccacggtggg aatcaaa | 327 |

<210> SEQ ID NO 216
<211> LENGTH: 327
<212> TYPE: DNA
<213> ORGANISM: Homo Sapiens

<400> SEQUENCE: 216

| ctagccgatg ttgtgatgac tcagtctcca tcctccctgt ctgcatctgt aggagacaga | 60 |
| gtcagcatca cttgccgggc aagtcggagc gttaagacct atttaaattg gtatcagcag | 120 |
| aaaccaggga aagcccctaa gctcctggtc tatggttcgt ccagtttgga aagtggggtc | 180 |
| ccatcaagat tcagtggcag tggatctggg acagatttca ctctcaccat cagcagtctg | 240 |
| caacctgagg attttgcaac ttactactgt caacagagtt cggtacccc ctacactttt | 300 |
| ggccagggga ccaagctgga caccaaa | 327 |

<210> SEQ ID NO 217
<211> LENGTH: 327
<212> TYPE: DNA
<213> ORGANISM: Homo Sapiens

<400> SEQUENCE: 217

| ctagccgaca tccagatgac ccagtctcca tcctccctgt ctgcatctgt aagtgacaga | 60 |
| gtcaccatta cttgccgggc aagtcagagc attaacaagt tcttaaactg gtatcagcag | 120 |
| aaaccaggga aagcccctca gctcctcatc tatgctgcaa ccaatttgca gagtggggtc | 180 |
| ccatcaaggt tcagtggcag tggatctggg acagacttca ctctcaccat cagcagtctg | 240 |
| caaactgaag attttgccac ttactactgt caacagagtt acgatatgcc tcggacgttc | 300 |

```
ggccaaggga ccaaggtgga gatcaaa                                            327
```

<210> SEQ ID NO 218
<211> LENGTH: 330
<212> TYPE: DNA
<213> ORGANISM: Homo Sapiens

<400> SEQUENCE: 218

```
ctagccgaaa ttgtgctgac tcagtctcca ggcaccctgt ctttgtctcc aggggaaaga       60
gccaccctct cctgcagggc cagtcggagt gtatacagca caacttagc ctggtatcag       120
cagaaacctg accaggctcc caggctcctc atgtatggtg catccagtag gccactggc       180
atcccagaca ggttcactgg cagtgggtct gggacagact tcactctcac catcagcaga      240
ctggagcctg aagattttgc agtgtattac tgtcatcagt ataacact                  300
tttggccagg ggaccaagct ggagatcaag                                        330
```

<210> SEQ ID NO 219
<211> LENGTH: 345
<212> TYPE: DNA
<213> ORGANISM: Homo Sapiens

<400> SEQUENCE: 219

```
ctagccgaca tccagatgac ccagtctcca gactccctgg ctgtgtctct gggcgagaag       60
gccaccatca actgcaagtc cagccagagt ctttttataca gctccaacaa taagaactac      120
ttagcttggt accagcagaa accaggacag cctcctaagt tgctcattta ctgggcatct      180
acccgggaat ccggggtccc tgaccgattc agtggcagcg ggtctgggac agatttcact      240
ctcaccatca gcagcctgca ggctgaagat gtggcagttt attactgtca gcaatattat      300
agtactcctc cgatgttcgg ccaagggacc aaggtggaaa tcaaa                       345
```

<210> SEQ ID NO 220
<211> LENGTH: 330
<212> TYPE: DNA
<213> ORGANISM: Homo Sapiens

<400> SEQUENCE: 220

```
ctagccgaaa ttgtgatgac gcagtctcct cctctctgt ctgcatctgt aggagacaga       60
gtcaccatct cttgccgggc gagtcagggc attagcaatt ttttagcctg gtttcagcag      120
aaaccaggtc aagttcctaa gctcctgatc tatgttgcat ccactttgca atcagggtc       180
ccatctcggt tcagtggcag tggatctggg acagatttca gtctcaccat caacggcctg      240
cagcctgagg atgttgcaac ttattactgt caaaggtatg acagtggcct gatattcact      300
ttcggccctg ggaccaaagt ggagatcaaa                                        330
```

<210> SEQ ID NO 221
<211> LENGTH: 327
<212> TYPE: DNA
<213> ORGANISM: Homo Sapiens

<400> SEQUENCE: 221

```
ctagccgaca tccagatgac ccagtctcca tcctccctgt ctgcatctgt aggagacaga       60
gtcaccatca cttgccgggc aagtcagacc attagcaacc atttaaattg gtatcagcag      120
aaaccaggga gagcccctaa gctcctgatc tatgttgggt ccagtctgcg aagtggggtc      180
ccatcaaggt tcagtggcag tggatctggg acagatttca ctctcaccat cagtggtctg      240
caacctgaag attttgcaac ttactactgt caacagagtt acagtccctc gtacactttt      300
```

```
ggccagggga ccaaggtgga gatcaaa                                        327

<210> SEQ ID NO 222
<211> LENGTH: 330
<212> TYPE: DNA
<213> ORGANISM: Homo Sapiens

<400> SEQUENCE: 222
ctagccgaaa ttgtgttgac acagtctcct tcctctctgt ctgcatctgt gggagacaga     60
gtcaccatca cttgccgggc gagtcagggc attagcaatt ttttagcctg gtatcagcag    120
aaaccaggga agttcctga gctccttatc tatggcgcat ccactttgca atcgggggtc    180
ccatctcggt tcagtggcag tggatctggg acagatttca ctctcaccat caacagcctg    240
cagcctgaag atgttgcaac ttattactgt caaaagtatg acagtggcct gagattcact    300
ttcggccctg gggccaaagt ggatatcaaa                                     330

<210> SEQ ID NO 223
<211> LENGTH: 327
<212> TYPE: DNA
<213> ORGANISM: Homo Sapiens

<400> SEQUENCE: 223
ctagccgatg ttgtgatgac tcagtctcca tcctccctgt ctgcatctgt aggagacaga     60
gtcagcatca cttgccgggc aagtcggagc gttaagacct atttaaattg gtatcagcag    120
aaaccaggga aagcccctaa gctcctggtc tatggttcgt ccagtttgga aagtggggtc    180
ccatcaagat tcagtggcag tggatctggg acagatttca ctctcaccat cagcagtctg    240
caacctgagg attttgcaac ttactgctgt caacagagtt cggtacccc ctacactttt     300 ggccagggga ccaagctgga catcaaa                                        327

<210> SEQ ID NO 224
<211> LENGTH: 330
<212> TYPE: DNA
<213> ORGANISM: Homo Sapiens

<400> SEQUENCE: 224
ctagccgaca tccagttgac ccagtctcct tcctctctgt ctgcatctgt gggagacaga     60
gtcaccatca cttgccgggc gagtcagggc attagcaatt ttttagcctg gtatcagcag    120
aaaccaggga agttcctga gctccttatc tatggtgcat ccaccttgca atcagggggtc   180 ccatctcggt tcagtggcag tggatctggg acagagttca ctctcaccat caacagcctg    240
cagcctgaag atgttgcgac ttattactgt caaaagtatg atagtggcct gagattcact    300
ttcggccctg ggaccaaagt ggatatcaaa                                     330

<210> SEQ ID NO 225
<211> LENGTH: 327
<212> TYPE: DNA
<213> ORGANISM: Homo Sapiens

<400> SEQUENCE: 225
ctagccgaca tccagatgac ccagtcttct tccaccctgt ctgcatctgt aggagacaga     60
gtcaccatca cttgccgggc cagtcagaat attaatatct ggttggcctg gtatcagcag    120
aaagcaggga agccccccaa actcctgatc tataaggcgt ctactttaga aggggggtc    180 ccctcaaggt tcagcggcag tggatctggg acagagttca ctctcaccat caccggcctg    240
```

```
cgccctgacg atttcggaag ttattattgc caacactatg atggtaattc actaacgttc    300
ggccaaggga ccagggtgga tatccaa                                        327
```

<210> SEQ ID NO 226
<211> LENGTH: 330
<212> TYPE: DNA
<213> ORGANISM: Homo Sapiens

<400> SEQUENCE: 226

```
ctagccgaca tccagttgac ccagtctcct tccaccctgt ctgcatctgt aggcgacaga    60
gtcaccatca cttgccgggc cagtcagagt attggtagct ggttggcctg gtatcaacag    120
aaaccaggga aagcccctaa actcctgatc tataaggcgt ctactttaca aagtgagacc    180
ccttcaaggt tccgcggcag tggatctggg accgaattca ctctcaccat cagcagcctg    240
cagcctgatg attttgcaac ttactactgc caacagttta atagtttttc tccgtggacg    300
ttcggccaag ggaccaaggc ggaattcaaa                                     330
```

<210> SEQ ID NO 227
<211> LENGTH: 123
<212> TYPE: PRT
<213> ORGANISM: homo sapiens

<400> SEQUENCE: 227

```
Gly Arg Ala Gln Val Gln Leu Val Gln Ser Gly Pro Glu Val Lys Lys
1               5                   10                  15

Pro Gly Ala Ser Val Arg Val Ser Cys Lys Ala Ser Gly Tyr Ser Phe
            20                  25                  30

Lys Asn Tyr Gly Ile His Trp Val Arg Gln Ala Pro Gly Gln Gly Leu
        35                  40                  45

Glu Trp Met Gly Trp Ile Ser Ala Asp Asn Gly Asp Thr Thr Thr Ala
    50                  55                  60

Leu Asn Leu Arg Gly Arg Val Ser Met Thr Thr Asp Thr Ser Thr Asn
65                  70                  75                  80

Thr Val Tyr Met Glu Val Lys Ser Leu Arg Ser Asp Asp Thr Ala Ile
                85                  90                  95

Tyr Phe Cys Ala Arg Asp Phe Tyr Ser Gly Ser Tyr Arg Ser Phe Asp
            100                 105                 110

Cys Trp Gly Gln Gly Thr Leu Val Thr Val Ser
        115                 120
```

<210> SEQ ID NO 228
<211> LENGTH: 126
<212> TYPE: PRT
<213> ORGANISM: homo sapiens

<400> SEQUENCE: 228

```
Gly Arg Ala Gln Val Gln Leu Gln Gln Ser Gly Gly Leu Val Lys
1               5                   10                  15

Pro Gly Gly Ser Leu Arg Leu Ser Cys Ala Ala Ser Gly Phe Thr Phe
            20                  25                  30

Ser Ser Tyr Ser Met Asn Trp Val Arg Gln Ala Pro Gly Lys Gly Leu
        35                  40                  45

Glu Trp Val Ser Ser Ile Ser Ser Ser Ser Tyr Ile Tyr Tyr Ala
    50                  55                  60

Asp Ser Val Lys Gly Arg Phe Thr Ile Ser Arg Asp Asn Ala Lys Asn
65                  70                  75                  80
```

```
Ser Leu Tyr Leu Gln Met Asn Ser Leu Arg Ala Glu Asp Thr Ala Val
                85                  90                  95

Tyr Tyr Cys Ala Arg Arg Pro Gly Trp Ala Ala Thr Arg Ala Ala Gly
            100                 105                 110

Ala Phe Asp Ile Trp Gly Gln Gly Thr Met Val Thr Val Ser
        115                 120                 125

<210> SEQ ID NO 229
<211> LENGTH: 119
<212> TYPE: PRT
<213> ORGANISM: homo sapiens

<400> SEQUENCE: 229

Gly Arg Ala Gln Val Gln Leu Val Gln Ser Gly Pro Glu Leu Lys Lys
1               5                   10                  15

Pro Gly Ala Ser Val Arg Ile Ser Cys Lys Ala Ser Glu Lys Cys Asp
            20                  25                  30

Ile His Trp Val Arg Gln Ala Pro Gly Gln Gly Leu Glu Trp Met Gly
        35                  40                  45

Trp Ile Ser Ala Asp Asp Gly Thr Thr Thr Ala Leu Asn Leu Arg
    50                  55                  60

Gly Arg Val Ser Met Thr Thr Asp Arg Ala Thr Asn Thr Val Tyr Met
65                  70                  75                  80

Glu Leu Lys Ser Leu Arg Ser Asp Thr Ala Ile Tyr Phe Cys Ala
                85                  90                  95

Arg Asp Phe Tyr Ser Gly Thr Tyr Arg Ser Phe Asp Tyr Trp Gly Gln
            100                 105                 110

Gly Thr Leu Val Thr Val Ser
        115

<210> SEQ ID NO 230
<211> LENGTH: 132
<212> TYPE: PRT
<213> ORGANISM: homo sapiens

<400> SEQUENCE: 230

Gly Arg Ala Lys Val Gln Leu Val Glu Ser Gly Gly Val Val Gln
1               5                   10                  15

Pro Gly Thr Ser Leu Arg Leu Ser Cys Val Val Ser Gly Phe Thr Phe
            20                  25                  30

Arg Thr Tyr Gly Met Asn Trp Val Arg Gln Ala Pro Gly Lys Gly Leu
        35                  40                  45

Glu Trp Leu Ala Phe Leu Ser Ser Asp Gly Ser Asp Glu Phe Tyr Ala
    50                  55                  60

Asp Ser Val Lys Gly Arg Phe Thr Val Ser Arg Asp Asn Ser Lys Ser
65                  70                  75                  80

Thr Leu Phe Leu Lys Met Asn Ser Leu Arg Pro Asp Asp Thr Ala Val
                85                  90                  95

Tyr Tyr Cys Ala Arg Asp Arg Gly Ala Gln Ile Thr Leu Phe Gly Ala
            100                 105                 110

Pro Leu Ile Arg Pro Ser Ser Phe Asp Ser Trp Gly Gln Gly Thr Leu
        115                 120                 125

Val Thr Val Ser
        130

<210> SEQ ID NO 231
<211> LENGTH: 121
```

```
<212> TYPE: PRT
<213> ORGANISM: homo sapiens

<400> SEQUENCE: 231

Gly Arg Ala Gln Val Gln Leu Gln Ser Gly Pro Glu Val Lys Lys
1               5                   10                  15

Pro Gly Ala Ser Val Lys Val Ser Cys Lys Ala Ser Gly Tyr Thr Phe
            20                  25                  30

Asn Ser Tyr Gly Ile Ala Trp Val Arg Gln Val Pro Gly Gln Gly Leu
        35                  40                  45

Glu Trp Met Gly Trp Ile Ser Pro Tyr Ser Gly His Thr Asn Tyr Ala
50                  55                  60

Glu Lys Val Gln Gly Arg Val Thr Met Thr Thr Asp Thr Ala Thr Ser
65                  70                  75                  80

Thr Ala Cys Met Glu Leu Thr Ser Leu Arg Ser Asp Asp Thr Ala Val
                85                  90                  95

Tyr Phe Cys Ala Arg Asp Tyr Ser Pro Tyr His Phe Asp Tyr Trp
            100                 105                 110

Gly Gln Gly Thr Trp Ser Pro Ser Arg
        115                 120

<210> SEQ ID NO 232
<211> LENGTH: 122
<212> TYPE: PRT
<213> ORGANISM: homo sapiens

<400> SEQUENCE: 232

Gly Arg Ala Gln Ile Thr Leu Lys Glu Ser Gly Pro Thr Leu Val Lys
1               5                   10                  15

Pro Thr Gln Thr Leu Thr Leu Thr Cys Thr Leu Ser Gly Phe Ser Leu
            20                  25                  30

Tyr Thr Thr Gly Val Gly Val Gly Trp Ile Arg Gln Pro Pro Gly Lys
        35                  40                  45

Ala Leu Glu Trp Leu Ala Arg Ile Tyr Trp Asp Asp Asp Glu Arg Tyr
50                  55                  60

Asn Pro Ser Leu Lys Ser Arg Leu Thr Ile Thr Lys Asp Ala Ser Lys
65                  70                  75                  80

Asn Gln Val Val Leu Lys Met Thr Asn Met Asp Pro Val Asp Thr Ala
                85                  90                  95

Thr Tyr Tyr Cys Ala Arg Thr Met Gly Val Val Leu Pro Phe Asp Tyr
            100                 105                 110

Trp Gly Gln Gly Thr Leu Val Thr Val Ser
        115                 120

<210> SEQ ID NO 233
<211> LENGTH: 117
<212> TYPE: PRT
<213> ORGANISM: homo sapiens

<400> SEQUENCE: 233

Gly Arg Ala Lys Val Gln Leu Val Glu Ser Gly Gly Leu Val Lys
1               5                   10                  15

Pro Gly Gly Ser Leu Arg Leu Ser Cys Val Val Ser Gly Phe Pro Leu
            20                  25                  30

Asn Arg Tyr Thr Met Asn Trp Val Arg Gln Ala Pro Gly Lys Gly Leu
        35                  40                  45

Glu Trp Leu Ser Ser Ile Ser Ser Thr Ser Ser Tyr Ile Tyr Tyr Ala
```

```
                    50                  55                  60
Asp Ser Val Lys Gly Arg Phe Thr Ile Ser Arg Asp Asn Ala Lys Asn
 65                  70                  75                  80

Ser Leu Phe Leu Gln Met Asn Ser Leu Arg Ala Asp Asp Thr Ala Leu
                     85                  90                  95

Tyr Phe Cys Ala Ser Gly Asn Thr His Asp Tyr Trp Gly Gln Gly Thr
                    100                 105                 110

Leu Val Thr Val Ser
                115

<210> SEQ ID NO 234
<211> LENGTH: 126
<212> TYPE: PRT
<213> ORGANISM: homo sapiens

<400> SEQUENCE: 234

Gly Arg Ala Gln Val Gln Leu Val Gln Ser Gly Ala Glu Val Lys Lys
  1               5                  10                  15

Leu Gly Thr Ser Val Arg Val Ser Cys Lys Thr Pro Gly Gly Tyr Val
                 20                  25                  30

Phe Ser Trp Val Arg Gln Ala Pro Gly Gln Gly Pro Glu Trp Met Gly
             35                  40                  45

Gly Ile Ile Thr Asn Phe Gly Thr Asn Tyr Ala Arg Lys Phe Gln
         50                  55                  60

Gly Arg Ile Thr Val Thr Ala Asp Lys Ser Thr Asn Thr Val Tyr Met
 65                  70                  75                  80

Asp Leu Ser Asn Leu Ala Ser Glu Asp Thr Ala Val Tyr Tyr Cys Ala
                 85                  90                  95

Arg Ala Pro Arg Gly Thr Ser Thr Ile Ala Ala Arg Phe Asn Arg Tyr
                100                 105                 110

Phe Phe Asp Ser Trp Gly Gln Gly Thr Leu Val Thr Val Ser
            115                 120                 125

<210> SEQ ID NO 235
<211> LENGTH: 132
<212> TYPE: PRT
<213> ORGANISM: homo sapiens

<400> SEQUENCE: 235

Gly Arg Ala Gln Val Gln Leu Gln Glu Ser Gly Gly Gly Val Val Gln
  1               5                  10                  15

Pro Gly Thr Ser Leu Arg Leu Ser Cys Val Val Ser Gly Phe Thr Phe
                 20                  25                  30

Arg Thr Tyr Gly Met Asn Trp Val Arg Gln Ala Pro Gly Lys Val Leu
             35                  40                  45

Glu Trp Leu Ala Phe Val Ser Ser Asp Gly Ser Asp Glu Phe Tyr Ala
         50                  55                  60

Asp Ser Val Lys Gly Arg Phe Thr Val Ser Arg Asp Asn Ser Lys Ser
 65                  70                  75                  80

Thr Leu Phe Leu Lys Met Asn Ser Leu Arg Ala Asp Asp Thr Ala Val
                 85                  90                  95

Tyr Tyr Cys Ala Arg Asp Arg Gly Ala Gln Ile Thr Leu Phe Gly Ala
                100                 105                 110

Pro Leu Ile Arg Pro Ser Ser Phe Asp Ser Trp Gly Gln Gly Thr Leu
            115                 120                 125

Val Thr Val Ser
```

<210> SEQ ID NO 236
<211> LENGTH: 126
<212> TYPE: PRT
<213> ORGANISM: homo sapiens

<400> SEQUENCE: 236

Gly Arg Ala Glu Val Gln Leu Val Glu Ser Gly Ala Glu Val Lys Lys
1               5                   10                  15
Pro Gly Thr Ser Val Arg Val Ser Cys Lys Thr Ser Gly Gly Tyr Val
            20                  25                  30
Phe Ser Trp Val Arg Gln Ala Pro Gly Gln Gly Pro Glu Trp Met Gly
        35                  40                  45
Gly Ile Ile Thr Ser Phe Gly Thr Ser Tyr Ala Gln Lys Phe Gln
    50                  55                  60
Gly Arg Val Thr Ile Thr Ala Asp Lys Ala Thr Asn Thr Val Tyr Met
65                  70                  75                  80
Asp Leu Ser Asp Leu Thr Ser Glu Asp Thr Ala Ile Tyr Tyr Cys Ala
                85                  90                  95
Lys Ala Pro Arg Gly Thr Ser Thr Ile Ala Ala Arg Phe Asn Arg Tyr
            100                 105                 110
Phe Phe Asp Ser Trp Gly Gln Gly Thr Leu Val Thr Val Ser
        115                 120                 125

<210> SEQ ID NO 237
<211> LENGTH: 122
<212> TYPE: PRT
<213> ORGANISM: homo sapiens

<400> SEQUENCE: 237

Gly Arg Ala Gln Val Gln Leu Gln Glu Ser Gly Pro Thr Leu Val Lys
1               5                   10                  15
Pro Thr Gln Thr Leu Thr Leu Thr Cys Ser Phe Ser Gly Phe Ser Leu
            20                  25                  30
Gly Thr Thr Gly Val Asn Val Gly Trp Ile Arg Gln Pro Pro Gly Lys
        35                  40                  45
Ala Leu Glu Trp Leu Ala Leu Ile Ser Trp Asp Gly Gly Lys His Tyr
    50                  55                  60
Ser Pro Ser Leu Asn Ser Arg Ile Thr Leu Thr Lys Asp Ala Ser Arg
65                  70                  75                  80
Glu Gln Val Val Val Pro Thr Met Thr Asn Met Asp Pro Ala Asp Thr
                85                  90                  95
Gly Arg Tyr Tyr Cys Ala Arg Ile Val Gly Thr His Gly Phe Asp Tyr
            100                 105                 110
Trp Gly Gln Gly Thr Leu Val Thr Val Ser
        115                 120

<210> SEQ ID NO 238
<211> LENGTH: 131
<212> TYPE: PRT
<213> ORGANISM: homo sapiens

<400> SEQUENCE: 238

Gly Arg Ala Lys Val Gln Leu Val Glu Ser Gly Ala Glu Val Lys Lys
1               5                   10                  15
Pro Gly Ala Thr Val Arg Val Ser Cys Lys Ala Ser Gly Tyr Arg Phe
            20                  25                  30

```
Asn Asp Tyr Cys Ile Ser Trp Val Arg Gln Ala Pro Gly Gln Gly Leu
            35                  40                  45

Glu Trp Met Gly Trp Ile Asn Gly Asn Asn Ala Asp Thr Phe Tyr Ala
 50                  55                  60

Pro Lys Leu Gln Gly Arg Val Thr Met Ser Thr Asp Thr Ser Thr Ser
 65                  70                  75                  80

Thr Ala Tyr Met Glu Leu Arg Asn Leu Arg Ser Asp Asp Thr Ala Val
                 85                  90                  95

Tyr Phe Cys Ala Arg Asp Arg Gly Arg Ile Thr Leu Phe Gly Glu Val
                100                 105                 110

Ile Leu Arg Ala Gly Trp Phe Asp Ser Trp Gly Gln Gly Thr Leu Val
            115                 120                 125

Thr Val Ser
    130

<210> SEQ ID NO 239
<211> LENGTH: 124
<212> TYPE: PRT
<213> ORGANISM: homo sapiens

<400> SEQUENCE: 239

Gly Arg Ala Gln Val Gln Leu Val Gln Ser Gly Gly Gly Leu Val Lys
 1               5                  10                  15

Pro Gly Gly Ser Leu Arg Leu Ser Cys Ala Ala Ser Gly Phe Ser Phe
             20                  25                  30

Ser Asn Asn Asn Met Asn Trp Val Arg Gln Thr Pro Gly Lys Gly Leu
         35                  40                  45

Glu Trp Val Ala Ser Ile Ser Phe Gly Ser His Tyr Ile Ser Tyr Ala
 50                  55                  60

Asp Ser Val Lys Gly Arg Phe Thr Ile Ser Arg Asp Asn Ala Arg Asn
 65                  70                  75                  80

Ala Val Tyr Leu Gln Met Asn Ser Leu Arg Val Glu Asp Thr Ala Val
                 85                  90                  95

Tyr Tyr Cys Thr Arg Cys Arg Gly Thr Arg Thr Tyr Tyr Tyr Met
                100                 105                 110

Asp Val Trp Gly Lys Gly Thr Leu Val Thr Val Ser
            115                 120

<210> SEQ ID NO 240
<211> LENGTH: 124
<212> TYPE: PRT
<213> ORGANISM: homo sapiens

<400> SEQUENCE: 240

Gly Arg Ala Lys Val Gln Leu Val Glu Ser Gly Gly Gly Leu Val Lys
 1               5                  10                  15

Pro Gly Gly Ser Leu Arg Leu Ser Cys Ala Ala Ser Gly Ser Ser Phe
             20                  25                  30

Ser Asn Asn Asn Met Asn Trp Val Arg Gln Thr Pro Gly Lys Gly Leu
         35                  40                  45

Glu Trp Val Ala Ser Ile Ser Phe Gly Ser His Tyr Ile Ser Tyr Ala
 50                  55                  60

Asp Ser Val Lys Gly Arg Phe Thr Ile Ser Arg Asp Asn Ala Arg Asn
 65                  70                  75                  80

Ala Val Tyr Leu Gln Met Asn Ser Leu Arg Val Glu Asp Thr Ala Val
                 85                  90                  95
```

```
Tyr Tyr Cys Thr Arg Cys Arg Gly Gly Thr Arg Thr Tyr Tyr Tyr Met
            100                 105                 110

Asp Val Trp Gly Lys Gly Thr Leu Val Thr Val Ser
        115                 120
```

<210> SEQ ID NO 241
<211> LENGTH: 130
<212> TYPE: PRT
<213> ORGANISM: homo sapiens

<400> SEQUENCE: 241

```
Gly Arg Ala Gln Met Gln Leu Val Gln Ser Gly Ala Glu Val Lys Lys
1               5                   10                  15

Pro Gly Ser Ser Val Lys Val Ser Cys Gln Ser Gly Gly Pro Pro
            20                  25                  30

Lys Ser Tyr Thr Leu Ser Trp Val Arg Gln Ala Pro Gly Gln Gly Pro
            35                  40                  45

Glu Trp Met Gly Gly Ile Ile Leu Ile Phe Gly Pro Pro Asn Tyr Ala
        50                  55                  60

Gln Lys Phe Gln Asp Arg Leu Thr Ile Thr Ala Asp Lys Ser Thr Asn
65                  70                  75                  80

Thr Val Tyr Met Glu Leu Ser Ser Leu Arg Ser Asp Asp Thr Ala Met
                85                  90                  95

Tyr Tyr Cys Val Thr Ala Pro Asp Asp Thr Gly Thr Ile Leu Ala Arg
            100                 105                 110

His Asn Arg Tyr Tyr Phe Asp Ser Trp Gly Gln Gly Thr Leu Val Thr
            115                 120                 125

Val Ser
    130
```

<210> SEQ ID NO 242
<211> LENGTH: 130
<212> TYPE: PRT
<213> ORGANISM: homo sapiens

<400> SEQUENCE: 242

```
Gly Arg Ala Lys Val Gln Leu Val Gln Ser Gly Ala Glu Val Lys Lys
1               5                   10                  15

Pro Gly Glu Ser Leu Lys Ile Ser Cys Gln Ala Ser Gly Tyr Gly Phe
            20                  25                  30

Thr Val Tyr Trp Ile Gly Trp Val Arg Gln Pro Pro Gly Lys Gly Leu
            35                  40                  45

Glu Trp Leu Gly Ile Ile Tyr Pro Gly Asp Ser Asp Thr Arg Tyr Asn
        50                  55                  60

Pro Ser Phe Gln Gly Gln Val Thr Ile Ser Ala Asp Lys Ser Val Ser
65                  70                  75                  80

Thr Thr Tyr Leu Gln Trp Ser Ser Leu Lys Ala Ser Asp Thr Ala Ile
                85                  90                  95

Tyr Tyr Cys Ala Arg His Leu Asp Ser Tyr Asp Val Phe Thr Gly Tyr
            100                 105                 110

Asn Leu Gly Gly Tyr Met Asp Val Trp Gly Lys Gly Thr Leu Val Thr
            115                 120                 125

Val Ser
    130
```

<210> SEQ ID NO 243

```
<211> LENGTH: 117
<212> TYPE: PRT
<213> ORGANISM: homo sapiens

<400> SEQUENCE: 243

Gly Arg Ala Lys Val Gln Leu Val Gln Ser Gly Gly Leu Val Lys
1               5                   10                  15

Pro Gly Gly Ser Leu Arg Leu Ser Cys Val Val Ser Gly Phe Pro Leu
            20                  25                  30

Asn Arg Tyr Ile Met Asn Trp Val Arg Gln Thr Pro Gly Lys Gly Leu
            35                  40                  45

Glu Trp Leu Ser Ser Ile Ser Ser Thr Ser Ser Tyr Ile Tyr Tyr Ala
50                  55                  60

Asp Ser Ala Lys Gly Arg Phe Thr Ile Ser Arg Asp Asn Ala Lys Asn
65                  70                  75                  80

Ser Leu Phe Leu Gln Met Asn Ser Leu Arg Ala Glu Asp Thr Gly Leu
                85                  90                  95

Tyr Tyr Cys Ala Ser Gly Asn Thr His Asp Tyr Trp Gly Gln Gly Thr
            100                 105                 110

Leu Val Thr Val Ser
        115

<210> SEQ ID NO 244
<211> LENGTH: 126
<212> TYPE: PRT
<213> ORGANISM: homo sapiens

<400> SEQUENCE: 244

Gly Arg Ala Gln Met Gln Leu Val Gln Ser Gly Ala Glu Val Lys Lys
1               5                   10                  15

Pro Gly Thr Ser Val Arg Val Ser Cys Lys Thr Ser Gly Gly Tyr Val
            20                  25                  30

Phe Ser Trp Val Arg Gln Ala Pro Gly Gln Gly Pro Glu Trp Met Gly
            35                  40                  45

Gly Ile Ile Thr Asn Phe Gly Thr Thr Asn Tyr Ala Gln Lys Phe Gln
50                  55                  60

Gly Arg Val Thr Ile Thr Ala Asp Lys Ser Thr Asn Thr Val Tyr Met
65                  70                  75                  80

Asp Leu Ser Asn Leu Thr Ser Glu Asp Thr Ala Val Tyr Tyr Cys Ala
                85                  90                  95

Arg Ala Pro Arg Gly Thr Ser Thr Ile Ala Ala Arg Phe Asn Arg Tyr
            100                 105                 110

Phe Phe Asp Ser Trp Gly Gln Gly Thr Leu Val Thr Val Ser
            115                 120                 125

<210> SEQ ID NO 245
<211> LENGTH: 124
<212> TYPE: PRT
<213> ORGANISM: homo sapiens

<400> SEQUENCE: 245

Gly Arg Ala Lys Val Gln Leu Val Glu Ser Gly Ala Glu Val Lys Lys
1               5                   10                  15

Pro Gly Ser Ser Val Lys Val Ser Cys Lys Ala Ser Gly Gly Ser Phe
            20                  25                  30

Ser Thr Tyr Ala Ile Thr Trp Val Arg Gln Ala Pro Gly Gln Gly Leu
            35                  40                  45
```

Glu Trp Met Gly Gly Ile Ile Pro Ile Phe Ala Ser Arg Asp Tyr Ala
    50                  55                  60

Gln Lys Phe Gln Gly Arg Val Thr Val Thr Ala Asp Glu Ser Thr Arg
65                  70                  75                  80

Thr Val Tyr Met Glu Leu Ser Ser Leu Arg Ser Asp Asp Thr Ala Val
                85                  90                  95

Tyr Tyr Cys Ala Arg Val Leu Gly Gly Thr Arg Leu Tyr Tyr Ala Leu
                100                 105                 110

Asn Val Trp Gly Gln Gly Thr Met Val Thr Val Ser
            115                 120

<210> SEQ ID NO 246
<211> LENGTH: 124
<212> TYPE: PRT
<213> ORGANISM: homo sapiens

<400> SEQUENCE: 246

Gly Arg Ala Lys Val Gln Leu Val Glu Ser Gly Ala Glu Val Lys Lys
1               5                   10                  15

Pro Gly Ser Ser Val Lys Val Ser Cys Lys Thr Ser Gly Gly Ser Phe
                20                  25                  30

Ser Thr Tyr Ser Ile Thr Trp Val Arg Gln Ala Pro Gly Gln Gly Leu
            35                  40                  45

Glu Trp Met Gly Gly Ile Asn Pro Ile Phe Ala Thr Arg Asp Tyr Ala
    50                  55                  60

Gln Lys Phe Gln Gly Arg Val Thr Ile Thr Ala Asp Glu Ser Thr Arg
65                  70                  75                  80

Thr Val Tyr Met Glu Leu Arg Asn Leu Arg Ser Glu Asp Thr Ala Val
                85                  90                  95

Tyr Tyr Cys Ala Arg Val Phe Gly Gly Thr Arg Leu Tyr Tyr Ala Leu
                100                 105                 110

Asn Val Trp Gly Gln Gly Thr Leu Val Thr Val Ser
            115                 120

<210> SEQ ID NO 247
<211> LENGTH: 126
<212> TYPE: PRT
<213> ORGANISM: homo sapiens

<400> SEQUENCE: 247

Gly Arg Ala Glu Val Gln Leu Val Gln Ser Gly Ala Glu Val Lys Lys
1               5                   10                  15

Pro Gly Thr Ser Val Arg Val Ser Cys Lys Thr Pro Gly Gly Tyr Val
                20                  25                  30

Phe Ser Trp Val Arg Gln Ala Pro Gly Gln Gly Pro Glu Trp Met Gly
            35                  40                  45

Gly Ile Ile Thr Asn Phe Gly Thr Thr Asn Tyr Ala Arg Lys Phe Gln
            50                  55                  60

Gly Arg Ile Thr Val Thr Ala Asp Lys Ser Thr Asn Thr Val Tyr Met
65                  70                  75                  80

Asp Leu Ser Asn Leu Ala Ser Glu Asp Thr Ala Val Tyr Tyr Cys Ala
                85                  90                  95

Arg Ala Pro Arg Gly Thr Ser Thr Ile Ala Ala Arg Phe Asn Arg Tyr
                100                 105                 110

Phe Phe Asp Ser Trp Gly Gln Gly Thr Leu Val Thr Val Ser
            115                 120                 125

```
<210> SEQ ID NO 248
<211> LENGTH: 124
<212> TYPE: PRT
<213> ORGANISM: homo sapiens

<400> SEQUENCE: 248

Gly Arg Ala Lys Val Gln Leu Val Glu Ser Gly Gly Leu Val Lys
1               5                   10                  15

Pro Gly Gly Ser Leu Arg Leu Ser Cys Ala Ala Ser Gly Phe Ser Phe
            20                  25                  30

Ser Asn Asn Met Asn Trp Val Arg Gln Thr Pro Gly Lys Gly Leu
        35                  40                  45

Glu Trp Val Ala Ser Ile Ser Phe Gly Ser His Tyr Ile Ser Tyr Ala
    50                  55                  60

Asp Ser Val Lys Gly Arg Phe Thr Ile Ser Arg Asp Asn Ala Arg Asn
65                  70                  75                  80

Ala Val Tyr Leu Gln Met Asn Ser Leu Arg Val Glu Asp Thr Ala Val
                85                  90                  95

Tyr Tyr Cys Thr Arg Cys Arg Gly Gly Thr Arg Thr Tyr Tyr Tyr Met
            100                 105                 110

Asp Val Trp Gly Lys Gly Thr Met Val Thr Val Ser
            115                 120

<210> SEQ ID NO 249
<211> LENGTH: 130
<212> TYPE: PRT
<213> ORGANISM: homo sapiens

<400> SEQUENCE: 249

Gly Arg Ala Lys Val Gln Leu Val Gln Ser Gly Ala Glu Val Lys Lys
1               5                   10                  15

Pro Gly Glu Ser Leu Lys Ile Ser Cys Gln Ala Ser Gly Tyr Gly Phe
            20                  25                  30

Thr Val Tyr Trp Ile Gly Trp Val Arg Gln Pro Pro Gly Lys Gly Leu
        35                  40                  45

Glu Trp Leu Gly Ile Ile Tyr Pro Gly Asp Ser Asp Thr Arg Tyr Asn
    50                  55                  60

Pro Ser Phe Gln Gly Gln Val Thr Ile Ser Ala Asp Lys Ser Val Ser
65                  70                  75                  80

Thr Thr Tyr Leu Gln Trp Ser Ser Leu Lys Ala Ser Asp Thr Ala Ile
                85                  90                  95

Tyr Tyr Cys Ala Arg His Leu Asp Ser Tyr Asp Val Phe Thr Gly Tyr
            100                 105                 110

Asn Leu Gly Gly Tyr Met Asp Val Trp Gly Lys Gly Thr Leu Val Thr
            115                 120                 125

Val Ser
    130

<210> SEQ ID NO 250
<211> LENGTH: 126
<212> TYPE: PRT
<213> ORGANISM: homo sapiens

<400> SEQUENCE: 250

Gly Arg Ala Gln Val Gln Leu Val Glu Ser Gly Ala Glu Val Lys Lys
1               5                   10                  15

Pro Gly Ser Ser Val Lys Val Ser Cys Lys Ser Ser Gly Gly Tyr Val
```

```
                 20                  25                  30
Phe Ser Trp Val Arg Gln Ala Pro Gly Gln Gly Leu Glu Trp Met Gly
             35                  40                  45

Gly Ile Ile Ser Asn Phe Arg Thr Ala Glu Tyr Ala Arg Lys Phe Gln
     50                  55                  60

Gly Arg Val Thr Met Thr Ala Asp Thr Ser Thr Asn Thr Ile Tyr Met
65                  70                  75                  80

Glu Leu Thr Ser Leu Thr Ser Glu Asp Thr Ala Val Tyr Phe Cys Val
                 85                  90                  95

Ser Ala Pro Arg Asp Thr Ser Thr Ile Ala Ala Arg Phe Asn Arg Tyr
            100                 105                 110

Phe Phe Asp Thr Trp Gly Gln Gly Thr Leu Val Thr Val Ser
            115                 120                 125

<210> SEQ ID NO 251
<211> LENGTH: 126
<212> TYPE: PRT
<213> ORGANISM: homo sapiens

<400> SEQUENCE: 251

Gly Arg Ala Gln Val Gln Leu Gln Gln Ser Gly Gly Val Val Gln
1               5                  10                  15

Pro Gly Arg Ser Leu Arg Leu Ser Cys Ala Ala Ser Gly Phe Ala Phe
             20                  25                  30

Arg Asp Tyr Ala Met His Trp Val Arg Gln Ala Pro Gly Lys Gly Leu
             35                  40                  45

Glu Trp Met Gly Val Ile Ser Phe Asn Gly Asp Gln Ile Phe Tyr Ala
     50                  55                  60

Asp Ser Met Lys Gly Arg Phe Thr Ile Ser Arg Glu Asn Ser Lys Asn
65                  70                  75                  80

Thr Leu His Leu Arg Met Asn Ser Leu Arg Pro Glu Asp Thr Ala Val
                 85                  90                  95

Tyr Tyr Cys Ala Arg Ala Arg Leu Leu Phe Cys Ser Gly Gly Arg Cys
            100                 105                 110

Asp Met Asp Ser Trp Gly Gln Gly Thr Leu Val Thr Val Ser
            115                 120                 125

<210> SEQ ID NO 252
<211> LENGTH: 126
<212> TYPE: PRT
<213> ORGANISM: homo sapiens

<400> SEQUENCE: 252

Gly Arg Ala Lys Val Gln Leu Val Gln Ser Gly Ala Glu Val Lys Lys
1               5                  10                  15

Pro Gly Thr Ser Val Arg Val Ser Cys Lys Thr Ser Gly Gly Tyr Val
             20                  25                  30

Phe Ser Trp Val Arg Gln Ala Pro Gly His Gly Pro Glu Trp Met Gly
             35                  40                  45

Gly Ile Ile Thr Asn Phe Gly Thr Ala Thr Tyr Ala Gln Lys Phe Gln
     50                  55                  60

Gly Arg Val Ser Ile Thr Ala Asp Thr Ser Thr Asn Thr Phe Tyr Met
65                  70                  75                  80

Asp Leu Asn Asn Leu Lys Ser Asp Asp Thr Ala Val Tyr Tyr Cys Ala
                 85                  90                  95

Ser Ala Pro Arg Asp Thr Ser Thr Ile Ala Ala Arg Phe Asn Arg Tyr
```

-continued

```
                100                 105                 110
Phe Phe Asp Phe Trp Gly Pro Gly Thr Leu Val Thr Val Ser
        115                 120                 125

<210> SEQ ID NO 253
<211> LENGTH: 116
<212> TYPE: PRT
<213> ORGANISM: homo sapiens

<400> SEQUENCE: 253

Gly Arg Ala Gln Val Gln Leu Val Gln Ser Gly Gly Leu Val Lys
1               5                   10                  15

Pro Gly Gly Ser Leu Arg Leu Ser Cys Ala Ala Ser Gly Phe Thr Phe
            20                  25                  30

Ser Asn Ala Trp Met Ser Trp Val Arg Gln Ala Pro Gly Lys Gly Leu
        35                  40                  45

Glu Trp Val Gly His Val Lys Ser Met Thr Asp Gly Thr Thr Asp
    50                  55                  60

Tyr Ala Ala Pro Val Lys Gly Arg Phe Thr Ile Ser Arg Asp Asp Ser
65                  70                  75                  80

Glu Asn Thr Leu Tyr Leu Gln Met Asn Ser Leu Lys Thr Asp Asp Thr
                85                  90                  95

Ala Val Tyr Tyr Cys Thr Thr His Asp Tyr Trp Gly Gly Thr Leu
            100                 105                 110

Val Thr Val Ser
        115

<210> SEQ ID NO 254
<211> LENGTH: 126
<212> TYPE: PRT
<213> ORGANISM: homo sapiens

<400> SEQUENCE: 254

Gly Arg Ala Lys Val Gln Leu Val Gln Ser Gly Ala Glu Val Lys Lys
1               5                   10                  15

Pro Gly Thr Ser Val Arg Val Ser Cys Lys Thr Pro Gly Gly Tyr Val
            20                  25                  30

Phe Ser Trp Val Arg Gln Ala Pro Gly Gln Gly Pro Glu Trp Met Gly
        35                  40                  45

Gly Ile Ile Thr Asn Phe Gly Thr Thr Asn Tyr Ala Arg Lys Phe Gln
    50                  55                  60

Gly Arg Ile Thr Val Thr Ala Asp Lys Ser Thr Asn Thr Val Tyr Met
65                  70                  75                  80

Asp Leu Ser Asn Leu Ala Ser Glu Asp Thr Ala Val Tyr Tyr Cys Ala
                85                  90                  95

Arg Ala Pro Arg Gly Thr Ser Thr Ile Ala Ala Arg Phe Asn Arg Tyr
            100                 105                 110

Phe Phe Asp Ser Trp Gly Gln Gly Thr Leu Val Thr Val Ser
        115                 120                 125

<210> SEQ ID NO 255
<211> LENGTH: 131
<212> TYPE: PRT
<213> ORGANISM: homo sapiens

<400> SEQUENCE: 255

Gly Arg Ala Gln Val Gln Leu Val Glu Ser Gly Ala Glu Met Lys Lys
1               5                   10                  15
```

```
Pro Gly Ser Ser Val Lys Val Ser Cys Gln Ala Ser Gly Gly Thr Phe
            20                  25                  30

Ser Asn Tyr Gly Ile Asn Trp Val Arg His Ala Pro Gly Gln Gly Leu
        35                  40                  45

Glu Trp Met Gly Gly Ile Val Pro Ile Tyr Gly Pro Pro Lys Tyr Ala
    50                  55                  60

Gln Lys Phe Gln Gly Arg Val Thr Ile Thr Ala Asp Thr Ser Thr Ser
65                  70                  75                  80

Thr Ala Tyr Met Glu Leu Ser Ser Leu Ser Ser Asp Asp Thr Ala Val
                85                  90                  95

Tyr Tyr Cys Ala Arg Leu Ser Arg Thr Val Phe Gly Ser Gly Thr Tyr
            100                 105                 110

Arg Pro Gly Tyr Tyr Met Asp Val Trp Gly Ile Gly Thr Thr Val
        115                 120                 125

Thr Val Ser
        130

<210> SEQ ID NO 256
<211> LENGTH: 124
<212> TYPE: PRT
<213> ORGANISM: homo sapiens

<400> SEQUENCE: 256

Gly Arg Ala Gln Val Gln Leu Gln Gln Ser Gly Gly Gly Leu Val Lys
1               5                   10                  15

Pro Gly Gly Ser Leu Arg Leu Ser Cys Ala Ala Ser Gly Phe Ser Phe
            20                  25                  30

Ser Asn Asn Asn Met Asn Trp Val Arg Gln Thr Pro Gly Lys Gly Leu
        35                  40                  45

Glu Trp Val Ala Ser Ile Ser Phe Gly Ser His Tyr Ile Ser Tyr Ala
    50                  55                  60

Asp Ser Val Lys Gly Arg Phe Thr Ile Ser Arg Asp Asn Ala Arg Asn
65                  70                  75                  80

Ala Val Tyr Leu Gln Met Asn Ser Leu Arg Val Glu Asp Thr Ala Val
                85                  90                  95

Tyr Tyr Cys Thr Arg Cys Arg Gly Gly Thr Arg Thr Tyr Tyr Tyr Met
            100                 105                 110

Asp Val Trp Gly Lys Gly Thr Leu Val Thr Val Ser
        115                 120

<210> SEQ ID NO 257
<211> LENGTH: 126
<212> TYPE: PRT
<213> ORGANISM: homo sapiens

<400> SEQUENCE: 257

Gly Arg Ala Lys Val Gln Leu Val Gln Ser Gly Ala Glu Val Lys Lys
1               5                   10                  15

Pro Gly Thr Ser Val Arg Val Ser Cys Lys Thr Ser Gly Gly Tyr Val
            20                  25                  30

Phe Ser Trp Val Arg Gln Ala Pro Gly Gln Gly Pro Glu Trp Met Gly
        35                  40                  45

Gly Ile Ile Thr Asn Phe Gly Thr Thr Asn Tyr Ala Gln Lys Phe Gln
    50                  55                  60

Gly Arg Val Thr Ile Thr Ala Asp Lys Ser Thr Asn Thr Val Tyr Met
65                  70                  75                  80
```

```
Asp Leu Ser Asn Leu Thr Ser Glu Asp Thr Ala Val Tyr Tyr Cys Ala
                85                  90                  95

Arg Ala Pro Arg Gly Thr Ser Thr Ile Ala Ala Arg Phe Asn Arg Tyr
            100                 105                 110

Phe Phe Asp Ser Trp Gly Gln Gly Thr Leu Val Thr Val Ser
        115                 120                 125

<210> SEQ ID NO 258
<211> LENGTH: 124
<212> TYPE: PRT
<213> ORGANISM: homo sapiens

<400> SEQUENCE: 258

Gly Arg Ala Glu Val Gln Leu Val Gln Ser Gly Ala Glu Val Lys Lys
1               5                   10                  15

Pro Gly Ser Ser Val Lys Val Ser Cys Lys Thr Glu Gly Gly Thr Phe
            20                  25                  30

Ser Thr Tyr Val Ile Ser Trp Met Arg Gln Ala Pro Gly Gln Gly Leu
            35                  40                  45

Glu Trp Met Gly Gly Ile Val Pro Ile Phe Asn Thr Pro Asn Tyr Ala
50                  55                  60

Gln Lys Phe Gln Gly Arg Val Thr Ile Thr Ala Asp Arg Ser Thr Ser
65                  70                  75                  80

Thr Ala Tyr Met Glu Leu Arg Ser Leu Gly Ser Glu Asp Thr Ala Val
                85                  90                  95

Tyr Tyr Cys Ala Arg Val Val Gly Gly Thr Arg Ser Tyr Tyr Ala Leu
            100                 105                 110

Gly Phe Trp Gly Gln Gly Thr Val Thr Val Ser
            115                 120

<210> SEQ ID NO 259
<211> LENGTH: 122
<212> TYPE: PRT
<213> ORGANISM: homo sapiens

<400> SEQUENCE: 259

Gly Arg Ala Gln Val Thr Leu Lys Glu Ser Gly Pro Thr Leu Val Lys
1               5                   10                  15

Pro Thr Gln Thr Leu Thr Leu Thr Cys Thr Phe Ser Gly Phe Ser Leu
            20                  25                  30

Gly Thr Thr Gly Val Asn Val Gly Trp Ile Arg Gln Pro Pro Gly Lys
            35                  40                  45

Ala Leu Glu Trp Leu Ala Leu Ile Ser Trp Gly Gly Gly Lys His Tyr
50                  55                  60

Ser Pro Ser Leu Asn Ser Arg Ile Thr Leu Thr Lys Asp Ala Ser Arg
65                  70                  75                  80

Glu Gln Val Val Val Leu Thr Met Ala Asn Met Asp Pro Val Asp Thr
                85                  90                  95

Gly Arg Tyr Tyr Cys Ala Arg Ile Val Gly Thr His Gly Phe Asp Tyr
            100                 105                 110

Trp Gly Gln Gly Thr Leu Val Thr Val Ser
            115                 120

<210> SEQ ID NO 260
<211> LENGTH: 124
<212> TYPE: PRT
<213> ORGANISM: homo sapiens
```

<400> SEQUENCE: 260

Gly Arg Ala Glu Val Gln Leu Val Gln Ser Gly Gly Val Val Arg
1               5                   10                  15

Pro Gly Gly Ser Leu Arg Leu Ser Cys Ala Gly Ser Gly Phe Thr Phe
            20                  25                  30

Asp Glu Tyr Ala Met Ser Trp Val Arg Gln Ala Pro Gly Lys Gly Leu
        35                  40                  45

Glu Trp Val Ala Phe Ile Asn Trp Asn Gly Asp Ser Thr Tyr Tyr Ala
    50                  55                  60

Asp Ser Val Lys Gly Arg Phe Thr Val Ser Arg Thr Asn Ala Lys Asn
65                  70                  75                  80

Ser Leu Tyr Leu Gln Met Asn Ser Leu Arg Ala Glu Asp Thr Ala Phe
                85                  90                  95

Tyr Tyr Cys Ala Arg Asp Pro Arg Thr Lys Leu Gly Met Ser Tyr Phe
            100                 105                 110

Asp Tyr Trp Gly Gln Gly Thr Leu Val Thr Val Ser
        115                 120

<210> SEQ ID NO 261
<211> LENGTH: 130
<212> TYPE: PRT
<213> ORGANISM: homo sapiens

<400> SEQUENCE: 261

Gly Arg Ala Glu Val Gln Leu Val Gln Ser Gly Ala Glu Val Lys Lys
1               5                   10                  15

Pro Gly Glu Ser Leu Lys Ile Ser Cys Gln Ala Ser Gly Tyr Gly Phe
            20                  25                  30

Thr Val Tyr Trp Ile Gly Trp Val Arg Gln Leu Pro Gly Lys Gly Leu
        35                  40                  45

Glu Trp Leu Gly Ile Ile Tyr Pro Gly Asp Ser Asp Thr Arg Tyr Asn
    50                  55                  60

Pro Ser Phe Gln Gly Gln Val Thr Ile Ser Ala Asp Lys Ser Val Ser
65                  70                  75                  80

Thr Thr Tyr Leu Gln Trp Ser Ser Leu Lys Ala Ser Asp Thr Ala Ile
                85                  90                  95

Tyr Tyr Cys Ala Arg His Leu Asp Ser Tyr Asp Val Phe Thr Gly Tyr
            100                 105                 110

Asn Leu Gly Gly Tyr Met Asp Val Trp Gly Lys Gly Thr Met Val Thr
        115                 120                 125

Val Ser
    130

<210> SEQ ID NO 262
<211> LENGTH: 123
<212> TYPE: PRT
<213> ORGANISM: homo sapiens

<400> SEQUENCE: 262

Gly Arg Ala Glu Val Gln Leu Val Gln Ser Gly Pro Glu Val Lys Lys
1               5                   10                  15

Pro Gly Ala Ser Val Arg Val Ser Cys Lys Ala Ser Gly Tyr Ser Leu
            20                  25                  30

Lys Asn Tyr Gly Ile His Trp Val Arg Gln Ala Pro Gly Gln Gly Leu
        35                  40                  45

-continued

Glu Trp Met Gly Trp Ile Ser Ala Asp Asn Gly Asp Thr Thr Thr Ala
50                  55                  60

Leu Asn Leu Arg Gly Arg Val Ser Met Thr Thr Asp Thr Ser Thr Asn
65                  70                  75                  80

Thr Val Tyr Met Glu Val Lys Ser Leu Arg Ser Asp Asp Thr Ala Ile
                85                  90                  95

Tyr Phe Cys Ala Arg Asp Phe Tyr Ser Gly Ser Tyr Arg Ser Phe Asp
            100                 105                 110

Tyr Trp Gly Gln Gly Thr Leu Val Thr Val Ser
            115                 120

<210> SEQ ID NO 263
<211> LENGTH: 126
<212> TYPE: PRT
<213> ORGANISM: homo sapiens

<400> SEQUENCE: 263

Gly Arg Ala Glu Val Gln Leu Val Gln Ser Gly Pro Gly Leu Val Lys
1               5                   10                  15

Pro Ser Glu Thr Leu Ser Leu Thr Cys Ala Val Ser Gly Ala Ser Val
                20                  25                  30

Ser Gly Gly Asp Tyr Tyr Trp Ser Trp Ile Arg Gln Pro Pro Gly Lys
            35                  40                  45

Ala Leu Glu Trp Ile Gly Tyr Ile Tyr Tyr Ile Gly Ser Thr Asn Tyr
        50                  55                  60

Asn Pro Ser Leu Lys Ser Arg Leu Ser Leu Ser Val Asp Thr Ala Lys
65                  70                  75                  80

Ser Gln Phe Ser Leu Lys Leu Ser Ser Val Thr Ala Ala Asp Thr Ala
                85                  90                  95

Ile Tyr Phe Cys Ala Arg Ala Arg Arg Thr Tyr Ser Gly Tyr Asp Ser
            100                 105                 110

Ala Phe Asp Tyr Trp Gly Gln Gly Thr Leu Val Thr Val Ser
        115                 120                 125

<210> SEQ ID NO 264
<211> LENGTH: 124
<212> TYPE: PRT
<213> ORGANISM: homo sapiens

<400> SEQUENCE: 264

Gly Arg Ala Gln Val Gln Leu Gln Gln Ser Gly Pro Gly Leu Val Lys
1               5                   10                  15

Pro Ser Glu Thr Leu Pro Leu Thr Cys Thr Val Ser Gly Gly Ser Phe
                20                  25                  30

Ser Thr Tyr Tyr Trp Ser Trp Ile Arg Gln Ser Pro Glu Lys Gly Leu
            35                  40                  45

Glu Trp Ile Gly Tyr Ile Gln Asn Ser Val Asn Thr Asn Tyr Asn Pro
        50                  55                  60

Ser Leu Lys Ser Arg Val Ile Ile Ser Val Asp Thr Ser Asn Asn Gln
65                  70                  75                  80

Phe Ser Leu Lys Leu Arg Ser Val Thr Ala Ala Asp Thr Ala Val Tyr
                85                  90                  95

Tyr Cys Ala Arg Val Ser Gly Trp Gly Pro Arg Gly Ile Tyr Phe
            100                 105                 110

Asp Tyr Trp Gly Gln Gly Thr Leu Val Thr Val Ser
        115                 120

-continued

```
<210> SEQ ID NO 265
<211> LENGTH: 126
<212> TYPE: PRT
<213> ORGANISM: homo sapiens

<400> SEQUENCE: 265
```

Gly Arg Ala Lys Val Gln Leu Val Gln Ser Gly Ala Glu Val Lys Lys
1               5                   10                  15

Pro Gly Ser Ser Val Lys Val Ser Cys Lys Ser Gly Gly Tyr Val
            20                  25                  30

Phe Ser Trp Val Arg Gln Ala Pro Gly Gln Gly Leu Glu Trp Met Gly
        35                  40                  45

Gly Ile Ile Ser Asn Phe His Thr Ala Glu Tyr Ala Gln Lys Phe Gln
    50                  55                  60

Gly Arg Val Thr Met Thr Ala Asp Thr Ser Thr Asn Thr Ile Tyr Met
65                  70                  75                  80

Glu Leu Thr Ser Leu Thr Ser Glu Asp Thr Ala Val Tyr Phe Cys Val
                85                  90                  95

Ser Ala Pro Arg Asp Thr Ser Thr Ile Ala Ala Arg Phe Asn Arg Tyr
            100                 105                 110

Phe Phe Asp Thr Trp Gly Gln Gly Thr Leu Val Thr Val Ser
        115                 120                 125

```
<210> SEQ ID NO 266
<211> LENGTH: 126
<212> TYPE: PRT
<213> ORGANISM: homo sapiens

<400> SEQUENCE: 266
```

Gly Arg Ala Glu Val Gln Leu Val Gln Ser Gly Ala Glu Val Lys Lys
1               5                   10                  15

Pro Gly Thr Ser Val Arg Val Ser Arg Lys Thr Pro Gly Gly Tyr Val
            20                  25                  30

Phe Ser Trp Val Arg Gln Ala Pro Gly Gln Gly Pro Glu Trp Met Gly
        35                  40                  45

Gly Ile Ile Thr Asn Phe Gly Thr Thr Asn Tyr Ala Arg Lys Phe Gln
    50                  55                  60

Gly Arg Ile Thr Val Thr Ala Asp Lys Ser Thr Asn Thr Val Tyr Met
65                  70                  75                  80

Asp Leu Ser Asn Leu Ala Ser Glu Asp Thr Ala Val Tyr Tyr Cys Ala
                85                  90                  95

Arg Ala Pro Arg Gly Thr Ser Thr Ile Ala Ala Arg Phe Asn Arg Tyr
            100                 105                 110

Phe Phe Asp Ser Trp Ser Gln Gly Thr Leu Val Thr Val Ser
        115                 120                 125

```
<210> SEQ ID NO 267
<211> LENGTH: 124
<212> TYPE: PRT
<213> ORGANISM: homo sapiens

<400> SEQUENCE: 267
```

Gly Arg Ala Glu Val Gln Leu Val Glu Ser Gly Ala Glu Val Lys Lys
1               5                   10                  15

Pro Gly Ser Ser Val Lys Val Ser Cys Lys Ala Ser Gly Gly Ser Phe
            20                  25                  30

Ser Thr Tyr Ile Phe Thr Trp Val Arg Gln Ala Pro Gly Gln Gly Leu

```
                35                  40                  45
Glu Trp Met Gly Gly Ile Asn Pro Ile Phe Ala Thr Arg Asp Tyr Pro
 50                  55                  60

Lys Lys Phe Gln Gly Arg Val Thr Ile Thr Ala Asp Glu Ser Thr Arg
65                   70                  75                  80

Thr Val Tyr Met Glu Leu Ser Ser Leu Thr Ser Glu Asp Thr Ala Val
                 85                  90                  95

Tyr Tyr Cys Ala Arg Val Leu Gly Gly Thr Arg Leu Tyr Tyr Ala Leu
            100                 105                 110

Asn Val Trp Gly Gln Gly Thr Thr Val Thr Val Ser
            115                 120

<210> SEQ ID NO 268
<211> LENGTH: 124
<212> TYPE: PRT
<213> ORGANISM: homo sapiens

<400> SEQUENCE: 268

Gly Arg Ala Glu Val Gln Leu Val Gln Ser Gly Gly Gly Val Val Arg
1               5                   10                  15

Pro Gly Gly Ser Leu Arg Leu Ser Cys Ala Gly Ser Gly Phe Thr Phe
            20                  25                  30

Asp Glu Tyr Ala Met Ser Trp Val Arg Gln Ala Pro Gly Lys Gly Leu
        35                  40                  45

Lys Trp Val Ala Phe Ile Asn Trp Asn Gly Asp Ser Thr Tyr Tyr Ala
 50                  55                  60

Asp Ser Val Lys Gly Arg Phe Thr Val Ser Arg Ser Asn Ala Lys Asn
65                   70                  75                  80

Ser Leu Tyr Leu Gln Met Asn Ser Leu Arg Ala Glu Asp Thr Ala Phe
                 85                  90                  95

Tyr Cys Cys Ala Arg Asp Pro Arg Thr Lys Leu Gly Met Ser Tyr Phe
            100                 105                 110

Asp Tyr Trp Gly Gln Gly Thr Leu Val Thr Val Ser
            115                 120

<210> SEQ ID NO 269
<211> LENGTH: 124
<212> TYPE: PRT
<213> ORGANISM: homo sapiens

<400> SEQUENCE: 269

Gly Arg Ala Glu Val Gln Leu Val Gln Ser Gly Ala Glu Val Lys Lys
1               5                   10                  15

Pro Gly Ser Ser Val Lys Val Ser Cys Lys Ala Ser Gly Gly Ser Phe
            20                  25                  30

Ser Thr Tyr Ala Ile Thr Trp Val Arg Gln Ala Pro Gly Gln Gly Leu
        35                  40                  45

Glu Trp Met Gly Gly Ile Ile Pro Ile Phe Ala Ser Arg Asp Tyr Ala
 50                  55                  60

Gln Lys Phe Gln Gly Arg Val Thr Ile Thr Ala Asp Glu Ser Thr Arg
65                   70                  75                  80

Thr Val Tyr Met Glu Pro Arg Ser Leu Arg Ser Glu Asp Thr Ala Val
                 85                  90                  95

Tyr Tyr Cys Ala Arg Val Leu Gly Gly Thr Arg Leu Tyr Tyr Ala Leu
            100                 105                 110

Asn Val Trp Gly Gln Gly Thr Leu Val Thr Val Ser
```

<210> SEQ ID NO 270
<211> LENGTH: 126
<212> TYPE: PRT
<213> ORGANISM: homo sapiens

<400> SEQUENCE: 270

Gly Arg Ala Glu Val Gln Leu Val Gln Ser Gly Pro Gly Leu Val Lys
1               5                   10                  15

Pro Ser Glu Thr Leu Ser Leu Thr Cys Ala Val Ser Gly Ala Ser Val
            20                  25                  30

Ser Gly Gly Asp Tyr Tyr Trp Ser Trp Ile Arg Gln Pro Pro Gly Lys
        35                  40                  45

Ala Leu Glu Trp Ile Gly Tyr Ile Tyr Tyr Ile Gly Ser Thr Asn Tyr
    50                  55                  60

Asn Pro Ser Leu Lys Ser Arg Leu Ser Leu Ser Val Asp Thr Ala Lys
65                  70                  75                  80

Ser Gln Phe Ser Leu Lys Leu Ser Ser Val Thr Ala Ala Asp Thr Ala
                85                  90                  95

Thr Tyr Phe Cys Ala Arg Ala Arg Arg Thr Tyr Ser Gly Tyr Asp Ser
            100                 105                 110

Ala Phe Asp Tyr Trp Gly Gln Gly Thr Leu Val Thr Val Ser
        115                 120                 125

<210> SEQ ID NO 271
<211> LENGTH: 124
<212> TYPE: PRT
<213> ORGANISM: homo sapiens

<400> SEQUENCE: 271

Gly Arg Ala Glu Val Gln Leu Val Glu Ser Gly Ala Glu Val Lys Lys
1               5                   10                  15

Pro Gly Ser Ser Val Lys Val Ser Cys Lys Ala Ser Gly Gly Ser Phe
            20                  25                  30

Ser Thr Tyr Ala Ile Thr Trp Val Arg Gln Ala Pro Gly Gln Gly Leu
        35                  40                  45

Glu Trp Met Gly Gly Ile Ile Pro Ile Phe Ala Ser Arg Asp Tyr Ala
    50                  55                  60

Gln Lys Phe Gln Gly Arg Val Thr Ile Thr Ala Asp Glu Ser Thr Arg
65                  70                  75                  80

Thr Val Tyr Met Glu Leu Ser Ser Leu Arg Ser Asp Asp Thr Ala Val
                85                  90                  95

Tyr Tyr Cys Ala Arg Val Leu Gly Gly Thr Arg Leu Tyr Tyr Ala Leu
            100                 105                 110

Asn Val Trp Gly Gln Gly Thr Thr Val Thr Val Ser
        115                 120

<210> SEQ ID NO 272
<211> LENGTH: 123
<212> TYPE: PRT
<213> ORGANISM: homo sapiens

<400> SEQUENCE: 272

Gly Arg Ala Gln Val Thr Leu Lys Glu Ser Gly Pro Thr Val Val Lys
1               5                   10                  15

Pro Thr Gln Thr Leu Thr Leu Thr Cys Ser Leu Ser Gly Phe Ala Leu
            20                  25                  30

```
Gly Thr Thr Gly Val Ala Val Gly Trp Ile Arg Gln Pro Pro Gly Lys
            35                  40                  45

Ala Leu Glu Trp Leu Gly Leu Ile Asp Trp Asn Asp Asp Arg Arg Tyr
 50                  55                  60

Arg Pro Ser Leu Lys Thr Arg Leu Thr Ile Thr Gln Asp Met Ser Arg
 65                  70                  75                  80

Asn Gln Val Val Leu Arg Leu Thr Asn Leu Asp Pro Leu Asp Thr Gly
                 85                  90                  95

Thr Tyr Phe Cys Ala Arg Ser Val Val Pro Ala Thr Arg Ala Phe Asp
            100                 105                 110

Phe Trp Gly Gln Gly Thr Leu Val Thr Val Ser
            115                 120

<210> SEQ ID NO 273
<211> LENGTH: 122
<212> TYPE: PRT
<213> ORGANISM: homo sapiens
<220> FEATURE:
<221> NAME/KEY: MISC_FEATURE
<222> LOCATION: (52)..(52)
<223> OTHER INFORMATION: Xaa unknown amino acid

<400> SEQUENCE: 273

Gly Arg Ala Gln Val Thr Leu Lys Glu Ser Gly Pro Thr Leu Val Lys
 1               5                  10                  15

Pro Thr Gln Thr Leu Thr Leu Thr Cys Thr Leu Ser Gly Phe Ser Leu
                 20                  25                  30

Tyr Thr Thr Gly Val Gly Val Gly Trp Ile Arg Gln Pro Pro Gly Lys
            35                  40                  45

Ala Leu Glu Xaa Leu Ala Arg Ile Tyr Trp Asp Asp Asp Glu Arg Tyr
 50                  55                  60

Asn Pro Ser Leu Lys Ser Arg Leu Thr Ile Thr Lys Asp Ala Ser Lys
 65                  70                  75                  80

Asn Gln Val Val Leu Lys Met Thr Asn Met Asp Pro Val Asp Thr Ala
                 85                  90                  95

Thr Tyr Tyr Cys Ala Arg Thr Met Gly Val Val Leu Pro Phe Asp Tyr
            100                 105                 110

Trp Gly Gln Gly Thr Leu Val Thr Val Ser
            115                 120

<210> SEQ ID NO 274
<211> LENGTH: 109
<212> TYPE: PRT
<213> ORGANISM: homo sapiens

<400> SEQUENCE: 274

Leu Ala Glu Ile Val Leu Thr Gln Ser Pro Ser Ser Leu Ser Ala Ser
 1               5                  10                  15

Leu Gly Asp Arg Val Thr Ile Thr Cys Arg Ala Ser Gln His Ile Ser
                 20                  25                  30

Asn Tyr Leu Asn Trp Tyr Gln Gln Lys Pro Gly Lys Ala Pro Lys Leu
            35                  40                  45

Leu Ile Cys Ala Ala Ser Ser Leu Gln Ser Gly Val Pro Ser Arg Phe
 50                  55                  60

Thr Gly Ser Gly Ser Gly Ala Asp Tyr Thr Leu Thr Ile Ser Ser Leu
 65                  70                  75                  80

Gln Pro Glu Asp Phe Ala Thr Tyr Tyr Cys Gln Gln Ser Tyr Ser Thr
```

```
                        85                  90                  95

Ser Trp Thr Phe Gly Gln Gly Thr Val Glu Ile Lys
            100                 105

<210> SEQ ID NO 275
<211> LENGTH: 109
<212> TYPE: PRT
<213> ORGANISM: homo sapiens

<400> SEQUENCE: 275

Leu Ala Glu Ile Val Leu Thr Gln Ser Pro Ser Ser Leu Ser Ala Ser
1               5                   10                  15

Val Gly Asp Arg Val Thr Ile Thr Cys Arg Ala Ser Gln Gly Ile Ser
            20                  25                  30

Asn Tyr Leu Ala Trp Tyr Gln Gln Lys Pro Gly Lys Val Pro Lys Leu
        35                  40                  45

Leu Ile Tyr Ala Ala Ser Thr Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Val Ala Thr Tyr Tyr Cys Gln Lys Tyr Asn Ser Ala
                85                  90                  95

Pro Tyr Thr Phe Gly Gln Gly Thr Lys Leu Glu Ile Lys
            100                 105

<210> SEQ ID NO 276
<211> LENGTH: 109
<212> TYPE: PRT
<213> ORGANISM: homo sapiens

<400> SEQUENCE: 276

Leu Ala Asp Val Val Met Thr Gln Ser Pro Ser Ser Leu Ser Ala Ser
1               5                   10                  15

Leu Gly Asp Arg Val Ser Ile Thr Cys Arg Ala Ser Gln His Ile Ser
            20                  25                  30

Asn Tyr Ile Asn Trp Tyr Gln Gln Lys Pro Gly Lys Ala Pro Lys Leu
        35                  40                  45

Leu Ile Tyr Ala Ala Ser Thr Leu Gln Ser Gly Val Pro Ser Arg Phe
    50                  55                  60

Thr Gly Ser Gly Ser Gly Ala Asp Tyr Thr Leu Thr Ile Thr Ser Leu
65                  70                  75                  80

Gln Pro Glu Asp Phe Ala Thr Tyr Tyr Cys Gln Gln Ser Tyr Gly Thr
                85                  90                  95

Ser Trp Thr Phe Gly Gln Gly Thr Val Glu Ile Lys
            100                 105

<210> SEQ ID NO 277
<211> LENGTH: 109
<212> TYPE: PRT
<213> ORGANISM: homo sapiens

<400> SEQUENCE: 277

Leu Ala Asp Val Val Met Thr Gln Ser Pro Ser Ser Leu Ser Ala Ser
1               5                   10                  15

Val Gly Asp Arg Val Thr Ile Thr Cys Gln Ala Ser Gln Asp Ile Thr
            20                  25                  30

Asn Tyr Leu Asn Trp Tyr Gln Gln Lys Pro Gly Lys Ala Pro Lys Leu
        35                  40                  45
```

Leu Ile Tyr Asp Ala Ser Asn Leu Gln Pro Gly Val Pro Ser Arg Phe
            50                  55                  60

Ser Gly Ser Gly Ser Val Thr Asp Phe Thr Phe Thr Ile Ser Ser Leu
65                  70                  75                  80

Arg Pro Glu Asp Ile Ala Thr Tyr Tyr Cys Gln Gln Tyr Asp Gly Pro
                85                  90                  95

Val Leu Thr Phe Gly Gly Gly Thr Lys Val Glu Ile Lys
            100                 105

<210> SEQ ID NO 278
<211> LENGTH: 109
<212> TYPE: PRT
<213> ORGANISM: homo sapiens

<400> SEQUENCE: 278

Leu Ala Asp Val Val Met Thr Gln Ser Pro Ser Ser Leu Ser Ala Ser
1               5                   10                  15

Val Gly Asp Arg Val Thr Ile Ser Cys Arg Ala Ser Gln Pro Ile Ser
            20                  25                  30

Thr Tyr Leu Asn Trp Tyr Gln Gln Lys Pro Gly Lys Ala Pro Lys Ile
        35                  40                  45

Leu Ile Phe Gly Ala Ser Arg Leu Gln Ser Gly Val Pro Ser Arg Phe
    50                  55                  60

Ser Gly Ser Gly Ser Gly Thr Asp Phe Ser Leu Thr Ile Thr Ser Leu
65                  70                  75                  80

Gln Pro Glu Asp Phe Ala Thr Tyr Ile Cys Gln Gln Ser Lys Ser Pro
                85                  90                  95

Pro Tyr Asn Phe Gly Arg Gly Thr Lys Leu Glu Ile Lys
            100                 105

<210> SEQ ID NO 279
<211> LENGTH: 110
<212> TYPE: PRT
<213> ORGANISM: homo sapiens

<400> SEQUENCE: 279

Leu Ala Glu Ile Val Leu Thr Gln Ser Pro Ser Thr Leu Ser Ala Ser
1               5                   10                  15

Val Gly Asp Arg Val Thr Ile Thr Cys Arg Ala Ser Gln Ser Ile Gly
            20                  25                  30

Ser Trp Leu Ala Trp Tyr Gln Gln Lys Pro Gly Lys Ala Pro Lys Leu
        35                  40                  45

Leu Ile Tyr Lys Ala Ser Thr Leu Gln Ser Glu Thr Pro Ser Arg Phe
    50                  55                  60

Arg Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Gln Gln Phe Asn Ser Phe
                85                  90                  95

Ser Pro Trp Thr Phe Gly Gln Gly Thr Lys Val Glu Phe Lys
            100                 105                 110

<210> SEQ ID NO 280
<211> LENGTH: 109
<212> TYPE: PRT
<213> ORGANISM: homo sapiens

<400> SEQUENCE: 280

```
Leu Ala Asp Val Val Met Thr Gln Ser Pro Ser Ser Leu Ser Ala Ser
1               5                   10                  15

Val Gly Asp Arg Val Thr Ile Thr Cys Arg Ala Ser Gln Ser Ile Asn
            20                  25                  30

Ile Asn Leu Asn Trp Phe Gln Gln Lys Pro Gly Lys Ala Pro Asn Leu
        35                  40                  45

Leu Ile Tyr Ser Ala Ser Thr Leu Gln Thr Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Glu Asp Phe Ala Thr Tyr Tyr Cys Gln Gln Ile Tyr Ser His
                85                  90                  95

Val Arg Thr Phe Gly Gln Gly Thr Lys Val Glu Ile Lys
                100                 105
```

<210> SEQ ID NO 281
<211> LENGTH: 115
<212> TYPE: PRT
<213> ORGANISM: homo sapiens

<400> SEQUENCE: 281

```
Leu Ala Asp Val Val Met Thr Gln Ser Pro Asp Ser Leu Ala Val Ser
1               5                   10                  15

Leu Gly Glu Arg Ala Thr Ile Asn Cys Lys Ser Ser Gln Ser Leu Leu
            20                  25                  30

Tyr Ser Ser Asn Asn Lys Asn Tyr Leu Ala Trp Tyr Gln Gln Lys Pro
        35                  40                  45

Gly Gln Pro Pro Lys Leu Leu Ile Tyr Trp Ala Ser Thr Arg Glu Ser
    50                  55                  60

Gly Val Pro Asp Arg Phe Ser Gly Ser Gly Ser Gly Thr Asp Phe Thr
65                  70                  75                  80

Leu Thr Ile Ser Ser Leu Gln Ala Glu Asp Val Ala Val Tyr Tyr Cys
                85                  90                  95

Gln Gln Tyr Tyr Ser Thr Pro Pro Met Phe Gly Gln Gly Thr Lys Val
                100                 105                 110

Glu Ile Lys
        115
```

<210> SEQ ID NO 282
<211> LENGTH: 109
<212> TYPE: PRT
<213> ORGANISM: homo sapiens

<400> SEQUENCE: 282

```
Leu Ala Glu Ile Val Leu Thr Gln Ser Pro Ser Ser Leu Ser Ala Ser
1               5                   10                  15

Val Gly Asp Arg Ile Thr Ile Thr Cys Gln Ala Ser Gln Asp Ile Thr
            20                  25                  30

Asn Tyr Leu Asn Trp Tyr Gln Gln Lys Pro Gly Lys Ala Pro Lys Leu
        35                  40                  45

Leu Ile Tyr Asp Ala Ser Asn Leu Gln Pro Gly Val Pro Ser Arg Phe
    50                  55                  60

Ser Gly Ser Arg Ser Gly Thr Asp Phe Thr Phe Thr Ile Ser Ser Leu
65                  70                  75                  80

Arg Pro Glu Asp Ile Ala Thr Tyr Tyr Cys Gln Gln Tyr Asp Gly Pro
                85                  90                  95
```

```
Val Leu Thr Phe Gly Gly Gly Thr Lys Val Glu Ile Lys
            100                 105

<210> SEQ ID NO 283
<211> LENGTH: 115
<212> TYPE: PRT
<213> ORGANISM: homo sapiens

<400> SEQUENCE: 283

Leu Ala Glu Ile Val Leu Thr Gln Ser Pro Asp Ser Leu Ala Val Ser
1               5                   10                  15

Leu Gly Glu Arg Ala Thr Ile Asn Cys Lys Ser Ser Gln Ser Leu Leu
            20                  25                  30

Tyr Ser Ser Asn Asn Lys Asn Tyr Leu Ala Trp Tyr Gln Gln Lys Pro
        35                  40                  45

Gly Gln Pro Pro Lys Leu Leu Ile Tyr Trp Ala Ser Thr Arg Glu Ser
    50                  55                  60

Gly Val Pro Asp Arg Phe Ser Gly Ser Gly Ser Gly Thr Asp Phe Thr
65                  70                  75                  80

Leu Thr Ile Ser Ser Leu Gln Ala Glu Asp Val Ala Val Tyr Tyr Cys
                85                  90                  95

Gln Gln Tyr Tyr Ser Thr Pro Pro Met Phe Gly Gln Gly Thr Lys Val
            100                 105                 110

Glu Ile Lys
        115

<210> SEQ ID NO 284
<211> LENGTH: 110
<212> TYPE: PRT
<213> ORGANISM: homo sapiens

<400> SEQUENCE: 284

Leu Ala Glu Ile Val Leu Thr Gln Ser Pro Ser Phe Leu Ser Ala Ser
1               5                   10                  15

Val Gly Asp Arg Val Thr Ile Thr Cys Arg Ala Ser Gln Gly Ile Gly
            20                  25                  30

Asn Phe Leu Ala Trp Tyr Gln Gln Lys Pro Gly Lys Ala Pro Lys Leu
        35                  40                  45

Leu Ile Ser Gly Ala Ser Thr Leu Gln Ser Trp Val Pro Ser Arg Phe
    50                  55                  60

Ser Gly Arg Gly Ser Gly Thr Glu Phe Thr Leu Thr Ile Ser Ser Leu
65                  70                  75                  80

Gln Pro Glu Asp Phe Ala Thr Tyr Tyr Cys Gln Gln Leu Asn Arg Tyr
                85                  90                  95

Pro Pro Tyr Thr Phe Gly Gln Gly Thr Lys Leu Glu Ile Lys
            100                 105                 110

<210> SEQ ID NO 285
<211> LENGTH: 109
<212> TYPE: PRT
<213> ORGANISM: homo sapiens

<400> SEQUENCE: 285

Leu Ala Glu Ile Val Met Thr Gln Ser Pro Ser Ser Leu Ser Ala Ser
1               5                   10                  15

Val Gly Asp Arg Val Thr Ile Thr Cys Gln Ala Ser Gln Asp Ile Ser
            20                  25                  30

Lys Tyr Leu Asn Trp Tyr Gln Gln Lys Pro Gly Arg Ala Pro Lys Leu
```

-continued

```
                35                  40                  45
Leu Ile Tyr Glu Ala Ser Asn Leu Glu Thr Gly Val Pro Pro Arg Phe
    50                  55                  60

Ser Gly Ser Gly Ser Gly Thr His Phe Thr Phe Thr Ile Thr Gly Leu
65                  70                  75                  80

Gln Pro Glu Asp Ile Ala Thr Tyr Tyr Cys Gln Gln Cys Asp Ser Leu
                85                  90                  95

Pro Pro Val Phe Gly Gln Gly Thr Lys Leu Glu Val Lys
            100                 105
```

<210> SEQ ID NO 286
<211> LENGTH: 110
<212> TYPE: PRT
<213> ORGANISM: homo sapiens

<400> SEQUENCE: 286

```
Leu Ala Glu Ile Val Leu Thr Gln Ser Pro Gly Thr Leu Ala Leu Ser
1               5                   10                  15

Pro Gly Asp Arg Ala Thr Leu Ser Cys Gly Ala Ser Gln Ser Val Phe
            20                  25                  30

Gly Asp Phe Leu Ala Trp Tyr Gln His Lys Pro Gly Gln Ala Pro Arg
        35                  40                  45

Leu Leu Ile Tyr Gly Ala Ser Thr Arg Ala Thr Gly Ile Pro Asp Arg
    50                  55                  60

Phe Ser Gly Ser Gly Ala Gly Thr Asp Phe Thr Leu Thr Ile Ser Arg
65                  70                  75                  80

Leu Glu Pro Glu Asp Phe Ala Val Tyr Phe Cys Gln Gln Tyr Gly Asp
                85                  90                  95

Ser Val Phe Thr Phe Gly Gln Gly Thr Lys Leu Gly Ile Lys
            100                 105                 110
```

<210> SEQ ID NO 287
<211> LENGTH: 110
<212> TYPE: PRT
<213> ORGANISM: homo sapiens

<400> SEQUENCE: 287

```
Leu Ala Glu Ile Val Met Thr Gln Ser Pro Gly Thr Leu Ala Leu Ser
1               5                   10                  15

Pro Gly Asp Arg Ala Thr Leu Ser Cys Gly Ala Ser Gln Ser Val Phe
            20                  25                  30

Gly Asp Phe Leu Ala Trp Tyr Gln His Lys Pro Gly Gln Ala Pro Arg
        35                  40                  45

Leu Leu Ile Tyr Gly Ala Ser Thr Arg Ala Thr Gly Ile Pro Asp Arg
    50                  55                  60

Phe Ser Gly Ser Gly Ala Gly Thr Asp Phe Thr Leu Thr Ile Ser Arg
65                  70                  75                  80

Leu Glu Pro Glu Asp Phe Ala Val Tyr Phe Cys Gln Gln Tyr Gly Asp
                85                  90                  95

Ser Val Phe Thr Phe Gly Gln Gly Thr Lys Leu Glu Ile Lys
            100                 105                 110
```

<210> SEQ ID NO 288
<211> LENGTH: 110
<212> TYPE: PRT
<213> ORGANISM: homo sapiens

<400> SEQUENCE: 288

```
Leu Ala Glu Ile Val Leu Thr Gln Ser Pro Gly Thr Leu Ser Leu Ser
1               5                   10                  15

Pro Gly Gln Arg Ala Thr Leu Ser Cys Arg Ala Ser Gln Ser Val Asn
                20                  25                  30

Arg Asp Tyr Leu Ala Trp Tyr Gln Gln Lys Pro Gly Gln Ala Pro Arg
            35                  40                  45

Leu Leu Ile Tyr Gly Ala Ser Ser Arg Ala Thr Gly Ile Pro Asp Arg
        50                  55                  60

Phe Ser Gly Ser Gly Ser Gly Thr Asp Phe Thr Leu Thr Ile Ser Arg
65                  70                  75                  80

Leu Glu Arg Asp Asp Phe Ala Val Tyr Phe Cys His Gln Tyr Gly Ser
                85                  90                  95

Ser Pro Asn Thr Phe Gly Gln Gly Thr Lys Leu Glu Ile Lys
            100                 105                 110

<210> SEQ ID NO 289
<211> LENGTH: 110
<212> TYPE: PRT
<213> ORGANISM: homo sapiens

<400> SEQUENCE: 289

Leu Ala Glu Thr Thr Leu Thr Gln Ser Pro Gly Thr Leu Ser Leu Ser
1               5                   10                  15

Pro Gly Glu Arg Ala Thr Leu Ser Cys Arg Ala Ser Gln Ser Val Ser
                20                  25                  30

Thr Asn Tyr Leu Ala Trp Tyr Arg Gln Lys Pro Gly Gln Ala Pro Arg
            35                  40                  45

Leu Leu Ile His Gly Ala Ser Ser Arg Ala Thr Gly Ile Pro Asp Arg
        50                  55                  60

Phe Ser Gly Ser Gly Ser Gly Thr Asp Phe Thr Leu Thr Ile Ser Arg
65                  70                  75                  80

Leu Glu Pro Glu Asp Phe Ala Val Tyr Phe Cys Gln Gln Tyr Gly Ser
                85                  90                  95

Ser Pro Gln Thr Phe Gly Gln Gly Thr Arg Leu Glu Ile Lys
            100                 105                 110

<210> SEQ ID NO 290
<211> LENGTH: 109
<212> TYPE: PRT
<213> ORGANISM: homo sapiens

<400> SEQUENCE: 290

Leu Ala Glu Ile Val Leu Thr Gln Ser Pro Ser Ser Leu Ser Ala Ser
1               5                   10                  15

Val Gly Asp Arg Val Thr Thr Cys Arg Thr Ser Gln Ser Ile Phe
                20                  25                  30

Ile Asn Leu Asn Trp Phe Gln Gln Lys Pro Gly Lys Ala Pro Lys Leu
            35                  40                  45

Leu Ile Tyr Ser Ala Ser Thr Leu Gln Thr Gly Val Pro Ser Arg Phe
        50                  55                  60

Ser Gly Ser Gly Ser Gly Thr Glu Phe Thr Leu Thr Ile Ser Ser Leu
65                  70                  75                  80

Gln Pro Glu Asp Phe Ala Thr Tyr Tyr Cys Gln Gln Ile Tyr Ser Gln
                85                  90                  95

Val Arg Thr Phe Gly Gln Gly Thr Lys Val Glu Ile Lys
            100                 105
```

<210> SEQ ID NO 291
<211> LENGTH: 110
<212> TYPE: PRT
<213> ORGANISM: homo sapiens

<400> SEQUENCE: 291

Leu Ala Asp Ile Gln Met Thr Gln Ser Pro Gly Thr Leu Ser Leu Ser
1               5                   10                  15

Pro Gly Glu Arg Ala Thr Leu Ser Cys Arg Ala Ser Gln Ser Val Asn
            20                  25                  30

Ser Asp Asn Leu Ala Trp Tyr Gln Gln Lys Pro Gly Gln Ala Pro Arg
        35                  40                  45

Leu Leu Met Ser Gly Ala Thr Ser Arg Ala Thr Asp Val Pro Asp Arg
50                  55                  60

Phe Ser Gly Ser Gly Ser Gly Thr Asp Phe Thr Leu Thr Ile Ser Arg
65                  70                  75                  80

Leu Glu Pro Glu Asp Phe Ala Val Tyr Tyr Cys His Gln Tyr Gly Ser
                85                  90                  95

Ser Asp Asn Thr Phe Gly Gln Gly Thr Lys Leu Glu Ile Lys
            100                 105                 110

<210> SEQ ID NO 292
<211> LENGTH: 110
<212> TYPE: PRT
<213> ORGANISM: homo sapiens

<400> SEQUENCE: 292

Leu Ala Asp Val Val Met Thr Gln Phe Pro Ser Ser Leu Ser Ala Ser
1               5                   10                  15

Val Gly Asp Arg Val Thr Ile Thr Cys Arg Ala Ser Gln Gly Ile Ser
            20                  25                  30

Asn Phe Leu Ala Trp Tyr Gln Gln Lys Pro Gly Lys Val Pro Glu Leu
        35                  40                  45

Leu Ile Tyr Gly Ala Ser Thr Leu Gln Ser Gly Val Pro Ser Arg Phe
50                  55                  60

Ser Gly Ser Gly Ser Gly Ala Glu Phe Thr Leu Thr Ile Asn Ser Leu
65                  70                  75                  80

Gln Pro Glu Asp Val Ala Thr Tyr Tyr Cys Gln Lys Tyr Asp Ser Gly
                85                  90                  95

Leu Arg Phe Thr Phe Gly Pro Gly Thr Lys Val Asp Ile Lys
            100                 105                 110

<210> SEQ ID NO 293
<211> LENGTH: 110
<212> TYPE: PRT
<213> ORGANISM: homo sapiens

<400> SEQUENCE: 293

Leu Ala Asp Val Val Met Thr Gln Ser Pro Ser Ser Leu Ser Ala Ser
1               5                   10                  15

Val Gly Asp Arg Val Thr Ile Thr Cys Arg Ala Ser Gln Gly Ile Ser
            20                  25                  30

Asn Phe Leu Ala Trp His Gln Gln Lys Pro Gly Gln Val Pro Lys Leu
        35                  40                  45

Leu Ile Tyr Gly Ala Ser Thr Leu Gln Ser Gly Val Pro Ser Arg Phe
50                  55                  60

```
Ser Gly Ser Gly Ser Gly Thr Asp Phe Thr Leu Thr Ile Asn Gly Leu
 65                  70                  75                  80

Gln Pro Glu Asp Val Ala Thr Tyr Tyr Cys Gln Lys Tyr Asp Ser Gly
                 85                  90                  95

Leu Ile Phe Thr Phe Gly Pro Gly Thr Arg Val Glu Ile Lys
            100                 105                 110

<210> SEQ ID NO 294
<211> LENGTH: 115
<212> TYPE: PRT
<213> ORGANISM: homo sapiens

<400> SEQUENCE: 294

Leu Ala Asp Val Val Met Thr Gln Ser Pro Asp Ser Leu Ala Val Ser
 1               5                  10                  15

Leu Gly Glu Arg Ala Thr Ile Asn Cys Lys Ser Ser Gln Ser Leu Leu
                 20                  25                  30

Tyr Ser Ser Asn Asn Lys Asn Tyr Leu Ala Trp Tyr Gln Gln Lys Pro
             35                  40                  45

Gly Gln Pro Pro Lys Leu Leu Ile Tyr Trp Ala Ser Thr Arg Glu Ser
 50                  55                  60

Gly Val Pro Asp Arg Phe Ser Gly Ser Gly Ser Gly Thr Asp Phe Thr
 65                  70                  75                  80

Leu Thr Ile Ser Ser Leu Gln Ala Glu Asp Val Ala Val Tyr Tyr Cys
                 85                  90                  95

Gln Gln Tyr Tyr Ser Thr Pro Pro Met Leu Gly Gln Gly Thr Lys Val
            100                 105                 110

Glu Ile Lys
        115

<210> SEQ ID NO 295
<211> LENGTH: 110
<212> TYPE: PRT
<213> ORGANISM: homo sapiens

<400> SEQUENCE: 295

Leu Ala Asp Val Val Met Thr Gln Ser Pro Gly Thr Leu Ala Leu Ser
 1               5                  10                  15

Pro Gly Asp Arg Ala Thr Leu Ser Cys Gly Ala Ser Gln Ser Val Phe
                 20                  25                  30

Gly Asp Phe Leu Ala Trp Tyr Gln His Lys Pro Gly Gln Ala Pro Arg
             35                  40                  45

Leu Leu Ile Tyr Val Ala Ser Thr Arg Ala Thr Gly Ile Pro Asp Arg
 50                  55                  60

Phe Ser Gly Ser Gly Ala Gly Thr Asp Phe Thr Leu Thr Ile Ser Arg
 65                  70                  75                  80

Leu Glu Pro Glu Asp Phe Ala Val Tyr Phe Cys Gln Gln Tyr Gly Asp
                 85                  90                  95

Ser Val Phe Thr Phe Gly Gln Gly Thr Lys Leu Glu Ile Arg
            100                 105                 110

<210> SEQ ID NO 296
<211> LENGTH: 110
<212> TYPE: PRT
<213> ORGANISM: homo sapiens

<400> SEQUENCE: 296

Leu Ala Glu Thr Thr Leu Thr Gln Ser Pro Gly Thr Leu Ser Leu Ser
```

```
                1               5                  10                 15
Pro Gly Glu Arg Ala Thr Leu Ser Cys Arg Ala Ser Gln Ser Val Ser
                20                 25                 30

Thr Asn Tyr Leu Ala Trp Tyr Arg Gln Lys Pro Gly Gln Ala Pro Arg
            35                 40                 45

Leu Leu Ile His Gly Ala Ser Ser Arg Ala Thr Gly Ile Pro Asp Arg
        50                 55                 60

Phe Ser Gly Ser Gly Ser Gly Thr Asp Phe Thr Leu Thr Ile Ser Arg
65                 70                 75                 80

Leu Glu Pro Glu Asp Phe Ala Val Tyr Phe Cys Gln Gln Tyr Gly Ser
                85                 90                 95

Ser Pro Gln Thr Phe Gly Gln Gly Thr Arg Leu Glu Ile Lys
                100                105                110
```

<210> SEQ ID NO 297
<211> LENGTH: 110
<212> TYPE: PRT
<213> ORGANISM: homo sapiens

<400> SEQUENCE: 297

```
Leu Ala Glu Ile Val Leu Thr Gln Ser Pro Gly Thr Leu Ser Leu Ser
1               5                  10                 15

Pro Gly Glu Arg Ala Thr Leu Ser Cys Arg Ala Ser Arg Ser Val Asn
                20                 25                 30

Ser Asn Asn Leu Ala Trp Tyr Gln Gln Lys Pro Asp Gln Ala Pro Arg
            35                 40                 45

Leu Leu Met Tyr Gly Ala Ser Ser Arg Ala Thr Gly Ile Pro Asp Arg
        50                 55                 60

Phe Thr Gly Ser Gly Ser Gly Thr Asp Phe Thr Leu Thr Ile Ser Arg
65                 70                 75                 80

Leu Glu Pro Glu Asp Phe Ala Val Tyr Tyr Cys His Gln Tyr Gly Ala
                85                 90                 95

Ser Asp Asn Thr Phe Gly Gln Gly Thr Lys Leu Glu Ile Lys
                100                105                110
```

<210> SEQ ID NO 298
<211> LENGTH: 109
<212> TYPE: PRT
<213> ORGANISM: homo sapiens

<400> SEQUENCE: 298

```
Leu Ala Glu Ile Val Met Thr Gln Ser Pro Ser Phe Leu Ser Ala Ser
1               5                  10                 15

Val Gly Asp Arg Val Thr Ile Thr Cys Arg Ala Ser Gln Asp Ile Ile
                20                 25                 30

Thr Tyr Leu Ala Trp Tyr Gln Gln Lys Pro Gly Lys Ala Pro Glu Val
            35                 40                 45

Leu Ile Phe Gly Ala Ser Thr Leu Gln Ser Gly Val Pro Ser Arg Phe
        50                 55                 60

Ser Gly Ser Gly Ser Gly Thr Glu Phe Thr Leu Thr Ile Ser Ser Leu
65                 70                 75                 80

Gln Pro Glu Asp Phe Ala Thr Tyr Tyr Cys Gln Gln Ile Ile Arg Tyr
                85                 90                 95

Pro Arg Thr Phe Gly Gln Gly Thr Arg Val Glu Ile Lys
                100                105
```

<210> SEQ ID NO 299
<211> LENGTH: 110
<212> TYPE: PRT
<213> ORGANISM: homo sapiens

<400> SEQUENCE: 299

Leu Ala Asp Val Val Met Thr Gln Ser Pro Gly Thr Leu Ser Leu Ser
1               5                   10                  15

Pro Gly Glu Arg Ala Thr Leu Ser Cys Arg Ala Ser Gln Ser Val Asn
            20                  25                  30

Ser Asn Asn Leu Ala Trp Tyr Gln Gln Lys Pro Gly Gln Ala Pro Arg
        35                  40                  45

Leu Leu Val Ser Gly Ala Thr Asn Arg Ala Thr Asp Ile Pro Asp Arg
    50                  55                  60

Phe Ser Gly Ser Gly Ser Gly Thr Asp Phe Thr Leu Thr Ile Ser Arg
65                  70                  75                  80

Leu Glu Pro Glu Asp Phe Ala Val Tyr Tyr Cys His Gln Tyr Gly Ser
                85                  90                  95

Ser Glu Asn Thr Phe Gly Gln Gly Thr Lys Leu Glu Ile Arg
            100                 105                 110

<210> SEQ ID NO 300
<211> LENGTH: 109
<212> TYPE: PRT
<213> ORGANISM: homo sapiens

<400> SEQUENCE: 300

Leu Ala Glu Ile Val Met Thr Gln Ser Pro Pro Phe Leu Ser Ala Ser
1               5                   10                  15

Val Gly Asp Arg Val Thr Ile Thr Cys Arg Ala Ser Gln Gly Leu Ser
            20                  25                  30

Thr Tyr Leu Ala Trp Tyr Gln Val Lys Pro Gly Lys Ala Pro Lys Leu
        35                  40                  45

Leu Ile Tyr Ala Ala Ser Thr Leu Gln Ser Gly Val Pro Ser Arg Phe
    50                  55                  60

Ser Gly Ser Gly Ser Gly Thr Glu Phe Thr Leu Thr Ile Asn Ser Leu
65                  70                  75                  80

Gln Pro Glu Asp Phe Ala Thr Tyr Tyr Cys Gln Gln Leu Asp Thr Tyr
                85                  90                  95

Pro Leu Thr Leu Gly Gly Gly Thr Lys Val Glu Ile Lys
            100                 105

<210> SEQ ID NO 301
<211> LENGTH: 115
<212> TYPE: PRT
<213> ORGANISM: homo sapiens

<400> SEQUENCE: 301

Leu Ala Glu Ile Val Leu Thr Gln Ser Pro Asp Ser Leu Ala Val Ser
1               5                   10                  15

Leu Gly Glu Arg Ala Thr Ile Asn Cys Lys Ser Ser Gln Ser Leu Leu
            20                  25                  30

Tyr Ser Ser Asn Asn Lys Asn Tyr Leu Ala Trp Tyr Gln Gln Lys Pro
        35                  40                  45

Gly Gln Pro Pro Lys Leu Leu Ile Tyr Trp Ala Ser Thr Arg Glu Ser
    50                  55                  60

Gly Val Pro Asp Arg Phe Ser Gly Ser Gly Ser Gly Thr Asp Phe Thr
65                  70                  75                  80

-continued

Leu Thr Ile Ser Ser Leu Gln Ala Glu Asp Val Ala Val Tyr Tyr Cys
                85                  90                  95

Gln Gln Tyr Tyr Ser Thr Pro Pro Met Phe Gly Gln Gly Thr Lys Val
            100                 105                 110

Glu Ile Lys
        115

<210> SEQ ID NO 302
<211> LENGTH: 115
<212> TYPE: PRT
<213> ORGANISM: homo sapiens

<400> SEQUENCE: 302

Leu Ala Asp Ile Gln Met Thr Gln Ser Pro Asp Ser Leu Ala Val Ser
1               5                   10                  15

Leu Gly Glu Arg Ala Thr Ile Asn Cys Lys Ser Ser Gln Ser Leu Leu
            20                  25                  30

Tyr Ser Ser Asn Asn Lys Asn Tyr Leu Ala Trp Tyr Gln Gln Lys Pro
        35                  40                  45

Gly Gln Pro Pro Lys Leu Leu Ile Tyr Trp Ala Ser Thr Arg Glu Ser
    50                  55                  60

Gly Val Pro Asp Arg Phe Ser Gly Ser Gly Ser Gly Thr Asp Phe Thr
65                  70                  75                  80

Leu Thr Ile Ser Ser Leu Gln Ala Glu Asp Val Ala Val Tyr Tyr Cys
                85                  90                  95

Gln Gln Tyr Tyr Ser Thr Pro Pro Met Phe Gly Gln Gly Thr Arg Val
            100                 105                 110

Glu Ile Lys
        115

<210> SEQ ID NO 303
<211> LENGTH: 110
<212> TYPE: PRT
<213> ORGANISM: homo sapiens

<400> SEQUENCE: 303

Leu Ala Glu Ile Val Met Thr Gln Ser Pro Gly Thr Leu Ala Leu Ser
1               5                   10                  15

Pro Gly Asp Arg Ala Thr Leu Ser Cys Gly Ala Ser Gln Ser Val Phe
            20                  25                  30

Gly Asp Phe Leu Ala Trp Tyr Gln His Lys Pro Gly Gln Ala Pro Arg
        35                  40                  45

Pro Leu Ile Tyr Gly Ala Ser Thr Arg Ala Thr Gly Ile Pro Asp Arg
    50                  55                  60

Phe Ser Gly Ser Gly Ala Gly Thr Asp Phe Thr Leu Thr Ile Ser Arg
65                  70                  75                  80

Leu Glu Pro Glu Asp Phe Ala Val Tyr Phe Cys Gln Gln Tyr Gly Asp
                85                  90                  95

Ser Val Phe Thr Phe Gly Gln Gly Thr Lys Leu Glu Ile Lys
            100                 105                 110

<210> SEQ ID NO 304
<211> LENGTH: 110
<212> TYPE: PRT
<213> ORGANISM: homo sapiens

<400> SEQUENCE: 304

```
Leu Ala Asp Val Val Met Thr Gln Ser Pro Gly Thr Leu Ser Leu Ser
1               5                   10                  15

Pro Gly Glu Arg Ala Thr Leu Ser Cys Arg Ala Ser Gln Ser Val Asn
            20                  25                  30

Ser Asp Asn Leu Ala Trp Tyr Gln Gln Lys Pro Gly Gln Ala Pro Arg
        35                  40                  45

Leu Leu Met Ser Gly Ala Thr Ser Arg Ala Thr Asp Ile Pro Asp Arg
50                  55                  60

Phe Ser Gly Ser Gly Ser Gly Thr Asp Phe Thr Leu Thr Ile Ser Arg
65                  70                  75                  80

Leu Glu Pro Glu Asp Phe Ala Val Tyr Tyr Cys His Gln Tyr Gly Ser
                85                  90                  95

Ser Asp Asn Thr Phe Gly Gln Gly Thr Lys Leu Glu Ile Lys
            100                 105                 110

<210> SEQ ID NO 305
<211> LENGTH: 110
<212> TYPE: PRT
<213> ORGANISM: homo sapiens

<400> SEQUENCE: 305

Leu Ala Asp Ile Gln Leu Thr Gln Ser Pro Ser Ser Leu Ser Ala Ser
1               5                   10                  15

Val Gly Asp Ser Val Thr Ile Thr Cys Arg Ala Ser Gln Gly Ile Ser
            20                  25                  30

Asn Phe Leu Ala Trp Tyr Gln Lys Lys Pro Gly Lys Val Pro Arg Leu
        35                  40                  45

Leu Ile Tyr Gly Ala Ser Thr Leu Gln Ser Gly Val Pro Ser Arg Phe
50                  55                  60

Ser Gly Ser Gly Ser Gly Thr Asp Phe Thr Leu Thr Ile Ser Ser Leu
65                  70                  75                  80

Gln Pro Glu Asp Val Ala Thr Tyr Tyr Cys Gln Glu Tyr Ser Asn Ala
                85                  90                  95

Leu Ile Phe Thr Phe Gly Pro Gly Thr Lys Val His Ile Lys
            100                 105                 110

<210> SEQ ID NO 306
<211> LENGTH: 110
<212> TYPE: PRT
<213> ORGANISM: homo sapiens

<400> SEQUENCE: 306

Leu Ala Glu Ile Val Met Thr Gln Ser Pro Ser Phe Leu Ser Ala Ser
1               5                   10                  15

Val Gly Asp Arg Val Thr Ile Thr Cys Arg Ala Ser Gln Gly Ile Gly
            20                  25                  30

Asn Phe Leu Ala Trp Tyr Gln Gln Lys Pro Gly Lys Ala Pro Lys Leu
        35                  40                  45

Leu Ile Ser Gly Ala Ser Thr Leu Gln Ser Trp Val Pro Ser Arg Phe
50                  55                  60

Ser Gly Arg Gly Ser Gly Thr Glu Phe Thr Leu Thr Ile Ser Ser Leu
65                  70                  75                  80

Gln Pro Glu Asp Phe Ala Thr Tyr Tyr Cys Gln Gln Leu Asn Arg Tyr
                85                  90                  95

Pro Pro Tyr Thr Phe Gly Gln Gly Thr Lys Leu Glu Ile Lys
            100                 105                 110
```

<210> SEQ ID NO 307
<211> LENGTH: 109
<212> TYPE: PRT
<213> ORGANISM: homo sapiens

<400> SEQUENCE: 307

Leu Ala Glu Ile Val Met Thr Gln Ser Pro Ser Ser Leu Ser Ala Ser
1               5                   10                  15

Val Gly Asp Arg Val Thr Ile Thr Cys Arg Ala Ser Gln Thr Ile Ser
                20                  25                  30

Asn His Leu Asn Trp Tyr Gln Gln Lys Pro Gly Arg Ala Pro Lys Leu
            35                  40                  45

Leu Ile Tyr Val Gly Ser Ser Leu Gln Ser Gly Val Pro Ser Arg Phe
50                  55                  60

Ser Gly Ser Gly Ser Gly Thr Asp Phe Thr Leu Thr Ile Ser Gly Leu
65                  70                  75                  80

Gln Pro Glu Asp Phe Ala Thr Tyr Tyr Cys Gln Gln Ser Tyr Ser Pro
                85                  90                  95

Ser Tyr Thr Phe Gly Gln Gly Thr Lys Val Glu Ile Lys
            100                 105

<210> SEQ ID NO 308
<211> LENGTH: 110
<212> TYPE: PRT
<213> ORGANISM: homo sapiens

<400> SEQUENCE: 308

Leu Ala Asp Ile Gln Leu Thr Gln Ser Pro Gly Thr Leu Ser Leu Ser
1               5                   10                  15

Pro Gly Glu Arg Ala Thr Leu Ser Cys Arg Ala Ser Gln Ser Val Ser
                20                  25                  30

Thr Asn Tyr Leu Ala Trp Tyr Arg Gln Lys Pro Gly Gln Ala Pro Arg
            35                  40                  45

Leu Leu Ile His Gly Ala Ser Ser Arg Ala Thr Gly Ile Pro Asp Arg
50                  55                  60

Phe Ser Gly Ser Gly Ser Gly Thr Asp Phe Thr Leu Thr Ile Ser Arg
65                  70                  75                  80

Leu Glu Pro Glu Asp Phe Ala Val Tyr Phe Cys Gln Gln Tyr Gly Ser
                85                  90                  95

Ser Pro Gln Thr Phe Gly Gln Gly Thr Arg Leu Glu Ile Lys
            100                 105                 110

<210> SEQ ID NO 309
<211> LENGTH: 109
<212> TYPE: PRT
<213> ORGANISM: homo sapiens

<400> SEQUENCE: 309

Leu Ala Asp Val Val Met Thr Gln Ser Pro Ser Ser Leu Ser Ala Ser
1               5                   10                  15

Leu Gly Asp Arg Val Thr Ile Thr Cys Arg Ala Ser Gln His Ile Ser
                20                  25                  30

Asn Tyr Leu Asn Trp Tyr Gln Gln Lys Pro Gly Lys Ala Pro Lys Leu
            35                  40                  45

Leu Ile Tyr Ala Ala Ser Ser Leu Gln Ser Gly Val Pro Ser Arg Phe
50                  55                  60

Thr Gly Ser Gly Ser Gly Ala Asp Tyr Thr Leu Thr Ile Ser Ser Leu

```
                65                  70                  75                  80
Gln Pro Glu Asp Phe Ala Thr Tyr Tyr Cys Gln Gln Ser Tyr Ser Thr
                85                  90                  95

Ser Trp Thr Phe Gly Gln Gly Thr Thr Val Gly Ile Lys
            100                 105

<210> SEQ ID NO 310
<211> LENGTH: 109
<212> TYPE: PRT
<213> ORGANISM: homo sapiens

<400> SEQUENCE: 310

Leu Ala Asp Val Val Met Thr Gln Ser Pro Ser Ser Leu Ser Ala Ser
1               5                   10                  15

Val Gly Asp Arg Val Ser Ile Thr Cys Arg Ala Ser Arg Ser Val Lys
            20                  25                  30

Thr Tyr Leu Asn Trp Tyr Gln Gln Lys Pro Gly Lys Ala Pro Lys Leu
        35                  40                  45

Leu Val Tyr Gly Ser Ser Ser Leu Glu Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Phe Gly Thr
                85                  90                  95

Pro Tyr Thr Phe Gly Gln Gly Thr Lys Leu Asp Thr Lys
            100                 105

<210> SEQ ID NO 311
<211> LENGTH: 109
<212> TYPE: PRT
<213> ORGANISM: homo sapiens

<400> SEQUENCE: 311

Leu Ala Asp Ile Gln Met Thr Gln Ser Pro Ser Ser Leu Ser Ala Ser
1               5                   10                  15

Val Ser Asp Arg Val Thr Ile Thr Cys Arg Ala Ser Gln Ser Ile Asn
            20                  25                  30

Lys Phe Leu Asn Trp Tyr Gln Gln Lys Pro Gly Lys Ala Pro Gln Leu
        35                  40                  45

Leu Ile Tyr Ala Ala Thr Asn Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Thr Glu Asp Phe Ala Thr Tyr Tyr Cys Gln Gln Ser Tyr Asp Met
                85                  90                  95

Pro Arg Thr Phe Gly Gln Gly Thr Lys Val Glu Ile Lys
            100                 105

<210> SEQ ID NO 312
<211> LENGTH: 110
<212> TYPE: PRT
<213> ORGANISM: homo sapiens

<400> SEQUENCE: 312

Leu Ala Glu Ile Val Leu Thr Gln Ser Pro Gly Thr Leu Ser Leu Ser
1               5                   10                  15

Pro Gly Glu Arg Ala Thr Leu Ser Cys Arg Ala Ser Arg Ser Val Tyr
            20                  25                  30
```

Ser Asn Asn Leu Ala Trp Tyr Gln Gln Lys Pro Asp Gln Ala Pro Arg
                35                  40                  45

Leu Leu Met Tyr Gly Ala Ser Ser Arg Ala Thr Gly Ile Pro Asp Arg
        50                  55                  60

Phe Thr Gly Ser Gly Ser Gly Thr Asp Phe Thr Leu Thr Ile Ser Arg
65                  70                  75                  80

Leu Glu Pro Glu Asp Phe Ala Val Tyr Tyr Cys His Gln Tyr Gly Ala
                85                  90                  95

Ser Asp Asn Thr Phe Gly Gln Gly Thr Lys Leu Glu Ile Lys
                100                 105                 110

<210> SEQ ID NO 313
<211> LENGTH: 115
<212> TYPE: PRT
<213> ORGANISM: homo sapiens

<400> SEQUENCE: 313

Leu Ala Asp Ile Gln Met Thr Gln Ser Pro Asp Ser Leu Ala Val Ser
1               5                   10                  15

Leu Gly Glu Lys Ala Thr Ile Asn Cys Lys Ser Ser Gln Ser Leu Leu
                20                  25                  30

Tyr Ser Ser Asn Asn Lys Asn Tyr Leu Ala Trp Tyr Gln Gln Lys Pro
            35                  40                  45

Gly Gln Pro Pro Lys Leu Leu Ile Tyr Trp Ala Ser Thr Arg Glu Ser
        50                  55                  60

Gly Val Pro Asp Arg Phe Ser Gly Ser Gly Ser Gly Thr Asp Phe Thr
65                  70                  75                  80

Leu Thr Ile Ser Ser Leu Gln Ala Glu Asp Val Ala Val Tyr Tyr Cys
                85                  90                  95

Gln Gln Tyr Tyr Ser Thr Pro Pro Met Phe Gly Gln Gly Thr Lys Val
                100                 105                 110

Glu Ile Lys
        115

<210> SEQ ID NO 314
<211> LENGTH: 110
<212> TYPE: PRT
<213> ORGANISM: homo sapiens

<400> SEQUENCE: 314

Leu Ala Glu Ile Val Met Thr Gln Ser Pro Ser Ser Leu Ser Ala Ser
1               5                   10                  15

Val Gly Asp Arg Val Thr Ile Ser Cys Arg Ala Ser Gln Gly Ile Ser
                20                  25                  30

Asn Phe Leu Ala Trp Phe Gln Gln Lys Pro Gly Gln Val Pro Lys Leu
            35                  40                  45

Leu Ile Tyr Val Ala Ser Thr Leu Gln Ser Gly Val Pro Ser Arg Phe
        50                  55                  60

Ser Gly Ser Gly Ser Gly Thr Asp Phe Ser Leu Thr Ile Asn Gly Leu
65                  70                  75                  80

Gln Pro Glu Asp Val Ala Thr Tyr Tyr Cys Gln Arg Tyr Asp Ser Gly
                85                  90                  95

Leu Ile Phe Thr Phe Gly Pro Gly Thr Lys Val Glu Ile Lys
                100                 105                 110

<210> SEQ ID NO 315

```
<211> LENGTH: 109
<212> TYPE: PRT
<213> ORGANISM: homo sapiens

<400> SEQUENCE: 315

Leu Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Thr Ile Ser
            20                  25                  30

Asn His Leu Asn Trp Tyr Gln Gln Lys Pro Gly Arg Ala Pro Lys Leu
        35                  40                  45

Leu Ile Tyr Val Gly Ser Ser Leu Arg Ser Gly Val Pro Ser Arg Phe
    50                  55                  60

Ser Gly Ser Gly Ser Gly Thr Asp Phe Thr Leu Thr Ile Ser Gly Leu
65                  70                  75                  80

Gln Pro Glu Asp Phe Ala Thr Tyr Tyr Cys Gln Gln Ser Tyr Ser Pro
                85                  90                  95

Ser Tyr Thr Phe Gly Gln Gly Thr Lys Val Glu Ile Lys
            100                 105

<210> SEQ ID NO 316
<211> LENGTH: 110
<212> TYPE: PRT
<213> ORGANISM: homo sapiens

<400> SEQUENCE: 316

Leu Ala Glu Ile Val Leu Thr Gln Ser Pro Ser Ser Leu Ser Ala Ser
1               5                   10                  15

Val Gly Asp Arg Val Thr Ile Thr Cys Arg Ala Ser Gln Gly Ile Ser
            20                  25                  30

Asn Phe Leu Ala Trp Tyr Gln Gln Lys Pro Gly Lys Val Pro Glu Leu
        35                  40                  45

Leu Ile Tyr Gly Ala Ser Thr Leu Gln Ser Gly Val Pro Ser Arg Phe
    50                  55                  60

Ser Gly Ser Gly Ser Gly Thr Asp Phe Thr Leu Thr Ile Asn Ser Leu
65                  70                  75                  80

Gln Pro Glu Asp Val Ala Thr Tyr Tyr Cys Gln Lys Tyr Asp Ser Gly
                85                  90                  95

Leu Arg Phe Thr Phe Gly Pro Gly Ala Lys Val Asp Ile Lys
            100                 105                 110

<210> SEQ ID NO 317
<211> LENGTH: 109
<212> TYPE: PRT
<213> ORGANISM: homo sapiens

<400> SEQUENCE: 317

Leu Ala Asp Val Val Met Thr Gln Ser Pro Ser Ser Leu Ser Ala Ser
1               5                   10                  15

Val Gly Asp Arg Val Ser Ile Thr Cys Arg Ala Ser Arg Ser Val Lys
            20                  25                  30

Thr Tyr Leu Asn Trp Tyr Gln Gln Lys Pro Gly Lys Ala Pro Lys Leu
        35                  40                  45

Leu Val Tyr Gly Ser Ser Leu Glu Ser Gly Val Pro Ser Arg Phe
    50                  55                  60

Ser Gly Ser Gly Ser Gly Thr Asp Phe Thr Leu Thr Ile Ser Ser Leu
65                  70                  75                  80
```

Gln Pro Glu Asp Phe Ala Thr Tyr Cys Cys Gln Gln Ser Phe Gly Thr
                85                  90                  95

Pro Tyr Thr Phe Gly Gln Gly Thr Lys Leu Asp Ile Lys
            100                 105

<210> SEQ ID NO 318
<211> LENGTH: 110
<212> TYPE: PRT
<213> ORGANISM: homo sapiens

<400> SEQUENCE: 318

Leu Ala Asp Ile Gln Leu Thr Gln Ser Pro Ser Ser Leu Ser Ala Ser
1               5                   10                  15

Val Gly Asp Arg Val Thr Ile Thr Cys Arg Ala Ser Gln Gly Ile Ser
            20                  25                  30

Asn Phe Leu Ala Trp Tyr Gln Gln Lys Pro Gly Lys Val Pro Glu Leu
        35                  40                  45

Leu Ile Tyr Gly Ala Ser Thr Leu Gln Ser Gly Val Pro Ser Arg Phe
    50                  55                  60

Ser Gly Ser Gly Ser Gly Thr Glu Phe Thr Leu Thr Ile Asn Ser Leu
65                  70                  75                  80

Gln Pro Glu Asp Val Ala Thr Tyr Tyr Cys Gln Lys Tyr Asp Ser Gly
                85                  90                  95

Leu Arg Phe Thr Phe Gly Pro Gly Thr Lys Val Asp Ile Lys
            100                 105                 110

<210> SEQ ID NO 319
<211> LENGTH: 109
<212> TYPE: PRT
<213> ORGANISM: homo sapiens

<400> SEQUENCE: 319

Leu Ala Asp Ile Gln Met Thr Gln Ser Ser Thr Leu Ser Ala Ser
1               5                   10                  15

Val Gly Asp Arg Val Thr Ile Thr Cys Arg Ala Ser Gln Asn Ile Asn
            20                  25                  30

Ile Trp Leu Ala Trp Tyr Gln Gln Lys Ala Gly Lys Ala Pro Lys Leu
        35                  40                  45

Leu Ile Tyr Lys Ala Ser Thr Leu Glu Arg Gly Val Pro Ser Arg Phe
    50                  55                  60

Ser Gly Ser Gly Ser Gly Thr Glu Phe Thr Leu Thr Ile Thr Gly Leu
65                  70                  75                  80

Arg Pro Asp Asp Phe Gly Ser Tyr Tyr Cys Gln His Tyr Asp Gly Asn
                85                  90                  95

Ser Leu Thr Phe Gly Gln Gly Thr Arg Val Asp Ile Gln
            100                 105

<210> SEQ ID NO 320
<211> LENGTH: 110
<212> TYPE: PRT
<213> ORGANISM: homo sapiens

<400> SEQUENCE: 320

Leu Ala Asp Ile Gln Leu Thr Gln Ser Pro Ser Thr Leu Ser Ala Ser
1               5                   10                  15

Val Gly Asp Arg Val Thr Ile Thr Cys Arg Ala Ser Gln Ser Ile Gly
            20                  25                  30

Ser Trp Leu Ala Trp Tyr Gln Gln Lys Pro Gly Lys Ala Pro Lys Leu

```
            35                  40                  45
Leu Ile Tyr Lys Ala Ser Thr Leu Gln Ser Glu Thr Pro Ser Arg Phe
 50                  55                  60

Arg Gly Ser Gly Ser Gly Thr Glu Phe Thr Leu Thr Ile Ser Ser Leu
 65                  70                  75                  80

Gln Pro Asp Asp Phe Ala Thr Tyr Tyr Cys Gln Gln Phe Asn Ser Phe
                 85                  90                  95

Ser Pro Trp Thr Phe Gly Gln Gly Thr Lys Ala Glu Phe Lys
            100                 105                 110

<210> SEQ ID NO 321
<211> LENGTH: 402
<212> TYPE: DNA
<213> ORGANISM: Artificial
<220> FEATURE:
<223> OTHER INFORMATION: Vector sequence

<400> SEQUENCE: 321
gctagcgctg gttgggcagc gagtaataac aatccagcgg ctgccgtagg caataggtat      60
ttcattatga ctgtctcctt ggcgactagc tagtttagaa ttaattcgtg aaattgttat     120
ccgctcacaa ttccacacaa catacgagcc ggaagcataa agtgtaaagc ctggggtgcc     180
taatgagtga gctaactcac attaattgcg ttgcgctcac tgcccgcttt ccagatctta     240
ctccccatcc ccctgttgac aattaatcat cggctcgtat gatgtgtgga attgtgagcg     300
gataacaatt tcacacagga aacaggagat atacatatga aatacctgct gccgaccgct     360
gctgctggtc tgctgctcct cgctgcccag ccggggcgcg cc                       402

<210> SEQ ID NO 322
<211> LENGTH: 37
<212> TYPE: DNA
<213> ORGANISM: Artificial
<220> FEATURE:
<223> OTHER INFORMATION: Primer sequence

<400> SEQUENCE: 322
tattggcgcg ccatggccgc ccagtctgtg acccagc                              37

<210> SEQ ID NO 323
<211> LENGTH: 36
<212> TYPE: DNA
<213> ORGANISM: Artificial
<220> FEATURE:
<223> OTHER INFORMATION: Primer sequence

<400> SEQUENCE: 323
tattggcgcg ccatggccgc ccagaagata actcaa                               36

<210> SEQ ID NO 324
<211> LENGTH: 36
<212> TYPE: DNA
<213> ORGANISM: Artificial
<220> FEATURE:
<223> OTHER INFORMATION: Primer sequence

<400> SEQUENCE: 324
tattggcgcg ccatggccga tgctaagacc acccag                               36

<210> SEQ ID NO 325
<211> LENGTH: 36
<212> TYPE: DNA
<213> ORGANISM: Artificial
```

```
<220> FEATURE:
<223> OTHER INFORMATION: Primer sequence

<400> SEQUENCE: 325
tattggcgcg ccatggccgc ccagacagtc actcag                                36

<210> SEQ ID NO 326
<211> LENGTH: 37
<212> TYPE: DNA
<213> ORGANISM: Artificial
<220> FEATURE:
<223> OTHER INFORMATION: Primer sequence

<400> SEQUENCE: 326
tattggcgcg ccatggccaa acaggaggtg acacaga                               37

<210> SEQ ID NO 327
<211> LENGTH: 37
<212> TYPE: DNA
<213> ORGANISM: Artificial
<220> FEATURE:
<223> OTHER INFORMATION: Primer sequence

<400> SEQUENCE: 327
tattggcgcg ccatggccgg agactcggtt acccaga                               37

<210> SEQ ID NO 328
<211> LENGTH: 37
<212> TYPE: DNA
<213> ORGANISM: Artificial
<220> FEATURE:
<223> OTHER INFORMATION: Primer sequence

<400> SEQUENCE: 328
tattggcgcg ccatggccgg agattcagtg acccaga                               37

<210> SEQ ID NO 329
<211> LENGTH: 37
<212> TYPE: DNA
<213> ORGANISM: Artificial
<220> FEATURE:
<223> OTHER INFORMATION: Primer sequence

<400> SEQUENCE: 329
tattggcgcg ccatggccag caattcagtc aagcaga                               37

<210> SEQ ID NO 330
<211> LENGTH: 36
<212> TYPE: DNA
<213> ORGANISM: Artificial
<220> FEATURE:
<223> OTHER INFORMATION: Primer sequence

<400> SEQUENCE: 330
tattggcgcg ccatggccgg acaaaacatt gaccag                                36

<210> SEQ ID NO 331
<211> LENGTH: 37
<212> TYPE: DNA
<213> ORGANISM: Artificial
<220> FEATURE:
<223> OTHER INFORMATION: Primer sequence

<400> SEQUENCE: 331
tattggcgcg ccatggccaa aaatgaagtg gagcaga                               37
```

<210> SEQ ID NO 332
<211> LENGTH: 37
<212> TYPE: DNA
<213> ORGANISM: Artificial
<220> FEATURE:
<223> OTHER INFORMATION: Primer sequence

<400> SEQUENCE: 332
tattggcgcg ccatggccga agaccaggtg acgcaga                              37

<210> SEQ ID NO 333
<211> LENGTH: 37
<212> TYPE: DNA
<213> ORGANISM: Artificial
<220> FEATURE:
<223> OTHER INFORMATION: Primer sequence

<400> SEQUENCE: 333
tattggcgcg ccatggccgg aatacaagtg gagcaga                              37

<210> SEQ ID NO 334
<211> LENGTH: 37
<212> TYPE: DNA
<213> ORGANISM: Artificial
<220> FEATURE:
<223> OTHER INFORMATION: Primer sequence

<400> SEQUENCE: 334
tattggcgcg ccatggccct acatacactg gagcaga                              37

<210> SEQ ID NO 335
<211> LENGTH: 37
<212> TYPE: DNA
<213> ORGANISM: Artificial
<220> FEATURE:
<223> OTHER INFORMATION: Primer sequence

<400> SEQUENCE: 335
tattggcgcg ccatggccga agacaaggtg gtacaaa                              37

<210> SEQ ID NO 336
<211> LENGTH: 37
<212> TYPE: DNA
<213> ORGANISM: Artificial
<220> FEATURE:
<223> OTHER INFORMATION: Primer sequence

<400> SEQUENCE: 336
tattggcgcg ccatggccga aaaccaggtg gagcaca                              37

<210> SEQ ID NO 337
<211> LENGTH: 36
<212> TYPE: DNA
<213> ORGANISM: Artificial
<220> FEATURE:
<223> OTHER INFORMATION: Primer sequence

<400> SEQUENCE: 337
tattggcgcg ccatggccca ggagaatgtg gagcag                               36

<210> SEQ ID NO 338
<211> LENGTH: 36
<212> TYPE: DNA
<213> ORGANISM: Artificial
<220> FEATURE:
<223> OTHER INFORMATION: Primer sequence

```
<400> SEQUENCE: 338
tattggcgcg ccatggccgg agagagtgtg gggctg                              36

<210> SEQ ID NO 339
<211> LENGTH: 37
<212> TYPE: DNA
<213> ORGANISM: Artificial
<220> FEATURE:
<223> OTHER INFORMATION: Primer sequence

<400> SEQUENCE: 339
tattggcgcg ccatggccgg agaggatgtg gagcaga                             37

<210> SEQ ID NO 340
<211> LENGTH: 37
<212> TYPE: DNA
<213> ORGANISM: Artificial
<220> FEATURE:
<223> OTHER INFORMATION: Primer sequence

<400> SEQUENCE: 340
tattggcgcg ccatggccag ccaaaagata gaacaga                             37

<210> SEQ ID NO 341
<211> LENGTH: 36
<212> TYPE: DNA
<213> ORGANISM: Artificial
<220> FEATURE:
<223> OTHER INFORMATION: Primer sequence

<400> SEQUENCE: 341
tattggcgcg ccatggccag tcaacaggga gaagag                              36

<210> SEQ ID NO 342
<211> LENGTH: 36
<212> TYPE: DNA
<213> ORGANISM: Artificial
<220> FEATURE:
<223> OTHER INFORMATION: Primer sequence

<400> SEQUENCE: 342
tattggcgcg ccatggccca acaaccagtg cagagt                              36

<210> SEQ ID NO 343
<211> LENGTH: 37
<212> TYPE: DNA
<213> ORGANISM: Artificial
<220> FEATURE:
<223> OTHER INFORMATION: Primer sequence

<400> SEQUENCE: 343
tattggcgcg ccatggccag ccaagaactg gagcaga                             37

<210> SEQ ID NO 344
<211> LENGTH: 37
<212> TYPE: DNA
<213> ORGANISM: Artificial
<220> FEATURE:
<223> OTHER INFORMATION: Primer sequence

<400> SEQUENCE: 344
tattggcgcg ccatggccgg tcaacagctg aatcaga                             37

<210> SEQ ID NO 345
```

```
<211> LENGTH: 37
<212> TYPE: DNA
<213> ORGANISM: Artificial
<220> FEATURE:
<223> OTHER INFORMATION: Primer sequence

<400> SEQUENCE: 345
tattggcgcg ccatggccac ccagctgctg gagcaga                               37

<210> SEQ ID NO 346
<211> LENGTH: 36
<212> TYPE: DNA
<213> ORGANISM: Artificial
<220> FEATURE:
<223> OTHER INFORMATION: Primer sequence

<400> SEQUENCE: 346
tattggcgcg ccatggccca gcagcaggtg aaacaa                                36

<210> SEQ ID NO 347
<211> LENGTH: 36
<212> TYPE: DNA
<213> ORGANISM: Artificial
<220> FEATURE:
<223> OTHER INFORMATION: Primer sequence

<400> SEQUENCE: 347
tattggcgcg ccatggccat actgaacgtg gaacaa                                36

<210> SEQ ID NO 348
<211> LENGTH: 36
<212> TYPE: DNA
<213> ORGANISM: Artificial
<220> FEATURE:
<223> OTHER INFORMATION: Primer sequence

<400> SEQUENCE: 348
tattggcgcg ccatggccga ccagcaagtt aagcaa                                36

<210> SEQ ID NO 349
<211> LENGTH: 36
<212> TYPE: DNA
<213> ORGANISM: Artificial
<220> FEATURE:
<223> OTHER INFORMATION: Primer sequence

<400> SEQUENCE: 349
tattggcgcg ccatggccgg acaacaggta atgcaa                                36

<210> SEQ ID NO 350
<211> LENGTH: 36
<212> TYPE: DNA
<213> ORGANISM: Artificial
<220> FEATURE:
<223> OTHER INFORMATION: Primer sequence

<400> SEQUENCE: 350
tattggcgcg ccatggccaa ggaccaagtg tttcag                                36

<210> SEQ ID NO 351
<211> LENGTH: 21
<212> TYPE: DNA
<213> ORGANISM: Artificial
<220> FEATURE:
<223> OTHER INFORMATION: Primer sequence

<400> SEQUENCE: 351
```
taggcagaca gacttgtcac t                                                    21

<210> SEQ ID NO 352
<211> LENGTH: 43
<212> TYPE: DNA
<213> ORGANISM: Artificial
<220> FEATURE:
<223> OTHER INFORMATION: Primer sequence

<400> SEQUENCE: 352
gccatggcgc gccaatagct agccggtgaa gaagtcgccc aga                            43

<210> SEQ ID NO 353
<211> LENGTH: 43
<212> TYPE: DNA
<213> ORGANISM: Artificial
<220> FEATURE:
<223> OTHER INFORMATION: Primer sequence

<400> SEQUENCE: 353
gccatggcgc gccaatagct agccgatgcc atggtcatcc aga                            43

<210> SEQ ID NO 354
<211> LENGTH: 43
<212> TYPE: DNA
<213> ORGANISM: Artificial
<220> FEATURE:
<223> OTHER INFORMATION: Primer sequence

<400> SEQUENCE: 354
gccatggcgc gccaatagct agccgaagcc caagtgaccc aga                            43

<210> SEQ ID NO 355
<211> LENGTH: 43
<212> TYPE: DNA
<213> ORGANISM: Artificial
<220> FEATURE:
<223> OTHER INFORMATION: Primer sequence

<400> SEQUENCE: 355
gccatggcgc gccaatagct agcccatgcc aaagtcacac aga                            43

<210> SEQ ID NO 356
<211> LENGTH: 43
<212> TYPE: DNA
<213> ORGANISM: Artificial
<220> FEATURE:
<223> OTHER INFORMATION: Primer sequence

<400> SEQUENCE: 356
gccatggcgc gccaatagct agccgacaca gccgtttccc aga                            43

<210> SEQ ID NO 357
<211> LENGTH: 43
<212> TYPE: DNA
<213> ORGANISM: Artificial
<220> FEATURE:
<223> OTHER INFORMATION: Primer sequence

<400> SEQUENCE: 357
gccatggcgc gccaatagct agccgaaacg ggagttacgc aga                            43

<210> SEQ ID NO 358
<211> LENGTH: 43
<212> TYPE: DNA

-continued

<213> ORGANISM: Artificial
<220> FEATURE:
<223> OTHER INFORMATION: Primer sequence

<400> SEQUENCE: 358
gccatggcgc gccaatagct agccgaacct gaagtcaccc aga          43

<210> SEQ ID NO 359
<211> LENGTH: 43
<212> TYPE: DNA
<213> ORGANISM: Artificial
<220> FEATURE:
<223> OTHER INFORMATION: Primer sequence

<400> SEQUENCE: 359
gccatggcgc gccaatagct agccgaagct gacatctacc aga          43

<210> SEQ ID NO 360
<211> LENGTH: 43
<212> TYPE: DNA
<213> ORGANISM: Artificial
<220> FEATURE:
<223> OTHER INFORMATION: Primer sequence

<400> SEQUENCE: 360
gccatggcgc gccaatagct agccatatct ggagtctccc aca          43

<210> SEQ ID NO 361
<211> LENGTH: 43
<212> TYPE: DNA
<213> ORGANISM: Artificial
<220> FEATURE:
<223> OTHER INFORMATION: Primer sequence

<400> SEQUENCE: 361
gccatggcgc gccaatagct agccgatgct ggaatcaccc aga          43

<210> SEQ ID NO 362
<211> LENGTH: 43
<212> TYPE: DNA
<213> ORGANISM: Artificial
<220> FEATURE:
<223> OTHER INFORMATION: Primer sequence

<400> SEQUENCE: 362
gccatggcgc gccaatagct agccaatgct ggtgtcactc aga          43

<210> SEQ ID NO 363
<211> LENGTH: 42
<212> TYPE: DNA
<213> ORGANISM: Artificial
<220> FEATURE:
<223> OTHER INFORMATION: Primer sequence

<400> SEQUENCE: 363
gccatggcgc gccaatagct agccagtgct gtcgtctctc aa           42

<210> SEQ ID NO 364
<211> LENGTH: 42
<212> TYPE: DNA
<213> ORGANISM: Artificial
<220> FEATURE:
<223> OTHER INFORMATION: Primer sequence

<400> SEQUENCE: 364
gccatggcgc gccaatagct agccgacgct ggagtcacac aa           42

-continued

<210> SEQ ID NO 365
<211> LENGTH: 43
<212> TYPE: DNA
<213> ORGANISM: Artificial
<220> FEATURE:
<223> OTHER INFORMATION: Primer sequence

<400> SEQUENCE: 365
gccatggcgc gccaatagct agccgatggt ggaatcactc agt             43

<210> SEQ ID NO 366
<211> LENGTH: 42
<212> TYPE: DNA
<213> ORGANISM: Artificial
<220> FEATURE:
<223> OTHER INFORMATION: Primer sequence

<400> SEQUENCE: 366
gccatggcgc gccaatagct agccactgct gggatcaccc ag              42

<210> SEQ ID NO 367
<211> LENGTH: 43
<212> TYPE: DNA
<213> ORGANISM: Artificial
<220> FEATURE:
<223> OTHER INFORMATION: Primer sequence

<400> SEQUENCE: 367
gccatggcgc gccaatagct agccgaagct ggagttgccc agt             43

<210> SEQ ID NO 368
<211> LENGTH: 43
<212> TYPE: DNA
<213> ORGANISM: Artificial
<220> FEATURE:
<223> OTHER INFORMATION: Primer sequence

<400> SEQUENCE: 368
gccatggcgc gccaatagct agccgaagct ggagtggttc agt             43

<210> SEQ ID NO 369
<211> LENGTH: 43
<212> TYPE: DNA
<213> ORGANISM: Artificial
<220> FEATURE:
<223> OTHER INFORMATION: Primer sequence

<400> SEQUENCE: 369
gccatggcgc gccaatagct agccgaagct ggagttactc agt             43

<210> SEQ ID NO 370
<211> LENGTH: 42
<212> TYPE: DNA
<213> ORGANISM: Artificial
<220> FEATURE:
<223> OTHER INFORMATION: Primer sequence

<400> SEQUENCE: 370
gccatggcgc gccaatagct agccgatgct gtagttacac aa              42

<210> SEQ ID NO 371
<211> LENGTH: 43
<212> TYPE: DNA
<213> ORGANISM: Artificial
<220> FEATURE:

<223> OTHER INFORMATION: Primer sequence

<400> SEQUENCE: 371
gccatggcgc gccaatagct agccgatgct ggagttatcc agt        43

<210> SEQ ID NO 372
<211> LENGTH: 42
<212> TYPE: DNA
<213> ORGANISM: Artificial
<220> FEATURE:
<223> OTHER INFORMATION: Primer sequence

<400> SEQUENCE: 372
gccatggcgc gccaatagct agccggtgct ggagtctccc ag         42

<210> SEQ ID NO 373
<211> LENGTH: 43
<212> TYPE: DNA
<213> ORGANISM: Artificial
<220> FEATURE:
<223> OTHER INFORMATION: Primer sequence

<400> SEQUENCE: 373
gccatggcgc gccaatagct agccgatgct gatgttaccc aga        43

<210> SEQ ID NO 374
<211> LENGTH: 43
<212> TYPE: DNA
<213> ORGANISM: Artificial
<220> FEATURE:
<223> OTHER INFORMATION: Primer sequence

<400> SEQUENCE: 374
gccatggcgc gccaatagct agcctctcag actattcatc aat        43

<210> SEQ ID NO 375
<211> LENGTH: 21
<212> TYPE: DNA
<213> ORGANISM: Artificial
<220> FEATURE:
<223> OTHER INFORMATION: Primer sequence

<400> SEQUENCE: 375
caggcacacc agtgtggcct t                                 21

<210> SEQ ID NO 376
<211> LENGTH: 36
<212> TYPE: DNA
<213> ORGANISM: Artificial
<220> FEATURE:
<223> OTHER INFORMATION: Primer sequence

<400> SEQUENCE: 376
caccttagag ctcttagagt ctctcagctg gtacac                 36

<210> SEQ ID NO 377
<211> LENGTH: 33
<212> TYPE: DNA
<213> ORGANISM: Artificial
<220> FEATURE:
<223> OTHER INFORMATION: Primer sequence

<400> SEQUENCE: 377
gacattatgc atgatctctg cttctgatgg ctc                    33